(12) United States Patent
Bolten et al.

(10) Patent No.: US 7,238,507 B2
(45) Date of Patent: Jul. 3, 2007

(54) ASPERGILLUS OCHRACEUS 11 ALPHA HYDROXYLASE AND OXIDOREDUCTASE

(75) Inventors: Suzanne L. Bolten, Kirkwood, MO (US); Robert A. Clayton, Foristell, MO (US); Alan M. Easton, Maryland Heights, MO (US); Leslie C. Engel, Des Peres, MO (US); Dean M. Messing, St. Louis, MO (US); John S. Ng, Thousand Oaks, CA (US); Beverly Reitz, Chesterfield, MO (US); Mark C. Walker, Chesterfield, MO (US); Ping T. Wang, Chesterfield, MO (US)

(73) Assignee: Pharmacia Corporation, St. Louis, MO (US)

( * ) Notice: Subject to any disclaimer, the term of this patent is extended or adjusted under 35 U.S.C. 154(b) by 79 days.

(21) Appl. No.: 10/900,856

(22) Filed: Jul. 28, 2004

(65) Prior Publication Data
US 2005/0003473 A1 Jan. 6, 2005

Related U.S. Application Data

(62) Division of application No. 10/021,425, filed on Oct. 30, 2001, now Pat. No. 7,033,807.

(60) Provisional application No. 60/244,300, filed on Oct. 30, 2000.

(51) Int. Cl.
C12N 9/02 (2006.01)
(52) U.S. Cl. .................... 435/189; 435/69.7
(58) Field of Classification Search .............. None
See application file for complete search history.

(56) References Cited

U.S. PATENT DOCUMENTS

| | | | | |
|---|---|---|---|---|
| 4,419,446 | A | 12/1983 | Howley et al. | 435/68 |
| 4,559,332 | A | 12/1985 | Grob et al. | 514/175 |
| 4,588,683 | A | 5/1986 | Goodhue et al. | 435/59 |
| 4,935,233 | A | 6/1990 | Bell et al. | 424/85.5 |
| 5,348,886 | A | 9/1994 | Lee et al. | 435/320.1 |
| 5,384,253 | A | 1/1995 | Krzyzek et al. | 435/172.3 |
| 5,422,262 | A | 6/1995 | Andersson et al. | 435/240.1 |
| 5,679,521 | A | 10/1997 | Andersson et al. | 435/6 |
| 5,869,283 | A | 2/1999 | Slijkhuis et al. | 435/69.1 |
| 6,046,023 | A | 4/2000 | Wiersma et al. | 435/60 |

FOREIGN PATENT DOCUMENTS

| | | |
|---|---|---|
| EP | 528 906 B1 | 10/1995 |
| WO | WO98/25948 | 6/1998 |

OTHER PUBLICATIONS

Altschul S F, et al; J. Molec Biol. (Oct. 5, 1990) p. 403-410.
Anfossi et al., Proc. Natl. Acad. Science (1989) 86:3379-3383.
Arfin et al., Proc. Natl. Acad. Science (1995) 92:7714-7718.
Armour et al., FEBS Lett. (1992) 307 : 113-115.
Baldwin et al., Gene Ther. (1997) 4:1142-1149.
Barany, Proc. Natl Acad. Science (1991) 88:189-193.
Zamechik et al. Proc. Natl. Acad. Sci. (1986) 83:4143-4146.
Baum et al., J. Hematother (1996) 5:323-329.
Becker et al., EMBO J. (1989) 8:3685-3691.
Ben-Bassat et al., J. Bacteriol. (1987) 169:751-757.
Berkner, BioTechniques (1988) 6:616-629.
Berkner, Current Top. Microbiol. Immunol. (1992) 158:39-66.
Blobel and Dobberstein, J. Cell Biol. (1975) 67:835-851.
Boris-Lawrie and Temin, Annal. New York Acad. Sci. (1944) 716:59-71.
Boris-Lawrie and Temin, Curr. Opin. Genet. Dev. (1993) 3:102-109.
Bostian et al., Cell (1984) 36:741-751.
Botstein et al., Ann. J. Hum. Genet. (1980) 32:314-331.
Bregni et al., Blood (1992) 80:1418-1422.
Breskvar Ket al., Biochem. Biophys. Res. Commun (1991) 178, 1078-1083.
Brody and Crystal, Annal. New York Acad. Sci. (1994) 716:90-103.
Capecchi, Cell (1980) 22:479-488.
Chen et al., Gene Ther. (1998) 5:50-58.
Clapp, Clin. Perinatol. (1993) 20:155-168.
Collins, W.P., Alternative Immunoassays, (1985) 1-38,77-86,103-184.
Corbi and Lopez-Rodriguez, Leuk. Lymphoma (1997) 25:415-425.
Crabeel et al., EMBO J. (1983) 2:205-212.
Curiel et al., Hum. Gen. Ther. (1992) 3:147-154.
John Wiley & Sons, N.Y., Current Protocols in Molecular Biology, (1989), contents, pp. 6.7.1-6.7.6.
Czerwinski, M. et al. Unpublished, Direct Submission [AAG09798].

(Continued)

*Primary Examiner*—Charles L. Patterson, Jr.
(74) *Attorney, Agent, or Firm*—Charles Ashbrook; Chris Slavinsky

(57) ABSTRACT

The present invention relates to a novel cytochrome P450-like enzyme (*Aspergillus ochraceus* 11 alpha hydroxylase) and an oxidoreductase (*Aspergillus ochraceus* oxidoreductase) isolated from cDNA library generated from the mRNA of *Aspergillus ochraceus* spores. When the cDNA encoding the 11 alpha hydroxylase was co-expressed in *Spodoptera frugiperda* (Sf-9) insect cells with the cDNA encoding human oxidoreductase as an electron donor, it successfully catalyzed the conversion of the steroid substrate 4-androstene-3,17-dione (AD) to 11 alpha-hydroxy-AD as determined by HPLC analysis. The invention also relates to nucleic acid molecules associated with or derived from these cDNAs including complements, homologues and fragments thereof, and methods of using these nucleic acid molecules, to generate, for example, polypeptides and fragments thereof. The invention also relates to the generation of antibodies that recognizes the *A. ochraceus* 11 alpha hydroxylase and oxidoreductase and methods of using these antibodies to detect the presence of these native and recombinant polypeptides within unmodified and transformed host cells, respectively. The invention also provides methods of expressing the *Aspergillus* 11 alpha hydroxylase gene separately, or in combination with human or *Aspergillus* oxidoreductase, in heterologous host cells, to facilitate the bioconversion of steroid substrates to their 11 alpha hydroxy-counterparts.

5 Claims, 25 Drawing Sheets

OTHER PUBLICATIONS

Datta et al., Proc. Natl. Acad. Sci. (1988) USA 85: 3324-2238 1.
Derynck et al., Nucleic Acids Res. (1983) 11:1819-1837.
Dobson et al., Nucleic Acids. Res. (1983) 11:2287-2302.
Dunbar et al., Blood (1995) 85:3048-3057.
Dutta TK et al. Biochem. Biophys. Res. Commun. (1993) 192:119-123.
Eglitis and Anderson, Biotechniques, (1988) 6:608-614.
Elshami et al., Cancer Gene Ther. (1997) 4:213-221.
Engel, L. et al. Dev Biol. (1990) 140: 196-208.
Fackrell, Clin. Immunoassay (1985) 8:213-219.
Fernandez de Henestrosa et al., FEMS Microbiol. Lett. (1997) 147:209-213.
Frohman, M.A. et al., Proc. Natl. Acad. Sci. (1988) (U.S.A.) 85:8998-9002.
Fromm et al., Nature 319:791 (1986).
Fromm et al., Proc. Natl. Acad. Sci. (U.S.A.) (1985) 82:5824-5828.
Gerwirtz et al., Science (1988) 242:1303-1306.
Ghosh D, et al. J. Steroid Biochem. 1981; 14, 1063-1067.
Goff et al., EMBO J. (1990) 9:2517-2522.
Goodchild et al., Proc. Natl. Acad. Sci. (U.S.A.) (1988) 85:5507-5511.
Goodhue, Charles T., Microb. Transform. Bioact. Compound, (1982) 1: 9-44.
Graham and van der Eb, Virology (1973) 54:536-539.
Gray et al., Proc. R. Acad. Soc. Lond. (1991) 243:241-253.
Griffith et al. Chem. Biol. (1997) 4:461-471.
Griffiths et al., Biochem. J. (1987) 241: 313-324.
Guarente and Ptashne, Proc. Natl. Acad. Sci. (1981) (U.S.A.) 78:2199-2203.
Gusella, Ann. Rev. Biochem. (1986) 55:831-854.
Hallek et al., Cytokines Mol. Ther. (1996) 2: 69-79.
Hames, B. D. et al. Nucleic Acid Hybridization, A Practical Approach, (1985) Table of Content, and pp. 3-15, 47-71, and 113-137.
Hasan et al., Gene (1987) 56:145-151.
Haniu, M., et al. Biochemistry (1989) 28 (21), 8639-8645 [P16435].
Harley and Reynolds, Nucleic Acids Res. (1987) 15:2343-2361.
Harlow and Lane, *In Antibodies: A Laboratory Manual*, Cold Spring Harbor Press, Cold Spring Harbor, New York (1988).
Harms and Splitter, Hum. Gene Ther. (1995) 6:1291-1297.
Hattori et al., Genes Dev. (1992) 6: 609-618.
Hawley and McClure, Nucleic Acids Res. (1983) 11:2237-2255.
Haniu,M., et al. Biochemistry (1986) 25 (24), 7906-7911 [P04175].
Hillel et al., Anim. Genet. (1989) 20:145-155.
Hillel et al., Genet. (1990) 124:783-789.
Hitzeman et al., Nature (1981) 293:717-722.
Holt et al., Molec. Cell. Biol. (1988) 8:963-973.
Ingber et al. Nature (1990) 348:555-557.
Janknecht et al., Carcinogenesis (1995) 16:443-450.
Janknecht Immunobiology (1995) 193:137-142.
Jayanthi CR, et al., Biochem. Biophys. Res. Commun.(1987) 106:1262-1268.
Jefferson et al., EMBO J. 6: 3901-3907.
Jefferson Plant Mol. Biol. Rep. (1987) 5: 387-405.
Jeffreys et al., Amer. J. Hum. Genet. (1986) 39:11-24.
Jeffreys et al., Anim. Genet. (1987) 18:1-15.
Jeffreys et al., Nature (1985) 316:76-79.
Johnston and Tang, Methods Cell Biol. (1994) 43:353-365.
Jones et al., Eur. J. Haematol. (1987) 39:144-147.
Julius et al., Cell (1983) 32:839-852.
Julius et al., Cell (1984) 36:309-318.
Katagiri,M. et al. J. Biochem. (1986) 100 (4), 945-954 [P00389].
Kemeny, D.M. et al.; ELISA & Other Solid Phase Immunoassays (1988) 265-78.
Kendall and Bradshaw, J. Biol. Chem. 267:20667-20673 (1992).
Kennedy, J. et al. Science (1999) In press LOCUS AAD34552 528 aa PLN Jun. 2, 1999.
Kieslich, K. et al.; Fed. Rep. Ger. Annu. Rep. Ferment. Processes, 3: 275-304, 1979.
Kieslich, Klaus. Fed. Rep. Ger. Econ. Microbiol. 5 (Microb. Enzymes Bioconvers.), 369-465, 1980.
King and Possee, The Baculovirus Expression System: A Laboratory Guide, London, Chapman & Hall (contents only).
Kurjan and Herskowitz, Cell (1982) 30:933-943.
Kusaka et al. ; Biochem. Biophys. Res. Commun. (1991) 174:1070-1076.
Kwoh et al., Proc. Natl. Acad. Sci. (U.S.A.) (1989) 86:1173.
Laboratory Techniques and Biochemistry in Molecular Biology, by Work, et al., North Holland Publishing Company, NY (1979) 8-259.
Lacour, Thierry, et al. Journal of Biological Chemistry (1998) 273, 23984-23992.
Landegren et al. ; Science (1988) 241:1077-1080.
Langer R. et al., Chem. Tech. (1982) 12:98.
Li and Chang, Biochem. Biophys. Res. Comm. (1989) 227: 152-159.
Lorz et al., Mol. Gen. Genet. (1985) 199:178.
Lu et al., J. Exp. Med. (1993) 178:2089-2096.
Luckow et al. ; J. Virol. (1993) 67: 4566-4579.
Luckow, V. Protein Eng. J. L. Cleland., Wiley-Liss, NY, NY (1996) 183-2180.
Makovec and Breskvar, Pflugers Arch—Eur J. Physiol 439(Suppl): R111-R112, 2000.
Makovec T, Breskvar K. Arch Biochem Biophys. (1998) 357, 310-6.
Marcotte et al., Nature 335:454-457 (1988).
Marsh, Nucleic Acids Res. (1986) 14:3603.
McCarty et al., Cell (1991) 66: 895-905.
McCowen et al., Science (1951) 113:202-203.
Miller Current Top. Microbiol. Immunol. (1992) 158:1-24.
Bazan et al., Proc. Natl. Acad. Sci. (U.S.A.) (1987) 91:2473-2477.
Moore et al., Genomics (1991) 10:654-660.
Mori and Prager, Leuk. Lymphoma (1997) 26:421-433.
Mouyna,I. Et al. Unpublished LOCUS CAA57874 294 aa PLN Jul. 21, 1997.
Mullis et al., Cold Spring Harbor Symp. Quant. Biol. (1986) 51:263-273.
Myers EW, Miller W. Bull Math Biol. (1989)51: 5-37.
Nelson DR, Koymans L, et al. Pharmacogenetics (1996) 6, 1-42.
Ngo et al., Enzyme Mediated Immunoassay, Plenum Press, NY (1985) 203-276.
Nickerson et al., Proc. Natl. Acad. Sci. (U.S.A.) 87:8923-8927 (1990).
No Authors. Genome sequence of the nematode C. elegans: a platform for investigating biology. The C. elegans Sequencing Consortium. Science 282 (5396), 2012-2018 (1998).
Norman et al., Vaccine (1997) 15:801-803.
Nussbaumer et al., FEMS Microbiol. Letter (1994) 118:57-63.
O'Neill et al., Transplant Proc. (1991) 23:2862-2866.
Obukowicz et al., Applied Environmental Microbiology (1992) 58:1511-1523.
Ohara et al., Proc. Natl. Acad. Sci. (U.S.A.) (1989) 86:5673-5677.
Ohgiya,S. et al. Biochim. Biophys. Acta 1186 (1-2),137-141 (1994).
O'Reilly et al., Baculovirus Expression Vectors: A Laboratory Manual. New York, W.H. Freeman and Company (1992) 98-100 and 102, 103.
Ow et al., Science (1986) 234: 856-859.
Peseckis et al., J. Biol. Chem. (1993) 267:5107-5114.
Porter,T.D. et al. Proc. Natl. Acad. Sci. U.S.A. 82 (4), 973-977 (1985).
Poulsen, et al., Mol. Gen. Genet. (1986) 205:193-200.
Rachal et al., EXS (1993) 64:330-342.
Ray et al., Adv. Exp. Med. Biol. (1990) 280:107-111.
Remington's Pharmaceutical Sciences, 16th ed., Osol, Ed., Mack, (1980), contents, 898-901, 936, 1283-1286.
Roderick and Matthews, Biochemistry (1993) 32:3907-3912.
Romanos et al., Yeast (1992) 8:423-488.
Rose et al., Proc. Natl. Acad. Sci. (U.S.A.) (1981) 78:2460-2464.
Rothman and Orci, Nature (1992) 355:409-415.
Samanta TB, et al. J Steroid Biochem (1987) 28, 327-32.
Samanta TB, Roy N, Chattopadhyay. An Improved 11 α-Hydroxylation of Progesterone by *Aspergillus ochraceus* TS. Biochem. J. 1978; 176, 593-594.

Sambrook et al., Molecular Cloning, A Laboratory Manual, Spring Harbor Press, Cold Spring Harbor, New York (1989) Book 1; 1.74-1.84, 5.3-5.89 and Book 2; 8.33-8.51, 9.31-9.57, 11.45-11.55, and 15.3-15.108.

[Published errata appear in Science Jan. 1, 1999;283(5398):35 and Mar. 26, 1999;283(5410):2103 and Sep. 3, 1999;285 (5433):1493]] LOCUS CAA91268 510 aa INV Jul. 13, 2000.

Schroeder,G., et al.; FEBS Lett. 458, 97-102 (1999) LOCUS CAB56503 495 aa PLN Sep. 23, 1999.

Schulte,U., Aign,V., Hoheisel,J., Brandt,P., Fartmann,B., Holland,R., Nyakatura,G., Mewes,H.W. and Mannhaupt,G., Unpublished LOCUS CAB91316 514 aa PLN May 11, 2000.

Serfing et al., Biochim. Biophys. Acta (1995) 1263:181-200.

Shannon et al., Crit. Rev. Immunol. (1997) 17:301-323.

Shephard,E.A., et al. Arch. Biochem. Biophys. 294 (1), 168-172 (1992) S90469 [AAB21814].

Sidman U. et al., Biopolymers (1983) 22:547.

Siminszky,B., et al. Proc. Natl. Acad. Sci. U.S.A. (1999) 96 (4), 1750-1755.

Sin et al. Proc. Natl. Acad. Sci. (U.S.A.) 94:6099-6103 (1997).

Skolnick, M.H. et al., Cytogen. Cell Genet. 32:58-67 (1982).

Yolken Rev. Infect. Dis. (1982) 4:35.

Smith KE, et al. *J Steroid Biochem Mol Biol* 49, 93-100 (1994).

Sonderfan, A.J., et al. Arch. Biochem. Biophys. (1987) 255:27-41.

Suh et al., Gene (1996) 169:17-23.

Sun et al., Curr. Top. Microbiol. Immunol (1996) 211:173-187.

Sutcliffe et al., Proc. Natl. Acad. Sci. (U.S.A.) (1978) 75: 3737-3741.

Takai et al., Princess Takamatsu Symp. (1991) 22:197-204.

Tan L, Falardeau P. 11α-Hydroxylation and Degradation of Progesterone-4-$^{14}$C by a Cell-Free Preparation from *Aspergillus ochraceus*. J. Steroid Biochem. (1970) 1: 221-227.

Thompson JD, et al. Comput Appl Biosci. (1994) 10:19-29.

Thompson, Julie D. et al. Nucleic Acids Research, (1994) 22(22):4673-4680.

Timberlake WE, Hamer JE. p. 1-29. In Setlow JK and Hollaender A (ed.), Genetic Engineering 1986; vol. 8., Plenum Publishing Corp., New York.

Tong et al., Anticancer Res. (1998) 18:719-725.

Tudzynski,B. et al. J. Biol. Chem. 277, 21246-21253, 2002.

Tudzynski,B. et al.Fungal Genet. Biol. (1998) 25 (3), 157-170.

Tuite et al., EMBO J. (1982) 1:603-608.

Uchimiya et al., Mol. Gen. Genet. (1986) 204:204.

Valenzuela et al., Nature (1982) 298:347-350.

van den Brink, Hans (J.) et al. Fungal Genetics and Biology (1998) 23, 1-17.

van den Brink, J., et al.; DNA Cell Biol 14,719-729, 1995.

Wagner et al., Proc. Natl. Acad. Science (U.S.A.) (1992) 89:6099-6103.

Walker et al., Proc. Natl. Acad. Sci. (U.S.A.) (1992) 89:392-396.

Wang, Regina W. et al. CYP3A4. Drug Metab. Dispos. 25(6), 762-767, 1997.

Weinberg et al., Gene (1993) 126:25-33.

Weisemann et al., Biochimie (1991) 73: 457-470.

Wickstrom et al., Proc. Natl. Acad. Sci. (U.S.A.) (1988) 85:1028-1032.

Wong and Neumann Biochem. & Biophys. Res. Commun. (1982) 107:584-587.

Wu et al., Journal of Biological Chemistry (1993) 268:10796-10781.

Wu, et al.; Genomics (1989) 4:560-569.

Yabusaki,Y., et al.; J. Biochem. (1988) 103 (6), 1004-1010.

Yamano,S., et al.; Molecular Pharmacology 36 (1), 83-88 (1989).

Yanish-Perron et al.; Gene (1985) 33:103-119.

K. M. Madyastha et al; Canadian Journal of Biochemistry & Cell Biology; 62 (2-3); 100-107; 1984.

J. M. Van Den Brink et al; Molecular & General Genetics; 263 (4); 601-609; May 2000.

D.K. Ghosh et al; Biochemical & Biophysical Research Communications; 113 (2); 497-505; 1983.

C. R. Jayanthi et al ; Biochemical & Biophysical Research Communications; 106 (4) ; 1262-1268 ; 1982.

S. Bak et al; Plant Molecular Biology; Nijoff Publishers, Dordecht, NL; 36 (6); 393-405; 1998.

J. S. Miles; Biochemical Journal; Portland Press; London,GB; 287; 195-200; 1992.

J.M. Van Den Brink et al; DNA and Cell Biology; 14(8); 719-729; 1995.

Figure 1A - Nucleotide and protein sequence of *Aspergillus ochraceus* 11 alpha hydroxylase

```
     tggaagtttt tacacttatt atgccggagc cgaaagattc tgagtcgagg ggttggggaa    60
     caacactata agacctacaa ccacttggat ttggtgaatt tacacgggca ttatcaaaac   120
     agccacaagc tgacagctca ttatc atg ccc ttc ttc act ggg ctt ctg gcg     172
                            Met Pro Phe Phe Thr Gly Leu Leu Ala
                             1              5 att tac cat agt ctc ata ctc gac aac cca gtc caa acc ctg agc acc     220
     Ile Tyr His Ser Leu Ile Leu Asp Asn Pro Val Gln Thr Leu Ser Thr
      10              15              20              25 att gtc gta ttg gcg gca gcg tac tgg ctc gca acg ctc cag ccg agc     268
     Ile Val Val Leu Ala Ala Ala Tyr Trp Leu Ala Thr Leu Gln Pro Ser
                  30              35              40 gac ctt cct gag ctg aat ccc gcc aaa cca ttc gag ttc acc aat cgt     316
     Asp Leu Pro Glu Leu Asn Pro Ala Lys Pro Phe Glu Phe Thr Asn Arg
              45              50              55 cgt cgt gtt cat gag ttt gtt gaa aat agt aag agc ttg ctt gct cgg     364
     Arg Arg Val His Glu Phe Val Glu Asn Ser Lys Ser Leu Leu Ala Arg
              60              65              70 ggg agg gaa ttg cac ggg cac gag ccg tac aga ctc atg tct gaa tgg     412
     Gly Arg Glu Leu His Gly His Glu Pro Tyr Arg Leu Met Ser Glu Trp
      75              80              85 gga tcc ttg att gtc ctg ccc cca gag tgc gcc gac gag ctg cgc aac     460
     Gly Ser Leu Ile Val Leu Pro Pro Glu Cys Ala Asp Glu Leu Arg Asn
      90              95             100             105 gac cca aga atg gac ttt gag acg ccc acc acc gac gac tcc cac gga     508
     Asp Pro Arg Met Asp Phe Glu Thr Pro Thr Thr Asp Asp Ser His Gly
                 110             115             120 tat atc cct ggc ttc gac gct ctc aac gca gac ccg aac ctg act aaa     556
     Tyr Ile Pro Gly Phe Asp Ala Leu Asn Ala Asp Pro Asn Leu Thr Lys
                 125             130             135 gtg gtc acc aag tac ctc aca aaa gca ttg aac aag ctt act gct ccg     604
     Val Val Thr Lys Tyr Leu Thr Lys Ala Leu Asn Lys Leu Thr Ala Pro
             140             145             150 atc tcg cat gaa gcg tcc atc gcc atg aaa gcg gtg ctg ggt gac gat     652
     Ile Ser His Glu Ala Ser Ile Ala Met Lys Ala Val Leu Gly Asp Asp
             155             160             165 cca gat tgg cgt gag atc tac cca gcc aga gac ttg ctc cag ctc gtc     700
     Pro Asp Trp Arg Glu Ile Tyr Pro Ala Arg Asp Leu Leu Gln Leu Val
     170             175             180             185 gcc cgg atg tcg aca aga gtg ttc ctt ggc gag gaa atg tgc aat aac     748
     Ala Arg Met Ser Thr Arg Val Phe Leu Gly Glu Glu Met Cys Asn Asn
                 190             195             200 cag gat tgg atc caa acc tca tca caa tac gcg gcc ctt gcc ttc ggt     796
     Gln Asp Trp Ile Gln Thr Ser Ser Gln Tyr Ala Ala Leu Ala Phe Gly
                 205             210             215 gtc ggt gac aag ctt aga ata tac ccg aga atg atc aga ccg ata gta     844
     Val Gly Asp Lys Leu Arg Ile Tyr Pro Arg Met Ile Arg Pro Ile Val
             220             225             230 cat tgg ttc atg cca tcc tgt tgg gag ctg cgc cga tcg ctg cga cgc     892
     His Trp Phe Met Pro Ser Cys Trp Glu Leu Arg Arg Ser Leu Arg Arg
             235             240             245 tgc cga cag att ctc acg ccg tac att cac aaa cgc aag tcc ctg aag     940
     Cys Arg Gln Ile Leu Thr Pro Tyr Ile His Lys Arg Lys Ser Leu Lys
     250             255             260             265 ggg acc acg gac gag cag ggc aag ccc ctt atg ttt gat gat tcc atc     988
     Gly Thr Thr Asp Glu Gln Gly Lys Pro Leu Met Phe Asp Asp Ser Ile
                 270             275             280
```

*Figure 1B - Nucleotide and protein sequence of
Aspergillus ochraceus 11 alpha hydroxylase*

```
gag tgg ttc gag cga gag ctg ggt ccc aac cac gac gcg gtc ctg aag      1036
Glu Trp Phe Glu Arg Glu Leu Gly Pro Asn His Asp Ala Val Leu Lys
        285                 290                 295 cag gtc acg ctc tcc ata gtt gct atc cac acc acg agt gac cta ctc      1084
Gln Val Thr Leu Ser Ile Val Ala Ile His Thr Thr Ser Asp Leu Leu
        300                 305                 310 ttg cag gcc atg agc gat ctc gcg cag aac ccg aaa gtg cta caa gca      1132
Leu Gln Ala Met Ser Asp Leu Ala Gln Asn Pro Lys Val Leu Gln Ala
        315                 320                 325 gtg cgc gag gag gtg gtc cga gtg ctg agc acc gag ggg ctc agc aag      1180
Val Arg Glu Glu Val Val Arg Val Leu Ser Thr Glu Gly Leu Ser Lys
330                 335                 340                 345 gtc tcg ctt cac agt ctc aag ctc atg gac agc gcg ttg aag gaa agc      1228
Val Ser Leu His Ser Leu Lys Leu Met Asp Ser Ala Leu Lys Glu Ser
                350                 355                 360 cag cgt ctc agg cct acg ctt ctc ggc tcc ttt cgt cgg cag gca acg      1276
Gln Arg Leu Arg Pro Thr Leu Leu Gly Ser Phe Arg Arg Gln Ala Thr
                365                 370                 375 aat gac atc aag ctg aag agc ggg ttt gtc ata aag aaa ggg act aga      1324
Asn Asp Ile Lys Leu Lys Ser Gly Phe Val Ile Lys Lys Gly Thr Arg
        380                 385                 390 gtc gtg atc gac agc acc cat atg tgg aat ccc gag tat tac act gac      1372
Val Val Ile Asp Ser Thr His Met Trp Asn Pro Glu Tyr Tyr Thr Asp
        395                 400                 405 cct ctc cag tac gac ggg tac cgc tac ttc aac aag cgg cag aca ccc      1420
Pro Leu Gln Tyr Asp Gly Tyr Arg Tyr Phe Asn Lys Arg Gln Thr Pro
410                 415                 420                 425 ggc gag gac aag aac gcg ttg ctc gtc agc aca agc gcc aac cac atg      1468
Gly Glu Asp Lys Asn Ala Leu Leu Val Ser Thr Ser Ala Asn His Met
                430                 435                 440 gga ttc ggt cac ggc gtt cac gcc tgt cct ggc aga ttc ttc gcc tcc      1516
Gly Phe Gly His Gly Val His Ala Cys Pro Gly Arg Phe Phe Ala Ser
                445                 450                 455 aac gag atc aag att gcc ttg tgt cat atc atc tta aat tat gag tgg      1564
Asn Glu Ile Lys Ile Ala Leu Cys His Ile Ile Leu Asn Tyr Glu Trp
        460                 465                 470 cgt ctt cca gac ggc ttc aag ccc cag cct ctc aac atc ggg atg act      1612
Arg Leu Pro Asp Gly Phe Lys Pro Gln Pro Leu Asn Ile Gly Met Thr
        475                 480                 485 tat ctg gcg gat ccc aat acc agg atg ctg atc agg cca cgc aag gcg      1660
Tyr Leu Ala Asp Pro Asn Thr Arg Met Leu Ile Arg Pro Arg Lys Ala
490                 495                 500                 505 gag atc gat atg gcg agt tta act gtg tag gtcgaacacg aagtcctgat       1710
Glu Ile Asp Met Ala Ser Leu Thr Val  *
                510 gaagtgttat tggtcagtgg gtgaagcaag tcgcagaaat gtgtaacaat ttataagaat    1770
aaaaaa                                                               1776
```

Figure 2A - Nucleotide and protein sequence of human oxidoreductase

```
atg gga gac tcc cac gtg gac acc agc tcc acc gtg tcc gag gcg gtg       48
Met Gly Asp Ser His Val Asp Thr Ser Ser Thr Val Ser Glu Ala Val
 1               5                  10                  15 gcc gaa gaa gta tct ctt ttc agc atg acg gac atg att ctg ttt tcg       96
Ala Glu Glu Val Ser Leu Phe Ser Met Thr Asp Met Ile Leu Phe Ser
                20                  25                  30 ctc atc gtg ggt ctc cta acc tac tgg ttc ctc ttc aga aag aaa aaa      144
Leu Ile Val Gly Leu Leu Thr Tyr Trp Phe Leu Phe Arg Lys Lys Lys
            35                  40                  45 gaa gaa gtc ccc gag ttc acc aaa att cag aca ttg acc tcc tct gtc      192
Glu Glu Val Pro Glu Phe Thr Lys Ile Gln Thr Leu Thr Ser Ser Val
        50                  55                  60 aga gag agc agc ttt gtg gaa aag atg aag aaa acg ggg agg aac atc      240
Arg Glu Ser Ser Phe Val Glu Lys Met Lys Lys Thr Gly Arg Asn Ile
65                  70                  75                  80 atc gtg ttc tac ggc tcc cag acg ggg act gca gag gag ttt gcc aac      288
Ile Val Phe Tyr Gly Ser Gln Thr Gly Thr Ala Glu Glu Phe Ala Asn
                85                  90                  95 cgc ctg tcc aag gac gcc cac cgc tac ggg atg cga ggc atg tca gcg      336
Arg Leu Ser Lys Asp Ala His Arg Tyr Gly Met Arg Gly Met Ser Ala
                100                 105                 110 gac cct gag gag tat gac ctg gcc gac ctg agc agc ctg cca gag atc      384
Asp Pro Glu Glu Tyr Asp Leu Ala Asp Leu Ser Ser Leu Pro Glu Ile
            115                 120                 125 gac aac gcc ctg gtg gtt ttc tgc atg gcc acc tac ggt gag gga gac      432
Asp Asn Ala Leu Val Val Phe Cys Met Ala Thr Tyr Gly Glu Gly Asp
        130                 135                 140 ccc acc gac aat gcc cag gac ttc tac gac tgg ctg cag gag aca gac      480
Pro Thr Asp Asn Ala Gln Asp Phe Tyr Asp Trp Leu Gln Glu Thr Asp
145                 150                 155                 160 gtg gat ctc tct ggg gtc aag ttc gcg gtg ttt ggt ctt ggg aac aag      528
Val Asp Leu Ser Gly Val Lys Phe Ala Val Phe Gly Leu Gly Asn Lys
                165                 170                 175 acc tac gag cac ttc aat gcc atg ggc aag tac gtg gac aag cgg ctg      576
Thr Tyr Glu His Phe Asn Ala Met Gly Lys Tyr Val Asp Lys Arg Leu
                180                 185                 190 gag cag ctc ggc gcc cag cgc atc ttt gag ctg ggg ttg ggc gac gac      624
Glu Gln Leu Gly Ala Gln Arg Ile Phe Glu Leu Gly Leu Gly Asp Asp
            195                 200                 205 gat ggg aac ttg gag gag gac ttc atc acc tgg cga gag cag ttc tgg      672
Asp Gly Asn Leu Glu Glu Asp Phe Ile Thr Trp Arg Glu Gln Phe Trp
        210                 215                 220 ccg gcc gtg tgt gaa cac ttt ggg gtg gaa gcc act ggc gag gag tcc      720
Pro Ala Val Cys Glu His Phe Gly Val Glu Ala Thr Gly Glu Glu Ser
225                 230                 235                 240 agc att cgc cag tac gag ctt gtg gtc cac acc gac ata gat gcg gcc      768
Ser Ile Arg Gln Tyr Glu Leu Val Val His Thr Asp Ile Asp Ala Ala
                245                 250                 255 aag gtg tac atg ggg gag atg ggc cgg ctg aag agc tac gag aac cag      816
Lys Val Tyr Met Gly Glu Met Gly Arg Leu Lys Ser Tyr Glu Asn Gln
                260                 265                 270 aag ccc ccc ttt gat gcc aag aat ccg ttc ctg gct gca gtc acc acc      864
Lys Pro Pro Phe Asp Ala Lys Asn Pro Phe Leu Ala Ala Val Thr Thr
            275                 280                 285 aac cgg aag ctg aac cag gga acc gag cgc cac ctc atg cac ctg gaa      912
Asn Arg Lys Leu Asn Gln Gly Thr Glu Arg His Leu Met His Leu Glu
        290                 295                 300 ttg gac atc tcg gac tcc aaa atc agg tat gaa tct ggg gac cac gtg      960
Leu Asp Ile Ser Asp Ser Lys Ile Arg Tyr Glu Ser Gly Asp His Val
```

Figure 2B - Nucleotide and protein sequence of human oxidoreductase

```
              305                 310                 315                 320
     gct gtg tac cca gcc aac gac tct gct ctc gtc aac cag ctg ggc aaa       1008
     Ala Val Tyr Pro Ala Asn Asp Ser Ala Leu Val Asn Gln Leu Gly Lys
                     325                 330                 335 atc ctg ggt gcc gac ctg gac gtc gtc atg tcc ctg aac aac ctg gat       1056
     Ile Leu Gly Ala Asp Leu Asp Val Val Met Ser Leu Asn Asn Leu Asp
                 340                 345                 350 gag gag tcc aac aag aag cac cca ttc ccg tgc cct acg tcc tac cgc       1104
     Glu Glu Ser Asn Lys Lys His Pro Phe Pro Cys Pro Thr Ser Tyr Arg
             355                 360                 365 acg gcc ctc acc tac tac ctg gac atc acc aac ccg ccg cgt acc aac       1152
     Thr Ala Leu Thr Tyr Tyr Leu Asp Ile Thr Asn Pro Pro Arg Thr Asn
         370                 375                 380 gtg ctg tac gag ctg gcg cag tac gcc tcg gag ccc tcg gag cag gag       1200
     Val Leu Tyr Glu Leu Ala Gln Tyr Ala Ser Glu Pro Ser Glu Gln Glu
     385                 390                 395                 400 ctg ctg cgc aag atg gcc tcc tcc tcc ggc gag ggc aag gag ctg tac       1248
     Leu Leu Arg Lys Met Ala Ser Ser Ser Gly Glu Gly Lys Glu Leu Tyr
                     405                 410                 415 ctg agc tgg gtg gtg gag gcc cgg agg cac atc ctg gcc atc ctg cag       1296
     Leu Ser Trp Val Val Glu Ala Arg Arg His Ile Leu Ala Ile Leu Gln
                 420                 425                 430 gac tgc ccg tcc ctg cgg ccc ccc atc gac cac ctg tgt gag ctg ctg       1344
     Asp Cys Pro Ser Leu Arg Pro Pro Ile Asp His Leu Cys Glu Leu Leu
             435                 440                 445 ccg cgc ctg cag gcc cgc tac tac tcc atc gcc tca tcc tcc aag gtc       1392
     Pro Arg Leu Gln Ala Arg Tyr Tyr Ser Ile Ala Ser Ser Ser Lys Val
         450                 455                 460 cac ccc aac tct gtg cac atc tgt gcg gtg gtt gtg gag tac gag acc       1440
     His Pro Asn Ser Val His Ile Cys Ala Val Val Val Glu Tyr Glu Thr
     465                 470                 475                 480 aag gcc ggc cgc atc aac aag ggc gtg gcc acc aac tgg ctg cgg gcc       1488
     Lys Ala Gly Arg Ile Asn Lys Gly Val Ala Thr Asn Trp Leu Arg Ala
                     485                 490                 495 aag gag cct gcc ggg gag aac ggc ggc cgt gcg ctg gtg ccc atg ttc       1536
     Lys Glu Pro Ala Gly Glu Asn Gly Gly Arg Ala Leu Val Pro Met Phe
                 500                 505                 510 gtg cgc aag tcc cag ttc cgc ctg ccc ttc aag gcc acc acg cct gtc       1584
     Val Arg Lys Ser Gln Phe Arg Leu Pro Phe Lys Ala Thr Thr Pro Val
             515                 520                 525 atc atg gtg ggc ccc ggc acc ggg gtg gca ccc ttc ata ggc ttc atc       1632
     Ile Met Val Gly Pro Gly Thr Gly Val Ala Pro Phe Ile Gly Phe Ile
         530                 535                 540 cag gag cgg gcc tgg ctg cga cag cag ggc aag gag gtg ggg gag acg       1680
     Gln Glu Arg Ala Trp Leu Arg Gln Gln Gly Lys Glu Val Gly Glu Thr
     545                 550                 555                 560 ctg ctg tac tac ggc tgc cgc cgc tcg gat gag gac tac ctg tac cgg       1728
     Leu Leu Tyr Tyr Gly Cys Arg Arg Ser Asp Glu Asp Tyr Leu Tyr Arg
                     565                 570                 575 gag gag ctg gcg cag ttc cac agg gac ggt gcg ctc acc cag ctc aac       1776
     Glu Glu Leu Ala Gln Phe His Arg Asp Gly Ala Leu Thr Gln Leu Asn
                 580                 585                 590 gtg gcc ttc tcc cgg gag cag tcc cac aag gtc tac gtc cag cac ctg       1824
     Val Ala Phe Ser Arg Glu Gln Ser His Lys Val Tyr Val Gln His Leu
             595                 600                 605 cta aag caa gac cga gag cac ctg tgg aag ttg atc gaa ggc ggt gcc       1872
     Leu Lys Gln Asp Arg Glu His Leu Trp Lys Leu Ile Glu Gly Gly Ala
```

Figure 2C - Nucleotide and protein sequence of human oxidoreductase

```
             610                615                 620
   cac atc tac gtc tgt ggg gat gca cgg aac atg gcc agg gat gtg cag    1920
   His Ile Tyr Val Cys Gly Asp Ala Arg Asn Met Ala Arg Asp Val Gln
   625             630                635                 640 aac acc ttc tac gac atc gtg gct gag ctc ggg gcc atg gag cac gcg    1968
   Asn Thr Phe Tyr Asp Ile Val Ala Glu Leu Gly Ala Met Glu His Ala
               645                650                 655 cag gcg gtg gac tac atc aag aaa ctg atg acc aag ggc cgc tac tcc    2016
   Gln Ala Val Asp Tyr Ile Lys Lys Leu Met Thr Lys Gly Arg Tyr Ser
           660                665                 670 ctg gac gtg tgg agc                                                 2031
   Leu Asp Val Trp Ser
           675
```

Figure 3A - Nucleotide and protein sequence of Aspergillus ochraceus oxidoreductase

```
cttatttcgt ttaggaagag caccggcttc ggtgtccttc cttaccctct tattcttcct      60
cttctgactc ccttttttgtt attgatcgcc catctcggtg aacatttggg atatctttcc   120
ctctccccct cccgccccga ccctccttat cttctcctcc cgtccagcat ttagctcgcc    180
atcgaattcg caattccttc ctcgtgactc ttcatcgctg agcgtcctca tc atg gcg   238
                                                            Met Ala
                                                              1
```

```
caa ctc gat act ctc gat ttg gtc gtc ctg gtg gcg ctc ttg gtg ggt      286
Gln Leu Asp Thr Leu Asp Leu Val Val Leu Val Ala Leu Leu Val Gly
      5              10                  15 agc gtg gcc tac ttc acc aag ggc acc tac tgg gcc gtc gcc aaa gac      334
Ser Val Ala Tyr Phe Thr Lys Gly Thr Tyr Trp Ala Val Ala Lys Asp
         20                  25                  30 cct tat gcc tcg gct ggt ccg gcg atg aat gga ggc gcc aag gcc ggc      382
Pro Tyr Ala Ser Ala Gly Pro Ala Met Asn Gly Gly Ala Lys Ala Gly
 35                  40                  45                  50 aag act cgc gac att gtt cag aaa atg gac gaa act ggc aaa aac tgt      430
Lys Thr Arg Asp Ile Val Gln Lys Met Asp Glu Thr Gly Lys Asn Cys
             55                  60                  65 gtg att ttc tac ggc tcg caa acc ggt acc gct gag gac tac gcg tcc      478
Val Ile Phe Tyr Gly Ser Gln Thr Gly Thr Ala Glu Asp Tyr Ala Ser
                 70                  75                  80 aga ctg gcc aag gaa ggc tcc cag cga ttc ggt ctc aag acc atg gtg      526
Arg Leu Ala Lys Glu Gly Ser Gln Arg Phe Gly Leu Lys Thr Met Val
         85                  90                  95 gcc gat ctg gag gac tac gac tac gaa aac ctg gaa aag ttc ccc gag      574
Ala Asp Leu Glu Asp Tyr Asp Tyr Glu Asn Leu Glu Lys Phe Pro Glu
    100                 105                 110 gac aag gtt gtt ttc ttc gtt ctg gcc act tat ggc gag ggt gaa ccc      622
Asp Lys Val Val Phe Phe Val Leu Ala Thr Tyr Gly Glu Gly Glu Pro
115                 120                 125                 130 acg gat aat gcg gtt gaa ttc tac cag ttc gtc acg ggc gaa gat gct      670
Thr Asp Asn Ala Val Glu Phe Tyr Gln Phe Val Thr Gly Glu Asp Ala
                135                 140                 145 gct ttc gag agc ggc gct acc gcc gac gat aag cct ctg tct tct ctc      718
Ala Phe Glu Ser Gly Ala Thr Ala Asp Asp Lys Pro Leu Ser Ser Leu
            150                 155                 160 aag tat gtc acg ttt ggt ctg ggt aac aac acc tat gag cac tac aac      766
Lys Tyr Val Thr Phe Gly Leu Gly Asn Asn Thr Tyr Glu His Tyr Asn
                165                 170                 175 gct atg gtt cgc aat gtg gac gcc gct ctc aca aag ttc ggc gcc caa      814
Ala Met Val Arg Asn Val Asp Ala Ala Leu Thr Lys Phe Gly Ala Gln
        180                 185                 190 cgc att ggc tct gct ggt gag ggt gac gac ggc gct ggt aca atg gaa      862
Arg Ile Gly Ser Ala Gly Glu Gly Asp Asp Gly Ala Gly Thr Met Glu
195                 200                 205                 210 gag gat ttc ctg gcc tgg aag gaa ccc atg tgg gct gcc ctt tct gag      910
Glu Asp Phe Leu Ala Trp Lys Glu Pro Met Trp Ala Ala Leu Ser Glu
                215                 220                 225 gcg atg aac ctg caa gag cgc gat gcg gtc tac gag ccg gtc ttc aat      958
Ala Met Asn Leu Gln Glu Arg Asp Ala Val Tyr Glu Pro Val Phe Asn
            230                 235                 240 gtc acc gag gac gag tcc ctg agc ccc gaa gat gag aac gtt tac ctc     1006
Val Thr Glu Asp Glu Ser Leu Ser Pro Glu Asp Glu Asn Val Tyr Leu
                245                 250                 255 ggt gag ccc act caa ggt cat ctc caa ggc gag ccc aag ggc ccg tac     1054
Gly Glu Pro Thr Gln Gly His Leu Gln Gly Glu Pro Lys Gly Pro Tyr
        260                 265                 270 tct gcg cac aac ccg ttc atc gct ccc atc tcc gaa tct cgt gaa ctg     1102
Ser Ala His Asn Pro Phe Ile Ala Pro Ile Ser Glu Ser Arg Glu Leu
275                 280                 285                 290
```

Figure 3B - Nucleotide and protein sequence of *Aspergillus ochraceus* oxidoreductase

```
ttc aac gtc aag gac cgc aac tgt ctg cac atg gaa atc agc atc gcc        1150
Phe Asn Val Lys Asp Arg Asn Cys Leu His Met Glu Ile Ser Ile Ala
            295                 300                 305 ggt agc aac ctc act tac cag act ggt gac cac atc gct gtt tgg ccc        1198
Gly Ser Asn Leu Thr Tyr Gln Thr Gly Asp His Ile Ala Val Trp Pro
        310                 315                 320 acc aac gcc ggt tcc gag gtc gat cgg ttc ctg cag gct ttt ggt ctc        1246
Thr Asn Ala Gly Ser Glu Val Asp Arg Phe Leu Gln Ala Phe Gly Leu
            325                 330                 335 gaa gga aag cgc cac tcc gtc atc aac att aag ggt atc gat gtg acc        1294
Glu Gly Lys Arg His Ser Val Ile Asn Ile Lys Gly Ile Asp Val Thr
        340                 345                 350 gct aag gtt ccg att ccc act cct acg acc tat gac gcc gca gtt cgc        1342
Ala Lys Val Pro Ile Pro Thr Pro Thr Thr Tyr Asp Ala Ala Val Arg
355                 360                 365                 370 tac tac ctg gaa gtc tgt gcc ccc gtt tcc cgt cag ttt gtc tcg act        1390
Tyr Tyr Leu Glu Val Cys Ala Pro Val Ser Arg Gln Phe Val Ser Thr
                375                 380                 385 ctc gct gcc ttt gcc cct gat gaa gcg acc aag gcg gag atc gtt cgt        1438
Leu Ala Ala Phe Ala Pro Asp Glu Ala Thr Lys Ala Glu Ile Val Arg
                390                 395                 400 ttg ggt ggc gac aag gac tat ttc cat gag aag att acc aac cga tgc        1486
Leu Gly Gly Asp Lys Asp Tyr Phe His Glu Lys Ile Thr Asn Arg Cys
            405                 410                 415 ttc aac atc gct cag gct ctc cag agc atc acg tcc aag cct ttc acc        1534
Phe Asn Ile Ala Gln Ala Leu Gln Ser Ile Thr Ser Lys Pro Phe Thr
        420                 425                 430 gcc gtc ccg ttc tcc ctg ctt atc gaa ggt atc acc aag ctt cag ccc        1582
Ala Val Pro Phe Ser Leu Leu Ile Glu Gly Ile Thr Lys Leu Gln Pro
435                 440                 445                 450 cgt tac tac tcg atc tcc tcg tct tcc ctg gtt cag aag gac aag att        1630
Arg Tyr Tyr Ser Ile Ser Ser Ser Ser Leu Val Gln Lys Asp Lys Ile
                455                 460                 465 agc att acc gcc gtt gtg gag tcg gtt cgc ttg cct ggt gag gaa cac        1678
Ser Ile Thr Ala Val Val Glu Ser Val Arg Leu Pro Gly Glu Glu His
            470                 475                 480 att gtc aag ggt gtg acc acg aac tat ctt ctc gcg ctc aag gaa aag        1726
Ile Val Lys Gly Val Thr Thr Asn Tyr Leu Leu Ala Leu Lys Glu Lys
        485                 490                 495 caa aac ggc gag cct tcc cct gac ccg cac ggc ttg act tac tct atc        1774
Gln Asn Gly Glu Pro Ser Pro Asp Pro His Gly Leu Thr Tyr Ser Ile
        500                 505                 510 act gga ccc cgt aac aag tac gat ggc atc cat gtc ccc gtt cac gtc        1822
Thr Gly Pro Arg Asn Lys Tyr Asp Gly Ile His Val Pro Val His Val
515                 520                 525                 530 cgc cac tcg aac ttc aaa ttg ccc tcg gat ccc tcg cga cct gtg atc        1870
Arg His Ser Asn Phe Lys Leu Pro Ser Asp Pro Ser Arg Pro Val Ile
                535                 540                 545 atg gtt gga ccc ggt act ggt gtt gct cct ttc cgt ggg ttt atc cag        1918
Met Val Gly Pro Gly Thr Gly Val Ala Pro Phe Arg Gly Phe Ile Gln
            550                 555                 560 gag cgt gct gcc ttg gcc gcg aag ggc gag aag gtc gga act acc ttg        1966
Glu Arg Ala Ala Leu Ala Ala Lys Gly Glu Lys Val Gly Thr Thr Leu
        565                 570                 575 ctt ttc ttc ggc tgc cgt aag tcc gac gaa gat ttc ttg tac aag gat        2014
Leu Phe Phe Gly Cys Arg Lys Ser Asp Glu Asp Phe Leu Tyr Lys Asp
        580                 585                 590 gaa tgg aag act ttt cag gag cag ctt ggc gac tcg ctc aag atc atc        2062
Glu Trp Lys Thr Phe Gln Glu Gln Leu Gly Asp Ser Leu Lys Ile Ile
```

Figure 3C - Nucleotide and protein sequence of Aspergillus ochraceus oxidoreductase

```
      595                    600                    605                    610
  act gcc ttc tct cgt gaa tcg gct gag aaa gtc tac gtc cag cac agg           2110
  Thr Ala Phe Ser Arg Glu Ser Ala Glu Lys Val Tyr Val Gln His Arg
                  615                    620                    625 ctg cgt gag cat gcc gag ctg gtc agt gac ctg ctg aag cag aaa gcc           2158
  Leu Arg Glu His Ala Glu Leu Val Ser Asp Leu Leu Lys Gln Lys Ala
                  630                    635                    640 act ttc tat gtt tgc ggt gac gct gcc aac atg gcc cgt gaa gtc aac           2206
  Thr Phe Tyr Val Cys Gly Asp Ala Ala Asn Met Ala Arg Glu Val Asn
                  645                    650                    655 ctc gtg ctt ggg caa atc att gcc aag cag cgc ggt ctc cct gcc gag           2254
  Leu Val Leu Gly Gln Ile Ile Ala Lys Gln Arg Gly Leu Pro Ala Glu
                  660                    665                    670 aag ggc gag gag atg gtg aag cac atg cgc agc agc ggc agc tac cag           2302
  Lys Gly Glu Glu Met Val Lys His Met Arg Ser Ser Gly Ser Tyr Gln
  675                    680                    685                    690 gac gat gtc tgg tcc taa aa                                                2322
  Asp Asp Val Trp Ser  *
                  695
```

Figure 4A - Amino acid homology alignment of A. ochraceus 11 alpha hydroxylase with the top 10 BLAST hits from GenBank

```
CAA75565    1  ---MANHSSSYYHEFYKDHSHTVL LMSEKPVILPSLILGTCAVLLCIQWLK--PQPLIM
CAB91316    1  ---------------MERLDIKSI DPSATPFSYLVTAFLLAVVV SLQGPRF-PKNIKH
CAB56503    1  -----------------------------LLFCFILSKTTKK GQNSQYS-NHDELP
AAB94588    1  --------------MVMELHNHTPF IYFITSILFIFFVFFKLVQRS--DSKTS-STCKLP
pMON45624   1  -----------MPFFTGLLAIYH LILDNPVQTLSTIVVLAAAY -LATLQ--PSDLPE
CAA75566    1  -------------MSIFNMITSYAG QLLPFYIAIFVFTLVPWAIR SWLELRK-GSVVPL
AAD34552    1  ---MTVDALTQPHHLLSLAWNDTQQHGSWFAPLVTTSAGLLCLLL LCSSGR--RSDLPV
CAA75567    1  ------------------------------------------------------------
CAA76703    1  MSKSNSMNSTSHETLFQQLVLGLDRMPLMDVHWLIYVAFGAWLCS VIHVLSSSSTVKVP
CAA57874    1  ------------------------------------------------------------
CAA91268    1  -----------------MALLIL SLVISIFTFFIYIILARRER KLREKIGLSGPEPH

CAA75565   56  VNGRKFGELSNV A RD TFGA QL EK LKMSPDKPF I G VGE H  PE KYA YE  N
CAB91316   45  LN KGPLEFSDT P KE VYGS Q ANWFKANPNKPC V S FGEA V P ERMANE  N
CAB56503   28  PG PQIPILGNA QLSGGH-TH I RDL KKYGPLMHL - G VST  ASS QIA E  FR
AAB94588   45  PG RTLPLIGNI QIVGSLPVHYY KNL DKYGPLMHL -  G VSN  TS EMA QE  MK
pMON45624  46  LN AKPFEFTNR RVHE VENS S AR RELHGHEPY L S WGS     PPECA DE  N
CAA75566   48  AN PD-SLFGTG T RS VKLS E AK RSLFPNEPF L T WGE V   PE DFADE  N
AAD34552   56  FN KTWWELTTM A RD DANAPSW ESWFSQN-DKPI F V SGYCT   SSMA DE F K
CAA75567    1  ------------------------------------------------------------
CAA76703   61  VVGYRSVFEPTWLL LR VWEGGS  GQ YNKFKDSIFQVRKLGTD V  PE NYIDE V K
CAA57874    1  ------------------------------------------------------------
CAA91268   43  WFLGNLKQTAER E LG DDAN WFNELHEQYGETFGIY-YGSQMN V  SNEKDIK E FI

CAA75565  116  NEK S TMAA--FKWFYAHLP G EG--FREGTNES I KL VARH QL T--- Q TL TGA S
CAB91316  105  DDR S TRWT--YKAF GHLP G EG--FGEASRES I QE IMRDL T-- Y NK TEP A
CAB56503   86  THD L ADRPSNLESF IVSYD SDMVVSPYGNYW Q R  SMME LSQ S QSFRSIRE
AAB94588  104  THD N SDRP-DFVLS IVSYNGSGIVFSQHGDYW Q R  CTVE LTA R QSFRSIRE
pMON45624 106  DPR D ETPT--TDDS GYIP G DA---LN-ADPN T VTKYL T-- A NK TAP S
CAA75566  107  DPR S SKAA--MQDN AGIP G FET--VALVGREDQL Q VARKQL T-- H SA IEP S
AAD34552  115  MKE CMYKFLG--TDF SHLP G FDG--FKEVTRDA L T VMNQFQ--TQAPKYVKP A
CAA75567    1  ---------------------------------------MKYT --CQ NIFPSLWS
CAA76703  121  LS----QDKTRSVEPFINDFA GQYT--RGMVFLQSDLQN V IQQRL T--PK VSI TKV K
CAA57874    1  ------------------------------------------------------------
CAA91268  102  KNFSN SDRS--VPSIYEANQLTASLLMNSYSSGW HTRSAIAPIF -TGK KA QET N

CAA75565  170  E CALV KD YTDSP--  HD TAKDAN K  ARI SRV  GKE C NPQW R  -ST A
CAB91316  159  Q TSMA EANLPKAANG WST N RSK  P VARI SRV GEE C NE WLK  -QQYT
CAB56503  146  E VLNF KS G---SKEG-TR N SKE SL YG I  RAAF GEKNKNTE   LDQLTK
AAB94588  163  E VAEL KK AATASEEGGSIFN TQS YS TFG  AA RAAF KKSRY QV  SNMHKQLM
pMON45624 156  H ASIA KA LGDDP-- RE YPARD L ARM S RV  GEE CNNQ   QTS -SQ A
CAA75566  161  R STLA SLNFGETT-- WRA R KPA  D ARI R   GDQ C NEA K  -KTYT
AAD34552  169  N ASGI TD FGDSN-- WHT VP VYNQC DL TRTV F M GSKI A NE WLD A-KHHA
CAA75567   17  MKTSFRWPRTS------K SS S YDM RT ALL G A    L P C E GW QA  -IG T
CAA76703  173  E LDYA TKEMPDMKND VE D SSI RL SRI SAR   GPEHC N Q    TT  -AE S
CAA57874    1  ------------------------------------------------------------
CAA91268  159  SKVDLF DI REKAS--SGQKWD YDDFQG TLD IG CAF IDSNC R RND FYHPVT

CAA75565  227   IAFRAVEE LR   -SWLRF  QWF HCTQS RAL QE RD   NP   E  -RREEK ---AEA
CAB91316  218   DGFGAAED LR    -AALRF VHW  SCQRA RAD V  SI  DP  K  -RQE    ---AAN
CAB56503  202  AVAEPNIAD  FPSL-KF QL  STSKYKIEKIH QFDVIVET   KGHKE  IN PLS--QEN
AAB94588  223   LGGFSVAD YPSS-R FQM GATG KLEKVH VTD VLQD  DEHK ---N NRS--SEE
pMON45624 213  ALAFGVGDK LR  F -R  RF VHW F SCWE  RRS RC Q  TF Y H  -R SL  --GTT
CAA75566  218  TNFYTASTN LR  F -RS RF AHW  PECRK RQER D  IGI  TP   E -RREL  --RAA
AAD34552  226   TMAIQARQ LR   E -V LRF  HWLE QGAK RAQ  R Q  DP  QE -RRAE   --DAC
CAA75567   70   QCVSIRDQ LFT S- P LRF  GP  SVRS RRH VF  AE  AP   SQALQDE QHRAD
CAA76703  232  ESLFITGFI R V  -H LRF  APL  SYRT LRN SS R R  GD   R----SQQ----
CAA57874    1  ----------MA-P LRF  YRF  ERAR  DQWTK RKR  MAS RE -- QE   --GGN
CAA91268  217   KITINNFTYFHSSSPGTFHF  EST QIHTTG CRNSTC RT KCV GF QD AKFCSDYE
```

Figure 4B - *Amino acid homology alignment of* A. ochraceus
*11 alpha hydroxylase with the top 10 BLAST hits from
GenBank*

```
CAA75565   283 ERTGEKV-TYNDAEELDDLAREK--VGYDPACAQLSLSVAA--HSTLDFFTQVMFD
CAB91316   274 ---GGKA-EHDDAIEWFERTA--K--CKYYDPAVAQLVLSLVA--IHTTSDLTCQVMTNL
CAB56503   259 G--EKKE-DLVDVLNIQRRNDFE--APLGDKNIKAIIFNLFSAGTETSSTTVDWAMCEM
AAB94588   276 R--EAVE-DLVDVLKFQKES--E--FRLTDDNIKAVIQDLFIGGGETSSVIEWMMSEL
pMON45624  269 DEQGKPL-MFDDSIEWFEREL-----PNHDAVIKQVTLSIVA--IHTTSDLLLQAMSDL
CAA75566   274 IAAGQPLPVFHDAIDWSEQEAEAAGTIASFDPVIFQLTLSLLA--IHTTYDLIQQTMIDL
AAD34552   282 RAKGIEPPRYVDSIQWFEDTAK----CKWYDAAGAQLAVDFAG--LYGTSDLLIGSLVDI
CAA75567   129 TLLADQTEGRGTFISLLRHLP--EELRTPEQVGLDQMLYSFAA--IHTTMALTKVVWEL
CAA76703   282 ---GDGN---EDILSWMRDAATGEE-KQIDNIAQRMLILSLAS--IHTTAMTTHAMYDL
CAA57874    44 --LEDPPTMLDHLSNGRNEHIA----DDVELQLLHQMTLIAVG--TVTFSSTTQATYDL
CAA91268   277 RRRGGEGSDSVDLIKLLLNREDDKS-KPMTKQEVIENCFEFLLAGYETTSTAITYCSYLL

CAA75565   338 AQNPEIIEPLREEIAVIGKQG------SKNSLYNLKLLDSVIKESQRIR-P-------
CAB91316   324 IQNPEFIAPLREEMIQVLSEGG------LKKTSLYNMKLLDSVIKESQRVT-P-------
CAB56503   314 LTNPTVMKKAQEEVRKVFNEEGN-----VDETKLHQLKYLQAVIKELLRH-P-------
AAB94588   329 LRNPRVMEEAQAEVRRVYDSKGY-----VDETELHQLIYLKSIIKEMMRLH-P-------
pMON45624  321 AQNEKVLCAVREEVVRVISTEG------LSKVSLHSLKLMDSALKESQRLM-P-------
CAA75566   332 GRHPEYIEPLRQEVVQLIREEG------VKKTILFKVKLLDSAIKESQRMK-P-------
AAD34552   336 VRHEHLIEPLRIEIRTVLGQGG------LTPASLYKLKLLDSCIKESQRVK-P-------
CAA75567   186 VARPEYIEPLRTELQDVFGPDAVSPDICINKEILSRLIKLDSFIREVQRWC-P-------
CAA76703   333 CACPEYIEPLRLEVKSVLGASG------LDKTALNRFLKLDSFIKESQRFN-P-------
CAA57874    96 VAHPEYITILREEVESVPRDPNGN----ITKDSTVAMDKLDSFLKESQRFNSPDLSMSNL
CAA91268   336 SKYENVQKLYEEIMEAKENGG------LTYDSIHNMKYLLCVYKELRFY-P-------

CAA75565   384 ----------IAIASMRRFTTHNLKLSDGVILPKNKLTLVSAIQHW---------DPEYYKD
CAB91316   370 ----------TGVASMRRYAEKDVTLSDGTFIPKGGFVAMSALDW---------NSPVMEQ
CAB56503   361 ----------PVPLLIPRECREQCKIK-GYTIESKSRVIVMNAWAIGR--------DENYIIE
AAB94588   376 ----------PVPLLVPRVSRERCQIN-GYELLSKTRILINAWAIGR--------NEKYIGE
pMON45624  367 ----------TLLGSFRRQATNDIKLKSGFVIKKGTRVVLDSTHIW---------NPEYTTD
CAA75566   378 ----------GSIVTMRRYVTEDITLSSGLTLKKGTRLNVDNERLD--------DEKIMDN
AAD34552   382 ----------VECAIMRSYALQDVTFSNGTFIPKGELVAVAADRMS--------NPEVMPE
CAA75567   238 ----------STFVIPSRRVMKSITLSNGIKLQRGTSIAFPAAIHMSEETPTFSEIFSSD
CAA76703   379 ----------VFLLIFNRIYHQSVTLSDGTNIESGTRLAVPSHALQ-------DSAHVPG
CAA57874   152 KNYKLCESLTGHSNIPTRTIADMKLPDGTFVPKGTKLEINTCSIHK-------DHKLYEN
CAA91268   382 ----------PHFSFIRRLCREDITIR-GQFYPKGAIVVCLPITVHR--------NPENADS

CAA75565   427 PLK-----FDGIRFFNIRREP--GRESKAQLVSATPDHMCFGYGLHACPGRFFASEEIKI
CAB91316   413 ADK-----IDGRRFLRIRETPGAGKENVAQLVSTAPDHLCFGHGQHACPGRFFAANEIKI
CAB56503   404 PEK-----FNPDRFPLES-------K---VDFKGNSFEYIPFGGGRRICPGITFALANIE
AAB94588   419 TES-----EKPERFLNS-------S---IDFRGIDFEFIPFGAGRRICPGITFAIPNIE
pMON45624  410 PLQ-----IDGVRIFNKFQTP--GEDKNALLVSTSANHMGFGHGVHACPGRFFASNBIKI
CAA75566   421 PEV-----ANPIRFYDIRSEA--GKDHGAQLVSTGSNHMGFGHGQHSCPGRFFAANEIKV
AAD34552   425 EAK-----LDPYRVMRLREDP--KAFSAQLENIMGCHLCFGWHPRACPGRFFASEIKM
CAA75567   289 FENPSPRIFDGIRVLNIRSIK--GQGSQHQAALTGPLYLIFNHGKHACPGRFFAISEIKM
CAA76703   423 PTP--PTEFDGIRYSKLRSDS--NYAQKYLFSMTDSSNMAFGYGKYACPGRFYASNENKI
CAA57874   205 PEQ-----FDGLRFHKWRKAP--GKEKRYMYSSIGTEDISNGFGRHACPGRYLSAINIKL
CAA91268   425 PEE-----EHPERFENWE------E------KSSSLKWIPFGVGPRYGVGMRFAEMEFKT

CAA75565   480 ALSHLLLYDLKPV-----EGSSMEPRKYGLNMNANPTAKLSVRRKK-EEIAI-----
CAB91316   468 AIVHLLLNYEWRLP-----EGSDPKIRTFGFSMGVDPSLIVEYLGRQ-PEIEL-----
CAB56503   449 PLAQLLFIDWQS----NTEKLNMKE-SRGVTVRREDDLYLTPVNFS-SSSPA-----
AAB94588   464 PLAQLLYIIDWKLPNKMKNEELDMTE-SNGITLRRQNDLCLIPITR----LP------
pMON45624  463 ALCHILINYEWRLP-----DGFKPQPLNIGLTYLADENTIMLIRPRK-AEIDMASLTV
CAA75566   474 ALCHILVKYDWKLC-----PDTETKPDTRGIAKSSPVTDLLLKRRESVELDLEAI--
AAD34552   478 MLAYLLIKYDWKVV-----PDEPLQYYRHSFSVLIHFTILMIRRD-EDIRLPGSL-
CAA75567   347 ILIELLAKYDIELE----DGKPGPELMRVGTETILDTKAGLEMRRR-----------
CAA76703   479 TLAILLIQFIEKLP-----DGKGRPRNITIDSDVIPDERARLCVRKRS---IRDE----
CAA57874   258 IVAELLLMNYDIKLP------DGLSRPKNIEFEVLASLNACANA---------------
CAA91268   468 TIVKLLDTILLKQF----EGEADLIPDCNGVIMRPNDPVILHLKPRN-----------

CAA75565   (SEQ ID NO: 27)
CAB91316   (SEQ ID NO: 28)
CAB56503   (SEQ ID NO: 29)
AAB94588   (SEQ ID NO: 30)
pMON45624  (SEQ ID NO: 02)
CAA75566   (SEQ ID NO: 31)
AAD34552   (SEQ ID NO: 32)
CAA75567   (SEQ ID NO: 33)
CAA76703   (SEQ ID NO: 34)
CAA57874   (SEQ ID NO: 35)
CAA91268   (SEQ ID NO: 36)
```

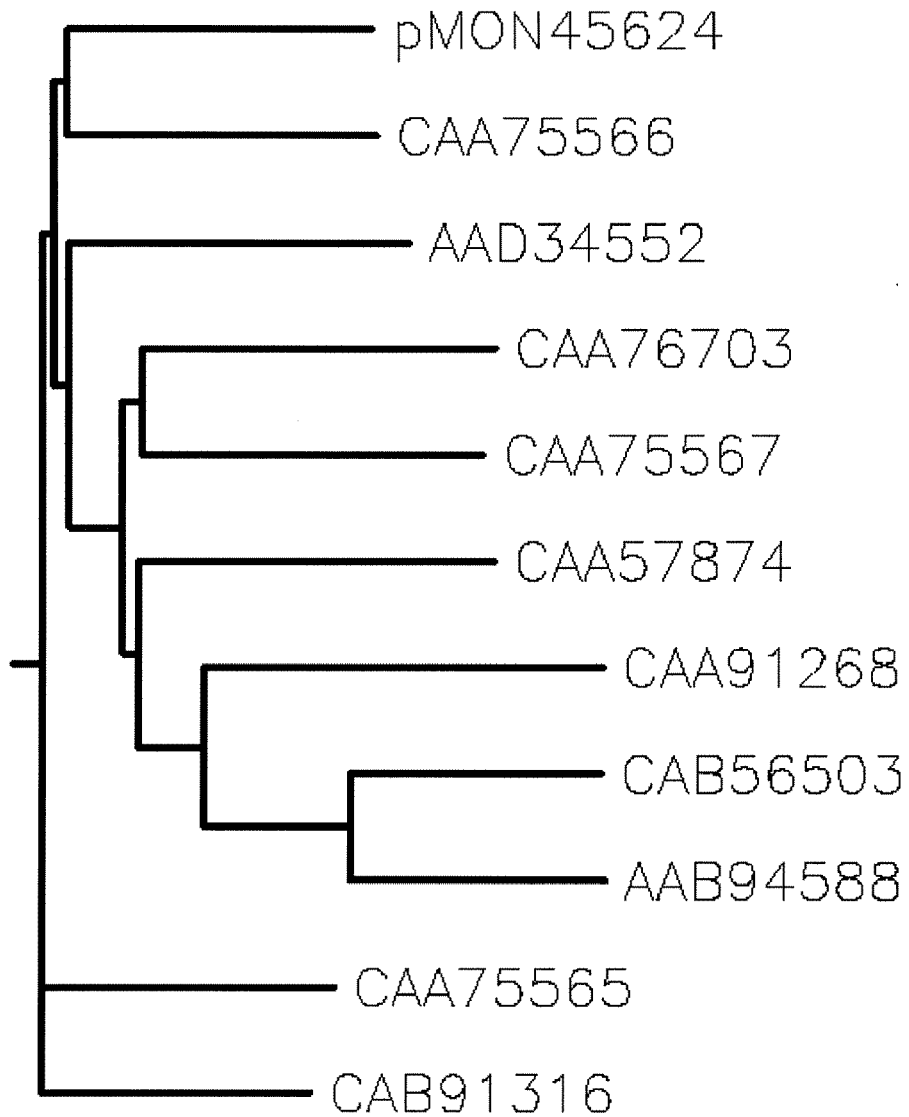
*Figure 5 - Phylogenetic tree showing the relatedness of Aspergillus ochraceus 11 alpha hydroxylase to the top 10 BLAST hits from GenBank*

*Figure 6 – Percent homology of* Aspergillus ochraceus *11 alpha hydroxylase to the top 10 BLAST hits from GenBank*

| Accession Number | Species | % ID to 11a OH |
| --- | --- | --- |
| CAB91316 | *Neurospora crassa* | 40 |
| CAA76565 | *Gibberella fujikuroi* | 37 |
| CAA75566 | *Gibberella fujikuroi* | 37 |
| AAD34552 | *Aspergillus terreus]* | 29 |
| CAA75567 | *Gibberella fujikuroi* | 24 |
| CAA57874 | *Fusarium oxysporum* | 24 |
| CAA76703 | *Gibberella fujikuroi* | 23 |
| CAB56503 | *Catharanthus roseus* | 14 |
| AAB94588 | *Glycine max* | 14 |
| CAA91268 | *Caenorhabditis elegans* | 12 |

Figure 7 A– Amino acid homology alignment of A. ochraceus and human oxidoreductase to NADPH cytochrome P450 reductases from A. niger, mouse, and S. cerevisiae

Figure 7B – Amino acid homology alignment of *A. ochraceus* and human oxidoreductase to NADPH cytochrome P450 reductases from *A. niger*, mouse, and *S. cerevisiae*

```
PMON45605  451 LQARYYSIASSSKVHPNSVHICAVVVEYETK----AGRINKGVATNWLRAKEP--AGE--
human      451 LQARYYSIASSSKVHPNSVHICAVVVEYETK----AGRINKGVATNWLRAKEP--AGE--
mouse      451 LQARYYSIASSSKVHPNSVHICAVAVEYEAK----SGRVNKGVATSWLRTKEP--AGE--
pMON45632  448 LQPRYYSISSSSLVQKLKSITAVVESVRLP---GEELIVKGVTTNYLLALKEKQNGEPS
niger      446 LQPRYYSISSSSLVQKLKSITAVVESVRLP---GASHMVKGVTTNMLLALKQKQNGRSL
yeast      436 MTPRYYSISSSSLSEKQTVHVTSTVENEPNPELP-DAPPGVGVTTNLLRNICLAQNNVNI PMON45605  503 -----------NGGR-----ALVPMFVRKSQFRLPFKATTPVIMVGPGTGVAPFIGFIQE
human      503 -----------NGGR-----ALVPMFVRKSQFRLPFKATTPVIMVGPGTGVAPFIGFIQE
mouse      503 -----------NGRR-----ALVPMFVRKSFRLPFKPTTPVIMVGPGTGVAPFMGFIQE
pMON45632  505 PDPHG-LTYSITGPRNKYDGIHVPVHVRHSNFKLPSDPSRPVIMVGPGTGVAPFRGFIQE
niger      503 SRPSR-LDLLHHGPRNKYDGIHVPVHVRHSNFLLPSDPSRPIIMVGPGTGVAPFRGFIQE
yeast      495 AETNLPVHYDLNGPRKLEANYKLPVHRRSNFRLPSNPGTPVIMIGPGTGVAPFRGFIRE PMON45605  547 RAWLRQ---QGKE---VGETLLYYGCRRSDEDYLYREELAQFHRD-GALTQLNVAFSRE-
human      547 RAWLRQ---QGKE---VGETLLYYGCRRSDEDYLYREELAQFHRD-GALTQLNVAFSRE-
mouse      547 RAWLRE---QGKE---VGETLLYYGCRRSDEDYLYREELARFHRD-GALTQLNVAFSRE-
pMON45632  564 RAALAA---KGEK---VGTTLLFFGCRSDEDFLYKDEWKTFQEQLGDSLKIITAFSRE-
niger      562 RAALAA---KGEK---VGPTVLFFGCRSDEDFLYKDEWKTYQDQLGDNLKIITAFSRE-
yeast      555 RVAFLESQKKGGNNVSLGKHLLFYGSRNQD-DELYQDEWPEYAKKLDCSFEMVVAHSRLP PMON45605  599 QSHKVYVQHLLKQDREHLWKLI-EGGAHIYVCGDARNMARDVQNTFYDIVAELGAMEHAQ
human      599 QSHKVYVQHLLKQDREHLWKLI-EGGAHIYVCGDARNMARDVQNTFYDIVAELGAMEHAQ
mouse      599 QAHKVYVQHLLKRDKEHLWKLIHEGGAHIYVCGDARNMAKDVQNTFYDIVAEFGPMEHTQ
pMON45632  617 SAEKVYVQHRLREHAELVSDLL-KQKATFYVCGDAANMAREVNLVLGQIIAKQRGLPAEK
niger      615 GPQKVYVQHRLRPHSELVSDLL-KQKATFYVCGDAANMAREVNLVLGQILAAQRGLPAEK
yeast      614 NPIKVYVQDKLKDYEDQVFEMI-NNGAFIYVCGDARGMAKGVSTALVGILSRGKSITTDE PMON45605  658 AVDYIKKLMTKGRYSLDVWS
human      658 AVDYIKKLMTKGRYSLDVWS
mouse      659 AVDYVKKLMTKGRYSLDVWS
pMON45632  676 GEEMVKHMRSSGSYQDDVWS
niger      674 GEEMVKHMRRGRYQEDVWS
yeast      673 ATELIKMLKTSGRYQEDVW- PMON45605      (SEQ ID NO: 03)
human          (SEQ ID NO: 06)
mouse          (SEQ ID NO: 39)
PMON45632      (SEQ ID NO: 05)
niger          (SEQ ID NO: 38)
yeast          (SEQ ID NO: 37)
```

*Figure 8 – Amino acid homology alignment of* A. ochraceus *oxidoreductase to NADPH cytochrome P450 reductases from* A. niger *and* S. cerevisiae

```
A.niger       1   -MAQLDTLDLVVLAVLLVGSVAYFTKGTYWAVAKQRMPLPAERMNGAAKAGKTRNIIEKM
A.ochraceus   1   -MAQLDTLDLVVLVALLVGSVAYFTKGTYWAVAKDPYASAEPAMNGGAKAGKTRDIVQKM
S.cerevisiae  1   MPFGIDNTDFTVLASLVLAVLLYVKENSIKEFLMSDDEDITAVSSG------NRDIACVW A.niger       60  EETGKNCVIFYGSQTGTAEDYASRLAKEGSQRFGLKTMVADLEEYDYENLQQFPEDKVAF
A.ochraceus   60  DETGKNCVIFYGSQTGTAEDYASRLAKEGSQRFGLKTMVADLEDYDYENLEKFPEDKVVF
S.cerevisiae  55  TENNKNYVLMASQTGTAEDYAKKFSKELVAKFNLNVMCADVENYDFESINDVP--VIVS A.niger       120 FVLATYGEGEPTDNAVEFYQFFTGIDVAFESAASADEKPLSKLKYVAFGLGNNTYEHYNA
A.ochraceus   120 FVLATYGEGEPTDNAVEFYQFVTGEDAAFESGATADDKPLSSLKYVTFGLGNNTYEHYNA
S.cerevisiae  113 IFLSTYGEGDFPDGAVNFEDFIC---------NALAGALSNLRYNMFGLGNSTYEFFNG A.niger       179 MVRQVDAAFQKLGEQRIGSAGEGDDGAGTMEEDFLAWKEPMWAALSESMDLEEREAVYEP
A.ochraceus   180 MVRAVDAALIKFGAQRIGSAGEGDDGAGTMEEDFLAWKEPMWAALSEANLQERDAVYEP
S.cerevisiae  163 AAKKAEKHLSAAGAIRIGKLGEADDGAGTTLEDYMAWKLSILEVLKCELHLDEQEAKITS A.niger       239 VFCVTENESLSPEDEIVYLGEPTQSHLQ---------GTPKGPYSAHNPFIAPIAESREL
A.ochraceus   240 VFAVTEDESLSPEDENVYLGEPTQGHLQ---------GEPKGPYSAHNPFIAPISESREL
S.cerevisiae  223 QFCYT---VLNEITDSMSLGEPSAHYLPSHQLNRNADGIQLGPEDLSQPYIAPIVKSREL A.niger       290 FLVKDRNCLHMEISIAGSNLSYQTGDHIAVWPTNAGAEVDRFLQVFGLEGKRDSVINIKG
A.ochraceus   291 FNVKDRNCLHMEISIAGSNLIYQTGDHIAVWPTNAGSEVDRFLQAFGLEGKRHSVINIKG
S.cerevisiae  280 FSSNDRNCIHSEFDLSGSNIKYSTGDHVAVWPSNPLEKVEQFLSIFNLEP--ETIFDLKP A.niger       350 IDVTAKVPIPTPTTYDAAVRYYMEVCAPVSRQFVATLAAFAPMRKAEQRLCWVAQG-LF
A.ochraceus   351 IDVTAKVPIPTPTTYDAAVRYYLEVCAPVSRQFVSTLAAFAPDEATKAEIVRLGEDKDYF
S.cerevisiae  338 LDPTVKVPFPTPTTIGAAERHYLETTCPVSRQLFSSLIQFAPNADVKEKLTLSKDKDQF A.niger       409 PREGHQPMLCHAQALQSITS-KPFSAVPFSLLIEGITKLQPRYYSISSSSLVQKDKISIT
A.ochraceus   411 HEKITIRCFNIAQALQSITS-KPFFAVPFSLLIEGITKLQPRYYSISSSSLVQKDKISIT
S.cerevisiae  398 AVEITSKYFNIADALKYLSDGAKQDNVEMQFLVESVPQLTPRYYSISSSSLSEKQTYHVT A.niger       468 AVVESVRLP--GASHMVKGVTTNYLLALKQKQNGRSLSRESR-LDLLHHGPRNKYDGIHV
A.ochraceus   470 AVVESVRLP--GEEHIVKGVTTNYLLALKEKQNGEPSPDHG-LTVSITGPRNKYDGIHV
S.cerevisiae  458 SIVENFPNEELPLAPPGVGVTTNLLRNIQLAQNNVNIAETNLPVHYDENGPRKLEANYKI A.niger       525 PVHVRHSNFKLPSDPSRPLIMVGPGTGVAPFRGFIQERAALAAKGEK------VGPTVLF
A.ochraceus   527 PVHVRHSNFKLPSDPSRPVIMVGPGTGVAPFRGFIQERAALAAKGEK------VGTTLLF
S.cerevisiae  518 PVHVRSNFKLPSNPSTPVIMIGPGTGVAPFRGFIRERVAFLESQKKGGNNVSLGKHILF A.niger       579 FGCRKSDEDFLYKDEWKTYQQQLGDNLKIITAFSRE-GPQKVYVQHRLREHSELVSDLLK
A.ochraceus   581 FGCRKSDEDFLYKDEWKTEQEQLGDSLKIITAFSRE-SABKVYVQHRLREHAELVSDLLK
S.cerevisiae  578 YGSRNTD-DFLYQDEWPEYAKKLDGSFEMVAHSRLPNTKKVYVQDKLLEYELQVFEMIN A.niger       638 QKATFYVCGDAANMAREVNLVLGQIIAAQRGLPAEKGEEMVKHMRRRGRYQEDVWS
A.ochraceus   640 QKATFYVCGDAANMAREVNLVLGQIIAKQRGLPAEKGEEMVKHMRSSGSYQDVWS
S.cerevisiae  637 NGAFIYVCGDAKGMAKGVSTALVGILSRGKSITTDEATELIKMLKISGRYQEDVW- A.ochraceus, PMON45632    (SEQ ID NO: 05)
A.niger                   (SEQ ID NO: 38)
S.cerevisiae, yeast       (SEQ ID NO: 37)
```

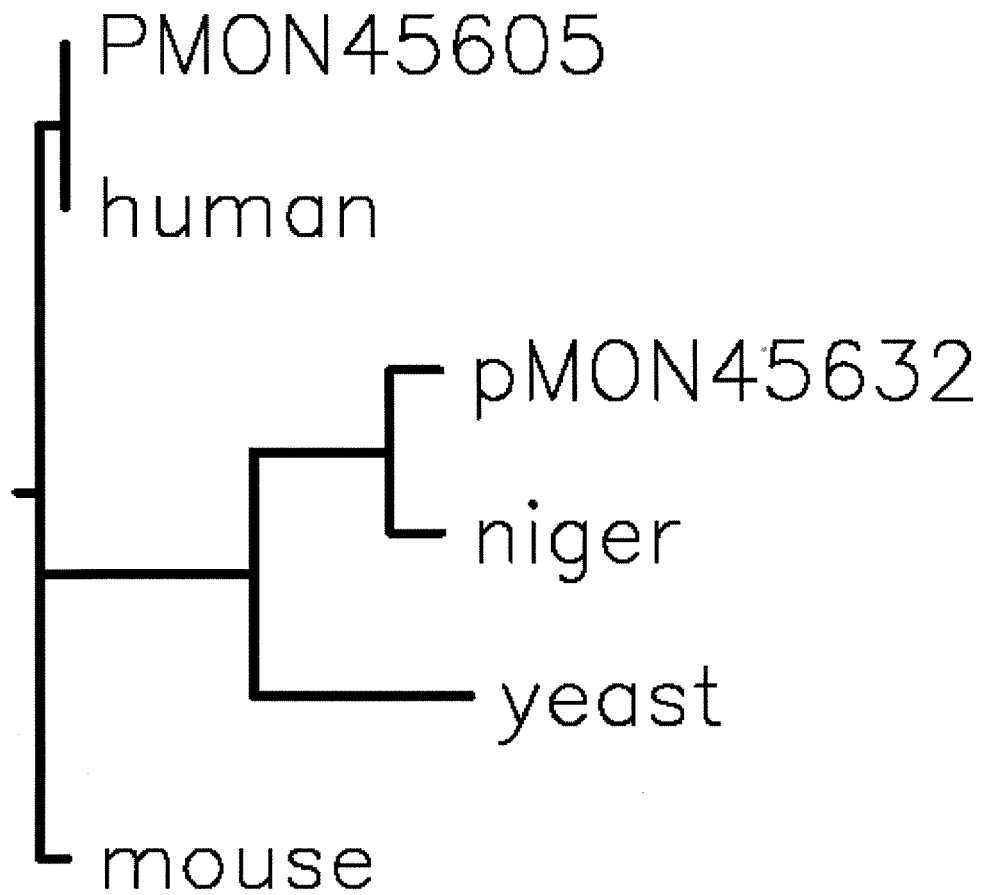
*Figure 9 – Phylogenetic tree showing the relatedness of* Aspergillus ochraceus and *human oxidoreductase to reductases from* A. niger, *yeast, and mouse.*

*Figure 10 – Percent homology between* Aspergillus ochraceus *oxidoreductase to reductases from* A. niger, *yeast, and mouse and human.*

| Accession number | organism | % id to A.och oxred |
|---|---|---|
| CAA81550 | *A. niger* | 84 |
| BAA02936 | *S. cerevisiae* | 37 |
| BAA04496 | mouse | 34 |
| AAB21814 | human | 33 |

Figure 11A – Amino acid homology alignment of human oxidoreductase with the top 4 hits from SwissProt

```
PMON45605   1   MGDSHVDTSSTVSEAVAEEVSLFSMTDMLFSLIVGLLTYWFFRKKKEEVPEFKIQTL
human       1   MGDSHVDTSSTVSEAVAEEVSLFSMTDMLFSLIVGLLTYWFFRKKKEEVPEFKIQTL
rabbit      1   MDSHGDTGATMPEAAAQEASVFSMTDVVLFSLIVGLITYWFFRKKKEEVPEFKIQAP
rat         1   MGDSHEDTSATMPEAVAEEVSLFSTTDMVLFSLIVGVLTYWFFRKKKEEIPEFSKIQTT
mouse       1   MGDSHEDTSATVPEAVAEEVSLFSTTDMVLFSLIVGVLTYWFFRKKKEEIPEFSKIQTT
pig         1   MGDSNVDTGTTTSEMVAEEVSLFSATDMVLFSLIVGLLTYWFFRKKKDEVPEFSKIETT PMON45605  61   TSS-VRESSFVEKMKKTGRNIIVFYGSQTGTAEEFANRLSKDAHRYGMRGMSADPEEYDL
human      61   TSS-VRESSFVEKMKKTGRNIIVFYGSQTGTAEEFANRLSKDAHRYGMRGMSADPEEYDL
rabbit     61   TSSSVKESSFVEKMKKTGRNIVFYGSQTGTAEEFANRLSKDAHRYGMRGMAADPEEYDL
rat        61   APP-VKESSFVEKMKKTGRNIIVFYGSQTGTAEEFANRLSKDAHRYGMRGMSADPEEYDL
mouse      61   APP-VKESSFVEKMKKTGRNIIVFYGSQTGTAEEFANRLSKDAHRYGMRGMSADPEEYDL
pig        61   TSS-VKDSSFVEKMKKTGRNIIVFYGSQTGTAEEFANRLSKDAHRYGMRGMAADPEEYDL PMON45605 120   ADLSSLPEIDNALVVFCMATYGEGDPTDNAQDFYDWLQETDVDLSGVKFAVFGLGNKTYE
human     120   ADLSSLPEIDNALVVFCMATYGEGDPTDNAQDFYDWLQETDVDLSGVKFAVFGLGNKTYE
rabbit    121   ADLSSLPEINNALAVFCMATYGEGDPTDNAQDFYDWLQETDVDLSGVKMAVFGLGNKTYE
rat       120   ADLSSLPEIDKSLVVFCMATYGEGDPTDNAQDFYDWLQETDVDLGVKFAVFGLGNKTYE
mouse     120   ADLSSLPEIDKSLVVFCMATYGEGDPTDNAQDFYDWLQETDVDLGVKFAVFGLGNKTYE
pig       120   SDLSSLPEINALAVFCMATYGEGDPTDNAQDFYDWLQEADVDLGVKMAVFGLGNKTYE PMON45605 180   HFNAMGKYVDKRLEQLGAQRIFELGLGDDDGNLEEDFITWREQFWPAVCEHFGVEATGEE
human     180   HFNAMGKYVDKRLEQLGAQRIFELGLGDDDGNLEEDFITWREQFWPAVCEHFGVEATGEE
rabbit    181   HFNAMGKYVDQRLEQLGAQRIFELGMGDDDANLEEDFITWREQFWPAVCEHFGVEATGEE
rat       180   HFNAMGKYVDQRLEQLGAQRIFELGLGDDDGNLEEDFITWREQFWPAVCBFFGVEATGEE
mouse     180   HFNAMGKYVDQRLEQLGAQRIFELGLGDDDGNLEEDFITWREQFWPAVCBFFGVEATGEE
pig       180   HFNAMGKYVDKRLEQLGAQRIFDLGLGDDDGNLEEDFITWREQFWPAVCEHFGVEATGEE PMON45605 240   SSIRQYELVVHTDIDAAKVYMGEMGRLKSYENQKPPFDAKNPFLAAVTTNRKLNQGTERH
human     240   SSIRQYELVVHTDIDAAKVYMGEMGRLKSYENQKPPFDAKNPFLAAVTTNRKLNQGTERH
rabbit    241   SSIRQYELVIHTDIDVAKVYQGEMGRLKSYENQKPPFDAKNPFLATVTTNRKLNQGTERH
rat       240   SSIRQYELVVHEDMDVAKVYTGEMGRLKSYENQKPPFDAKNPFLAAVTANRKLNQGTERH
mouse     240   SSIRQYELVVHEDMDTAKVYTGEMGRLKSYENQKPPFDAKNPFLAAVTTNRKLNQGTERH
pig       240   SSIRQYELVVHTDMDTAVVYTGEMGRLKSYENQKPPFDAKNPFLAVVTTNRKLNQGTERH PMON45605 300   LMHLELDISDSKIRYESGDHVAVYPANDSALVNQLGKILGADLDVVMSLNNLDEESNKKH
human     300   LMHLELDISDSKIRYESGDHVAVYPANDSALVNQLGKILGADLDVVMSLNNLDEESNKKH
rabbit    301   LMHLELDISDSKIRYESGDHVAVYPANDSALVNQLGEILGADLDVVMSLNNLDEESNKKH
rat       300   LMHLELDISDSKIRYESGDHVAVYPANDSALVNQIGEILGADLDVIMSLNNLDEESNKKH
mouse     300   LMHLELDISDSKIRYESGDHVAVYPANDSTLVNQIGEILGADLDVIMSLNNLDEESNKKH
pig       300   LMHLELDISDSKIRYESGDHVAVYPANDSALVNQLGEILGTDLDIVMSLNNLDEESNKRH PMON45605 360   PFPCPTSYRTALTYYLDITNPPRTNVLYELAQYASEPSEQELLRKMASSSGEGKELYLSW
human     360   PFPCPTSYRTALTYYLDITNPPRTNVLYELAQYASEPSEQELLRKMASSSGEGKELYLSW
rabbit    361   PFPCPTSYRTALTYYLDITNPPRTNVLYELAQYAADPAEQEQLRKMASSSGEGKELYLSW
rat       360   PFPCPTTYRTALTYYLDITNPPRTNVLYELAQYASEPSEQEHLKMASSSGEGKELYLSW
```

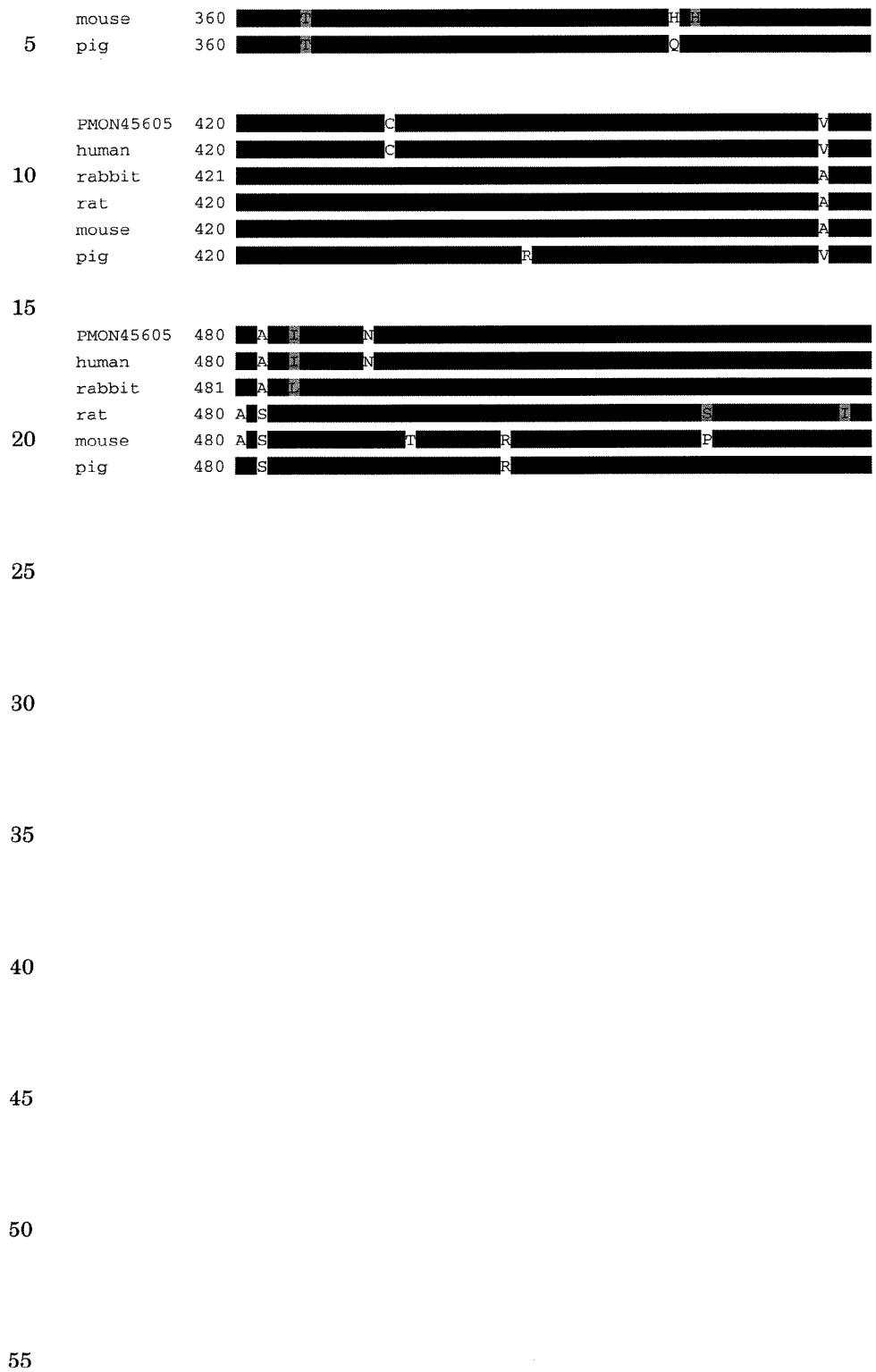
*Figure 11B – Amino acid homology alignment of human oxidoreductase with the top 4 hits from SwissProt*

*Figure 11C - Amino acid homology alignment of human oxidoreductase with the top 4 hits from SwissProt*

```
    PMON45605  540  FIGFIQERAWLRQQGKEVGETLLYYGCRRSDEDYLYREELAQFHRDGALTQLNVAFSREQ
    human      540  FIGFIQERAWLRQQGKEVGETLLYYGCRRSDEDYLYREELAQFHRDGALTQLNVAFSREQ
    rabbit     541  FIGFIQERAWLRQQGKEVGETLLYYGCRRAAEDYLYREELAGFQKDGTLSQLNVAFSREQ
    rat        540  FMGFIQERAWLREQGKEVGETLLYYGCRRSDEDYLYREELARFHKDGALTQLNVAFSREQ
    mouse      540  FMGFIQERAWLREQGKEVGETLLYYGCRRSDEDYLYREELARFHKDGALTQLNVAFSREQ
    pig        540  FIGFIQERAWLQEQGKEVGETLLYYGCRRSDEDYLYREELAQFHAKGALTRLSVAFSREQ PMON45605  600  SHKVYVQHLLKQDREHLWKLI-EGGAHIYVCGDARNMARDVQNTFYDIVAELGAMEHAQA
    human      600  SHKVYVQHLLKQDREHLWKLI-EGGAHIYVCGDARNMARDVQNTFYDIVAELGAMEHAQA
    rabbit     601  AQKVYVQHLLRRDKEHLWRLIHEGGAHIYVCGDARNMARDVQNTFYDIVAELGAMEHAQA
    rat        600  AHKVYVQHLLKRDREHLWKLIHEGGAHIYVCGDARNMAKDVQNTFYDIVAEFGPMEHTQA
    mouse      600  AHKVYVQHLLKRDKEHLWKLIHEGGAHIYVCGDARNMAKDVQNTFYDIVAEFGPMEHTQA
    pig        600  PQKVYVQHLLKRDKEHLWKLIHDGGAHIYICGDARNMARDVQNTFCDIVAEQGPMEHAQA PMON45605  659  VDYIKKLMTKGRYSLDVWS  (SEQ ID NO: 03)
    human      659  VDYIKKLMTKGRYSLDVWS  (SEQ ID NO: 52)
    rabbit     661  VDYVKKLMTKGRYSLDVWS  (SEQ ID NO: 53)
    rat        660  VDYVKKLMTKGRYSLDVWS  (SEQ ID NO: 54)
    mouse      660  VDYVKKLMTKGRYSLDVWS  (SEQ ID NO: 55)
    pig        660  VDYVKKLMTKGRYSLDVWS  (SEQ ID NO: 56)
```

*Figure 12 – Phylogenetic tree showing the relatedness of human oxidoreductase (P16435) with top 4 hits from SwissProt*
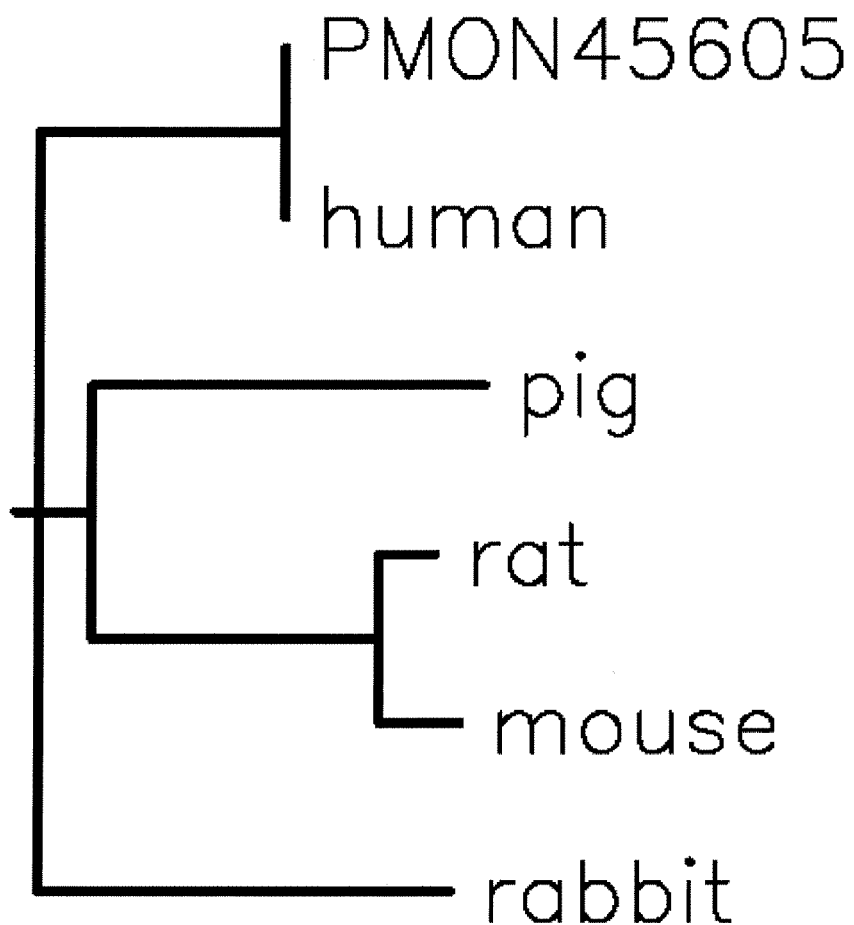

*Figure 13 – Percent homology between human oxidoreductase and top 4 hits from SwissProt*

| Accession number | Species | % id to human oxred |
|---|---|---|
| P00388 | rat | 92 |
| P00389 | rabbit | 92 |
| P37040 | mouse | 92 |
| P04175 | pig | 91 |

Figure 14 - Expression of Aspergillus ochraceus 11 alpha hydroxylase in transfected Sf9 insect cells
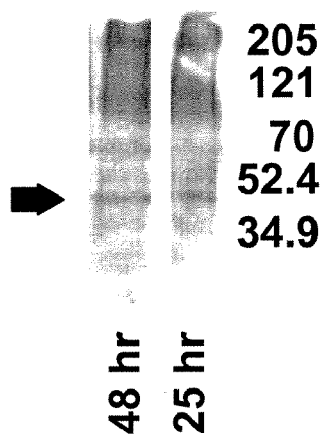

*Figure 15 - Expression of Aspergillus ochraceus P450 oxidoreductase in transfected Sf9 insect cells*
Expression of Fungal P-450 Oxidoreductase in Transfected Sf9 Cells
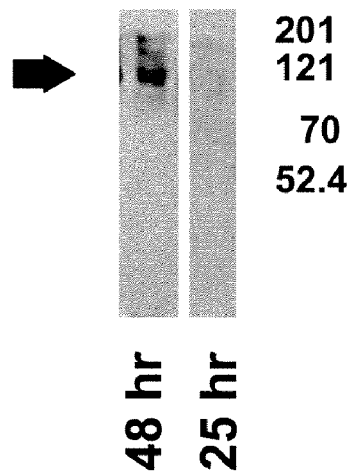

*Figure 16 - Conversion of androstenedione to 11 alpha hydroxy androstenedione monitored by HPLC*
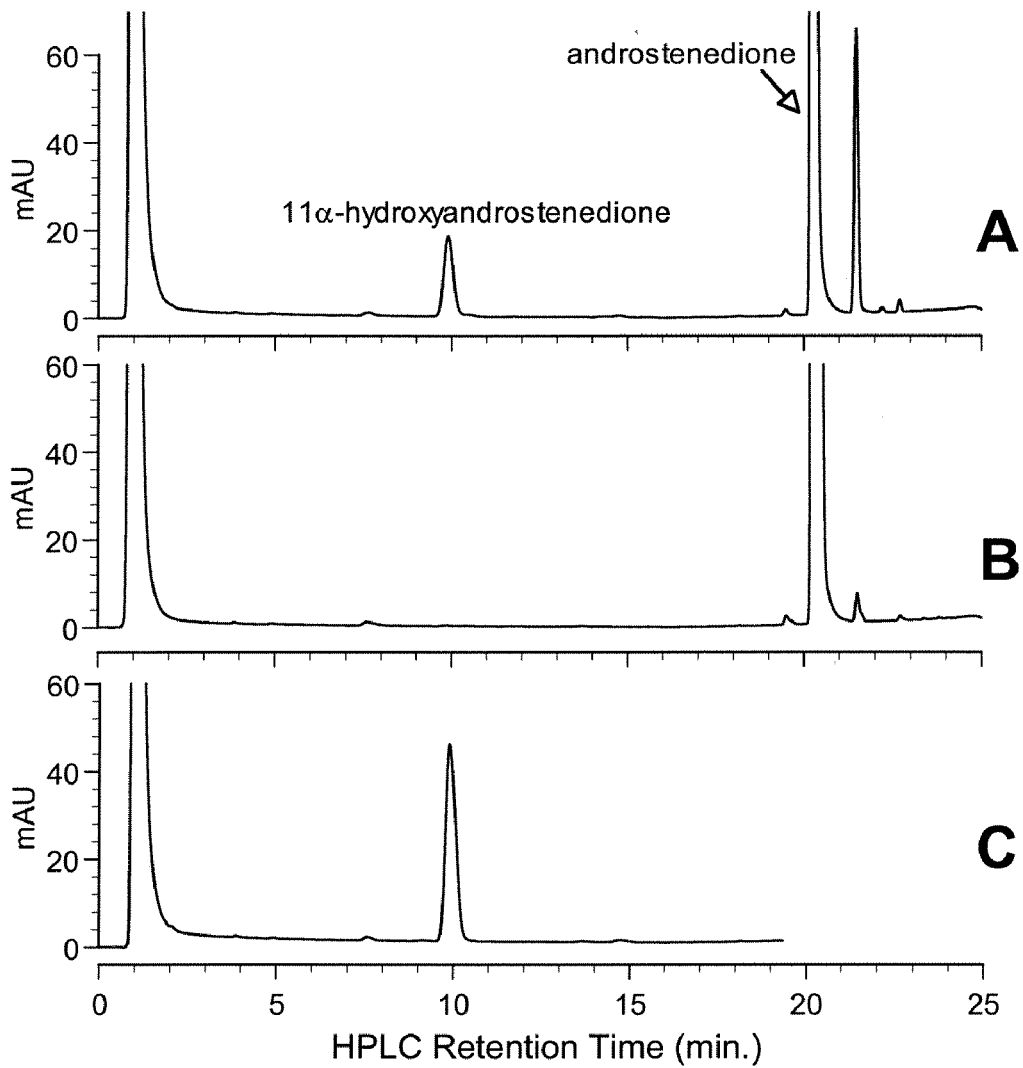

ASPERGILLUS OCHRACEUS 11 ALPHA HYDROXYLASE AND OXIDOREDUCTASE

PRIORITY

This is a division of application Ser. No. 10/021,425 filed Oct. 30, 2001 now U.S. Pat. No. 7,033,807, claims priority under Title 35, United States Code, § 119 of U.S. Provisional Application Ser. No. 60/244,300, filed Oct. 30, 2000.

FIELD OF THE INVENTION

The present invention relates to a novel cytochrome P450-like enzyme (*Aspergillus ochraceus* 11 alpha hydroxylase) and an oxidoreductase (*Aspergillus ochraceus* oxidoreductase) isolated from cDNA library generated from the mRNA of *Aspergillus ochraceus* spores. When the cDNA encoding the 11 alpha hydroxylase was co-expressed in *Spodoptera frugiperda* (Sf-9) insect cells with the cDNA encoding human oxidoreductase as an electron donor, it successfully catalyzed the conversion of the steroid substrate 4-androstene-3,17-dione (AD) to 11 alpha-hydroxy-AD as determined by HPLC analysis. The invention also relates to nucleic acid molecules associated with or derived from these cDNAs including complements, homologues and fragments thereof, and methods of using these nucleic acid molecules, to generate, for example, polypeptides and fragments thereof. The invention also relates to the generation of antibodies that recognize the *A. ochraceus* 11 alpha hydroxylase and oxidoreductase and methods of using these antibodies to detect the presence of these native and recombinant polypeptides within unmodified and transformed host cells, respectively. The invention also provides methods of expressing the *Aspergillus* 11 alpha hydroxylase gene separately, or in combination with human or *Aspergillus* oxidoreductase, in heterologous host cells, to facilitate the bioconversion of steroid substrates to their 11 alpha hydroxy-counterparts.

BACKGROUND OF THE INVENTION

Microbial transformation or bioconversion reactions have long been used to facilitate the chemical synthesis of a wide variety of pharmaceutical products. Stereospecific reactions carried out under mild enzymatic conditions frequently offer advantages over comparable chemical processes which result in undesireable side products. Microorganisms also have the ability to carry out simultaneous independent or sequential reactions on a substrate molecule, minimizing the number of distinct steps in a synthesis and reducing the total cost of the desired intermediate or end product.

General features of microbial systems used as biocatalysts for the transformation of organic compounds has been reviewed (See e.g., Goodhue, Charles T., *Microb. Transform. Bioact. Compd.*, 1:9-44, 1982). Biotransformations can be carried out, for example, in continuous cultures or in batch cultures. Enzymes secreted from the microorganism react with a substrate, and the product can be recovered from the medium. Intracellular enzymes can also react with a substrate if it is able to enter cells by an active or a passive diffusion process. Immobilized, dried, permeabilized, and resting cells, and spores have also been used for microbial transformations. The use of cell extracts and purified enzymes in solution, or immobilized on carriers, may eventually offer significant cost or control advantages over traditional fermentation methods.

Bioconversion reactions have been widely used in the field of steroids (Kieslich, K.; Sebek, O. K. *Annu. Rep. Ferment. Processes* 3:275-304, 1979; Kieslich, Klaus. *Econ. Microbiol.*, 5 (Microb. Enzymes Bioconvers.): 369-465, 1980). A variety of reactions have been characterized, including hydroxylation, epoxidation, oxidation, dehydrogenation, ring and side chain degradation, reduction, hydrolysis, and isomerization reactions. Many types of microorganisms have also been used including species as diverse, for example, as *Acremonium, Aspergillus, Rhizopus, Fusarium, Penicillium, Streptomyces, Actinomyces, Nocardia, Pseudomonas, Mycobacterium, Arthrobacter* and *Bacillus*.

A variety of approaches have been used to facilitate the hydroxylation of intermediates used in the synthesis of commercially-important steroid compounds. U.S. Pat. No. 4,588,683, for example, describes a method of preparing 11 beta, 17 alpha, 20, 21 tetrahydroxy steroids by incubating substrate compounds in a medium comprising a fungal culture of the genus *Curvularia* capable of effecting 11 beta hydroxylation. *Aspergillus ochraceus* cultures and preparations of mycelia have also been used to convert progesterone and other steroids to their corresponding 11 alpha hydroxy forms (Tan, L. and Falardeau, P., 1970; Tan L., and Falardeau P., *J. Steroid Biochem.* 1:221-227, 1970; Samanta, T. B. et al., *Biochem. J.* 176, 593-594, 1978; Jayanthi, C. R. et al., *Biochem. Biophys. Res. Commun.* 106:1262-1268, 1982).

The advent of new and expanded clinical uses of steroids for the treatment of a wide variety of disorders has created a need for improved methods for the production of steroid compounds and their intermediates on a commercial scale. U.S. Pat. No. 4,559,332, for example, describes a number of methods for the preparation of 20-spiroxane series of steroid compounds, including methods for the preparation of eplerenone methyl hydrogen 9,11α-epoxy-17α-hydroxy-3-oxopregn-4-ene-7α,21-dicarboxylate, γ-lactone (also referred to as eplerenone or epoxymexrenone) and related compounds. WO 98/25948 and U.S. application Ser. No. 09/319,673 describe novel processes for the preparation of 9,11-epoxy steroid compounds, especially those of the 20-spiroxane series and their analogs, novel intermediates useful in the preparation of steroid compounds, and processes for the preparation of such novel intermediates. U.S. Pat. No. 6,046,023 discloses improved methods for the microbial transformation of canrenone or estr-4-ene-3,17-dione into its 11 α-hydroxy analogue using microorganisms of the genus *Aspergillus, Rhizopus,* and *Pestelotia,* using steroid substrates having a purity of less than 97% and more than 90% at a concentration greater than 10 g/L.

Many modern, systematic approaches needed to optimize bioconversion of particular steroid intermediates are often hindered by insufficient biochemical knowledge of the enzymes involved in their synthesis and degradation. Eukaryotic cytochromes P450 appear to be associated with the endoplasmic reticulum (ER) or mitochondrial membranes. The electron donor for ER-associated cytochrome P450 enzymes is often an FAD/FMN-dependent NADPH-cytochrome P450 oxidoreductase. Electron transfer in the mitochondrial cytochromes P450 is usually mediated by an NADPH-ferredoxin oxidoreductase and ferrodoxin. The specific electron donors known to be involved in mammalian steroidogenesis, are also called adrenodoxin reductase and adrenodoxin, respectively.

While fungal biotransformations are known to be mediated by cytochrome P450 enzymes, many of these enzymes are extremely difficult to purify in an enzymatically-active form (van den Brink et al., *Fungal Genetics and Biology* 23, 1-17, 1998). Many fungal P450 enzymes appear to be associated with the endoplasmic reticulum (van den Brink et al., *Fungal Genetics and Biology* 23, 1-17, 1998). Yeast have an adrenodoxin reductase homologue which was shown to couple with a mammalian 11 beta hydroxylase in vitro. (Lacour et al., *Journal of Biological Chemistry* 273, 23984-23992, 1998). In contrast, the electron donor which couples with *Aspergillus ochraceus* 11 alpha hydroxylase was predicted to be an NADPH-cytochrome P450 oxidoreductase (Samanta and Ghosh, *J Steroid Biochem* 28, 327-32, 1987). The steroid 11 alpha hydroxylation complex in *Rhizopus nigricans* also appears to require an NADPH-cytochrome p450 oxidoreductase (Makovec and Breskvar, *Arch Biochem Biophys*. 357, 310-6, 1998). Amplification of cytochrome *R. nigricans* P450 and NADPH-cytochrome P450 reductase activities in preparations of progesterone-induced fungal mycelia may the facilitate biochemical characterization of both enzymes (Makovec and Breskvar, *Pflugers Arch—Eur J. Physiol* 439(Suppl): R111-R112, 2000).

*Aspergillus ochraceus* spores have been shown to catalyze the 11 alpha hydroxylation of steroid substrates such as progesterone (Dutta T K, Datta J, Samanta T B, *Biochem. Biophys. Res. Commun*. 192:119-123, 1993). *A. fumigatus* is also known to exhibit a steroid 11 alpha hydroxylase activity (Smith et al., *J Steroid Biochem Mol Biol* 49:93-100, 1994). The *A. fumigatus* enzyme is distinguished from the *A. ochraceus* enzyme, in that it appears to be a cytochrome P450 with dual site-specificity for 11 alpha and 15 beta hydroxylation and, unlike the *A. ochraceus* hydroxylase, appears to be non-inducible.

Despite recent advances in sequencing technologies, detailed knowledge about the structural relationships of fungal cytochrome P450s gleaned from nucleotide sequence data remains primitive. Breskvar et al., (*Biochem. Biophys. Res. Commun* 1991; 178, 1078-1083, 1991) have described a genomic DNA sequence from *Rhizopus nigricans* for a putative P-450 encoding an 11α-hydroxylase for progesterone. This sequence may not be complete, however, since the predicted amino acid sequence lacks the canonical heme-binding motif, FxxGxxxCxG, which is common to almost all known cytochrome P-450 enzymes. (Nelson et al, *Pharmacogenetics* 6:1-42, 1996).

The cloning and characterization of the NADPH cytochrome P450 oxidoreductase (cprA) gene of *Aspergillus niger* has been described (van den Brink, J., et al., Genbank accession numbers Z26938, CAA81550, 1993, unpublished). The primary structure of *Saccharomyces cereuisiae* NADPH-cytochrome P450 reductase has also been deduced from the nucleotide sequence of its cloned gene (Yabusaki et al., *J. Biochem*. 103(6): 1004-1010, 1988).

Several other approaches have been used to facilitate the cloning and analysis of steroid enzymes. U.S. Pat. Nos. 5,422,262, 5,679,521, and European patent EP 0 528 906 B1, for example, describes the expression cloning of steroid 5 alpha reductase, type 2. U.S. Pat. No. 5,869,283, for example, describes an expression cassette comprising heterologous DNAs encoding two or more enzymes, each catalyzing an oxidation step involved conversion of cholesterol into hydrocortisone, including the conversion of cholesterol to pregnenolone; the conversion of pregnenolone to progesterone; the conversion of progesterone to 17 α-hydroxy-progesterone; the conversion of 17α-hydroxyprogesterone to cortexolone; and the conversion of cortexolone to hydrocortisone.

The sequences of *Aspergillus ochraceus* 11 alpha hydroxylase and *A. ochraceus* oxidoreductase have not been reported. Knowledge about their sequence could greatly facilitate the development of expression vectors and recombinant host strains that can carry out more efficient bioconversions of steroid intermediates and the synthesis of end products on a commercial scale without the problems associated with partially-characterized host strains or an incomplete understanding of the enzymes involved in steroidogenesis. The present invention overcomes many of the limitations discussed above by identifying enzymes capable of carrying out the 11 alpha hydroxylation of steroids. This approach not only greatly facilitates the use of 11 alpha hydroxylation, but also permits the development of new strategies for the identification of similar enzymes from other fungi, the cloning of other enzymes involved in steroidogenesis from *Aspergillus ochraceus* and other microorganisms, and the development of improved host strains or methods using free cells or immobilized cells or enzymes in bioconversion reactions. Similar approaches could also be developed to aid in the construction of expression vectors and recombinant host strains that are more amenable to propagation and control than wild-type microorganisms now commonly used for bioconversion in large scale bioreactors.

SUMMARY OF THE INVENTION

In its broadest scope, the present invention provides a method to clone enzymes involved in steroid metabolism and use of these enzymes to produce novel steroid intermediates and end-products. One aspect of the claimed invention is to provide a novel enzyme 11 alpha hydroxylase and oxidoreductase, and their nucleic acids, proteins, peptides, fragments, and homologues. The invention also relates to methods of identifying and cloning other enzymes involved in steroid metabolism. The invention also covers novel vectors and host cells, a novel method for making heterologous proteins by using the above vectors, and a method for identifying the substrate specificity of the cloned enzymes.

The invention provides a means for determining the substrate specificity of the cloned 11 alpha hydroxylase, allelic variants, muteins, and fusion proteins thereof, permitting evaluation of a broad array of steroid substrates including 3 keto delta 4,5 steroids (3 keto delta 4 steroids); 3 keto delta 4, 5 delta 6, 7 steroids (3 keto delta 4 delta 6 steroids); 3 keto delta 6, 7 steroids (3 keto delta 6 steroids); or 3 keto delta 1, 2 delta 4, 5 steroids (3 keto delta 1 delta 4 steroids). Preferred substrates for testing include (a) canrenone; (b) androstenedione; (c) aldona; (d) ADD (1,4 androstenedienedione) (e) mexrenone; (f) 6 beta mexrenone; (g) 9 alpha mexrenone; (h) 12 beta mexrenone; (i) delta 12 mexrenone; (j) testosterone; (k) progesterone; (l) mexrenone 6,7-bis-lactone; and (m) mexrenone 7,9-bislactone. Preferably the cloned 11 alpha hydroxylase, allelic variants, muteins, and fusion proteins thereof do not also catalyze a second hydroxylation selected from the group consisting of 15 alpha or beta hydroxylation, 6 alpha or beta hydroxylation, 7 alpha or beta hydroxylation, 9 alpha or beta hydroxylation, 12 alpha or beta hydroxylation, and 17 alpha or beta hydroxylation of substrates selected from the group consisting of 3 keto delta 4,5 steroids; 3 keto delta 4, 5 delta 6, 7 steroids; or 3 keto delta 6, 7 steroids. Most preferably the cloned 11 alpha hydroxylase, allelic variants, muteins, and fusion proteins thereof do not catalyze the 15 beta hydroxylation of substrates selected from the group consisting of 3 keto delta 4,5 steroids; 3 keto delta 4, 5 delta 6, 7 steroids; or 3 keto delta 6, 7 steroids.

The invention provides an isolated and purified nucleic acid, encoding *Aspergillus ochraceus* 11 alpha hydroxylase. It also provides an isolated DNA, cDNA, gene, and an allele of the gene encoding *Aspergillus ochraceus* 11 alpha hydroxylase. Preferably the isolated and purified nucleic acid is as set forth in SEQ ID NO: 01. Preferably the isolated DNA, cDNA, gene, and an allele of the gene is as set forth in SEQ ID NO: 01.

The invention provides an isolated protein having the amino acid sequence of *Aspergillus ochraceus* 11 alpha hydroxylase. It also provides an isolated variant of *Aspergillus ochraceus* 11 alpha hydroxylase, and a fusion protein comprising this hydroxylase. Preferably the protein is as set forth in SEQ ID NO: 2. It also provides for variant of the protein set forth in SEQ ID NO: 2.; a polypeptide which comprises SEQ ID NO: 2 with at least one conservative amino acid substitution; polypeptides, with an amino acid sequence at least 99%, 95%, 90%, 75%, and 50% identical to SEQ ID NO: 2.

The invention provides an isolated and purified nucleic acid, encoding *Aspergillus ochraceus* 11 alpha oxidoreductase. It also provides an isolated DNA, cDNA, gene, and allele of the gene encoding *Aspergillus ochraceus* oxidoreductase. Preferably, the isolated and purified nucleic acid, wherein said nucleic acid sequence is as set forth in SEQ ID NO: 5. It also provides for an isolated DNA, cDNA, gene, and allele of the gene set forth in SEQ ID NO: 5.

The invention provides an isolated protein having the amino acid sequence of *Aspergillus ochraceus* oxidoreductase. It also provides an isolated variant of the protein having the amino acid sequence of *Aspergillus ochraceus* oxidoreductase, and a fusion protein comprising the amino acid sequence of *Aspergillus ochraceus* oxidoreductase. Preferably the isolated protein has the amino acid sequence set forth in SEQ ID NO: 6. It also provides an isolated variant of a protein set forth in SEQ ID NO: 6. a purified polypeptide, the amino acid sequence of which comprises SEQ ID NO: 6 with at least one conservative amino acid substitution; and a polypeptides with an amino acid sequence at least 99%, 95%, 90%, 75%, and 50% identical to SEQ ID NO: 6.

The invention provides an isolated and purified nucleic acid encoding an enzyme that can catalyze the 11 alpha hydroxylation of 3 keto delta 4,5 steroids (3 keto delta 4 steroids); 3 keto delta 4, 5 delta 6, 7 steroids (3 keto delta 4 delta 6 steroids); 3 keto delta 6,7 steroids (3 keto delta 6 steroids); or 3 keto delta 1, 2 delta 4, 5 steroids (3 keto delta 1 delta 4 steroids). Preferably the enzyme does not catalyze the 15 beta hydroxylation of 3 keto delta 4,5 steroids; 3 keto delta 4, 5 delta 6, 7 steroids; or 3 keto delta 6, 7 steroids. More preferably, the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; (d) ADD (1,4 androstenedienedione) to 11 alpha hydroxy ADD; (e) mexrenone to 11 alpha hydroxy mexrenone; (f) 6 beta mexrenone to 11 alpha hydroxy 6 beta mexrenone; (g) 9 alpha mexrenone to 11 alpha hydroxy 9 alpha mexrenone; (h) 12 beta mexrenone to 11 alpha hydroxy 12 beta mexrenone; (i) delta 12 mexrenone to 11 alpha hydroxy delta 12 mexrenone; (j) testosterone to 11 alpha hydroxy testosterone; (k) progesterone to 11 alpha hydroxy progesterone; (l) mexrenone 6,7-bis-lactone to 11 alpha hydroxy mexrenone 6,7-bis-lactone; and (m) mexrenone 7,9-bislactone to 11 alpha hydroxy mexrenone 7,9-bislactone. More preferably, the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; and (d) ADD (1,4 androstenedienedione) to 11 alpha hydroxy ADD. Most preferably the hydroxylation is from canrenone to 11 alpha hydroxy canrenone.

The invention also provides a method of expressing a protein that can catalyze the 11 alpha hydroxylation of 3 keto delta 4,5 steroids; 3 keto delta 4, 5 delta 6, 7 steroids; 3 keto delta 6, 7 steroids; or 3 keto delta 1, 2 delta 4, 5 steroids comprising; (a) transforming or transfecting host cells with an expression cassette comprising a promoter operably linked to a nucleic acid that encodes said protein, and (b) expressing said protein in said host cells. The invention also provides for a method of producing the protein further comprising the step of recovering said protein. Preferably, this protein is *Aspergillus ochraceus* 11 alpha hydroxylase. More preferably, this method further comprises expressing an electron donor protein, wherein said electron donor protein can donate electrons to said protein that can catalyze the 11 alpha hydroxylation of 3 keto delta 4,5 steroids; 3 keto delta 4, 5 delta 6, 7 steroids; 3 keto delta 6, 7 steroids; or 3 keto delta 1, 2 delta 4, 5 steroids. Preferably, the electron donor protein is selected from the group consisting of human oxidoreductase and *Aspergillus ochraceus* oxidoreductase. More preferably the electron donor protein is *Aspergillus ochraceus* oxidoreductase. More preferably, the nucleic acid encoding said steroid 11 alpha hydroxylase and said electron donor protein are on separate expression cassettes. More preferably, the nucleic acid encoding said steroid 11 alpha hydroxylase and said electron donor protein are on the same expression cassettes. Even more preferably, the steroid 11 alpha hydroxylase is *Aspergillus ochraceus* 11 alpha hydroxylase and said electron donor protein is human oxidoreductase. Even more preferably, the steroid 11 alpha hydroxylase is *Aspergillus ochraceus* 11 alpha hydroxylase and said electron donor protein is *Aspergillus ochraceus* oxidoreductase. Preferably, the expression cassette is on an expression vector. More preferably, the expression vector is a baculovirus. Even more preferably, the baculovirus is a nuclear polyhedrosis virus is selected from the group consisting of *Autographa californica* nuclear polyhedrosis virus and *Bombyx mori* nuclear polyhedrosis virus. Most preferably, the nuclear polyhedrosis virus is *Autographa californica* nuclear polyhedrosis virus. Preferably, the host cells are insect cells. More preferably, the insect cells are selected from the group consisting of *Spodoptera frugiperda, Trichoplusia ni, Autographa californica,* and *Manduca sexta* cells. Most preferably the insect cells are *Spodoptera frugiperda* cells. The invention also provides a for a method of expressing a protein wherein the *Aspergillus ochraceus* 11 alpha hydroxylase is SEQ ID NO: 2; the human oxidoreductase is SEQ ID NO: 4; and the *Aspergillus ochraceus* oxidoreductase is SEQ ID NO: 6.

The invention also provides for an isolated and purified polypeptide that can catalyze the 11 alpha hydroxylation of 3 keto delta 4,5 steroids (3 keto delta 4 steroids); 3 keto delta 4, 5 delta 6, 7 steroids (3 keto delta 4 delta 6 steroids); 3 keto delta 6, 7 steroids (3 keto delta 6 steroids); or 3 keto delta 1, 2 delta 4, 5 steroids (3 keto delta 1 delta 4 steroids). Preferably, the polypeptide does not catalyze the 15 beta hydroxylation of 3 keto delta 4,5 steroids; 3 keto delta 4, 5 delta 6, 7 steroids; or 3 keto delta 6, 7 steroids. More preferably, the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; (d) ADD (1,4 androstenedienedione) to 11 alpha hydroxy ADD; (e)

mexrenone to 11 alpha hydroxy mexrenone; (f) 6 beta mexrenone to 11 alpha hydroxy 6 beta mexrenone; (g) 9 alpha mexrenone to 11 alpha hydroxy 9 alpha mexrenone; (h) 12 beta mexrenone to 11 alpha hydroxy 12 beta mexrenone; (i) delta 12 mexrenone to 11 alpha hydroxy delta 12 mexrenone; (j) testosterone to 11 alpha hydroxy testosterone; (k) progesterone to 11 alpha hydroxy progesterone; (l) mexrenone 6,7-bis-lactone to 11 alpha hydroxy mexrenone 6,7-bis-lactone; and (m) mexrenone 7,9-bislactone to 11 alpha hydroxy mexrenone 7,9-bislactone. More preferably, the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; and (d) ADD (1,4 androstenedienedione) to 11 alpha hydroxy ADD. Most preferably the hydroxylation is from canrenone to 11 alpha hydroxy canrenone.

The invention also provides for an expression cassette comprising a promoter operably linked to an isolated and purified nucleic acid encoding a polypeptide that can catalyze the 11 alpha hydroxylation of 3 keto delta 4,5 steroids (3 keto delta 4 steroids); 3 keto delta 4, 5 delta 6, 7 steroids (3 keto delta 4 delta 6 steroids); 3 keto delta 6, 7 steroids (3 keto delta 6 steroids); or 3 keto delta 1, 2 delta 4, 5 steroids (3 keto delta 1 delta 4 steroids). More preferably, the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; (d) ADD (1,4 androstenedienedione) to 11 alpha hydroxy ADD; (e) mexrenone to 11 alpha hydroxy mexrenone; (f) 6 beta mexrenone to 11 alpha hydroxy 6 beta mexrenone; (g) 9 alpha mexrenone to 11 alpha hydroxy 9 alpha mexrenone; (h) 12 beta mexrenone to 11 alpha hydroxy 12 beta mexrenone; (i) delta 12 mexrenone to 11 alpha hydroxy delta 12 mexrenone; (j) testosterone to 11 alpha hydroxy testosterone; (k) progesterone to 11 alpha hydroxy progesterone; (l) mexrenone 6,7-bis-lactone to 11 alpha hydroxy mexrenone 6,7-bis-lactone; and (m) mexrenone 7,9-bislactone to 11 alpha hydroxy mexrenone 7,9-bislactone. More preferably, the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; and (d) ADD (1,4 androstenedienedione) to 11 alpha hydroxy ADD. Most preferably the hydroxylation is from canrenone to 11 alpha hydroxy canrenone.

The invention also provides for an expression cassette comprising a promoter operably linked to an isolated and purified nucleic acid encoding *Aspergillus ochraceus* oxidoreductase. Preferably the nucleic acid is SEQ ID NO: 6.

The invention also provides for an expression cassette comprising a heterologous DNA encoding an enzyme from the metabolic pathway for the synthesis of sitosterol to eplerenone wherein said enzyme catalyzes at least one conversion selected from the group consisting of: (a) canrenone to 11 alpha hydroxy canrenone; (b) androstenedione to 11 alpha hydroxy androstenedione; (c) aldona to 11 alpha hydroxy aldona; (d) ADD (1,4 androstenedienedione) to 11 alpha hydroxy ADD; (e) mexrenone to 11 alpha hydroxy mexrenone; (f) 6 beta mexrenone to 11 alpha hydroxy 6 beta mexrenone; (g) 9 alpha mexrenone to 11 alpha hydroxy 9 alpha mexrenone; (h) 12 beta mexrenone to 11 alpha hydroxy 12 beta mexrenone; (i) delta 12 mexrenone to 11 alpha hydroxy delta 12 mexrenone; (j) testosterone to 11 alpha hydroxy testosterone; and (k) progesterone to 11 alpha hydroxy progesterone; (l) mexrenone 6,7-bis-lactone to 11 alpha hydroxy mexrenone 6,7-bis-lactone; and (m) mexrenone 7,9-bislactone to 11 alpha hydroxy mexrenone 7,9-bislactone and wherein the heterologous DNA is operably linked to control sequences required to express the encoded enzymes in a recombinant host. Preferably the heterologous DNA coding sequences in the expression cassette are selected from the group consisting of the following genus and species: *Aspergillus ochraceus, Aspergillus ochraceus, Aspergillus niger, Aspergillus nidulans, Rhizopus oryzae, Rhizopus stolonifer, Streptomyces fradiae, Bacillus megaterium, Pseudomonas cruciviae, Trichothecium roseum, Fusarium oxysporum Rhizopus arrhizus, Absidia coerula, Absidia glauca, Actinomucor elegans, Aspergillus flavipes, Aspergillus fumigatus, Beauveria bassiana, Botryosphaeria obtusa, Calonectria decora, Chaetomium cochliodes, Corynespora cassiicola, Cunninghamella blakesleeana, Cunninghamella echinulata, Cunninghamella elegans, Curvularia clavata, Curvularia lunata, Cylindrocarpon radicicola, Epicoccum humicola, Gongronella butleri, Hypomyces chrysospermus, Monosporium olivaceum, Mortierella isabellina, Mucor mucedo, Mucor griseocyanus, Myrothecium verrucaria, Nocardia corallina, Paecilomyces carneus, Penicillum patulum, Pithomyces atroolivaceus, Pithomyces cynodontis, Pycnosporiuin sp., Saccharopolyspora erythrae, Sepedonium chrysospermum, Stachylidium bicolor, Streptomyces hyqroscopicus, Streptomyces purpurascens, Syncephalastrum racemosum, Thamnostylum piriforme, Thielavia terricola,* and *Verticillium theobromae, Cephalosporium aphidicola, Cochliobolus lunatas, Tieghemella orchidis, Tieghemella hyalospora, Monosporium olivaceum, Aspergillus ustus, Fusarium graminearum, Verticillium glaucum,* and *Rhizopus nigricans*. More preferably, the genus and species are selected from the group consisting of *Aspergillus ochraceus, Aspergillus ochraceus, Aspergillus niger, Aspergillus nidulans, Rhizopus oryzae, Rhizopus stolonifer, Streptomyces fradiae, Bacillus megaterium, Pseudomonas cruciviae, Trichothecium roseum, Fusarium oxysporum, Rhizopus arrhizus,* and *Monosporium olivaceum*. Most preferably, genus and species is *Aspergillus ochraceus*.

Preferably, the recombinant host cell and progeny thereof comprise at least one expression cassette. More preferably, the host is a microorganism. Most preferably, the host is a bacterium. The invention also provides for a process for making one or more enzymes from the metabolic pathway for the transformation of sitosterol to eplerenone comprising incubating the recombinant host cell in a nutrient medium under conditions where the one or more enzymes encoded by the heterologous DNA are expressed and accumulate. More preferably the process comprises the steps of: (a) incubating the compound to be oxidized in the presence the recombinant host cells under conditions where the compound is hydroxylated and the hydroxylated product accumulates, and (b) recovering the hydroxylated product. Most preferably, the process comprises the steps of: (a) incubating the compound to be oxidized in the presence of the enzymes produced under conditions where the compound is hydroxylated and the hydroxylated product accumulates, and (b) recovering the hydroxylated product. The invention also provides for a host cells harboring an expression cassette. More preferably the expression cassette is integrated into the chromosome of said host cell. More preferably, the expression cassette is integrated into an expression vector.

The invention also provides for a method of determining the specific activity of a cloned 11 alpha hydroxylase comprising the steps of; (a) transforming host cells with an expression vector comprising a nucleic acid that encodes said 11 alpha hydroxylase, (b) expressing said 11 alpha hydroxylase in said host cells; (c) preparing subcellular membrane fractions from said cells, (d) incubating said subcellular membrane fractions with a steroid substrate, and (e) monitoring conversion of the steroid substrate to its 11 alpha hydroxy steroid counterpart. Preferably, the further comprises transforming host cells with an expression vector nucleic acid that encodes an oxidoreductase, and expressing said oxidoreductase in said host cells. More preferably, the oxidoreductase is human or *Aspergillus ochraceus*. Most preferably the oxidoreductase is human oxidoreductase. Most preferably the oxidoreductase is *Aspergillus ochraceus* oxidoreductase.

The invention also provides for a protein having SEQ ID NO: 2 and variants thereof that are at least 95% identical to SEQ ID NO: 2 and catalyze the 11 alpha hydroxylation of 3 keto delta 4,5 steroids; 3 keto delta 4, 5 delta 6, 7 steroids; 3 keto delta 6, 7 steroids; or 3 keto delta 1, 2 delta 4, 5 steroids, wherein said hydroxylation is selected from the group consisting of: (a) canrenone to 11 alpha hydroxy canrenone; (b) androstenedione to 11 alpha hydroxy androstenedione; (c) aldona to 11 alpha hydroxy aldona; (d) ADD (1,4 androstenedienedione) to 11 alpha hydroxy ADD; (e) mexrenone to 11 alpha hydroxy mexrenone; (f) 6 beta mexrenone to 11 alpha hydroxy 6 beta mexrenone; (g) 9 alpha mexrenone to 11 alpha hydroxy 9 alpha mexrenone; (h) 12 beta mexrenone to 11 alpha hydroxy 12 beta mexrenone; (i) delta 12 mexrenone to 11 alpha hydroxy delta 12 mexrenone; (j) testosterone to 11 alpha hydroxy testosterone; and (k) progesterone to 11 alpha hydroxy progesterone. Preferably the enzyme does not catalyze the 15 beta hydroxylation of 3 keto delta 4,5 steroids; 3 keto delta 4, 5 delta 6, 7 steroids; or 3 keto delta 6, 7 steroids.

The invention provides an isolated and purified nucleic acid encoding an enzyme that can catalyze the 11 alpha hydroxylation of 3 keto delta 4,5 steroids (3 keto delta 4 steroids); 3 keto delta 4, 5 delta 6, 7 steroids (3 keto delta 4 delta 6 steroids); 3 keto delta 6, 7 steroids (3 keto delta 6 steroids); or 3 keto delta 1, 2 delta 4, 5 steroids (3 keto delta 1 delta 4 steroids) wherein the hydroxylation is selected from the group consisting of: (a) canrenone to 11 alpha hydroxy canrenone; (b) androstenedione to 11 alpha hydroxy androstenedione; (c) aldona to 11 alpha hydroxy aldona; (d) ADD (1,4 androstenedienedione) to 11 alpha hydroxy ADD; (e) mexrenone to 11 alpha hydroxy mexrenone; (f) 6 beta mexrenone to 11 alpha hydroxy 6 beta mexrenone; (g) 9 alpha mexrenone to 11 alpha hydroxy 9 alpha mexrenone; (h) 12 beta mexrenone to 11 alpha hydroxy 12 beta mexrenone; (i) delta 12 mexrenone to 11 alpha hydroxy delta 12 mexrenone; (j) testosterone to 11 alpha hydroxy testosterone; and (k) progesterone to 11 alpha hydroxy progesterone. Preferably the enzyme does not catalyze the 15 beta hydroxylation of 3 keto delta 4,5 steroids; 3 keto delta 4, 5 delta 6, 7 steroids; or 3 keto delta 6, 7 steroids.

The invention also provides for a purified polypeptide, the amino acid sequence of which is selected from the group consisting of SEQ ID NO: 23, SEQ ID NO: 24, SEQ ID NO: 25.

The invention provides for a purified immunogenic polypeptide, the amino acid sequence of which comprises at least ten consecutive residues of SEQ ID NO: 2.

The invention provides for an isolated and purified antibody having a binding specificity for 11 alpha hydroxylase having an amino acid sequence as shown in SEQ ID NO: 2. Preferably the antibody binds to a protein region selected from the group consisting of (a) the N-terminal amino acids 1-10 of SEQ ID NO: 2; (b) the last 10 C-terminal amino acids of SEQ ID NO: 2; (c) amino acids SEQ ID NO: 23; (d) amino acids SEQ ID NO: 24; and (e) amino acids SEQ ID NO: 25. Preferably the antibody is purified on a peptide column, wherein said peptide is selected from the group consisting of: (a) the N-terminal amino acids 1-10 of SEQ ID NO: 2; (b) the last 10 C-terminal amino acids of SEQ ID NO: 2; (c) amino acids SEQ ID NO: 23; (d) amino acids SEQ ID NO: 24; and (e) amino acids SEQ ID NO: 25.

The invention also provides for a purified polypeptide, the amino acid sequence of which is selected from the group consisting of SEQ ID NO: 26.

The invention also provides for a purified immunogenic polypeptide, the amino acid sequence of which comprises at least ten consecutive residues of SEQ ID NO: 6.

The invention also provides for an isolated and purified antibody having a binding specificity for 11 alpha hydroxylase having an amino acid sequence as shown in SEQ ID NO: 6. Preferably the antibody binds to a protein region selected from the group consisting of (a) the N-terminal amino acids 1-10 of SEQ ID NO: 6; (b) the last 10 C-terminal amino acids of SEQ ID NO: 6; and (c) amino acids SEQ ID NO: 26. More preferably, the antibody is purified on a peptide column, wherein said peptide is selected from the group consisting of: (a) the N-terminal amino acids 1-10 of SEQ ID NO: 6; (b) the last 10 C-terminal amino acids of SEQ ID NO: 6; and (c) amino acids SEQ ID NO: 26.

The invention also provides for a composition comprising an antibody described above in an effective carrier, vehicle, or auxiliary agent. It also provides for a composition comprising such an antibody and a solution. The antibody may be a polyclonal antibody. The antibody may also be a monoclonal antibody. The antibody may be conjugated to an immunoaffinity matrix. The invention also provides for a method of using an immunoaffinity matrix to purify a polypeptide from a biological fluid or cell lysate. Preferably the immunoaffinity matrix is SEPHAROSE 4B. More preferably the method of using an immunoaffinity matrix to purify a polypeptide from a biological fluid or cell lysate uses SEPHAROSE 4B as an immunoaffinity matrix. More preferably, the method of using an immunoaffinity matrix to purify a polypeptide from a biological fluid or cell lysate uses SEPHAROSE 4B as an immunoaffinity matrix.

The invention also provides for a method of using a peptide column to purify an antibody, wherein said peptide is selected from the group consisting of: (a) the N-terminal amino acids 1-10 of SEQ ID NO: 2; (b) the last 10 C-terminal amino acids of SEQ ID NO: 2; (c) amino acids SEQ ID NO: 23; (d) amino acids SEQ ID NO: 24; and (e) amino acids SEQ ID NO: 25.

The invention also provides for a method of using a peptide column to purify an antibody, wherein said peptide is selected from the group consisting of: (a) the N-terminal amino acids 1-10 of SEQ ID NO: 6; (b) the last 10 C-terminal amino acids of SEQ ID NO: 6; and (c) amino acids SEQ ID NO: 26.

The invention also provides for a method of detecting a first polypeptide in a biological fluid, wherein said first polypeptide is selected from the group consisting of 11 alpha hydroxylase and oxidoreductase, comprising the following steps: (a) contacting said fluid with a second polypeptide, having a binding specificity for said first polypeptide, and (b) assaying the presence of said second polypeptide to determine the level of said first polypeptide. Preferably, the second polypeptide is an antibody. More preferably, the second polypeptide is radiolabeled.

The invention also provides for a process for producing an isolated nucleic acid comprising hybridizing SEQ ID NO: 1 to genomic DNA in 6×SSC and 65° C. and isolating the nucleic acid detected with SEQ ID NO: 1. The invention also provides for an isolated DNA nucleic acid prepared according to this process.

The invention also provides for an isolated nucleic acid that specifically hybridizes under highly stringent conditions to the complement of the sequence set forth in SEQ ID NO: 1.

The invention also provides for a process for producing an isolated nucleic comprising hybridizing SEQ ID NO: 5 to genomic DNA in 6×SSC and 65° C. and isolating the nucleic acid detected with SEQ ID NO: 5. The invention also provides for an isolated DNA nucleic acid prepared according to this process.

The invention also provides for an isolated nucleic acid that specifically hybridizes under highly stringent conditions to the complement of the sequence set forth in SEQ ID NO: 5.

The invention also provides for a DNA construct which alters the expression of a 11 alpha hydroxylase gene not normally expressed in a cell when said DNA construct is inserted into chromosomal DNA of the cell, said DNA construct comprising: (a) a targeting sequence; (b) a regulatory sequence; and (c) the structural gene for a steroid 11 alpha hydroxylase. The invention also provides for a host cell harboring this DNA construct.

The invention also provides for a DNA construct which alters the expression of a 11 alpha hydroxylase gene not normally expressed in a cell when said DNA construct is inserted into chromosomal DNA of the cell, said DNA construct comprising: (a) a targeting sequence; (b) a regulatory sequence; and (c) the structural gene for a steroid oxidoreductase. The invention also provides for a host cell harboring this DNA construct.

The invention also provides for use of a host cell harboring a cloned 11 alpha hydroxylase for the manufacture of a medicament for therapeutic application to treat heart disease, inflammation, arthritis, or cancer.

The invention also provides for a composition comprising from about 0.5-to about 500 g/L molasses, 0.5-50 g/L cornsteep liquid, 0.5-50 g/L $KH_2PO_4$, 2.5-250 g/L NaCl, 2.5-250 g/L glucose, and 0.04-4 g/L progesterone, pH 3.5-7. Preferably, this composition is comprised of from about 10-250 g/L molasses, 1-25 g/L cornsteep liquid, 1-25 g/L $KH_2PO_4$, 5-125 g/L NaCl, 5-125 g/L glucose, and 0.08-2 g/L progesterone, pH 4.5-6.5. More preferably, the composition is comprised of from about 25-100 g/L molasses, 2.5-10 g/L cornsteep liquid, 2.5-10 g/L $KH_2PO_4$, 12.5-50 g/L NaCl, 12.5-50 g/L glucose, and 0.2-0.8 g/L progesterone, pH 5.5-6.0. Most preferably the composition comprises about 50 g/L molasses, 5 g/L cornsteep liquid, 5 g/L $KH_2PO_4$, 25 g/L NaCl, 25 g/L glucose, 20 g/L agar, and 0.4 g/L progesterone, pH 5.8.

The invention also provides for a semisolid formulation of any of the compositions described above, further comprising from about 4-100 g/L agar. Preferably the agar is at a concentration of from about 10-40 g/L agar. More preferably, the agar is about 20 g/L agar.

The invention also provides for the use of any of the compositions describe above to produce spores from the microorganism selected from the group consisting of *Aspergillus ochraceus, Aspergillus niger, Aspergillus nidulans, Rhizopus oryzae, Rhizopus stolonifer,* and *Trichothecium roseum, Fusarium oxysporum Rhizopus arrhizus, Monosporium olivaceum. Penicillum chrysogenum,* and *Absidia coerula.* Preferably, the composition is used to produce spores from *Aspergillus ochraceus.*

DEFINITIONS

The following is a list of abbreviations and the corresponding meanings as used interchangeably herein:

11 alpha hydroxycanrenone=11 alpha hydroxy-4-androstene-3,17-dione ($C_{22}H_{28}O_4$, MW 356.46)

AcNPV=*Autographa californica* nuclear polyhedrosis virus, a member of the Baculoviridae family of insect viruses AD=androstenedione or 4-androstene-3,17-dione ($C_{22}H_{28}O_3$, MW 340.46)

aldadiene=canrenone

Amp=ampicillin attTn7=attachment site for Tn7 (a preferential site for Tn7 insertion into bacterial chromosomes)

bacmid=recombinant baculovirus shuttle vector isolated from *E. coli*

Bluo-gal=halogenated indolyl-β-D-galactoside bp=base pair(s)

Cam=chloramphenicol cDNA=complementary DNA

DMF=N,N-dimethylformamide ds=double-stranded eplerenone or epoxymexrenone=methyl hydrogen 9,11α-epoxy-17α-hydroxy-3-oxopregn-4-ene-7α,21-dicarboxylate, γ-lactone (MW 414.5)

g=gram(s)

Gen=gentamicin hoxr=human oxidoreductase

HPLC=high performance liquid chromatography hydroxycanrenone=11 alpha- or 11 beta-hydroxycanrenone IPTG=isopropyl-β-D-thiogalactopyranoside Kan=kanamycin kb=kilobase(s), 1000 bp(s)

mb=megabase(s)

Me=methyl mg=milligram(s)

ml or mL=milliliter(s)

mm=millimeter mM=millimolar

NMR=nuclear magnetic resonance oxr=oxidoreductase

PCR=polymerase chain reaction r=resistant or resistance

RP-HPLC=reverse phase high performance liquid chromatography

RT=room temperature

RT-PCR=reverse transcriptase polymerase chain reaction s=sensitive

SDS-PAGE=sodium dodecyl sulfate polyacrylamide gel electrophoresis

Spc/Str=spectinomycin/streptomycin

Tet=tetracycline

Tn=transposon ts=temperature-sensitive

U=units ug or μg=microgram(s)

ul or μl=microliter(s)

X-gal=5-bromo-3-chloro-indolyl-β-D-galactopyranoside

X-gluc=5-bromo-3-chloro-indolyl-β-D-glucopyranoside

The following is a list definitions of various terms used herein:

The species "*Aspergillus ochraceus* NRRL 405" means the filamentous fungus *Aspergillus ochraceus* NRRL 405, accession number 18500, obtained from the American Type Culture Collection (ATCC). *A. ochraceus* NRRL 405 and *A. ochraceus* ATCC 18500 are the same strain, catalogued differently.

The term "amino acid(s)" means all naturally occurring L-amino acids, including norleucine, norvaline, homocysteine, and ornithine.

The term "degenerate" means that two nucleic acid molecules encode for the same amino acid sequences but comprise different nucleotide sequences.

The term "fragment" means a nucleic acid molecule whose sequence is shorter than the target or identified nucleic acid molecule and having the identical, the substantial complement, or the substantial homologue of at least 10 contiguous nucleotides of the target or identified nucleic acid molecule.

The term "fusion protein" means a protein or fragment thereof that comprises one or more additional peptide regions not derived from that protein.

The term "probe" means an agent that is utilized to determine an attribute or feature (e.g. presence or absence, location, correlation, etc.) of a molecule, cell, tissue, or organism.

The term "promoter" is used in an expansive sense to refer to the regulatory sequence(s) that control mRNA production. Such sequences include RNA polymerase binding sites, enhancers, etc.

The term "protein fragment" means a peptide or polypeptide molecule whose amino acid sequence comprises a subset of the amino acid sequence of that protein.

The term "recombinant" means any agent (e.g., DNA, peptide, etc.), that is, or results from, however indirectly, human manipulation of a nucleic acid molecule.

The term "selectable or screenable marker genes" means genes whose expression can be detected by a probe as a means of identifying or selecting for transformed cells.

The term "specifically bind" means that the binding of an antibody or peptide is not competitively inhibited by the presence of non-related molecules.

The term "specifically hybridizing" means that two nucleic acid molecules are capable of forming an anti-parallel, double-stranded nucleic acid structure.

The term "substantial complement" means that a nucleic acid sequence shares at least 80% sequence identity with the complement.

The term "substantial fragment" means a nucleic acid fragment which comprises at least 100 nucleotides.

The term "substantial homologue" means that a nucleic acid molecule shares at least 80% sequence identity with another.

The term "substantially hybridizing" means that two nucleic acid molecules can form an anti-parallel, double-stranded nucleic acid structure under conditions (e.g., salt and temperature) that permit hybridization of sequences that exhibit 90% sequence identity or greater with each other and exhibit this identity for at least about a contiguous 50 nucleotides of the nucleic acid molecules.

The term "substantially-purified" means that one or more molecules that are or may be present in a naturally-occurring preparation containing the target molecule will have been removed or reduced in concentration.

The following is a list of steroids, corresponding terms, and their structures, as used interchangeably herein:

| # | Name | CA Index Name: | Other Names | Formula | Structure |
|---|---|---|---|---|---|
| 1 | Eplerenone | Pregn-4-ene-7,21-dicarboxylic acid, 9,11-epoxy-17-hydroxy-3-oxo-, γ-lactone, methyl ester, (7α,11α,17α)-(9CI) | Spiro[9,11-epoxy-9H-cyclopenta[a]phenanthrene-17(2H),2'(3'H)-furan], pregn-4-ene-7,21-dicarboxylic acid deriv.; CGP30083; Eplerenone; SC66110 | $C_{24}H_{30}O_6$ | 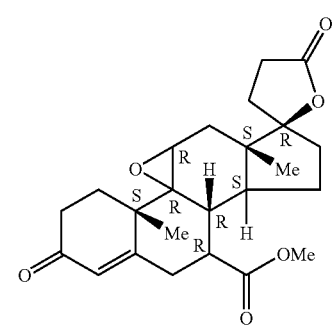 |
| 2 | Aldadiene; Canrenone | Pregna-4,6-diene-21-carboxylic acid, 17-hydroxy-3-oxo-, γ-lactone, (17α)-(9CI) | 17α-Pregna-4,6-diene-21-carboxylic acid, 17-hydroxy-3-oxo-, γ-lactone (6CI, 7CI, 8CI);Spiro[17H-cyclopenta[a]phenanthrene-17,2'(5'H)-furan], pregna-4,6-diene-21-carboxylic acid deriv.; 11614R.P.; 17β-Hydroxy-3-oxopregna-4,6-diene-21-carboxylic acid; 20-Spiroxa-4,6-diene-3,21-dione;Aldadiene; Canrenone; Phanurane; SC9376; Spirolactone SC14266 | $C_{22}H_{28}O_3$ | 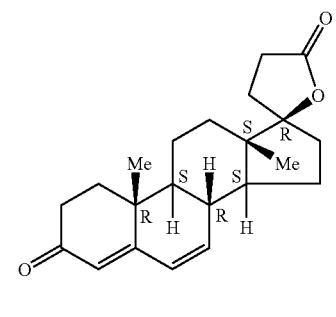 |

-continued

| # | Name | CA Index Name: | Other Names | Formula | Structure |
|---|---|---|---|---|---|
| 3 | 11α-Hydroxycanrenone | Pregna-4,6-diene-21-carboxylic acid, 11,17-dihydroxy-3-oxo-, γ-lactone, (11α,17α)-(9CI) | 11α-Hydroxycanrenone | C22H28O4 | 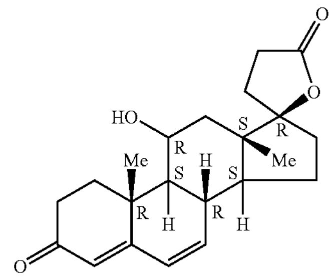 |
| 5 | Aldona ethyl enol ether | Pregna-4,6-diene-21-carboxylic acid, 3-ethoxy-17-hydroxy-, γ-lactone (9CI) | Spiro[17H-cyclopenta[a]phenanthrene-17,2'5'H)-furan], pregna-4,6-diene-21-carboxylic acid deriv.; Aldona ethyl enol ether | C24H34O3 | 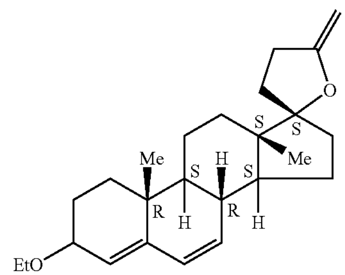 |
| 6 | Androstenedione | Androst-4-ene-3,17-dione(8CI,9CI) | Δ4-Androstene-3,17-dione; 17-Ketotestosterone; 3,17-Dioxoandrost-4-ene; Androstenedione; Fecundin; SKF2170 | C19H26O2 | 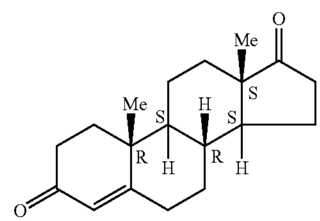 |
| 7 | 11α-Hydroxy-androstenedione | Androst-4-ene-3,17-dione, 11-hydroxy-,(11α)-(9CI) | Androst-4-ene-3,17-dione, 11α-hydroxy-(8CI); 11α-Hydroxyandrostendione; 11α-Hydroxyandrostenedione | C19H26O3 | 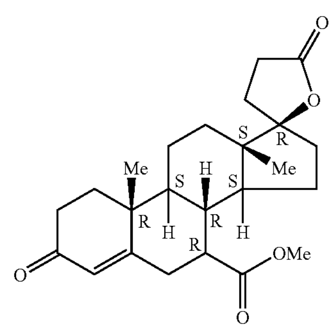 |
| 8 | Mexrenone | Pregn-4-ene-7,21-dicarboxylic acid, 17-hydroxy-3-oxo-, γ-lactone, methyl ester, (7α,17α)-(9CI) | Spiro[17H-cyclopenta[a]phenanthrene-17,2'(5'H)-furan], pregn-4-ene-7,21-dicarboxylic acid deriv.; Mexrenone; SC25152; ZK32055 | C24H32O5 | 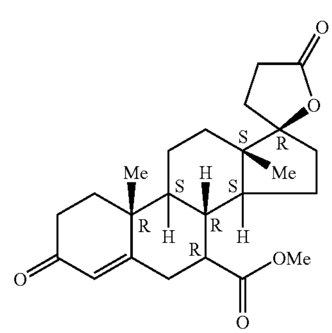 |

| # | Name | CA Index Name: | Other Names | Formula | Structure |
|---|------|----------------|-------------|---------|-----------|
| 9 | 11β-Hydroxymexrenone | Pregn-4-ene-7,21-dicarboxylic acid, 11,17-dihydroxy-3-oxo-, γ-lactone, methyl ester, (7α,11β,17α)-(9CI) | 11β-Hydroxymexrenone | C24H32O6 | 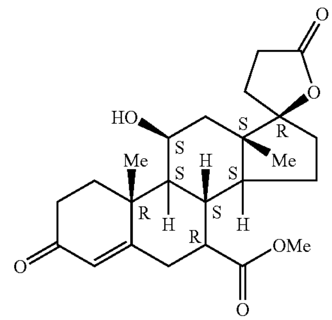 |
| 10 | 12β-Hydroxymexrenone | Pregn-4-ene-7,21-dicarboxylic acid, 12,17-dihydroxy-3-oxo-, γ-lactone, methyl ester, (7α,12β,17α)-(9CI) | 12β-Hydroxymexrenone | C24H32O6 | 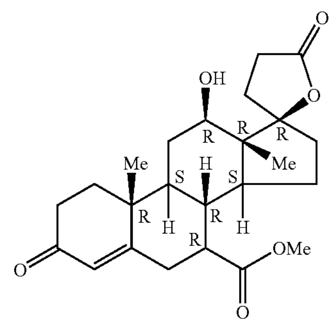 |
| 11 | 9α-Hydroxymexrenone | Pregn-4-ene-7,21-dicarboxylic acid, 9,17-dihydroxy-3-oxo-, 21,17-lactone, 7-methyl ester, (7α,17α)-(9CI) | 9α-Hydroxymexrenone | C24H32O6 | 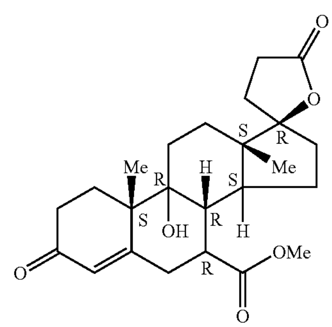 |
| 12 | 6β-Hydroxymexrenone | Pregn-4-ene-7,21-dicarboxylic acid, 6,17-dihydroxy-3-oxo-, γ-lactone, methyl ester, (6β,7α,17α)-(9CI) | Spiro[17H-cyclopenta[a]phenanthrene-17,2'(3'H)-furan], pregn-4-ene-7,21-dicarboxylic acid deriv.; 6β-Hydroxymexrenone | C24H32O6 | 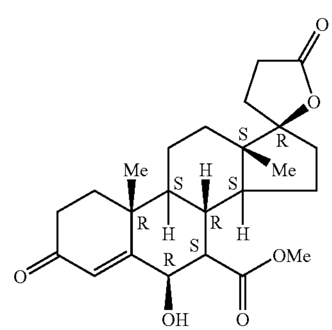 |
| 13 | Progesterone | Pregn-4-ene-3,20-dione (9CI) | Progesterone (8CI); Δ4-Pregnene-3,20-dione; and >70 other names | C21H30O2 | 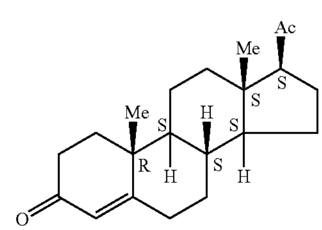 |

| # | Name | CA Index Name: | Other Names | Formula | Structure |
|---|------|----------------|-------------|---------|-----------|
| 14 | Estr-4-ene-3,17-dione | Estr-4-ene-3,17-dione (6CI, 8CI, 9CI) | (+)-19-Norandrost-4-ene-3,17-dione;Δ4-Estrene-3,17-dione; 19-Norandrost-4-ene-3,17-dione | $C_{18}H_{24}O_2$ | (structure shown) |
| 15 | delta 1,4-androstadiene-3,17-dione(ADD) | Androsta-1,4-diene-3,17-dione(7CI, 8CI, 9CI) | Δ1,4-Androstadiene-3,17-dione; 1-Dehydroandrostenedione; Androstadienedione; Androstane-1,4-diene-3,17-dione | $C_{19}H_{24}O_2$ | (structure shown) |
| 16 | 11α-Hydroxyandrosta-1,4-diene-3,17-dione (11 alpha hydroxy ADD) | Androsta-1,4-diene-3,17-dione, 11-hydroxy-, (11α)-(9CI) | Androsta-1,4-diene-3,17-dione, 11α-hydroxy-(6CI, 7CI, 8CI); 11α-Hydroxyandrosta-1,4-diene-3,17-dione; Kurchinin | $C_{19}H_{24}O_3$ | (structure shown) |
| 17 | aldona | | | | Compound 5 (aldonaethyl enol ether) with O= in place of EtO— at position 3 |
| 18 | mexrenone 6,7-bislactone | | | | Compound 12 with cyclic bis-lactone ring (—O—C=O—) formed between carbons at positions 6 and 7 (See U.S. Pat. No. 5,981,744 for discussion of similar lactone rings) |
| 19 | 11 alpha hydroxy mexrenone 6,7-bislactone | | | | 11 alpha hydroxy version of Compound 18 |
| 20 | mexrenone 7,9-bislactone | | | | Compound 11 with cyclic bis-lactone ring (—O—C=O—) formed between carbons at positions 7 and 9 (See U.S. Pat. No. 5,981,744 for discussion of similar lactone rings) |
| 21 | 11 alpha hydroxy mexrenone 7,9-bislactone | | | | 11 alpha hydroxy version of Compound 20 |

FIG. 1—Nucleotide and protein sequence of *Aspergillus ochraceus* 11 alpha hydroxylase The nucleotide and protein sequences of *Aspergillus ochraceus* 11 alpha hydroxylase (SEQ ID NO: 1, SEQ ID NO: 2, respectively) are displayed.

FIG. 2—Nucleotide and protein sequence of human oxidoreductase

The nucleotide and protein sequences of human oxidoreductase (SEQ ID NO: 3, SEQ ID NO: 4, respectively) are displayed. The predicted amino acid sequence of human oxidoreductase independently cloned from a cDNA library prepared by RT-PCR using the RNA from a human HepG2 cells as a template, as disclosed in this specification, matches that previous reported by three different laboratories. The GenBank accession numbers for these loci include A60557 (NADPH—ferrihemoprotein reductase (EC 1.6.2.4)—human); AAG09798 (NADPH-cytochrome P450 reductase [*Homo sapiens*]), and P16435 (NADPH-CYTOCHROME P450 REDUCTASE (CPR) (P450R)).

The amino acid sequence of AAB21814 (cytochrome P450 reductase {EC 1.6.2.41} [human, placenta, Peptide Partial, 676 aa]), differs from human oxidoreductase A60557 and P16435 at 4 residues: A→V at 500, F→L at 518, V→W at 537, and A→H at 538. The initial methionine is also missing from AAB21814. The cognate nucleic acid for AA21814 (S90469 |cytochrome P450 reductase [human, placenta, mRNA Partial, 2403 nt]) lacks the ATG codon for the initial methionine and includes a C→T change at 1496, a C→A, change at 1551, and a frameshift due to a missing G at 1605 which is resolved by the addition of a T at 1616.

References for these loci are as follows: A60557 [Yamano, S., Aoyama, T., McBride, O. W., Hardwick, J. P., Gelboin, H. V. and Gonzalez, F. J. Human NADPH-P450 oxidoreductase: complementary DNA cloning, sequence and vaccinia virus-mediated expression and localization of the CYPOR gene to chromosome 7 Mol. Pharmacol. 36 (1), 83-88 (1989)]; AAG09798 [Czerwinski, M., Sahni, M., Madan, A. and Parkinson, A. Polymorphism of human CYPOR: Expression of new allele. Unpublished, Direct Submission], and P16435 [Haniu, M., McManus, M. E., Birkett, D. J., Lee, T. D. and Shively, J. E. Structural and functional analysis of NADPH-cytochrome P-450 reductase from human liver: complete sequence of human enzyme and NADPH-binding sites. Biochemistry 28 (21), 8639-8645 (1989)]; AAB21814 [Shephard, E. A., Palmer, C. N., Segall, H. J. and Phillips, I. R. Quantification of cytochrome P450 reductase gene expression in human tissues. Arch. Biochem. Biophys. 294 (1), 168-172 (1992)]; S90469 [Shephard, E. A., Palmer, C. N., Segall, H. J. and Phillips, I. R. Quantification of cytochrome P450 reductase gene expression in human tissues. Arch. Biochem. Biophys. 294 (1), 168-172 (1992)].

FIG. 3—Nucleotide and protein sequence of *Aspergillus ochraceus* oxidoreductase The nucleotide and protein sequences of *Aspergillus ochraceus* 11 oxidoreductase (SEQ ID NO: 5, SEQ ID NO: 6, respectively) are displayed.

FIG. 4—Amino acid homology alignment of *A. ochraceus* 11 alpha hydroxylase with the top 10 BLAST hits from GenBank

*Aspergillus ochraceus* steroid 11 alpha hydroxylase (SEQ ID NO: 02), cloned into plasmid pMON45624 (SEQ ID NO: 01), was aligned with related enzymes found in GenBank using the BLASTP program that implements a heuristic matching algorithm (Altschul et al., *J Mol Biol* October 5;215(3):403-10, 1990). The GenBank accession numbers (its probable function, [genus and species]) for the top 10 matches are as follows: CAA75565 (cytochrome P450 monooxygenase [*Gibberella fujikuroi*]; CAB91316 (probable cytochrome P450 monooxygenase (lovA) [*Neurospora crassa*]); CAB56503 (cytochrome P450 [*Catharanthus roseus*]); AAB94588 (CYP71D10p [*Glycine max*]); CAA75566 (cytochrome P450 monooxygenase [*Gibberella fujikuroi*]); AAD34552 (cytochrome P450 monooxygenase [*Aspergillus terreus*]); CAA75567 (cytochrome P450 monooxygenase [*Gibberella fujikuroi*]); CAA76703 (cytochrome P450 [*Gibberella fujikuroi*]); CAA57874 (unnamed protein product [*Fusarium oxysporum*]); CAA91268 (similar to cytochrome P450-cDNA EST yk423b11.3 comes from this gene [*Caenorhabditis elegans*]).

References for these loci are as follows: CAA75565 [Tudzynski, B. and Holter, K., Gibberellin biosynthetic pathway in *Gibberella fujikuroi*: evidence for a gene cluster. *Fungal Genet. Biol.* 25 (3), 157-170 (1998)]; CAB91316 [Schulte, U., Aign, V., Hoheisel, J., Brandt, P., Fartmann, B., Holland, R., Nyakatura, G., Mewes, H. W. and Mannhaupt, G., Unpublished]; CAB56503 [Schroeder, G., Unterbusch, E., Kaltenbach, M., Schmidt, J., Strack, D. and Schroeder, J. Light-induced cytochrome P450-dependent enzyme in indole alkaloid biosynthesis: tabersonine 16-hydroxylase *FEBS Lett.* 458, 97-102 (1999)]; AAB94588 [Siminszky, B., Corbin, F. T., Ward, E. R., Fleischmann, T. J. and Dewey, R. E. Expression of a soybean cytochrome P450 monooxygenase cDNA in yeast and tobacco enhances the metabolism of phenylurea herbicides. *Proc. Natl. Acad. Sci. U.S.A.* 96 (4), 1750-1755 (1999)]; CAA75566 [Tudzynski, B. and Holter, K. Gibberellin biosynthetic pathway in *Gibberella fujikuroi*: evidence for a gene cluster. *Fungal Genet. Biol.* 25 (3), 157-170 (1998)]; AAD34552 [Kennedy, J., Auclair, K., Kendrew, S. G., Park, C., Vederas, J. C. and Hutchinson, C. R. Accessory Proteins Modulate Polyketide Synthase Activity During Lovastatin Biosynthesis. *Science* (1999) In press]; CAA75567 [Tudzynski, B. and Holter, K. Gibberellin biosynthetic pathway in *Gibberella fujikuroi*: evidence for a gene cluster. *Fungal Genet. Biol.* 25 (3), 157-170 (1998)]; CAA76703 [Tudzynski, B. and Hoelter, K. Characterization of P450 monooxygenase genes from *Gibberella fujikuroi*. Unpublished]; CAA57874 [Mouyna, I. and Brygoo, Y. Disruption of a *Fusarium oxysporum* f.sp. *elaeidis* cytochrome P450 gene by a repetitive sequence. Unpublished]; and CAA91268 [No Authors. Genome sequence of the nematode *C. elegans*: a platform for investigating biology. The *C. elegans* Sequencing Consortium. Science 282 (5396), 2012-2018 (1998) [Published errata appear in *Science* Jan. 1, 1999;283(5398):35 and Mar. 26, 1999;283 (5410):2103 and Sep. 3, 1999;285(5433): 1493]]].

FIG. 5—Phylogenetic tree showing the relatedness of *Aspergillus ochraceus* 11 alpha hydroxylase to the top 10 BLAST hits from GenBank A phylogenetic tree displaying the genetic relatedness of *Aspergillus ochraceus* steroid 11 alpha hydroxylase, cloned into plasmid pMON45624, was aligned with related enzymes found in GenBank. BLAST was used to find the related enzymes within GenBank, and ClustalW was used generate the multiple sequence alignment and phylogenetic tree depicted in this figure. Descriptions of the GenBank accession numbers used as labels in the figure are the same as that described above for the legend to FIG. 4.

FIG. 6—Percent homology between *Aspergillus ochraceus* 11 alpha hydroxylase and the top 10 BLAST hits from GenBank The percent homology between *Aspergillus ochraceus* steroid 11. alpha hydroxylase and the top 10 enzymes found in GenBank using BLAST was calculated using CLUSTAL (Thompson et al., *Comput. Appl. Biosci.* 10:19-29, 1994).

FIG. 7—Amino acid homology alignment of *Aspergillus ochraceus* and human oxidoreductase to NADPH cytochrome P450 reductases from *A. niger*, mouse, and *S. cerevisiae*

The amino acid sequences of *Aspergillus ochraceus* steroid oxidoreductase (SEQ ID NO: 06) cloned into plasmid pMON45632 (SEQ ID NO: 05), and human oxidoreductase (SEQ ID NO: 03), cloned into plasmid pMON45605 (SEQ ID NO: 04) were aligned with related enzymes from *A. niger*, mouse, and *S. cervisiase*, as described above. The GenBank accession numbers (probable function, [genus and species]) are as follows: BAA02936 (NADPH-cytochrome P450 reductase precursor [*Saccharomyces cerevisiae*]); CAA81550 NADPH cytochrome P450 oxidoreductase [*Aspergillus niger*]; P16435 (NADPH-CYTOCHROME P450 REDUCTASE (CPR) (P450R) [human]); BAA04496 (NADPH-cytochrome P450 oxidoreductase [*Mus musculus*]).

References for these loci are as follows: BAA02936 [Yabusaki, Y., Murakami, H. and Ohkawa, H. Primary structure of *Saccharomyces cerevisiae* NADPH-cytochrome P450 reductase deduced from nucleotide sequence of its cloned gene. *J. Biochem.* 103 (6), 1004-1010 (1988)]; CAA81550 [van den Brink, J., van Zeijl, C., van den Hondel, C. and van Gorcom, R. Cloning and characterization of the NADPH cytochrome P450 oxidoreductase (cprA) gene of *Aspergillus niger*. Unpublished]; P16435 [Haniu, M., McManus, M. E., Birkett, D. J., Lee, T. D. and Shively, J. E. Structural and functional analysis of NADPH-cytochrome P-450 reductase from human liver: complete sequence of human enzyme and NADPH-binding sites *Biochemistry* 28 (21), 8639-8645 (1989)]; BAA04496 [Ohgiya, S., Shinriki, N., Kamataki, T. and Ishizaki, K. Mouse NADPH-cytochrome P-450 oxidoreductase: molecular cloning and functional expression in yeast. *Biochim. Biophys. Acta* 1186 (1-2), 137-141 (1994)].

FIG. 8—Amino acid homology alignment of *A. ochraceus* oxidoreductase to NADPH cytochrome P450 reductases from *A. niger*, mouse, and *S. cerevisiae*

The amino acid sequence of *Aspergillus ochraceus* steroid oxidoreductase (SEQ ID NO: 06) cloned into plasmid pMON45632 (SEQ ID NO: 05), was aligned with related fungal enzymes from *A. niger* and *S. cervisiae*, as described above. Descriptions of the GenBank accession numbers used as labels in the figure are the same as that described above for the legend to FIG. 7, above.

FIG. 9—Phylogenetic tree showing the relatedness of *Aspergillus ochraceus* and human oxidoreductase to reductases from *A. niger*, yeast, and mouse.

A phylogenetic tree displaying the genetic relatedness of *Aspergillus ochraceus* oxidoreductase (SEQ ID NO: 06), cloned into plasmid pMON45632 (SEQ ID NO: 05), was aligned with related enzymes. BLAST was used to find the related enzymes within GenBank, and ClustalW was used generate the multiple sequence alignment and phylogenetic tree depicted in this figure. Descriptions of the GenBank accession numbers used as labels in the figure are the same as that described above for the legend to FIG. 7, above.

FIG. 10—Percent identity between *Aspergillus ochraceus* oxidoreductase and reductases from *A. niger*, yeast, and mouse.

The percent identity between *Aspergillus ochraceus* oxidoreductase and the oxidoreductases from *A. niger*, yeast, and mouse was calculated using Clustal W and Boxshade.

FIG. 11—Alignment of human oxidoreductase with top 4 hits from SwissProt

The amino acid sequences of human steroid oxidoreductase (SEQ ID NO: 04), cloned into plasmid pMON45605 (SEQ ID NO: 03), which corresponds to the amino acid sequence of the corrected sequence reported for P16435 below, was aligned with the top 4 hits from the SWISSPROT protein sequence database, as described above. The SWISSPROT accession numbers {locus} [common name] and species]) probable function) are as follows: P16435 {NCPR_HUMAN} [human] NADPH-CYTOCHROME P450 REDUCTASE; P00389 {NCPR_RABIT} [rabbit] NADPH-CYTOCHROME P450 REDUCTASE; P00388 {NCPR_RAT} [rat] NADPH-CYTOCHROME P450 REDUCTASE; P37040 {NCPR_MOUSE} [mouse] NADPH-CYTOCHROME P450 REDUCTASE; P04175 {NCPR_PIG} [pig] (NADPH-CYTOCHROME P450 REDUCTASE.

References for these loci are as follows: P16435 [Haniu, M., McManus, M. E., Birkett, D. J., Lee, T. D. and Shively, J. E. Structural and functional analysis of NADPH-cytochrome P-450 reductase from human liver: complete sequence of human enzyme and NADPH-binding sites. *Biochemistry* 28 (21), 8639-8645 (1989)]; P00389 [Katagiri, M., Murakami, H., Yabusaki, Y., Sugiyama, T., Okamoto, M., Yamano, T. and Ohkawa, H. Molecular cloning and sequence analysis of full-length cDNA for rabbit liver NADPH-cytochrome P-450 reductase mRNA. *J. Biochem.* 100 (4), 945-954 (1986)]; P00388 [Porter, T. D. and Kasper, C. B. Coding nucleotide sequence of rat NADPH-cytochrome P-450 oxidoreductase cDNA and identification of flavin-binding domains. *Proc. Natl. Acad. Sci. U.S.A.* 82 (4), 973-977 (1985)]; P37040 [Ohgiya, S., Shinriki, N., Kamataki, T. and Ishizaki, K. Mouse NADPH-cytochrome P-450 oxidoreductase: molecular cloning and functional expression in yeast. *Biochim. Biophys. Acta* 1186 (1-2), 137-141 (1994)]; P04175 [Haniu, M., Iyanagi, T., Miller, P., Lee, T. D. and Shively, J. E. Complete amino acid sequence of NADPH-cytochrome P-450 reductase from porcine hepatic microsomes. *Biochemistry* 25 (24), 7906-7911 (1986)].

FIG. 12—Phylogenetic tree showing the relatedness of human oxidoreductases with top 4 hits from SwissProt A phylogenetic tree displaying the genetic relatedness of human oxidoreductase (SEQ ID NO: 04), cloned into plasmid pMON45604 (SEQ ID NO: 03), was aligned with related enzymes found in SWISSPROT. BLAST was used to find the related enzymes within SWISSPROT, and ClustalW was used generate the multiple sequence alignment and phylogenetic tree depicted in this figure. Descriptions of the SWISPROT accession numbers used as labels in the figure are the same as that described above for the legend to FIG. 11, above.

FIG. 13—Percent identity between human oxidoreductase and top 4 hits from SwissProt The percent identity between human oxidoreductase and the top 4 hits found in SWISSPROT was calculated using Clustal W and Boxshade.

FIG. 14: Expression of *Aspergillus ochraceus* 11 alpha hydroxylase in transfected Sf9 insect cells Baculovirus-infected insect cells expressing *Aspergillus ochraceus* 11 alpha hydroxylase were harvested at 25 and 48 hours post infection and microsomal membrane fractions were prepared and separated by SDS-polyacrylamide gel electrophoresis. The proteins in the gel were electrophoretically transferred to 0.2 um nitrocellulose membrane (Schleicher & Schuell Grimsehlstrasse 23 37574 Einbeck Germany) and probed with antibodies GN-1187 and GN-1188 prepared from peptide 11aOH peptide 2 CRQILTPYIHKRKSLKGTTD (SEQ ID NO: 24).

FIG. 15: Expression of *Aspergillus ochraceus* P450 oxidoreductase in transfected Sf9 insect cells Baculovirus-infected insect cells expressing *Aspergillus ochraceus* 11 oxidoreductase were harvested at 25 and 48 hours post infection and microsomal membrane fractions were prepared and separated by SDS-polyacrylamide gel electrophoresis. The proteins in the gel were electrophoretically transferred to 0.2 um nitrocellulose membrane (Schleicher & Schuell Grimsehlstrasse 23 37574 Einbeck Germany) and probed with antibodies GN-2023 and GN-12024 prepared from oxr peptide 1 CTYWAVAKDPYASAGPAMNG (SEQ ID NO: 26).

FIG. 16—Conversion of androstenedione to 11 alpha hydroxy androstenedione monitored by HPLC Microsomal and mitochondrial subcellular fractions were prepared from insect cells co-infected with recombinant baculoviruses expressing recombinant *Aspergillus ochraceus* 11 alpha hydroxylase and human oxidoreductase cloned from HepG2 cell RNA. The subcellular fractions were incubated with 250 µM androstenedione (AD) in the presence of an NADPH-generating system for 120 minutes, and the resulting products were separated by HPLC and monitored by ultraviolet detection at 247 nm. Hydroxlase activity was found in the microsomal fraction, as expected, but also appeared in the mitochondrial fraction. These results suggest that the 11 alpha hydroxylase may have a tendency to stick to membranes in disrupted cells, or that the separation of the subcellular fractions in this experiment was insufficient. Panel A illustrates a reaction carried out using enzyme prepared from a mitochondrial fraction. The peak in panel A that elutes after AD appears to be testosterone. When a microsomal fraction was used, almost as much AD was converted to 11 alpha hydroxy AD, but relatively more testosterone was also produced. Panel B illustrates the same reaction carried out for 120 minutes without a source of enzyme. Panel C illustrates an HPLC tracing with 11α-hydroxyandrostenedione standard added to incubation buffer.

DETAILED DESCRIPTION OF THE INVENTION

The present invention encompasses enzymes that facilitate the biosynthesis of steroid molecules, particularly enzymes possessing cytochrome P450 or oxidoreductase activities. The present invention is directed, in part, to the isolation of a nucleic acid encoding *Aspergillus ochraceus* 11 alpha hydroxylase, which exhibits sequence homology to the highly conserved residues that correspond to cytochrome P450 enzymes. It also directed to the isolation of nucleic acids encoding human and *Aspergillus ochraceus* oxidoreductase. Biological activities of the cloned hydroxylases and oxidoreductases of the present invention can be determined by a variety of assays, including incubation of steroid substrates in the presence of microsomes prepared from recombinant baculovirus-infected insect cells and monitoring the conversion to their 11 alpha hydroxy-counterparts by high pressure liquid chromatography (HPLC). The present invention, comprising novel 11 alpha hydroxylase and oxidoreductase nucleic acids, proteins, peptides, homologues, and fragments of either, provides new and advantageous methods to convert steroid intermediates to their 11 alpha hydroxy counterparts.

The present invention also includes the DNA sequences which code for the 11 alpha hydroxylases and oxidoreductases, DNA sequences which are substantially similar and perform substantially the same function, and DNA sequences which differ from the DNAs encoding the hydroxylases and oxidoreductases of the invention only due to the degeneracy of the genetic code. Also included in the present invention are the oligonucleotide intermediates used to construct mutated versions of these DNAs and the polypeptides encoded by these oligonucleotides and mutant DNAs.

The present invention also includes antibodies which bind specifically to *A. ochraceus* 11 alpha hydroxylase or *A. ochraceus* oxidoreductase, including anti-peptide antibodies, methods of using these anti-peptide antibodies to purify these and other related polypeptides, methods of using the purified polypeptides to generate polyclonal or monoclonal antibodies to the full-length polypeptides, and methods of using antibodies to the full-length polypeptides to assess the presence of the polypeptides in recombinant and non-recombinant host cells. The antibodies can be used to identify related polypeptides in any of a variety of host organisms that possess the biological activities associated with these polypeptides.

Among the preferred organisms that can be used in this hydroxylation step are *Aspergillus ochraceus* NRRL 405, *Aspergillus ochraceus* ATCC 18500, *Aspergillus niger* ATCC 16888 and ATCC 26693, *Aspergillus nidulans* ATCC 11267, *Rhizopus oryzae* ATCC 11145, *Rhizopus stolonifer* ATCC 6227b, *Streptomyces fradiae* ATCC 10745, *Bacillus megaterium* ATCC 14945, *Pseudomonas cruciviae* ATCC 13262, and *Trichothecium roseum* ATCC 12543. Other preferred organisms include *Fusarium oxysporum f.* sp. *cepae* ATCC 11171 and *Rhizopus arrhizus* ATCC 11145.

Other organisms that have exhibited activity for this reaction include *Absidia coerula* ATCC 6647, *Absidia glauca* ATCC 22752, *Actinomucor elegans* ATCC 6476, *Aspergillus flavipes* ATCC 1030, *Aspergillus fumigatus* ATCC 26934, *Beauveria bassiana* ATCC 7159 and ATCC 13144, *Botryosphaeria obtusa* IMI 038560, *Calonectria decora* ATCC 14767, *Chaetomium cochliodes* ATCC 10195, *Corynespora cassiicola* ATCC 16718, *Cunninghamella blakesleeana* ATCC 8688a, *Cunninghamella echinulata* ATCC 3655, *Cunninghamella elegans* ATCC 9245, *Curvularia clavata* ATCC 22921, *Curvularia lunata* ACTT 12071, *Cylindrocarpon radicicola* ATCC 1011, *Epicoccum humicola* ATCC 12722, *Gongronella butleri* ATCC 22822, *Hypomyces chrysospermus, Mortierella isabellina* ATCC 42613, *Mucor mucedo* ATCC 4605, *Mucor griseocyanus* ATCC 1207A, *Myrothecium verrucaria* ATCC 9095, *Nocardia corallina, Paecilomyces carneus* ATCC 46579, *Penicillum patulum* ATCC 24550, *Pithomyces atroolivaceus* IFO 6651, *Pithomyces cynodontis* ATCC 26150, *Pycnosporium* sp. ATCC 12231, *Saccharopolyspora erythrae* ATCC 11635, *Sepedonium chrysospermum* ATCC 13378, *Stachylidium bicolor* ATCC 12672, *Streptomyces hyqroscopicus* ATCC 27438, *Streptomyces purpurascens* ATCC 25489, *Syncephalastrum racemosum* ATCC 18192, *Thamnostylum piriforme* ATCC 8992, *Thielavia terricola* ATCC 13807, and *Verticillium theobromae* ATCC 12474.

Additional organisms that may be expected to show activity for the 11α hydroxylation include *Cephalosporium aphidicola* (*Phytochemistry* (1996), 42(2), 411-415), *Cochliobolus lunatas* (*J. Biotechnol.* (1995), 42(2), 145-150), *Tieghemella orchidis* (*Khim.-Farm.Zh.* (1986), 20(7), 871-876), *Tieghemella hyalospora* [*Khim.-Farm.Zh.* (1986), 20(7), 871-876), *Monosporium olivaceum* (*Acta Microbiol. Pol.*, Ser. B. (1973), 5(2), 103-110), *Aspergillus ustus* (*Acta Microbiol. Pol.*, Ser. B. (1973), 5(2), 103-110), *Fusarium graminearum* (*Acta Microbiol. Pol.*, Ser. B. (1973), 5(2), 103-110), *Verticillium glaucum* (*Acta Microbiol. Pol.*, Ser. B. (1973), 5(2), 103-110), and *Rhizopus nigricans* (*J. Steroid Biochem.* (1987), 28(2), 197-201).

FIG. 1 sets forth the nucleotide and protein sequence of *Aspergillus ochraceus* 11 alpha hydroxylase (SEQ ID NO: 1, SEQ ID NO: 2, respectively). FIG. 2 sets forth the nucleotide and protein sequence of human oxidoreductase (SEQ ID NO: 3, SEQ ID NO: 4, respectively). FIG. 3 sets forth the nucleotide and protein sequence of *Aspergillus ochraceus* oxidoreductase (SEQ ID NO: 5, SEQ ID NO: 6, respectively).

FIG. 4 sets forth an amino acid homology alignment of *A. ochraceus* 11 alpha hydroxylase cloned in pMON45624 and aligned with related enzymes found in GenBank using BLAST. FIG. 5 is a phylogenetic tree showing the this relationship graphically. FIG. 6 shows the percent homology between *Aspergillus ochraceus* steroid 11 alpha hydroxylase and the top 10 enzymes found in GenBank using BLAST, calculated using Clustal W and Boxshade.

FIG. 7 sets forth the amino acid homology of *Aspergillus ochraceus* and human oxidoreductase to NADPH cytochrome P450 reductases from *A. niger,* mouse, and *S. cerevisiae* (yeast). FIG. 8 sets forth the amino acid alignment for *A. ochraceus, A. niger,* and *S. cerevisiae* oxidoreductases. FIG. 9 is a phylogenetic tree showing the relatedness of *Aspergillus ochraceus* and human oxidoreductase to reductases from *A. niger,* yeast, and mouse. FIG. 10 shows the percent homology between *Aspergillus ochraceus* steroid 11 alpha hydroxylase and the oxidoreductases from *A. niger,* yeast, and mouse, calculated using Clustal W and Boxshade.

FIG. 11—Alignment of human oxidoreductase with top 4 hits from SwissProt. FIG. 12 sets forth a phylogenetic tree displaying the genetic relatedness of human oxidoreductase, to these hits. FIG. 13 shows the percent identity between human oxidoreductase and top 4 hits from SwissProt.

FIG. 14 sets forth an immunoblot illustrating expression of *Aspergillus ochraceus* P450 11 alpha hydroxylase in baculovirus-infected insect cells harvested at 25 and 48 hours post infection. The nitrocellulose membrane was probed with a 1:1 mixture of antibodies prepared from two rabbits immunized with a conjugated synthetic peptide, 11aOH peptide 2 (SEQ ID NO 24).

FIG. 15 sets forth an immunoblot illustrating expression of *Aspergillus ochraceus* P450 oxidoreductase in baculovirus-infected insect cells harvested at 25 and 48 hours post infection. The nitrocellulose membrane was probed with a 1:1 mixture of antibodies prepared two rabbits immunized with a conjugated synthetic peptide, oxr peptide 1 (SEQ ID NO 26).

FIG. 16 sets forth an HPLC tracing illustrating the conversion of androstenedione (AD) to its 11 alpha hydroxy counterpart after incubating AD with subcellular fractions prepared from baculovirus-infected insect cells expressing *Aspergillus ochraceus* 11 alpha hydroxylase and human oxidoreductase.

Cloning Techniques

Genetic engineering techniques now standard in the art (U.S. Pat. No. 4,935,233 and Sambrook et al., "Molecular Cloning A Laboratory Manual", Cold Spring Harbor Laboratory, 1989) may be used in the construction of the DNA sequences of the present invention. One such method is cassette mutagenesis (Wells et al., *Gene* 34:315-323, 1985) in which a portion of the coding sequence in a plasmid is replaced with synthetic oligonucleotides that encode the desired amino acid substitutions in a portion of the gene between two restriction sites.

Pairs of complementary synthetic oligonucleotides encoding the desired gene can be made and annealed to each other. The DNA sequence of the oligonucleotide would encode sequence for amino acids of desired gene with the exception of those substituted and/or deleted from the sequence.

Plasmid DNA can be treated with the chosen restriction endonucleases then ligated to the annealed oligonucleotides. The ligated mixtures can be used to transform competent *E. coli* cells which will confer resistance to an appropriate antibiotic. Single colonies can be picked and the plasmid DNA examined by restriction analysis or by DNA sequencing to identify plasmids with the desired genes.

Cloning of DNA sequences encoding novel proteins and fusion proteins may be accomplished by the use of intermediate vectors. Linkers and adapters can be used to join DNA sequences, and to replace lost sequences, where a restriction site is internal to the region of interest. DNA encoding a single polypeptide or a fusion protein (comprising a first polypeptide, a peptide linker, and a second polypeptide) is inserted into a suitable expression vector which is then transformed or transfected into appropriate bacterial, fungal, insect, or mammalian host cells. The transformed organism or host cell line is grown and the recombinant protein isolated by standard techniques. Recombinant fusion proteins have all or a portion of a first protein joined by a linker region to a all or a portion of second protein.

Hybridization

Nucleic acid molecules and fragment nucleic acid molecules encoding 11 alpha hydroxylases or oxidoreductases can specifically hybridize with other nucleic acid molecules. Two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule, if they exhibit complete complementarity. Molecules exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook, et al., *Molecular Cloning*, A Laboratory Manual, 2nd Ed., Cold Spring Harbor Press, Cold Spring Harbor, N.Y. (1989), and by Haymes, et al. *Nucleic Acid Hybridization, A Practical Approach*, IRL Press, Washington, D.C., 1985). Departures from complete complementarity are therefore permissible, as long as such departures do not completely preclude the capacity of the molecules to form a double-stranded structure.

Appropriate stringency conditions which promote DNA hybridization are well known to those skilled in the art, or can be found in *Current Protocols in Molecular Biology*, John Wiley & Sons, N.Y., 6.3.1-6.3.6, (1989). Basic conditions would include, for example, 6× sodium saline citrate (SSC) at about 45° C., followed by a wash of 2×SSC at 50° C. Stringency can be varied, for example, by altering the salt concentration in the wash step from about 2×SSC at 50° C. (moderately low stringency) to about 0.2×SSC at 50° C. (high stringency). Stringency can also be altered by changing the temperature in the wash step, from room temperature, about 22° C. (low stringency conditions), to about 65° C. (high stringency conditions). Both temperature and salt may be varied, or either the temperature or the salt concentration may be held constant while the other variable is changed.

Expression Vectors

Another aspect of the present invention includes plasmid DNA vectors for use in the expression of these novel hydroxylases and oxidoreductases. These vectors contain the novel DNA sequences described above which code for the novel polypeptides of the invention. Appropriate vectors which can transform microorganisms or cell lines capable of expressing the hydroxylases and oxidoreductases include expression vectors comprising nucleotide sequences coding for the hydroxylases and oxidoreductases joined to transcriptional and translational regulatory sequences which are selected according to the host cells used.

Vectors incorporating modified sequences as described above are included in the present invention and are useful in the production of the hydroxylases and oxidoreductases. The vector employed in the method also contains selected regulatory sequences in operative association with the DNA coding sequences of the invention and which are capable of directing the replication and expression thereof in selected host cells.

Methods for producing the hydroxylases and oxidoreductases is another aspect of the present invention. The method of the present invention involves culturing suitable cells or cell lines, which has been transformed with a vector containing a DNA sequence encoding novel hydroxylases and oxidoreductases. Suitable cells or cell lines may be bacterial cells. For example, various strains of *E. coli* are well-known as host cells in the field of biotechnology. Examples of such strains include *E. coli* strains DH5 alpha, DH10B and MON105 (Obukowicz et al., *Applied Environmental Microbiology* 58:1511-1523, 1992). Also included in the present invention is the expression of the hydroxylases and oxidoreductases utilizing a chromosomal expression vector for *E. coli* based on the bacteriophage Mu (Weinberg et al., *Gene* 126:25-33, 1993). Various other strains of bacteria, including the Enteric bacteria (e.g., *Salmonella* sp.) and *B. subtilis*, may also be employed in this method.

When expressed in the *E. coli* cytoplasm, the gene encoding the proteins of the present invention may also be constructed such that at the 5' end of the gene codons are added to encode $Met^{-2}$-$Ala^{-1}$, $Met^{-2}$-$Ser^{-1}$, $Met^{-2}$-$Cys^{-1}$, or $Met^{-1}$ at the N-terminus of the protein. The N termini of proteins made in the cytoplasm of *E. coli* are affected by post-translational processing by methionine aminopeptidase (Ben Bassat et al., *J. Bacteriol.* 169:751-757, 1987), and possibly by other peptidases, so that upon expression the methionine is cleaved off the N-terminus. The proteins of the present invention may include polypeptides having $Met^{-1}_{-2}$, $Ala^{-1}$, $Ser^{-1}$, $Cys^{-1}$, $Met^{-2}$-$Ala^{-1}$, $Met^{-2}$-$Ser^{-1}$, or $Met^{-2}$-$Cys^{-1}$ at the N-terminus. These mutant proteins may also be expressed in *E. coli* by fusing a secretion signal peptide to the N-terminus. This signal peptide is cleaved from the polypeptide as part of the secretion process.

Yeast

Many strains of yeast cells known to those skilled in the art are also available as host cells for expression of the polypeptides of the present invention. Under another embodiment, the protein or fragment thereof of the present invention is expressed in a yeast cell, preferably *Saccharomyces cerevisiae*. The proteins or fragments thereof of the present invention can be expressed in *S. cerevisiae* by fusing it to the N-terminus of the URA3, CYC1 or ARG3 genes (Guarente and Ptashne, *Proc. Natl. Acad. Sci.* (U.S.A.) 78:2199-2203 (1981); Rose et al., *Proc. Natl. Acad. Sci.* (U.S.A.) 78:2460-2464 (1981); and Crabeel et al., *EMBO J.* 2:205-212 (1983)). Alternatively, proteins or fragments thereof of the present invention can be fused to either the PGK or TRP1 genes (Tuite et al., *EMBO J.* 1:603-608 (1982); and Dobson et al., *Nucleic Acids. Res.* 11:2287-2302 (1983)). More preferably, the protein or fragment thereof of the present invention is expressed as a mature protein (Hitzeman et al., *Nature* 293:717-722 (1981); Valenzuela et al., *Nature* 298:347-350 (1982); and Derynck et al., *Nucleic Acids Res.* 11:1819-1837 (1983)).

Native and engineered yeast promoters suitable for use in the present invention have been reviewed by Romanos et al., *Yeast* 8:423-488 (1992). Most preferably, the protein or fragment thereof of the present invention is secreted by the yeast cell (Blobel and Dobberstein, *J. Cell Biol.* 67:835-851 (1975); Kurjan and Herskowitz, *Cell* 30:933-943 (1982); Bostian et al., *Cell* 36:741-751 (1984); Rothman and Orci, *Nature* 355:409-415 (1992); Julius et al., *Cell* 32:839-852 (1983); and Julius et al., *Cell* 36:309-318 (1984)).

Mammalian

General methods for expression of foreign genes in mammalian cells have been reviewed (Kaufman, R. J., 1987, "Genetic Engineering, Principles and Methods", Vol. 9, J. K. Setlow, editor, Plenum Press, New York; Colosimo et al., *Biotechniques* 29:314-331, 2000). Recombinant proteins are generally targeted to their natural locations within the host cell (e.g., cytoplasm, nucleus, or various membrane compartments), or are secreted, if a signal peptide is present. An expression vector is constructed in which a strong promoter capable of functioning in mammalian cells drives transcription of a eukaryotic secretion signal peptide coding region, which is translationally joined to the coding region for the desired protein. For example, plasmids such as pcDNA I/Neo, pRc/RSV, and pRc/CMV (obtained from Invitrogen Corp., San Diego, Calif.) can be used. The eukaryotic secretion signal peptide coding region can be from the gene itself or it can be from another secreted mammalian protein (Bayne, M. L. et al., *Proc. Natl. Acad. Sci. USA* 84:2638-2642, 1987). After construction of the vector containing the gene, the vector DNA is transfected into mammalian cells such as the COS7, HeLa, BHK, Chinese hamster ovary (CHO), or mouse L lines. The cells can be cultured, for example, in DMEM media (JRH Scientific). The polypeptide secreted into the media can be recovered by standard biochemical approaches following transient expression for 24-72 hours after transfection of the cells or after establishment of stable cell lines following selection for antibiotic resistance. The selection of suitable mammalian host cells and methods for transformation, culture, amplification, screening and product production and purification are known in the art. See, e.g., Gething and Sambrook, *Nature*, 293:620-625, 1981, or alternatively, Kaufman et al, *Mol. Cell. Biol.*, 5(7):1750-1759, 1985) or Howley et al., and U.S. Pat. No. 4,419,446. Other suitable mammalian cell lines are the monkey COS-1 cell line and the CV-1 cell line.

Mammalian cells can also be used to express the nucleic acid molecules of the present invention. The nucleic acid molecules of the present invention can be cloned into a suitable retroviral vector (see, e.g., Dunbar et al., *Blood* 85:3048-3057 (1995); Baum et al., *J. Hematother.* 5:323-329 (1996); Bregni et al., *Blood* 80:1418-1422 (1992); Boris-Lawrie and Temin, *Curr. Opin. Genet. Dev.* 3:102-109 (1993); Boris-Lawrie and Temin, *Annal. New York Acad. Sci.* 716:59-71 (1994); Miller, *Current Top. Microbiol. Immunol.* 158:1-24 (1992)), adenovirus vector (Berkner, *BioTechniques* 6:616-629 (1988); Berkner, *Current Top. Microbiol. Immunol.* 158:39-66 (1992); Brody and Crystal, *Annal. New York Acad. Sci.* 716:90-103 (1994); Baldwin et al., *Gene Ther.* 4:1142-1149 (1997)), RSV, MuSV, SSV, MuLV (Baum et al., *J. Hematother.* 5: 323-329 (1996)), AAV (Chen et al., *Gene Ther.* 5:50-58 (1998); Hallek et al., *Cytokines Mol. Ther.* 2:69-79 (1996)), AEV, AMV, or CMV (Griffiths et al., *Biochem. J.* 241:313-324 (1987)).

Transformation and Transfection

In another aspect, the invention provides a transformed cell having a nucleic acid molecule which comprises an exogenous promoter region which functions in a cell to cause the production of an mRNA molecule which is linked to a structural nucleic acid molecule, wherein the structural nucleic acid molecule encodes an 11 alpha hydroxylase or oxidoreductase gene or fragment thereof. This nucleic acid molecule is linked to a 3' non-translated sequence that functions in a cell to cause termination of transcription and addition of polyadenylated ribonucleotides to a 3' end of the mRNA molecule.

Methods and compositions for transforming eukaryotic cells, bacteria and other microorganisms are known in the art (see, for example, Sambrook et al., *Molecular Cloning: A Laboratory Manual,* Second Edition, Cold Spring Harbor Laboratory Press, Cold Spring Harbor, N.Y., (1989); Colosimo et al., *Biotechniques* 29:314-331, 2000).

Technology for introduction of DNA into cells is well known to those of skill in the art. Four general methods for delivering a gene into cells have been described: (1) chemical methods (Graham and van der Eb, *Virology* 54:536-539 (1973)); (2) physical methods such as microinjection (Capecchi, *Cell* 22:479-488 (1980)), electroporation (Wong and Neumann, *Biochem. Biophys. Res. Commun.* 107:584-587 (1982); Fromm et al., *Proc. Natl. Acad. Sci.* (U.S.A.) 82:5824-5828 (1985); U.S. Pat. No. 5,384,253); and the gene gun (Johnston and Tang, *Methods Cell Biol.* 43:353-365 (1994); (3) viral vectors (Clapp, *Clin. Perinatol.* 20:155-168 (1993); Lu et al., *J. Exp. Med.* 178:2089-2096 (1993); Eglitis and Anderson, *Biotechniques*, 6:608-614 (1988)); and (4) receptor-mediated mechanisms (Curiel et al., *Hum. Gen. Ther.* 3:147-154 (1992), Wagner et al., *Proc. Natl. Acad. Sci.* (U.S.A.) 89:6099-6103 (1992)). Other methods well known in the art can also be used.

Transformation can be achieved using methods based on calcium phosphate precipitation, polyethylene glycol treatment, electroporation, and combinations of these treatments (see for example Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988)).

Assays for gene expression based on the transient expression of cloned nucleic acid constructs have been developed by introducing the nucleic acid molecules into cells by polyethylene glycol treatment, electroporation, or particle bombardment (Marcotte et al., *Nature* 335:454-457 (1988); McCarty et al., *Cell* 66:895-905 (1991); Hattori et al., *Genes Dev.* 6:609-618 (1992); Goff et al., *EMBO J.* 9:2517-2522 (1990)). Transient expression systems may be used to functionally dissect the regulatory and structural features of expression cassettes comprising operably-linked genetic elements.

Insect Cell Expression

Insect cells may be used as host cells to express recombinant proteins of the present invention (See, e.g., Luckow, V. A., *Protein Eng.* J. L. Cleland., Wiley-Liss, New York, N.Y.: 183-218, 1996, and references cited therein). General methods for expression of foreign genes in insect cells using baculovirus vectors have been described (O'Reilly, D. R., L. K. Miller et al. *Baculovirus Expression Vectors: A Laboratory Manual*. New York, W.H. Freeman and Company, 1992; and King, L. A. and R. D. Possee, *The Baculovirus Expression System: A Laboratory Guide*, London, Chapman & Hall).

A baculovirus expression vector can be constructed by inserting the desired gene (e.g., 11 alpha hydroxylase or oxidoreductase) into a baculovirus transfer vector which can recombine into the baculovirus genome by homologous recombination. Many transfer vectors use a strong baculovirus promoter (such as the polyhedrin promoter) to drive transcription of the desired gene. Some vectors permit the expression of fusion proteins or direct the secretion of proteins from the cell by fusing a eukaryotic secretion signal peptide coding region to the coding region of the desired gene. The plasmid pVL1393 (obtained from Invitrogen Corp., San Diego, Calif.) can be used, for example, to direct transcription of nonfused foreign genes in baculovirus-infected insect cells. The baculovirus transfer vector containing the desired gene is transfected into *Spodoptera frugiperda* (Sf9) insect cells along with circular or linearized genomic baculovirus DNA, and recombinant baculoviruses purified and amplified after one or more plaque assays.

Recombinant baculoviruses can also be created using the baculovirus shuttle vector system (Luckow, V. A. et al., *J. Virol.* 67(8):4566-4579, 1993; U.S. Pat. No. 5,348,886) now marketed as the Bac-To-Bac™ Expression System (Life Technologies, Inc., Rockville, Md.). The desired genes are inserted downstream from the polyhedrin promoter in mini-Tn7 cassettes that are transposed in vivo into a baculovirus shuttle vector genome propagated in *E. coli*. Composite viral DNAs are isolated from *E. coli* and transfected into Sf9 cells and stocks of recombinant baculoviruses are rapidly prepared without the need for multiple rounds of tedious plaque purification common to methods that rely on homologous recombination.

Recombinant baculoviruses can also created using the Gateway Recombinational Cloning System (Life Technologies) of shuttling genes from vector to vector using modified genetic elements (attachment sites) and modified proteins (e.g., int, IHF, xis) that are involved in the site-specific integration and excision of bacteriophage lambda.

Pure recombinant baculoviruses carrying the 11 alpha hydroxylase or oxidoreductase gene are used to infect cells cultured, for example, in Excell 401 serum-free medium (JRH Biosciences, Lenexa, Kans.) or Sf900-II (Life Technologies). Hydroxylases or oxidoreductases that are localized to membranes can be prepared using standard protocols that fractionate and enrich for enzymes in mitochondrial or microsomal fractions (Engel and White, *Dev Biol.* 140:196-208, 1990). Hydroxylases or oxidoreductases that are secreted or leak into the medium can also be recovered by standard biochemical approaches.

Simultaneous expression of two or more recombinant proteins in baculovirus-infected insect cells can be carried out by two general approaches. The simplest approach is to coinfect insect cells with titered stocks of recombinant baculoviruses harboring a single heterologous gene under the control of a strong baculovirus promoter, such as the polyhedrin or the p10 promoter. These promoters are highly transcribed during the late stages of infection when most host cell protein synthesis has been shut down. Earlier baculovirus promoters or other insect or eukaryotic cell promoters can also be used to direct synthesis at other times, which generally result in lower expression levels. Varying the ratio of two or more recombinant viruses used in a coinfection or selecting viruses that use different promoters to drive expression of the recombinant protein will permit one skilled in the art to select conditions suitable for optimal expression of the desired recombinant proteins.

Construction of dual- or multiple-expression vectors will also permit the expression of two or more recombinant proteins in baculovirus-infected insect cells. Generally, these vectors permit the introduction two or more gene cassettes into a single locus in the baculovirus genome. The structures of a variety of dual expression vectors have been described (O'Reilly, D. R., L. K. Miller et al. *Baculovirus Expression Vectors: A Laboratory Manual*. New York, W.H. Freeman and Company, 1992; and King, L. A. and R. D. Possee, *The Baculovirus Expression System: A Laboratory Guide*, London, Chapman & Hall).

Materials and Methods

General Methods

General methods of cloning, expressing, and characterizing proteins are found in T. Maniatis, et al., *Molecular Cloning, A Laboratory Manual*, Cold Spring Harbor Laboratory, 1982, and references cited therein, incorporated herein by reference; and in J. Sambrook, et al., *Molecular Cloning, A Laboratory Manual*, $2^{nd}$ edition, Cold Spring Harbor Laboratory, 1989, and references cited therein, incorporated herein by reference. General features and maps of a wide variety of cloning and expression vectors have been also been published (Gacesa, P. and Ramji, D. P., Vectors: Essential Data, John Wiley & Sons, 1994). General methods for the cloning and expression of genes in mammalian cells are also found in Colosimo et al., *Biotechniques* 29:314-331, 2000. General and specific conditions and procedures for the construction, manipulation and isolation of polyclonal and monoclonal antibodies are well known in the art (See, for example, Harlow and Lane, *Antibodies: A Laboratory Manual*, Cold Spring Harbor Press, Cold Spring Harbor, N.Y., 1988).

Unless noted otherwise, all specialty chemicals were obtained from Sigma (St. Louis, Mo.). Restriction endonucleases and T4 DNA ligase were obtained from Life Technologies (Rockville, Md.), New England Biolabs (Beverly, Mass.), Roche Molecular Biochemicals (Indianapolis, Ind.), or Promega (Madison, Wis.). All parts are by weight and temperatures are in degrees centigrade (° C.), unless otherwise indicated.

Strains, Plasmids, and Sequence Cross Listings

The bacterial strains used in these studies are listed in Table 1. Plasmids used or constructed for this study are listed in Table 2. Brief descriptions of sequences of relevant oligonucleotides, genes, or proteins are listed in Table 3.

TABLE 1

Strains

| Designation | Description or Genotype | Reference/Source |
|---|---|---|
| DH5α ™ | F−, phi80 dlacZdeltaM15, delta(lacZYA-argF)U169, deoR, recA1, endA1, hsdR17 (rk−, mk+), phoA, supE44, lambda-, thi-1, gyrA96, relA1 | Life Technologies, Rockville, Maryland |
| DH10B ™ | F−, mcrA D(mrr-hsdRMS-mcrBC) phi80 dlacZDM15 DlacX74 endA1 recA1 deoR D(ara, leu)7697 araD139 galU galK nupG rpsL | Life Technologies, Rockville, Maryland |
| DH10Bac ™ | DH10B harboring the baculovirus shuttle vector bMON14272 (Kan$^R$) and the helper plasmid pMON7124 (Tet$^R$) | Life Technologies, Rockville, Maryland; See also Luckow et al., J. Virol. 67: 4566–4579 (1993) |

TABLE 2

Plasmids

| Plasmid | SEQ ID NO. | Marker | Description | Source |
|---|---|---|---|---|
| pFastBac1 | | Amp$^R$ Gent$^R$ | Baculovirus donor plasmid containing multiple cloning site downstream of an AcNPV polyhedrin promoter within a mini-Tn7 transposable element capable of being transposed to a baculovirus shuttle vector | Life Technologies Inc. (Rockville, MD); See also Luckow et al., J. Virol. 67: 4566-4579 (1993) |
| pBluescript II SK | | Amp$^R$ | Multifunctional phagemid cloning vector derived from pUC19. | Stratagene, La Jolla, CA |
| pCRII-TOPO | | Amp$^R$ Kan$^R$ | Multifunctional cloning vector for direct cloning of polymerase chain reaction products using the T overhang | Invitrogen, Carlsbad, CA |
| pSport1 | | Amp$^R$ | Multifunctional cloning vector for cloning and in vitro transcription from either strand using SP6 or T7 promoters | Life Technologies, Rockville, MD |
| pGEM-T | | Amp$^R$ | A derivative of pGEM-5Zf(+) with single 5' T overhangs at the insertion site to improve the efficiency of PCR product ligation | Promega, Madison, WI |
| pMON45624 | #1 | Amp$^R$ Gent$^R$ | pFastBac1 EcoRI/XbaI + PCR fragment EcoRI/XbaI encoding *Aspergillus ochraceus* 11 alpha hydroxylase | This work |
| pMON45603 | | Amp$^R$ | pBluescriptII SK BamHI/HincII + BamHI/HincII 5' segment of human oxidoreductase | This work |

TABLE 2-continued

Plasmids

| Plasmid | SEQ ID NO. | Marker | Description | Source |
|---|---|---|---|---|
| pMON45604 | | Amp$^R$ | pBluescriptII SK HincII/KpnI + HincII/KpnI 3' segment of human oxidoreductase | This work |
| pMON45605 | #3 | Amp$^R$ Gent$^R$ | pFastBac1 BamHI/KpnI + BamHI/KpnI complete coding region of human oxidoreductase cDNA. | This work |
| pMON45630 | | Amp$^R$ Kan$^R$ | pCRII-TOPO SalI/BamHI + SalI/BamHI 5' segment of *A. ochraceus* oxidoreductase cDNA | This work |
| pMON45631 | | Amp$^R$ Kan$^R$ | pCRII-TOPO BamHI/XhoI + BamHI/XhoI 3' segment of *A. ochraceus* oxidoreductase cDNA which lacked the intron. | This work |
| pMON45632 | #5 | Amp$^R$ Gent$^R$ | pFastBac1 SalI/XhoI + containing assembled coding region of *Aspergillus ochraceus* oxidoreductase | This work |

TABLE 3

Table of Sequences

| SEQ ID NO | Description | Length/Sequence | Type |
|---|---|---|---|
| (SEQ ID NO: 01) | Nucleotide sequence of *Aspergillus ochraceus* 11alphaOH gene from pMON45624 | 1776 | DNA |
| (SEQ ID NO: 02) | *Aspergillus ochraceus* 11alphaOH protein sequence from pMON45624 | 514 | Protein |
| (SEQ ID NO: 03) | Nucleotide sequence of human oxidoreductase gene from pMON45605 | 2031 | DNA |
| (SEQ ID NO: 04) | Human oxidoreductase protein sequence from pMON45605 | 677 | Protein |
| (SEQ ID NO: 05) | Nucleotide sequence of *Aspergillus ochraceus* oxidoreductase gene from pMON45632 | 2322 | DNA |
| (SEQ ID NO: 06) | *Aspergillus ochraceus* oxidoreductase protein sequence from pMON45632 | 705 | Protein |
| (SEQ ID NO: 07) | Primer H. oxred 1A | gatcggatccaatATGG GAGACTCCCACGTGGAC AC | DNA |
| (SEQ ID NO: 08) | Primer H. oxred 1B | CAGCTGGTTGACGAGAG CAGAG | DNA |
| (SEQ ID NO: 09) | Primer H. oxred 2A | CTCTGCTCTCGTCAACC AGCTG | DNA |
| (SEQ ID NO: 10) | Primer H. oxred 2B | gatcggtaccttaGCTC CACACGTCCAGGGAGTA G | DNA |
| (SEQ ID NO: 11) | Primer A. oxred-for1 | GACGGIGCIGGTACAAT GGA | DNA |
| (SEQ ID NO: 12) | Primer A. oxred-rev1 | TTAIGACCAIACATCIT CCTGGTAGC | DNA |
| (SEQ ID NO: 13) | Primer pSport-for1 | CAAGCTCTAATACGACT CACTATAGGGA | DNA |

TABLE 3-continued

Table of Sequences

| SEQ ID NO | Description | Length/Sequence | Type |
|---|---|---|---|
| (SEQ ID NO: 14) | Primer A. oxred-rev2 | CAGGAACCGATCGACCT CGGAA | DNA |
| (SEQ ID NO: 15) | Primer A. oxred-rev3 | GTCACCCTCACCAGCAG AGCCAATG | DNA |
| (SEQ ID NO: 16) | Primer A. oxred-rev4 | CCACATTGCGAACCATA GCGTTGTAGTG | DNA |
| (SEQ ID NO: 17) | Primer pSport-for2 | GCCAAGCTCTAATACGA CTCACTATAGGGAAAGC | DNA |
| (SEQ ID NO: 18) | Primer A. oxred-for2 | gtcgacATGGCGCAACT CGATACTCTC | DNA |
| (SEQ ID NO: 19) | Primer A. oxred-rev5 | ctcgagttaGGACCAGA CATCGTCCTGGTAG | DNA |
| (SEQ ID NO: 20) | Primer A. oxred-for3 | GGATCCCTCGCGACCTG TGATCAT | DNA |
| (SEQ ID NO: 21) | Primer A. oxred-for4 | CGAAGATTTCTTGTACA AGGATGAATGGAAGACT TTTC | DNA |
| (SEQ ID NO: 22) | Primer A. oxred-rev6 | CTGAAAAGTCTTCCATT CATCCTTGTACAAGAAA TC | DNA |
| (SEQ ID NO: 23) | 11aOH peptide 1 | AAAYWLATLQPSDLPEL N | Protein |
| (SEQ ID NO: 24) | 11aOH peptide 2 | CRQILTPYIHKRKSLKG TTDE | Protein |
| (SEQ ID NO: 25) | 11aOH peptide 3 | HMGFGHGVHACPGRFFA SNEI | Protein |
| (SEQ ID NO: 26) | oxr peptide 1 | CTYWAVAKDPYASAGPA MNG | Protein |
| (SEQ ID NO: 27) | CAA75565; cytochrome P450 monooxygenase [*Gibberella fujikuroi*] | | Protein |
| (SEQ ID NO: 28) | CAB91316; probable cytochrome P450 monooxygenase (lovA) [*Neurospora crassa*] | | Protein |
| (SEQ ID NO: 29) | CAB56503; cytochrome P450 [*Catharanthus roseus*] | | Protein |
| (SEQ ID NO: 30) | AAB94588; CYP71D10p [*Glycine max*] | | Protein |
| (SEQ ID NO: 31) | CAA75566; cytochrome P450 monooxygenase [*Gibberella fujikuroi*] | | Protein |
| (SEQ ID NO: 32) | AAD34552; cytochrome P450 monooxygenase [*Aspergillus terreus*] | | Protein |
| (SEQ ID NO: 33) | CAA75567; cytochrome P450 monooxygenase [*Gibberella fujikuroi*] | | Protein |
| (SEQ ID NO: 34) | CAA76703; cytochrome P450 [*Gibberella fujikurol*] | | Protein |
| (SEQ ID NO: 35) | CAA57874; unnamed protein product [*Fusarium oxysporum*] | | Protein |

TABLE 3-continued

Table of Sequences

| SEQ ID NO | Description | Length/Sequence | Type |
|---|---|---|---|
| (SEQ ID NO: 36) | CAA91268; similar to cytochrome P450~cDNA EST yk423b11.3 comes from this gene; [*Caenorhabditis elegans*] | | Protein |
| (SEQ ID NO: 37) | BAA02936 NADPH-cytochrome P450 reductase precursor [*Saccharomyces cerevisiae*] | | Protein |
| (SEQ ID NO: 38) | CAA81550 NADPH cytochrome P450 oxidoreductase [*Aspergillus niger*] | | Protein |
| (SEQ ID NO: 39) | BAA04496 NADPH-cytochrome P450 oxidoreductase [*Mus musculus*] | | Protein |
| (SEQ ID NO: 40) | Universal bacteriophage M13 reverse primer | CAG GAA ACA GCT ATG AC | DNA |
| (SEQ ID NO: 41) | Universal bacteriophage T7 promoter primer | TAA TAC GAC TCA CTA TAG GG | DNA |
| (SEQ ID NO: 42) | *Aspergillus ochraceus* Primer 11alphaOH-for | gatcgaattcATGCCCT TCTTCACTGGGCT | DNA |
| (SEQ ID NO: 43) | *Aspergillus ochraceus* Primer 11alphaOH-rev | gatctctagattacaca gttaaactcgccaTATC GAT | DNA |
| (SEQ ID NO: 44) | pFastBac1 Primer Bacfwd | CTGTTTTCGTAACAGTT TTG | DNA |
| (SEQ ID NO: 45) | pFastBac1 Primer PolyA | CCTCTACAAATGTGGTA TG | DNA |
| (SEQ ID NO: 46) | *Aspergillus ochraceus* Primer 45624-for1 | GAGATCAAGATTGCCTT | DNA |
| (SEQ ID NO: 47) | *Aspergillus ochraceus* Primer 45624-for2 | CTTCGACGCTCTCAA | DNA |
| (SEQ ID NO: 48) | *Aspergillus ochraceus* Primer 45624-rev1 | GCAATCTTGATCTCGTT | DNA |
| (SEQ ID NO: 49) | S90469 human cytochrome P450 reductase [placental, mRNA Partial, 2403 nt]. | 2403 | DNA |
| (SEQ ID NO: 50) | AAB21814 human cytochrome P450 reductase, placental, partial | 676 | Protein |
| (SEQ ID NO: 51) | A60557 human NADPH-ferrihemoprotein reductase | 677 | Protein |
| (SEQ ID NO: 52) | P16435 Human NADPH-cytochrome P450 reductase | 677 | Protein |
| (SEQ ID NO: 53) | P00389 Rabbit NADPH-cytochrome P450 reductase | 679 | Protein |
| (SEQ ID NO: 54) | P00388 Rat NADPH-cytochrome P450 reductase | 678 | Protein |
| (SEQ ID NO: 55) | P37040 Mouse NADPH-cytochrome P450 reductase | 678 | Protein |
| (SEQ ID NO: 56) | P04175 Pig NADPH-cytochrome P450 reductase | 678 | Protein |
| (SEQ ID NO: 57) | Universal bacteriophage SP6 primer | gatttaggtgacactat ag | DNA |

TABLE 3-continued

Table of Sequences

| SEQ ID NO | Description | Length/Sequence | Type |
|---|---|---|---|
| (SEQ ID NO: 58) | NotI-poly-dT adapter | 5'-pGACTAGT TCTAGA TCGCGA GCGGCCGC CC (T)$_{15}$-3' | DNA |
| (SEQ ID NO: 59) | SalI adapter, top strand | 5'-TCGACCCACGCGTCCG-3' | DNA |
| (SEQ ID NO: 60) | SalI adapter, bottom strand | 3'-GGGTGCGCAGGCp-5' | DNA |
| (SEQ ID NO: 61) | Primer oxred 1C | GTGGACCACAAGCTCGT ACTG | DNA |
| (SEQ ID NO: 62) | Primer oxred 2C | CATCGACCACCTGTGTG AGCTG | DNA |
| (SEQ ID NO: 63) | Primer oxred 2D | GTACAGGTAGTCCTCAT CCGAG | DNA |
| (SEQ ID NO: 64) | *Aspergillus niger* NADP CYP450 oxidoreductase Z26838 | 3710 | DNA |
| (SEQ ID NO: 65) | *Aspergillus niger* NADP CYP450 oxidoreductase CAA81550 | 693 | Protein |

Specific Methods

Transformation of *E. coli* Strains

*E. coli* strains such as DH5 alpha and DH10B (Life Technologies, Rockville, Md.) are routinely used for transformation of ligation reactions and are the hosts used to prepare plasmid DNA for transfecting mammalian cells. *E. coli* strains, such as DH10B and MON105 (Obukowicz, et al., *Appl. and Envir. Micr.*, 58:1511-1523, 1992) can be used for expressing the proteins of the present invention in the cytoplasm or periplasmic space.

DH10B and DH5alpha subcloning efficiency cells are purchased as competent cells and are ready for transformation using the manufacturer's protocol. Other *E. coli* strains are rendered competent to take up DNA using a CaCl$_2$ method. Typically, 20 to 50 mL of cells are grown in LB medium (1% Bacto-tryptone, 0.5% Bacto-yeast extract, 150 mM NaCl) to a density of approximately 1.0 absorbance unit at 600 nanometers (OD600) as measured by a Baush & Lomb Spectronic spectrophotometer (Rochester, N.Y.). The cells are collected by centrifugation and resuspended in one-fifth culture volume of CaCl$_2$ solution [50 mM CaCl$_2$, 10 mM Tris-Cl ((10 mM 2-amino-2-(hydroxymethyl) 1,3-propanediol hydrochloride, pH 7.4] and are held at 4° C. for 30 minutes. The cells are again collected by centrifugation and resuspended in one-tenth culture volume of CaCl$_2$ solution. Ligated DNA is added to 0.1 ml of these cells, and the samples are held at 4° C. for 30-60 minutes. The samples are shifted to 42° C. for 45 seconds and 1.0 ml of LB is added prior to shaking the samples at 37° C. for one hour. Cells from these samples are spread on plates (LB medium plus 1.5% Bacto-agar) containing either ampicillin (100 micrograms/mL, ug/ml) when selecting for ampicillin-resistant transformants, or spectinomycin (75 ug/ml) when selecting for spectinomycin-resistant transformants. The plates are incubated overnight at 37° C. Colonies are picked and inoculated into LB plus appropriate antibiotic (100 ug/ml ampicillin or 75 ug/ml spectinomycin) and are grown at 37° C. while shaking.

DNA Isolation and Characterization

Plasmid DNA can be isolated by a number of different methods and using commercially available kits known to those skilled in the art. Plasmid DNA is isolated using the Promega Wizard™ Miniprep kit (Madison, Wis.), the Qiagen QIAwell Plasmid isolation kits (Chatsworth, Calif.) or Qiagen Plasmid Midi or Mini kit. These kits follow the same general procedure for plasmid DNA isolation. Briefly, cells are pelleted by centrifugation (5000×g), the plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted. After screening for the colonies with the plasmid of interest, the *E. coli* cells are inoculated into 50-100 ml of LB plus appropriate antibiotic for overnight growth at 37° C. in an air incubator while shaking. The purified plasmid DNA is used for DNA sequencing, further restriction enzyme digestion, additional subcloning of DNA fragments and transfection into *E. coli*, mammalian cells, or other cell types.

DNA Sequencing Protocols

Purified plasmid DNA is resuspended in dH$_2$O and its concentration is determined by measuring the absorbance at 260/280 nm in a Baush and Lomb Spectronic 601 UV spectrometer. DNA samples are sequenced using ABI PRISM™ DyeDeoxy™ terminator sequencing chemistry (Applied Biosystems Division of Perkin Elmer Corporation, Lincoln City, Calif.) kits (Part number 401388 or 402078) according to the manufacturer's suggested protocol. Occasionally, 5% DMSO is added to the mixture in repeat experiments, to facilitate the sequencing of difficult templates.

Sequencing reactions are performed in a DNA thermal cycler (Perkin Elmer Corporation, Norwalk, Conn.) following the recommended amplification conditions. Typically, DNA samples were prepared containing 500 ng of template DNA and 100 ng of primer of choice in thin-walled 0.2 mL PCR tubes that have been brought to 12 uL with Millipore milli-Q (mQ)-quality water. 2 ul of 2 mM $Mg^{++}$ was added to each tube. Tubes were denatured for 5 minutes at 96° C. in a Perkin-Elmer System 9700 thermal cycler. After denaturation, the tubes were chilled to a temperature of 4° C. by the thermal cycler. 6 ul of ABI Prism Big Dye Terminator Cycle Sequencing Ready Reaction Kit was added to each tube. The samples were returned to the thermal cycler and cycle-sequenced using the following program: (1) 96° C. for 30 sec; (2) 50° C. for 5 sec; (3) 60° C. for 4 min, followed by step (1) for 24 additional cycles and then held at 4° C. Cycle sequencing was complete after about 2.5 hours.

Samples are purified to remove excess dye terminators with using Centri-Sep™ spin columns (Princeton Separations, Adelphia, N.J.) or purified through a Millipore MAHV N45 50 Multiscreen-HV filtration plate which had been filled with 25 uL Sephadex G-50 superfine resin and 300 uL mQ water. Before loading samples onto filtration plates, the plate was prespun in a centrifuge at 750×g for 2 min to remove excess water. The samples were loaded onto the resin and the plate spun again at 750×g for 4 min. The purified sample was collected into a 96-well plate that was placed directly underneath the Sephadex-filled plate during the spin. The liquid in the 96-well plate was dried at room temperature in a Speed Vac. After 45-60 min the DNA was dried and pelleted at the bottom of the plate. Samples were resuspended in 3 uL of a formamide/blue Dextran loading dye and were heated for 2 minutes (see p.33 of Perkin-Elmer Big Dye manual for loading buffer recipe). Samples were loaded onto 48 cm well-to-read length 4.5% acrylamide gels and sequenced for 7 hr using ABI automated DNA sequencers (typically run module Seq Run 48E-1200 and dye set DT, Program BD, Set Any-Primer).

Overlapping DNA sequence fragments are analyzed and assembled into master DNA contigs using Sequencher DNA Analysis software (Gene Codes Corporation, Ann Arbor, Mich.) or the Perkin-Elmer Data Collection and Sequence Analysis programs to assign bases to the data collected.

BLAST, ClustalW, and Boxshade Homology Alignment Tools

A variety of programs can be used to align nucleotide or peptide sequences to each other and to facilitate homology searches in large sequence databases. BLAST (Basic Local Alignment Search Tool), which implements the statistical matching theory by Karlin and Altschul (*Proc. Natl. Acad. Sci. USA* 87:2264-2268, 1990; *Proc. Natl. Acad. Sci. USA* 90:5873-5877, 1993), is a widely used program for rapidly detecting ungapped nucleotide or peptide subsequences that match a given query sequence (Available from the National Center for Biotechnology Information, http://www.ncbi.nlm.nih.gov). BLAST uses a heuristic algorithm which seeks local as opposed to global alignments and is therefore able to detect relationships among sequences which share only isolated regions of similarity (Altschul et al., *J. Mol. Biol.* 215:403-410, 1990).

Two parameters can be varied which alter the sensitivity and quantity of BLAST search results. Parameter B (with a default value of 10) regulates the number of high-scoring segment pairs (alignments) reported in the results. Parameter V (with a default value of 10) is the maximum number of database sequences (hits) for which one-line descriptions will be reported. Matches are based on high-scoring segment pairs (HSPs). Two sequences may share more than one HSP, if the HSPs are separated by gaps. The BLAST algorithm is sensitive to ambiguities in the sequence and is not well-suited for sequences that contain many gaps.

The program blastp compares an amino acid query sequence against a protein sequence database. blastn compares a nucleotide query sequence against a nucleotide sequence database. blastx compares a nucleotide query sequence translated in all reading frames against a protein sequence database. You could use this option to find potential translation products of an unknown nucleotide sequence. tblastn compares a protein query sequence against a nucleotide sequence database dynamically translated in all reading frames. tblastx compares the six-frame translations of a nucleotide query sequence against the six-frame translations of a nucleotide sequence database (See http://www.ncbi.nlm.nih.gov/Education/BLASTinfo/ for more information on BLAST, related programs, and pattern matching algorithms).

Nucleotides searches performed with BLAST, score=98-557, word length 514 letters, were used to obtain nucleotide sequences homologous to nucleic acid molecules of the present invention. Protein searches are performed with BLASTP, score=50, word length=3 to obtain amino acid sequences homologous to a reference polypeptide (e.g., SEQ ID NO: 2).

Clustal W version 1.74, which implements a different algorithm for alignment of multiple DNA or protein sequences, was also used to prepare alignments and to assign percent identities between different sequences. This program improves the sensitivity of progressive multiple sequence alignment through sequence weighting, position specific gap penalties and weight matrix choice (Thompson et al., *Nucleic Acids Research*, 22(22):4673-4680, 1994). The default parameters for version 1.74 were used facilitate alignments and to assign percent identities between two sequences. The input consisted of sequences in FASTA format and the output is the alignment shown in the figures. For nucleic acid sequences, the iub DNA weight matrix was used. For amino acid sequences, the blosum protein weight matrix was used (See http://www.ncbi.nlm.nih.gov/Education/BLASTinfo/ for more information on BLAST, related programs, and pattern matching algorithms.

Boxshade v 3.31 is a public domain program for creating nicely formatted printouts from muliple-aligned protein or DNA sequences. Boxshade, by itself, does not create alignments, but applies shading or coloring to files that were previously prepared by other sequence alignment programs. The inputs to Boxshade are the alignments created by ClustalW and the threshold values for the residues to be colored or shaded. In most cases, except where specified, a 50% identity value was used. With this setting, if a position has greater than or equal to half of the sequences sharing an identical residue, then it is shaded. Boxshade is available by ftp from ftp. or by e-mail from Kay Hofmann (khofmann@isrec-sun1-unil.ch or Michael D. Baron (michael.baron@bbsrc.ac.uk).

Protein Purification and Characterization

Protein purification can be accomplished using any of a variety of chromatographic methods such as: ion exchange, gel filtration or hydrophobic chromatography or reversed phase HPLC. In some cases, proteins which are properly folded can be affinity-purified using affinity reagents, such as monoclonal antibodies or receptor subunits attached to a suitable matrix. These and other protein purification methods are described in detail in Methods in Enzymology, Volume 182 "Guide to Protein Purification" edited by Murray Deutscher, Academic Press, San Diego, Calif., 1990.

The purified protein can be analyzed by RP-HPLC, electrospray mass spectrometry, and SDS-PAGE. Protein quantitation is done by amino acid composition, RP-HPLC, and/or Bradford protein dye-binding assays. In some cases, tryptic peptide mapping is performed in conjunction with electrospray mass spectrometry to confirm the identity of the protein.

EXAMPLES

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

Example 1

Preparation of *A. ochraceus* Spores for RNA Extraction

*Aspergillus ochraceus* ATCC 18500 stock culture (50 ul) was grown for 3-4 days on plates containing sporulation medium: 50 g/L molasses, 5 g/L cornsteep liquid, 5 g/L $KH_2PO_4$, 25 g/L NaCl, 25 g/L glucose, 20 g/L agar, and 0.4 g/L progesterone, pH 5.8. Progesterone was included in the media to induce the steroid 11 α-hydroxylase. Spores were scraped from the plates into 5 to 7 ml saline, washed in saline, collected by centrifugation, and suspended in saline containing 15% glycerol. The spores were frozen on dry ice and stored at −80° C. Approximately 0.8 g spores were incubated at 30° C. in a 1 liter flask containing 400 ml 1% glucose, 50 mM $KH_2PO_4$ and 0.1 g canrenone, pH 7.0. This treatment prior to spore disruption has three benefits: (1) to induce the steroid 11 α-hydroxylase by incubation with canrenone; (2) to determine whether the spores were catalyzing the 11 α-hydroxylation of canrenone; (3) and to soften the spore wall. After approximately 26 hours of incubating with shaking at 30° C. to provide better aeration, the spores were collected by centrifugation. Visual inspection with the aid of a microscope indicated that very few had started to germinate. The spore pellets were flash frozen in liquid nitrogen and stored at −80° C. The media was analyzed for presence of 11 alpha hydroxy canrenone by HPLC to determine whether spores used for library construction demonstrated the desired activity.

Example 2

*A. ochraceus* Spores Catalyze 11 α-hydroxylation of Canrenone

Approximately 160 ml of media from the spore induction was extracted three times with 70 ml ethyl acetate to collect the steroid substrate and products. The organic phase was dried over anhydrous magnesium sulfate, filtered, and evaporated to dryness. The residue was dissolved in 8 ml methanol so that the final concentration of canrenone was approximately 15 mM (assuming quantitative recovery). The media extract was diluted 10- to 15-fold into 50% methanol for HPLC analysis. Stock solutions of canrenone and 11 α-hydroxy canrenone were prepared in methanol. Standards for HPLC analysis were prepared from these stock solutions by diluting to a final concentration of 750 uM with 50% methanol. Media extract and standards were chromatographed over a C-4 reverse phase HPLC column. The media exhibited a component with the same retention time as the 11 α-hydroxy canrenone standard, as monitored at 254 nm (data not shown).

Example 3

Growth of *A. ochraceus* Mycelia for RNA Extraction

Liquid cultures of *Aspergillus ochraceus* mycelia were grown in 10 g/L peptone, 10 g/L yeast extract and 10 g/L glucose containing 20 g/L canrenone for 24 to 72 hours at 28° C. in a volume of 160 ml. Ten ml samples of cells were filtered, washed with cold water, frozen, and stored at −80° C.

Example 4

Extraction of Total RNA from Induced Spores

Approximately 0.4 g spores were disrupted in 40 ml Trizol reagent (Life Technologies, Rockville, Md.) using a Mini-Beadbeater™ model 3110 (Biospec Products, Bartlesville, Okla.). Briefly, spore-Trizol mixture was subjected to four 30 second pulses at low speed. Between pulses, tubes containing spores were chilled on ice. Visual inspection with the aid of a microscope indicated that the majority of the spores were disrupted by this treatment. The debris was pelleted by low-speed centrifugation and the total RNA in the supernatant was extracted following the manufacturer's recommended protocols for use with Trizol. Briefly, 2 ml chloroform was added for each 10 ml Trizol in 11 ml polypropylene centrifuge tubes. Following a 3 minute extraction of proteins, phase separation was done by centrifugation and the aqueous phase containing the RNA was transferred to a clean tube for precipitation with an equal volume of isopropanol. The precipitated RNA was recovered by centrifugation and washed with 70% ethanol. The RNA was resuspended in 10 ml water, re-extracted with chloroform and precipitated with ethanol overnight at −20° C. Total RNA (3 mg) was recovered by centrifugation and rehydrated in 2 ml water, and precipitated on ice by adding an equal volume of cold 4 M lithium chloride. This precipitation was done to remove DNA, carbohydrates, heme, and other impurities which can carry over from guanidine methods. The RNA was recovered by a 25 minute centrifugation.

Example 5

Extraction of Total RNA from Induced Mycelia

Approximately 0.5 g wet weight cells were pulverized to a fine powder under liquid nitrogen with a mortar and pestle pre-chilled in dry ice. The powder was added to 10 ml Trizol Reagent (Life Technologies) and homogenized with a Kinematica polytron (Kinematica AG, Lucerne, Switzerland) at setting #4. Cellular debris was removed by centrifugation prior to chloroform extraction. The aqueous phase containing nucleic acids was precipitated with isopropanol for 10 minutes at room temperature. The precipitate was collected by centrifugation and washed with 70% ethanol. The RNA was rehydrated in water and re-extracted with chloroform to remove any residual proteins. The aqueous phase was precipitated at −20° C. with ⅒ volume of 3 M sodium acetate and 2.5 volumes absolute ethanol. The final yield was 424 ug. Approximately 4 ug and 16 ug of total RNA were separated by electrophoresis through a 1.2% agarose gel and visualized by staining in ethidium bromide. Chromosomal DNA was present as a minor contaminant.

Example 6

Extraction of Total RNA from HepG2 Cells

Hepatocellular human liver carcinoma cells (HepG2), ATCC HB-8065, were maintained in DMEM high glucose media supplemented with Penstrep, glutamate and 10% fetal bovine serum (Life Technologies, Rockville, Md.). Cells were induced overnight with 0.05% ethanol and harvested for RNA extraction by trypsinization. Briefly, the cell pellet was resuspended in >10× volumes of 4 M guanidine isothiocyanate, 50 mM Tris-HCl, pH 7.5, 25 mM EDTA (solution D, Life Technologies) and then vortexed. Water and sodium acetate, pH 4.1, were added such that the final concentration of sodium acetate was 0.1 M. The RNA solution was extracted with one half volume of chloroform and placed on ice for 15 minutes. The aqueous phase was re-extracted with chloroform and precipitated overnight with isopropanol. Total RNA was resuspended in solution D and re-precipitated with isopropanol, followed by two precipitations in water containing 0.3 M sodium acetate pH 5.5 and 2.5 volumes of ethanol. PolyA$^+$ selection was performed twice as described below.

Example 7

PolyA$^+$ Selection of mRNA

PolyA$^+$ RNA was selected from total RNA with an Eppendorf 5Prime, Inc. kit (Boulder Colo.). Briefly, each 1 mg of total RNA was selected twice over a column containing oligo dT cellulose. The column slurry was packed by gentle centrifugation and equilbrated with 0.5 M NaCl. RNA was allowed to bind to the dT cellulose for 15 minutes at room temperature. The columns were washed once with 0.5 M NaCl, and twice with 0.1 M NaCl. PolyA$^+$ RNA was eluted in 0.5 ml 10 mM Tris-HCl, 1 mM EDTA, pH 7.5. The selection by oligo dT cellulose was performed twice. The mRNA was precipitated at −20° C. with 0.3 M sodium acetate in 50% ethanol, with glycogen added as carrier.

Example 8

CDNA Synthesis and Library Construction

The Superscript™ Plasmid System for cDNA Synthesis and Plasmid Cloning kit (Life Technologies) was used for cDNA systhesis and library construction. Superscript II reverse transcriptase catalyzed the first strand of cDNA in a 20 ul reaction for 1 hour at 42° C. The final composition was 50 mM Tris-HCl, pH 8.3, 75 mM KCl, 3 mM MgCl$_2$, 10 mM DTT, 50 uM each dATP, dCTP, dGTP and dTTP, 50 ug/ml oligo-dT-NotI primer-adaptors that were phosphorylated at their 5' end (Life Technologies) and 50,000 units/ml Superscript II reverse transcriptase.

```
oligo-dT-NotI primer-adapter      (SEQ ID NO: 58)
5'-pGACTAGT TCTAGA TCGCGA GCGGCCGC CC (T)15-3'
     SpeI    XbaI   NruI     NotI
```

A radiolabeled tracer ([Δ-$^{32}$P]dCTP) was not added. The second strand of cDNA was synthesized in a reaction volume of 150 ul. The final composition of this mixture including the first strand reaction was 25 mM Tris-HCl, pH 7.5, 100 mM KCl, 5 mM (NH$_4$)$_2$SO$_4$, 0.15 mM B-NAD$^+$, 250 uM each dATP, dCTP, dGTP and dTTP, 1.2 mM DTT, 65 units/ml E. coli DNA ligase, 250 units/ml E. coli DNA polymerase I and 13 units/ml E. coli Rnase H. After a 2 hour incubation at 16° C., 10 units of T4 DNA polymerase was added, and incubated 5 minutes at 16° C. The reaction was stopped with 10 ul 0.5 M EDTA and the cDNA was separated from cDNAs smaller than 300 base pairs, primer-adaptors and deoxynucleotides with GENECLEAN II (BIO 101 Inc. La Jolla, Calif.). Annealed Sal I adaptors (Life Technologies) that were phosphorylated at their 5' blunt end were ligated to the cDNA overnight at 16° C.

```
5'-TCGACCCACGCGTCCG -3'        (SEQ ID NO: 59)

3'-     GGGTGCGCAGGCp-5'       (SEQ ID NO: 60)
```

GENECLEAN II was used to remove the adaptors. The cDNA was then digested with NotI. QIAquick columns (QIAGEN, Valencia, Calif.) were used to remove small DNA fragments from the cDNA, which was ethanol precipitated.

Example 9

Size Fractionation of CDNA

The cDNA was enriched for species approximately 1.5 kb and larger by gel electrophoresis through 0.8% Sea-Plaque agarose (FMC BioProducts, Rockland Me.) in TAE buffer. The preparative gel had a lane of DNA size markers which was excised from the gel after electrophoresis and stained with ethidum bromide for visualization under ultraviolet light next to a ruler so that the appropriate region of the cDNA could be recovered from the gel. GENECLEAN II was used to extract the cDNA, which was eluted in 20 ul water.

Example 10

Library Construction in Vector pSport1 and Electroporation into E. coli

An aliquot of the size-selected cDNA was ligated overnight at 4° C. with pSport1 (Life Technologies, Inc., Rockville, Md.) predigested with NotI and SalI in a 20 ul reaction containing 50 mM Tris-HCl, pH 7.6, 10 mM MgCl$_2$, 1 mM ATP, 5% (w/v) PEG 8000, 1 mM DTT, 2.5 ug/ml pSport1, approximately 0.5 ug/ml cDNA, and 50 units/ml T4 DNA ligase. The ligation mixture was precipitated by the addition of 12.5 ul 7.5 M ammonium acetate, 5 ul yeast tRNA carrier and 70 ul absolute ethanol. The ligated cDNA was recovered by centrifugation at room temperature for 20 minutes and rehydrated in 5 ul sterile water. One ul of the ligated cDNA was introduced into ElectroMAX DH10B E. coli (Life Technologies) by electroporation. Cells were allowed to recover in 1 ml SOC medium (Life Technologies) for 1 hour at 37° C., before plating an aliquot on LB with 100 ug/ml ampicillin. The titer of the *Aspergillus ochraceus* spore library (designated LIB3025) was determined by preparing serial dilutions of the cell suspension in SOC. The equivalent of 1 ul, 0.1 ul and 0.01 ul samples of the cell suspension were plated, and the resulting titer was calculated to be 1.75×10⁶/ml colony forming units.

Example 11

Identification of Clones Encoding Cytochrome P450 Enzymes by DNA Sequence Analysis and Construction of Plasmid pMON45624 Encoding *Aspergillus ochraceus* 11 Alpha Hydroxylase Cloning of 11 Alpha Hydroxylase from *Aspergillus ochraceus*

Approximately 2,000 colonies were selected on LB agar plates containing 100 ug/ml ampicillin and miniprep plasmid DNA samples were prepared for sequencing. Unidirectional sequencing was performed from the 3' end of the expressed sequence tags (ESTs) beginning at the NotI site encompassing part of the poly dT primer used for cDNA synthesis. Two universal primers were used to facilitate the sequencing:

```
M13 reverse:
CAG GAA ACA GCT ATG AC        (SEQ ID NO: 40)

T7 promoter:
TAA TAC GAC TCA CTA TAG GG    (SEQ ID NO: 41)
```

Most known cytochrome p450s contain a conserved heme-binding region approximately 50 amino acid residues (150 nucleotides) upstream of the stop codon (Nelson et al, *Pharmacogenetics* 6:1-42, 1996). The 2,000 ESTs were screened for sequences encoding the canonical heme-binding motif (FXXGXXXCXG, where "X" is any amino acid) in the appropriate region using BLASTX and visual inspection of the sequences scored as hydroxylases for the canonical heme-binding motif. Only fifteen ESTs had the heme-binding motif. One EST was unique and the other fourteen appeared to be overlapping sequences. The cDNA inserts from seven clones encoding putative cytochrome p450 enzymes were then sequenced to completion. All seven encoded the same enzyme.

Gene Amplification of *Aspergillus ochraceus* 11 Alpha Hydroxylase

The coding region of the 11 alpha hydroxylase was amplified by PCR using a unique clone from the *A. ochraceus* cDNA spore library (LIB3025) as a template. The primers included recognition sites for EcoRI (forward) and XbaI (reverse) for directional cloning into pFastbac1. Amplification was carried out for 32 cycles using a PCR core kit (Roche) and 50 pmol of each primer. One cycle consisted of a denaturation step at 94° C. for 45 seconds, an annealing step at 60° C. for 45 seconds, and an elongation step at 72° C. for 60 seconds.

```
Primer 11alphaOH-for:
gatcgaattcATGCCCTTCTTCACTGGGCT    (SEQ ID NO: 42)

Primer 11alphaOH-rev:
gatctctagaTTACACAGTTAAACTCGCCATATC (SEQ ID NO: 43)
GAT
```

Construction of pMON45624

The amplified fragments described above were purified through a QIAquick column (Qiagen, Valencia Calif.) and digested with EcoRI and XbaI prior to ligation into pFastBac1 cleaved with EcoRI and XbaI. The resulting plasmid was designated pMON45624 and the DNA sequence verified using primers based on the vector sequence and internal primers based on the 11 alpha hydroxylase sequence (shown below).

```
Primer BacfWd:
CTGTTTTCGTAACAGTTTTG      (SEQ ID NO: 44)

Primer PolyA:
CCTCTACAAATGTGGTATG       (SEQ ID NO: 45)

Primer 45624-for1:
GAGATCAAGATTGCCTT         (SEQ ID NO: 46)

Primer 45624-for2:
CTTCGACGCTCTCAA           (SEQ ID NO: 47)

Primer 45624-rev1:
GCAATCTTGATCTCGTT         (SEQ ID NO: 48)
```

The nucleotide and predicted amino acid sequences of the cloned 11 alpha hydroxylase are displayed in FIG. 1 as SEQ ID NO: 1 and SEQ ID NO: 2, respectively.

FIG. 4 sets forth an amino acid homology alignment of *A. ochraceus* 11 alpha hydroxylase cloned in pMON45624 and aligned with related enzymes found in GenBank using BLAST. FIG. 5 is a phylogenetic tree showing the this relationship graphically. FIG. 6 shows the percent homology between *Aspergillus ochraceus* steroid 11 alpha hydroxylase and the top 10 enzymes found in GenBank using BLAST, calculated using Clustal W and Boxshade.

Example 12

Amplification of cDNA Encoding Human NADPH Cytochrome P450 Reductase and Cloning into Plasmids pMON45603, pMON45604, and pMON45605

Gene Amplification of human oxidoreductase

Approximately 1 ug polyA⁺ mRNA from HepG2 cells was heated to 65° C. for 10 minutes with 100 ng random hexamers (Invitrogen, Carlsbad, Calif.) in an 11 ul reaction. The mixture was chilled on ice, then incubated at 42° C. for 75 minutes in a 20 ul reaction containing 1 ul RNase inhibitor (Promega, Madison, Wis.), 0.01 M DTT, 5 mM dNTPs, 50 mM Tris-HCl, pH 8.3, 75 mM KCl, 3 mM MgCl$_2$ and 1 ul SuperScriptII enzyme (Life Technologies). The reverse transcriptase was inactivated by heating to 95° C. for 2 minutes. First strand cDNA was stored at −20° C. Forward and reverse primers were based on the nucleotide sequence of accession number S90469 (human placental partial mRNA encoding cytochrome P450 reductase (SEQ ID NO: 49)). The accession number of the corresponding protein sequence is AAB21814 (SEQ ID NO: 50). The human oxidoreductase was cloned in two pieces which were assembled in pFastBac1 (Life Technologies) by ligation at an internal HincII site. The primers included restriction sites for directional subcloning into pFastBac1.

```
Primer H. oxred 1A:
gatcggatccaatATGGGAGACTCCCACGTGGAC (SEQ ID NO: 07)
AC
```

-continued

```
Primer H. oxred 1B:
CAGCTGGTTGACGAGAGCAGAG            (SEQ ID NO: 08)

Primer H. oxred 2A:
CTCTGCTCTCGTCAACCAGCTG            (SEQ ID NO: 09)

Primer H. oxred 2B:
gatcggtaccttaGCTCCACACGTCCAGGGAGTA (SEQ ID NO: 10)
G
```

The second strand was synthesized using 400 uM dNTP and 167 nM of each primer set per 150 ul reaction. Amplification was performed with Deep Vent polymerase (New England Biolabs, Beverly, Mass.). The reaction for segment 2 (the 3' half of the oxidoreductase cDNA) was adjusted to 5% DMSO. The amplification included an initial cycle of denaturation at 94° C. for 90 seconds, followed by annealing at 62° C. for 2 minutes and elongation at 72° C. for 2 minutes. This was followed by 30 cycles, consisting of a 45 second denaturation step, a 45 second annealing step, and a 60 second elongation step. The elongation step was extended to 5 minutes for the final cycle.

Construction of pMON45603, pMON45604, pMON45605

The PCR fragments for the 5' half of the oxidoreductase cDNA were digested with BamHI and HincII. The PCR fragments for the 3' half of the oxidoreductase cDNA were digested with HincII and KpnI and ligated into pBluescript II (Stratagene, La Jolla, Calif.) for sequencing. The resulting plasmids were designated pMON45603 (5' segment) and pMON45604 (3' segment). The BamHI/HincII fragment from pMON45603 and the HincII/KpnI fragment from pMON45604 were ligated into pFastbac1 cut with BamHI and KpnI, to generate pMON45605.

Sequencing primers were based on the sequence of GenBank accession number S90469 (SEQ ID NO 49), a cDNA encoding cytochrome P450 reductase [human, placenta, mRNA Partial, 2403 nt]. The cognate protein sequence is: AAB21814 (SEQ ID NO 50) cytochrome P450 reductase {EC 1.6.2.4} {human, placenta, Peptide Partial, 676 aa} [*Homo sapiens*]. The cDNA insert of pMON45603 was sequenced using primer oxred 1C, and the cDNA insert of pMON45604 was sequenced using primer oxred 2C and 2D. Universal T7 (SEQ ID NO: 41) and M13 reverse (SEQ ID NO: 40) primers, which annealed to vector sequences flanking the cDNA inserts were also used for sequencing.

```
Primer oxred 1C:
GTGGACCACAAGCTCGTACTG             (SEQ ID NO: 61)

Primer oxred 2C:
CATCGACCACCTGTGTGAGCTG            (SEQ ID NO: 62)

Primer oxred 2D:
GTACAGGTAGTCCTCATCCGAG            (SEQ ID NO: 63)
```

The nucleotide and predicted amino acid sequences of the cloned human oxidoreductase are displayed in FIG. 2 as SEQ ID NO: 3 and SEQ ID NO: 4, respectively. FIG. 11 sets forth an alignment of human oxidoreductase with top 4 hits from SwissProt. FIG. 12 sets forth a phylogenetic tree displaying the genetic relatedness of human oxidoreductase, to these hits. FIG. 13 shows the percent identity between human oxidoreductase and top 4 hits from SwissProt.

Example 13

Amplification of cDNA Encoding NADPH Cytochrome P450 Reductase from *A. ochraceus* and Cloning into Plasmids pMON45630, pMON45631, and pMON45632

Gene Amplification of *Aspergillus Ochraceus* Oxidoreductase

An alignment of sequences from the *Aspergillus niger* cprA gene accession number Z26938 (SEQ ID NO: 65) and a partial cDNA clone 804561639F1 from *Aspergillus fumigatus* (PathoSeq Database, Incyte Pharmaceuticals) was visually scanned to select regions of high homology for the design of primers for PCR. A primer set was selected which spanned the coding region of the cprA gene product from amino acids 203 to 693.

Primers were selected from the 5' most region of overlap where the amino acid sequence was identical between both and the nucleic acid sequence differed by 2 positions in the $3^{rd}$ codon position. For the 3' primer, the nucleic acid encoding the stop codon, last 7 amino acid residues and 2 additional bases corresponding to second and third positions in the codon of the amino acid residue 8 positions from the stop codon encodes ARG in *A. niger* and SER in *A. fumigatis* (CGC vs. AGC). Inosines replaced the third base in codons when there was a discrepancy between the *A. niger* and *A. fumigatus* sequence.

```
Primer A. oxred-for1:
GACGGIGCIGGTACAATGGA              (SEQ ID NO: 11)

Primer A. oxred-rev1:
TTAIGACCAIACATCITCCTGGTAGC        (SEQ ID NO: 12)
(where I = Inosine)
```

A partial cDNA clone was amplified from approximately 5 ug of total RNA extracted from *A. ochraceus* mycelia. Before the first strand synthesis, the RNA was heated to 65° C. for 10 minutes with 100 ng random hexamers (Promega Madison Wis.) in an 11 ul reaction mixture. The mixture was chilled on ice, then incubated at 42° C. for 75 minutes in a 20 ul reaction containing 1 ul RNase inhibitor (Promega), 0.01 M DTT, 5 mM dNTPs, 50 mM Tris-HCl, pH 8.3), 75 mM KCl, 3 mM $MgCl_2$ and 1 ul SuperScriptII (LTI). The reverse transcriptase was inactivated by heating to 95° C. for 2 minutes. The first strand cDNA was stored at −20° C. The second strand was synthesized using 5 ul of the first strand as template. The reaction included 500 nM primers, 200 uM each dNTP, and Taq polymerase and buffer as supplied in PCR core kit (Roche Molecular Biochemicals, Indianapolis, Ind.). Amplification was performed using 32 cycles of a 30 second denaturation step at 94° C., a 30 second annealing step at 60° C. and a 60 second elongation step at 72° C. The amplified DNA products were cloned into pGEM-T (Promega, Madison, Wis.) and sequenced using universal T7 (SEQ ID NO: 41) and SP6 (SEQ ID NO: 57) primers.

```
Primer SP6
GATTTAGGTGACACTATAG               (SEQ ID NO: 57)
```

Alignment of the sequences with the *A. niger* cprA gene revealed that the *A. ochraceus* clones had an intron in the same position as the intron in the *A. niger* gene. This indicated that the *A. ochraceus* PCR products might have been amplified from a genomic DNA contaminant of the total RNA. A reverse primer based on the *A. ochraceus* sequence was designed to amplify the approximately 600 missing bp including the initial methionine. The *A. ochraceus* cDNA library was then used as a template for PCR. The forward primer was based on the reverse complement of vector pSport1 (Life Technologies) bases 299 to 326. The other primer, A.oxred-rev2 was bases on the *A. ochraceus* sequence encoding residues 326-333.

```
Primer pSport-for1:
CAAGCTCTAATACGACTCACTATAGGGA      (SEQ ID NO: 13)

Primer A. oxred-rev2:
CAGGAACCGATCGACCTCGGAA            (SEQ ID NO: 14)
```

The *A. ochraceus* spore library size made from gel-purified fragments >1.5 kb in size was then used as a template for amplifying the final 200 bases of coding region. Two new reverse primers were designed from the A.oxred sequence, and a new forward primer based on pSport1 (bases 295-328) was also used.

```
Primer A. oxred-rev3:
GTCACCCTCACCAGCAGAGCCAATG         (SEQ ID NO: 15)

Primer A. oxred-rev4:
CCACATTGCGAACCATAGCGTTGTAGTG      (SEQ ID NO: 16)

Primer pSport-for2:
GCCAAGCTCTAATACGACTCACTATAGGGAAAGC (SEQ ID NO: 17)
```

Amplification was performed using an Elongase polymerase kit (Life Technologies, Rockville Md) for 35 cycles consisting of a denaturation step at 94° C. for 30 seconds, an annealing step at 63° C. for 30 seconds, and an elongation step at 68° C. for 5 minutes. The PCR products were cloned directly into pCRII TOPO (Invitrogen). Twelve clones were sequenced, and the composite sequence, extended for 232 bases upstream of the initial methionine, and included 2 in-frame stop codons (Data not shown).

Primers incorporating the complete coding region of A.oxred were designed with a 5' SalI site and a 3' XhoI site for ligation into expression vector pFastBac1.

```
Primer A. oxred-for2:
gtcgacATGGCGCAACTCGATACTCTC       (SEQ ID NO: 18)

Primer A. oxred-rev5:
ctcgagttaGGACCAGACATCGTCCTGGTAG   (SEQ ID NO: 19)
```

*A. ochraceus* total RNA was used as a template for PCR with these primers and the Elongase kit. Amplification consisted of 35 cycles with a 30 second denaturation step at 94° C., a 30 second annealing step at 64° C., and a 5 minute elongation step at 68° C. An aliquot of the cDNA from reaction ran as a single band of approximately 2.1 kb.

Construction of pMON45630

The PCR products were cloned directly into pCRII-TOPO (Invitrogen, Carlsbad, Calif.). All clones contained the internal intron noted earlier. One clone was designated pMON45630.

Construction of pMON45631 and pMON45632

A strategy based on two step PCR from an internal BamHI site approximately 170 bp upstream of the 5' splice site was employed to generate clones lacking the intron.

```
Primer A. oxred-for3:
GGATCCCTCGCGACCTGTGATCAT          (SEQ ID NO: 20)

Primer A. oxred-for4:
CGAAGATTTCTTGTACAAGGATGAATGGAAGACTTTTC (SEQ ID NO: 21)

Primer A. oxred-rev6:
CTGAAAAGTCTTCCATTCATCCTTGTACAAGAAATC (SEQ ID NO: 22)
```

Primers A.oxred-for4 and rev6 were complementary and flanked the intron. The first PCR reaction used an A.oxred clone linearized at the internal BamHI site as template. Polymerase and buffers were supplied by the PCR core kit (Roche Molecular Biochemicals, Indianapolis, Ind.). Primer and dNTP concentrations were 500 nM and 200 uM, respectively. Two reactions were performed, using a combination of A.oxred-for3 with A.oxred-rev6, and A.oxred-for4 with A.oxred-rev5. Following a 2 minute initial denaturation, 28 cycles of PCR amplification were performed. One cycle included a 45 second denaturation at 94° C., a 45 second denaturation step at 62° C. and a 45 second elongation step at 72° C. One ul of each reaction served as template for the second PCR amplification with primers A.oxred-for3 and A.oxred-rev5 using Elongase enzyme and buffers. Amplification consisted of 30 cycles with a 30 second denaturation step at 94° C., a 30 second annealing step at 62° C., and a 5 minute elongation step at 68° C. The PCR products were directly cloned into pCRII-TOPO. DNA sequencing demonstrated that the intron had been removed. This clone was designated pMON45631.

Plasmid pMON45632 was constructed in a three-way ligation by ligating the SalI/BamHI fragment from pMON45630 with the BamHI/XhoI fragment from pMON45631 and vector pFastBac1, which had been cut with SalI and XhoI and de-phosphorylated to enhance the recovery of vectors with the desired inserts.

The nucleotide and amino acid sequences of the cloned *Aspergillus ochraceus* 11 oxidoreductase are displayed in FIG. 3 as SEQ ID NO: 5 and SEQ ID NO: 6, respectively. FIG. 7 sets forth the amino acid homology of *Aspergillus ochraceus* and human oxidoreductase to NADPH cytochrome P450 reductases from *A. niger*, mouse, and *S. cerevisiae*. FIG. 8 sets forth the amino acid alignment for *A. ochraceus*, *A. niger*, and *S. cerevisiae* oxidoreductases. FIG. 9 is a phylogenetic tree showing the relatedness of *Aspergillus ochraceus* and human oxidoreductase to reductases from *A. niger*, yeast, and mouse. FIG. 10 shows the percent homology between *Aspergillus ochraceus* steroid 11 alpha hydroxylase and the oxidoreductases from *A. niger*, yeast, and mouse, calculated using Clustal W and Boxshade.

Example 15

Generation of Polyclonal Antibodies Recognizing *Aspergillus ochraceus* 11 Alpha Hydroxylase and *Aspergillus ochraceus* NADPH Cytochrome p450 Reductase Generation of Anti-11-α-hydroxylase Antibodies Polyclonal antibodies against *Aspergillus ochraceus* 11 alpha hydroxylase and NADPH cytochrome p450 reductase were raised in rabbits against synthetic peptides (prepared by Sigma/Genosis, The Woodlands, Tex.) corresponding to several regions of the following predicted protein sequences:

```
11aOH peptide 1:
AAAYWLATLQPSDLPELN          (SEQ ID NO: 23)

11aOH peptide 2:
CRQILTPYIHKRKSLKGTTD        (SEQ ID NO: 24)

11aOH peptide 3:
HMGFGHGVHACPGRFFASNEI       (SEQ ID NO: 25)

oxr peptide 1:
CTYWAVAKDPYASAGPAMNG        (SEQ ID NO: 26)
```

The 11aOH peptide 2 (SEQ ID NO: 24) corresponds to the G helix, G/H loop, and H helix region present in an alignment of the amino acid sequence of 11 alpha hydroxylase with the corresponding sequence of CYP3A4 described by Wang and Lu, (Drug Metab. Dispos. 25(6), 762-767, 1997). The 11aOH peptide 3 (SEQ ID NO: 25) corresponded to the peptide fragment from the heme-binding domain.

Immunological grade peptides were monitored for purity using reverse phase high performance liquid chromatography (HPLC). Each peptide was conjugated to keyhole limpet hemacyanin (KLH) and suspended in Complete Freund's Adjuvant. The conjugated peptide was then injected subcutaneously at multiple sites into rabbits. Each conjugated peptide was injected into two rabbits. All subsequent immunizations were given in incomplete Freund's Adjuvant. In general, five subsequent injections were given at two-week intervals following the initial immunization. IgG fractions were affinity-purified using a Sepharose-Protein A column. Fractions from the two rabbits injected with each peptide were combined at a 1:1 ratio. The pooled anti-11 alpha hydroxylase (rabbits GN 1187/1188) was 0.34 mg/ml IgG. The pooled anti-oxred (rabbits GN 2023/2024) was 0.26 mg/ml IgG. The combined IgGs were each diluted 1:10, 1:100 and 1:1,000 for a pilot experiment to determine which was dilution was optimal for probing Western blots. The 1:10 dilution gave the best results and was used for probing subsequent Westerns.

Example 16

Insect Cell Infection and Heterologous Expression

Proteins were expressed in Sf9 insect cells using baculovirus shuttle vectors (Luckow et al., J. Virol. 67:4566-4579, 1993). The baculovirus shuttle vector (bacmid) contains a mini-F replicon for expression in bacterial cells, a kanamycin resistance marker for selection, and attTn7 [the target site for the bacterial Tn7 transposon) within the lacZα sequence. Each of these elements is inserted into the polyhedrin locus of the Autographa californica nuclear polyhedrosis virus (AcNPV, the native baculovirus) genome. A donor plasmid (pFastBac1, Life Technologies) was used to deliver the gene to be expressed and was inserted into the bacmid via the bacterial Tn7 transposition elements. pFastBac1 contains the Tn7 left and right ends flanking the polyhedrin promoter, a polylinker cloning sequence, the SV40 polyA transcription termination sequence, and the gentamicin resistance gene for selection. Recombinant viruses were generated following transformation of the pFastBac1 plasmid, which contained a single 11 alpha hydroxylase or oxidoreductase cDNA, into DH10Bac E. coli cells (Life Technologies) that contained the bacmid and helper plasmid.

Transfections were performed using CellFectin™ reagent (Life Technologies) following the manufacturer's protocol for Spodoptera frugigperda (Sf9) cells. Cells were seeded in 6-well tissue culture plates at $9 \times 10^5$ cells per well in SF-900 serum-free medium (Life Technologies) and allowed to attach for at least one hour. The transfection mixtures were made following the addition of 5 ul miniprep DNA and 5 μl Cellfectin to polystyrene tubes that contained 200 ul SF-900 medum. The mixtures were allowed to incubate for 15-30 minutes at room temperature. Prior to transfection, 800 ul SF-900 medium was added to each tube. The cells were washed one time with 2 ml SF-900 medium, and the DNA mixtures were added to the cells. The cultures were allowed to incubate for 5 hours at 27° C. Following the 5 hr incubation period, the transfection mixture was removed and the cultures were replenished with 3 ml per well IPL-41 medium (Life Technologies) supplemented with 10% fetal bovine serum. Following a three day incubation period, the cells were harvested, centrifuged, and the supernatant that contained recombinant virus (designated as passage 1 or P1 stock) was removed and stored at 4° C. A larger viral stock was made by infecting 100 ml fresh Sf9 cells at $5 \times 10^5$ cells per ml with 0.5 ml of the P1 medium. This larger (P2) stock was then titered using a plaque assay protocol (O'Reilly et al., 1992), and used for production of the 11 alpha hydroxylase or oxidoreductase enzymes, separately or in combination with each other.

FIG. 14 sets forth an immunoblot illustrating expression of Aspergillus ochraceus P450 11 alpha hydroxylase in baculovirus-infected insect cells harvested at 25 and 48 hours post infection. The nitrocellulose membrane was probed with a 1:1 mixture of antibodies prepared two rabbits immunized with a conjugated synthetic peptide 11aOH peptide 2 (SEQ ID NO 24).

FIG. 15 sets forth an immunoblot illustrating expression of Aspergillus ochraceus P450 oxidoreductase in baculovirus-infected insect cells harvested at 25 and 48 hours post infection. The nitrocellulose membrane was probed with a 1:1 mixture of antibodies prepared two rabbits immunized with a conjugated synthetic peptide oxr peptide 1 (SEQ ID NO 26).

Example 17

Co-infection Baculoviruses Expressing of Aspergillus ochraceus 11 Alpha Hydroxylase and Human Oxidoreductase Sf9 cells were co-infected with virus particles that contained the steroid 11 alpha hydroxylase cDNA and a separate virus containing a human NADPH P450-oxidoreductase. Both viruses were added at a multiplicity of infection (MOI) ratio of 0.1:0.01 (11 aOH to oxr). One day after infection, 0.9 μg/ml hemin chloride was added to the culture. The cells were harvested by centrifugation three days after infection (unless specified differently), and the washed cell pellets were frozen until processed for sub-cellular fractions.

Example 18

Co-infection Baculoviruses Expressing of Aspergillus ochraceus 11 Alpha Hydroxylase and Aspergillus ochraceus oxidoreductase Sf9 cells are co-infected with virus particles that contain the steroid 11 alpha hydroxylase cDNA and a separate virus containing A. Ochraceus NADPH P450-oxidoreductase. Both viruses are added at a multiplicity of infection (MOI) ratio of 0.1:0.01 (11 aOH to oxr). One day after infection, 0.9 μg/ml hemin chloride is added to the culture. The cells are harvested by centrifugation three days after infection (unless specified differently), and the washed cell pellets are frozen until needed in subsequent experiments that require processing into for sub-cellular fractions.

Example 19

Preparation of Subcellular Fractions from Baculovirus-infected Insect Cells

One half gram of the cell pastes from infected sf9 cells and uninfected control cells were thawed and suspended in 40 ml of 0.25 M sucrose with 10 mM KHPO4, adjusted to pH 7.4. The suspensions were homogenized using a Fisher Sonic Dismembrator, model 300 probe sonicator (Fisher Scientific, St. Louis, Mo.). The samples were transferred to a conical centrifuge tube (Corning Costar Corporation, Cambridge, Mass.) and subjected to centrifugation at 500×g at 5° C. for 15 minutes. The pellets were resuspended in the same volume of fresh buffer and viewed under a microscope to confirm complete lysis. Few or no whole cells were observed. The supernatants were then subjected to centrifugation at 10,000×g for 30 minutes at 5° C. to collect mitochondria, Golgi and other subcellular organelles. The pellets were resuspended in fresh buffer and subjected to centrifugation at 7,800×g for 30 minutes at 5° C. to collect mitochondria.

The mitochondrial pellets were resuspended in buffer as described about and the centrifugation was repeated. The mitochondrial pellets were resuspended in 2 ml buffered sucrose solution and stored at −80° C. in 100 ul aliquots.

The supernatants from the original mitochondrial fractionation were subjected to centrifugation at 200,000×g for 1 hour at 5° C. The microsomal pellets were resuspended in 2 ml buffered sucrose solution and stored at −80° C. in 100 ul aliquots.

Microsomal Incubations

Incubation mixtures consisted of Sf9 microsomes (1.0 mg of protein/mL final concentration), an NADPH-generating system and 250 uM substrate (AD) in 100 mM potassium phosphate buffer, pH 7.4 or 150 mM HEPES buffer, pH 7.4. The NADPH-generating system was composed of the following at the indicated final concentrations: $MgCl_2$ (7.5 mM), D-glucose-6-phosphate (7.5 mM), NADP (0.80 mM), and glucose-6-phosphate dehydrogenase (1.0 units/mL). Incubations were carried out for the indicated times at 37° C. in a water bath. Following incubation, reactions were terminated by the addition of 0.3 ml methanol. The samples were vortexed three times for two seconds and placed on ice, or stored at −70° C. for later analysis.

Example 20

HPLC Assays to Measure Conversion of Steroid Substrates to Their Hydroxylated Counterparts High Performance Liquid Chromatography (HPLC)

The HPLC method used to separate hydroxylated steroid compounds from steroid substrates, such as 11α-hydroxyandrostenedione from androstenedione, is a modified version of the testosterone hydroxylase assay, described by Sonderfan et al., Arch. Biochem. Biophys. 255:27-41, 1987). The standards for androstenedione and 11-beta-hydroxyandrostenedione were obtained from Sigma. 11-alpha-hydroxyandrostenedione (89.5% pure, with the major impurity being androstenedione) was provided by Searle Medicinal Chemistry. HPLC grade water and methanol were obtained from Burdick & Jackson.

The HPLC system consisted of a Model 1050 series pump, autoinjector and variable wavelength detector (Hewlett-Packard, Naperville, Ill.), and a Model TC-50 temperature controller and Model CH-30 column heater (both Eppendorf, Madison, Wis.).

Cell membrane fractions derived from insect cells transfected with recombinant baculoviruses expressing 11-hydroxylase and complementary electron transport proteins were analyzed for 11-hydroxylase activity in a reaction mixture containing 80 mM phosphate buffer, pH 7.4, 8 mM $MgCl_2$, and 0.9 mM $NADP^+$ in a final volume of 200 ul. In order to insure an adequate source of reducing equivalents, an NADPH regenerating system was provided by adding glucose-6-phosphate dehydrogenase (1.5 U/ml) and 8 mM glucose-6-phosphate. Steroid substrate (e.g., androstenedione) was provided at a final concentration of 0.3 mM.

Reaction mixtures were incubated at 37° C. for 30 min. The reactions were terminated by the addition of 200 ul methanol and then placed on ice. Samples were pelleted by centrifugation to remove precipitated protein.

On one occasion, the incubation was carried out in a volume of 0.5 ml in siliconized polypropylene 1.5 ml microcentrifuge tubes at 37° C. for 120 minutes. The enzyme, prepared from microsomal or mitochondrial fractions, was added and the substrate added at a concentration of 250 μM (e.g., 25 mM methanol stock solution of AD). The cofactor buffer was 100 mM potassium phosphate, pH 7.4, 7.5 mM $MgCl_2$, 7.5 mM glucose-6-phosphate, 0.80 mM NADP, and 1.0 units/mL glucose-6-phosphate dehydrogenase. HPLC samples were prepared by terminating the 0.5 ml reaction mixture by addition of 0.3 ml methanol, vortexing three times for 2 seconds and storing on ice. The tubes were spun for 5 minutes at ~20,000×g in a microcentrifuge and the samples transferred to autosampler vials and capped.

Steroid components present in reaction mixtures and media extract were separated and analyzed by reverse phase HPLC using a 250 mm×4 mm Vydac analytical C-4 column. Chromatograms were developed using a solvent gradient from 40% to 100% methanol over a ten minute time period and holding at 100% methanol for 5 minutes before re-equilibration to initial conditions. The column effluent was monitored for UV absorbance at both 254 and 220 nm.

Androstenedione, testosterone and monohydroxylated androstenedione metabolites were resolved on a Nova-pak C18 column, 4 micron, 3.9×150 mm (Waters Chromatography, Milford, Mass.) equipped with a 0.22 micron Rheodyne precolumn filter at 40° C. and 1.0 ml mobile phase/min. A stepped gradient was utilized with water as mobile phase solvent A and methanol as solvent B. The initial concentration of solvent B was 42% for 6 min. The percentage of B was increased linearly to 45% over 4 minutes and then held for 3 minutes. The percentage of B was then increased linearly to 80% over 10 minutes and held there for an additional 2 minutes for a total run time of 25 minutes. The ultraviolet detection wavelength was 247 nm and the injection volume was 200 ul.

Both the "mitochondria" sample and the "microsomal" sample produced peaks matching the HPLC retention time of the 11α-hydroxyandrostenedione standard, while other fractions did not. These "mitochondria" and "microsomal" peaks were 3.2 and 2.3%, respectively, of the total peak area quantitated at 247 nm. The 11α-hydroxyandrostenedione standard was also spiked into a blank microsomal incubation sample at a concentration of 5.0 µg/mL. The concentration of the "mitochondria" and "microsomal" 11α-hydroxyandrostenedione peaks were 1.75 and 1.31 µg/mL, after correcting for the purity of the standard (89.5%). These concentrations represent 2.3 and 1.7% of substrate converted to 11α-hydroxyandrostenedione, using a substrate concentration of 250 µM.

FIG. 16 sets forth an HPLC tracing illustrating the conversion of androstenedione (AD) to its 11 alpha hydroxy counterpart after incubating AD with subcellular fractions prepared from baculovirus-infected insect cells expressing *Aspergillus ochraceus* 11 alpha hydroxylase and human oxidoreductase.

Example 21

Recognition of *Aspergillus ochraceus* 11 Alpha Hydroxylase and *Aspergillus ochraceus* NADPH Cytochrome p450 Reductase by Immunoblotting Using Polyclonal Antibodies Generated Against Synthetic Peptides Proteins from Sf9 cell lysates (obtained from uninfected and recombinant baculovirus-infected cells) were loaded onto lanes of a 10% gradient acrylamide mini gel (BioRad, Hercules, Calif.) at equal concentrations (10 µg per well). The proteins were separated by electrophoresis at 16 mAmps constant current for approximatley 1 hr in a Trisglycine buffer containing 0.1% SDS (Sigma, St. Louis, Mo.). The proteins were transferred to nitrocellulose (Schleicher & Schuell, Keene, N.H.) for 40 min at 70 mAmp constant current. Primary antibodies were diluted 1:10 (from stock concentrations of 0.34 mg/ml IgG for anti-11 alpha hydroxylase (antibodies GN-1187 and GN-1188 prepared from peptide 11aOH peptide 2 CRQILTPYIHKRKSLKGTTD (SEQ ID NO: 24)), and 0.26 mg/ml IgG for anti-oxred (antibodies GN-2023 and GN-12024 prepared from oxr peptide 1 CTYWAVAKDPYASAGPAMNG (SEQ ID NO: 26)) and used to probe the nitrocellulose membrane. The antigens were detected using anti-rabbit horseradish peroxidase (HRP)-linked secondary antibody as recommended by the manufacturer (New England Biolabs, Beverly, Mass.). Chemilumiescence was detected using luminol and peroxide reagents (New England Biolabs, Beverly, Mass.) following the protocol provided by the vendor. Light emission was recorded using X-OMAT AR film (Eastman Kodak Company, Rochester, N.Y.). Images were recorded using a Minolta Dimage V digital camera (Minolta Corporation, Ramsey, N.J.).

Example 22

Characterization of the *Aspergillus ochraceus* Genomic DNA Encoding 11 Alpha Hydroxylase and Oxidoreductase The approaches described above can be used to facilitate the identification of genes encoding steroid hydroxylases and oxidoreductases within the genome of *Aspergillus ochraceus* and closely related microorganisms, including *Aspergillus niger* and *Aspergillus nidulans*. Other preferred organisms are *Rhizopus oryzae, Rhizopus stolonifer, Streptomyces fradiae, Bacillus megaterium, Pseudomonas cruciviae, Trichothecium roseum, Fusarium oxysporum f.* sp. *cepae, Rhizopus arrhizus,* and *Monosporium olivaceum*. Other preferred organisms that are known to have steroid 11 alpha hydroxylase activity are described in the detailed description of the invention, above.

Briefly, genomic DNA is prepared and shotgun cloned into low copy artificial chromosomes propagated in bacteria. A large number of clones are sequenced to ensure statistical representation of the entire genome, and the sequences of overlapping clones merged to produce the final map and sequence of the genome. Analysis of the open reading frames, will reveal regions which are homologous to the steroid hydroxylase and oxidoreductase genes of the present invention, and regions of the translated open reading frames which are homologous to these enzymes using programs designed to facilitate multiple sequence alignments of nucleotide and protein sequence data such as BLAST, CLUSTAL W, and BoxShade. Genes which encode these proteins are obtained from the artificial chromosomes and recloned into expression vectors such as pFastBac1, transformed into appropriate host cells, which are assayed for the presence of enzymes capable of carrying out the conversion of steroid substrates to their oxidized counterparts.

It is intended that the scope of the present invention be determined by reference to the appended claims. It is recognized that a number of variations can be made to this invention as it is currently described but which do not depart from the scope and spirit of the invention without compromising any of its advantages. These include isolation of homologous genes from microorganisms known to carry out 11 alpha hydroxylation of steroid substrates, preferably fungi and bacteria. This invention is also directed to any substitution of analogous components. This includes, but is not restricted to use of these techniques to isolate other P450s which are involved in steroidogenesis, including hydroxylases that act at other positions in the core molecule, and use of these enzymes to facilitate bioconversion of steroid intermediates in modified host microorganisms.

All references, patents, or applications cited herein are incorporated by reference in their entirety, as if written herein.

REFERENCES

Altschul S F; Gish W; Miller W; Myers E W; Lipman D J Basic local alignment search tool. J. Molec. Biol. (Oct. 5, 1990), 215(3), 403-10.
Anfossi et al., Proc. Natl. Acad. Sci. (U.S.A.) 86:3379-3383 (1989)
Arfin et al. Proc. Natl. Acad. Sci. (U.S.A.) 92:7714-7718 (1995)
Armour, et al., FEBS Lett. 307:113-115 (1992)
Baldwin et al., Gene Ther. 4:1142-1149 (1997)
Barany, Proc. Natl. Acad. Sci. (U.S.A.) 88:189-193 (1991)
Bassat et al., J. Bacteriol. 169:751-757 (1987)
Baum et al., J. Hematother. 5: 323-329 (1996)
Becker et al., EMBO J. 8:3685-3691 (1989)
Ben-Bassat et al., J. Bacteriol. 169:751-757 (1987)
Berkner, BioTechniques 6:616-629 (1988)
Berkner, Current Top. Microbiol. Immunol. 158:39-66 (1992)
Blobel and Dobberstein, J. Cell Biol. 67:835-851 (1975)
Boris-Lawrie and Temin, Annal. New York Acad. Sci. 716:59-71 (1994)
Boris-Lawrie and Temin, Curr. Opin. Genet. Dev. 3:102-109 (1993)
Bostian et al., Cell 36:741-751 (1984)
Botstein et al., Ann. J. Hum. Genet. 32:314-331 (1980)
Bregni et al., Blood 80:1418-1422 (1992)
Breskvar K, Cresnar B, Plaper A, Hudnik-Plevnik T. Localization of the Gene Encoding Steroid Hydroxylase Cytochrome P-450 from *Rhizopus Nigricans* inside a HindIII Fragment of Genomic DNA. *Biochem. Biophys. Res. Commun* 1991; 178, 1078-1083.
Brody and Crystal, Annal. New York Acad. Sci. 716:90-103 (1994)
Capecchi, Cell 22:479-488 (1980)
Chen et al., Gene Ther. 5:50-58 (1998)
Clapp, Clin. Perinatol. 20:155-168 (1993)
Collins, In: Alternative Immunoassays, John Wiley & Sons, NY (1985)
Corbi and Lopez-Rodriguez, Leuk. Lymphoma 25:415-425 (1997)
Crabeel et al., EMBO J. 2:205-212 (1983)
Curiel et al., Hum. Gen. Ther. 3:147-154 (1992)
Current Protocols in Molecular Biology, John Wiley & Sons, N.Y. (1989)
Czerwinski, M., Sahni, M., Madan, A. and Parkinson, A. Polymorphism of human CYPOR: Expression of new allele. Unpublished, Direct Submission [AAG09798]
Datta et al., Proc. Natl. Acad. Sci. USA 85:3324-2238 1(1988)
Derynck et al., Nucleic Acids Res. 11:1819-1837 (1983)
Dobson et al., Nucleic Acids. Res. 11:2287-2302 (1983)
Dunbar et al., Blood 85:3048-3057 (1995)
Dutta T K, Datta J, Samanta T B: Onset of new catalytic activity in immobilized spores of *Aspergillus ochraceus* TS due to in situ germination: C17-C20 lysis accompanies 11 alpha-hydroxylation of steroid. *Biochem. Biophys. Res. Commun.* 192:119-123 (1993).
Eglitis and Anderson, Biotechniques, 6:608-614 (1988)
ELISA and Other Solid Phase Immunoassays (Kemeny, et al., Eds.), John Wiley & Sons, NY (1988)
Elshami et al., Cancer Gene Ther. 4:213-221 (1997)
Engel, L. and White, J. Antibodies to 100- and 60-kDa surface proteins inhibit substratum attachment and differentiation of rodent skeletal myoblasts. *Dev Biol.* 140:196-208, 1990
Fackrell, Clin. Immunoassay 8:213-219 (1985)
Fernandez de Henestrosa et al., FEMS Microbiol. Lett. 147:209-213 (1997)
Frohman, M. A. et al., Proc. Natl. Acad. Sci. (U.S.A.) 85:8998-9002 (1988)
Fromm et al., Nature 319:791 (1986)
Fromm et al., Proc. Natl. Acad. Sci. (U.S.A.) 82:5824-5828 (1985)
Gerwirtz et al., Science 242:1303-1306 (1988)
Ghosh D, Samanta T B. 11α-hydroxylation of Progesterone by Cell Free Preparation of *Aspergillus ochraceus* TS. *J. Steroid Biochem.* 1981; 14, 1063-1067.
Goff et al., EMBO J. 9:2517-2522 (1990)
Goodchild et al., Proc. Natl. Acad. Sci. (U.S.A.) 85:5507-5511 (1988)
Goodhue, Charles T. "The methodology of microbial transformation of organic compounds." Editor(s): Rosazza, John P. Microb. Transform. Bioact. Compd., 1:9-44, 1982.
Graham and van der Eb, Virology 54:536-539 (1973)
Gray et al., Proc. R. Acad. Soc. Lond. 243:241-253 (1991)
Griffith et al. Chem. Biol. 4:461-471 (1997)
Griffiths et al., Biochem. J. 241:313-324 (1987)
Guarente and Ptashne, Proc. Natl. Acad. Sci. (U.S.A.) 78:2199-2203 (1981)
Gusella, Ann. Rev. Biochem. 55:831-854 (1986)
Hallek et al., Cytokines Mol. Ther. 2:69-79 (1996)
Haniu, M., Iyanagi, T., Miller, P., Lee, T. D. and Shively, J. E. Complete amino acid sequence of NADPH-cytochrome P-450 reductase from porcine hepatic microsomes. *Biochemistry* 25 (24), 7906-7911 (1986) {P04175}
Haniu, M., McManus, M. E., Birkett, D. J., Lee, T. D. and Shively, J. E. Structural and functional analysis of NADPH-cytochrome P-450 reductase from human liver: complete sequence of human enzyme and NADPH-binding sites Biochemistry 28 (21), 8639-8645 (1989) [P16435].
Harley and Reynolds, Nucleic Acids Res. 15:2343-2361 (1987)
Harlow and Lane, *In Antibodies: A Laboratory Manual*, Cold Spring Harbor Press, Cold Spring Harbor, N.Y. (1988)
Harms and Splitter, Hum. Gene Ther. 6:1291-1297 (1995)
Hasan et al., Gene 56:141-151 (1987)
Hattori et al., Genes Dev. 6:609-618 (1992)
Hawley and McClure, Nucleic Acids Res. 11:2237-2255 (1983)
Haymes, et al. Nucleic Acid Hybridization, A Practical Approach, IRL Press, Washington, D.C. (1985)
Hillel et al., Anim. Genet. 20:145-155 (1989)
Hillel et al., Genet. 124:783-789 (1990)
Hitzeman et al., Nature 293:717-722 (1981)
Holt et al., Molec. Cell. Biol. 8:963-973 (1988)
Ingber et al. Nature 348:555-557, (1990)
Janknecht et al., Carcinogenesis 16:443-450 (1995)
Janknecht Immunobiology 193:137-142 (1995)
Jayanthi C R, Madyastha P, Madyastha K M. Microsomal 11α-Hydroxylation of Progesterone in *Aspergillus ochraceus*: Part I: Characterization of the Hydroxylase System. *Biochem. Biophys. Res. Commun.* 106:1262-1268, 1982.
Jefferson et al., EMBO J. 6:3901-3907 (1987)
Jefferson Plant Mol. Biol. Rep. 5:387-405 (1987)
Jeffreys et al., Amer. J. Hum. Genet. 39:11-24 (1986)
Jeffreys et al., Anim. Genet. 18:1-15 (1987)
Jeffreys et al., Nature 316:76-79 (1985)
Johnston and Tang, Methods Cell Biol. 43:353-365 (1994)
Jones et al., Eur. J. Haematol. 39:144-147 (1987)
Julius et al., Cell 32:839-852 (1983)
Julius et al., Cell 36:309-318 (1984)
Katagiri, M., Murakami, H., Yabusaki, Y., Sugiyama, T., Okamoto, M., Yamano, T. and Ohkawa, H. Molecular cloning and sequence analysis of full-length cDNA for rabbit liver NADPH-cytochrome P-450 reductase mRNA. *J. Biochem.* 100 (4), 945-954 (1986) [P00389]
Kendall and Bradshaw, J. Biol. Chem. 267:20667-20673 (1992)
Kennedy, J., Auclair, K., Kendrew, S. G., Park, C., Vederas, J. C. and Hutchinson, C. R. Accessory Proteins Modulate Polyketide Synthase Activity During Lovastatin Biosynthesis. Science (1999) In press LOCUS AAD34552 528 aa PLN 02 Jun. 1999
Kieslich, K.; Sebek, O. K. "Microbial transformations of steroids." Ges. Biotechnol. Forsch Braunschweig-Stoeckheim, Fed. Rep. Ger. Annu. Rep. Ferment. Processes, 3:275-304., 1979.
Kieslich, Klaus. "Steroid conversions." Ges. Biotechnol. Forsch. m.b.H., Braunschweig-Stoeckheim, Fed. Rep. Ger. Econ. Microbiol. 5 (Microb. Enzymes Bioconvers.), 369-465, 1980.
King and Possee, The Baculovirus Expression System: A Laboratory Guide, London, Chapman & Hall
Kurjan and Herskowitz, Cell 30:933-943 (1982)
Kusaka et al., Biochem. Biophys. Res. Commun. 174:1070-1076 (1991)
Kwoh et al., Proc. Natl. Acad. Sci. (U.S.A.) 86:1173 (1989)

Laboratory Techniques and Biochemistry in Molecular Biology, by Work, et al., North Holland Publishing Company, NY (1978)

Lacour, Thierry, Tilman Achstetter and Bruno Dumas. "Characterization of Recombinant Adrenodoxin Reductase Homologue (Arh1p) from Yeast" *Journal of Biological Chemistry* 273, 23984-23992 (1998).

Landegren et al., Science 241:1077-1080 (1988)

Langer R. et al., Chem. Tech. 12:98 (1982)

Li and Chang, Biochem. Biophys. Res. Comm. 227:152-159 (1989)

Lorz et al., Mol. Gen. Genet. 199:178 (1985)

Lu et al., J. Exp. Med. 178:2089-2096 (1993)

Luckow et al., J. Virol. 67:4566-4579 (1993)

Luckow, V. A. In: Protein Eng. J. L. Cleland., Wiley-Liss, New York, N.Y.: 183-2180 (1996)

Makovec and Breskvar, Purification of cytochrome P450 from filamentous fungus *Rhizopus nigricans*. Pflugers Arch—Eur J. Physiol 439(Suppl): R111-R112, 2000.

Makovec T, Breskvar K. "Purification and characterization of NADPH-cytochrome P450 reductase from filamentous fungus *Rhizopus nigricans*." Arch Biochem Biophys. 357, 310-6 (1998)

Marcotte et al., Nature 335:454-457 (1988)

Marsh, Nucleic Acids Res. 14:3603 (1986)

McCarty et al., Cell 66:895-905 (1991)

McCowen et al., Science 113:202-203 (1951)

Miller Current Top. Microbiol. Immunol. 158:1-24 (1992)

Miller et al., Proc. Natl. Acad. Sci. (U.S.A.) 91:2473-2477 (1987)

Moore et al., Genomics 10:654-660 (1991)

Mori and Prager, Leuk. Lymphoma 26:421-433 (1997)

Mouyna, I. and Brygoo, Y. Disruption of a *Fusarium oxysporum* f.sp. *elaeidis* cytochrome P450 gene by a repetitive sequence. Unpublished LOCUS CAA57874 294 aa PLN 21 Jul. 1997

Mullis et al., Cold Spring Harbor Symp. Quant. Biol. 51:263-273 (1986)

Myers E W, Miller W. "Approximate matching of regular expressions" *Bull Math Biol*. 51:5-37 (1989).

Nelson D R, Koymans L, Kamataki T, Stegeman J J, Feyereisen R, Waxman D J, Waterman M R, Gotoh O, Coon M J, Estabrook R W, Gunsalus I C, and Nebert D W. P450 superfamily: Update on New Sequences, Gene Mapping, Accession Numbers and Nomenclature. *Pharmacogenetics* 1996; 6, 1-42.

Ngo et al., In: Enzyme Mediated Immunoassay, Plenum Press, NY (1985)

Nickerson et al., Proc. Natl. Acad. Sci. (U.S.A.) 87:8923-8927 (1990)

No Authors. Genome sequence of the nematode *C. elegans*: a platform for investigating biology. The *C. elegans* Sequencing Consortium. Science 282 (5396), 2012-2018 (1998) [Published errata appear in Science Jan. 1, 1999; 283(5398):35 and Mar. 26, 1999;283(5410):2103 and Sep. 3, 1999;285(5433):1493]] LOCUS CAA91268 510 aa INV 13 Jul. 2000

Norman et al., Vaccine 15:801-803 (1997)

Nussbaumer et al., FEMS Microbiol. Lett. 118:57-63 (1994)

O'Neill et al., Transplant Proc. 23:2862-2866 (1991)

Obukowicz et al., Applied Environmental Microbiology 58:1511-1523 (1992)

Ohara et al., Proc. Natl. Acad. Sci. (U.S.A.) 86:5673-5677 (1989)

Ohgiya, S., Shinriki, N., Kamataki, T. and Ishizaki, K. Mouse NADPH-cytochrome P-450 oxidoreductase: molecular cloning and functional expression in yeast. Biochim. *Biophys. Acta* 1186 (1-2), 137-141 (1994) [BAA04496 P37040].

O'Reilly et al., Baculovirus Expression Vectors: A Laboratory Manual. New York, W.H. Freeman and Company (1992)

Ow et al., Science 234:856-859 (1986)

Peseckis et al., J. Biol. Chem. 267:5107-5114 (1993)

Porter, T. D. and Kasper, C. B. Coding nucleotide sequence of rat NADPH-cytochrome P-450 oxidoreductase cDNA and identification of flavin-binding domains. *Proc. Natl. Acad. Sci. U.S.A.* 82 (4), 973-977 (1985) [P00388]

Potrykus et al., Mol. Gen. Genet. 205:193-200 (1986)

Rachal et al., EXS 64:330-342 (1993)

Ray et al., Adv. Exp. Med. Biol. 280:107-111 (1990)

Remington's Pharmaceutical Sciences, 16th ed., Osol, Ed., Mack, Easton Pa. (1980)

Roderick and Matthews, Biochemistry 32:3907-3912 (1993)

Romanos et al., Yeast 8:423-488 (1992)

Rose et al., Proc. Natl. Acad. Sci. (U.S.A.) 78:2460-2464 (1981)

Rothman and Orci, Nature 355:409-415 (1992)

Samanta T B, Ghosh D K Characterization of progesterone 11 alpha-hydroxylase of *Aspergillus ochraceus* TS: a cytochrome P-450 linked monooxygenase. *J Steroid Biochem* 28, 327-32 (1987)

Samanta T B, Roy N, Chattopadhyay. An Improved 11 α-Hydroxylation of Progesterone by *Aspergillus ochraceus* TS. *Biochem. J.* 1978; 176, 593-594.

Sambrook et al., Molecular Cloning, A Laboratory Manual, 2nd Ed., Cold Spring Harbor Press, Cold Spring Harbor, N.Y. (1989)

Schroeder, G., Unterbusch, E., Kaltenbach, M., Schmidt, J., Strack, D. and Schroeder, J. Light-induced cytochrome P450-dependent enzyme in indole alkaloid biosynthesis: tabersonine 16-hydroxylase FEBS Lett. 458, 97-102 (1999) LOCUS CAB56503 495 aa PLN 23 Sep. 1999

Schulte, U., Aign, V., Hoheisel, J., Brandt, P., Fartmann, B., Holland, R., Nyakatura, G., Mewes, H. W. and Mannhaupt, G., Unpublished LOCUS CAB91316 514 aa PLN 11 May 2000

Serfing et al., Biochim. Biophys. Acta 1263:181-200 (1995)

Shannon et al., Crit. Rev. Immunol. 17:301-323 (1997)

Shephard, E. A., Palmer, C. N., Segall, H. J. and Phillips, I. R. Quantification of cytochrome P450 reductase gene expression in human tissues. Arch. Biochem. Biophys. 294 (1), 168-172 (1992) S90469 [AAB21814]

Sidman U. et al., Biopolymers 22:547 (1983)

Siminszky, B., Corbin, F. T., Ward, E. R., Fleischmann, T. J. and Dewey, R. E,. Expression of a soybean cytochrome P450 monooxygenase cDNA in yeast and tobacco enhances the metabolism of phenylurea herbicides. Proc. Natl. Acad. Sci. U.S.A. 96 (4), 1750-1755 (1999) LOCUS AAB94588 510 aa PLN 02 Mar. 1999

Sin et al. Proc. Natl. Acad. Sci. (U.S.A.) 94:6099-6103 (1997) Skolnick, M. H. et al., Cytogen. Cell Genet. 32:58-67 (1982)

Slijkhuis, Herman; Smaal, Eric Bastiaan; Selten, Gerardus Cornelis Maria. (Roussel-UCLAF, Fr.). Hydrocortisone biosynthesis enzyme expression cassette operable in a recombinant host. U.S. (1999), 102 pp., Cont.-in-part of U.S. Ser. No. 54,185, abandoned. CODEN: USXXAM U.S. Pat. No. 5,869,283 A 19990209.

Smith K E, Ahmed F, Williams R A, Kelly S L. "Microbial transformations of steroids—VIII. Transformation of progesterone by whole cells and microsomes of *Aspergillus fumigatus*". *J Steroid Biochem Mol Biol* 49, 93-100 (1994).

Sonderfan, A. J., Arlotto, M. P., Dutton, D. R., McMillen, S. K., and Parkinson, A. J. Regulation of Testosterone Hydroxylation by Rat Liver Microsomal Cytochrome P-450. Arch. Biochem. Biophys. (1987) 255:27-41.

Suh et al., Gene 169:17-23 (1996)

Sun et al., Curr. Top. Microbiol. Immunol 211:173-187 (1996)

Sutcliffe et al., Proc. Natl. Acad. Sci. (U.S.A.) 75:3737-3741 (1978)

Takai et al., Princess Takamatsu Symp. 22:197-204 (1991)

Tan L, Falardeau P. 11α-Hydroxylation and Degradation of Progesterone-4-$^{14}$C by a Cell-Free Preparation from *Aspergillus ochraceus*. *J. Steroid Biochem.* 1:221-227, 1970.

Thompson J D, Higgins D G, Gibson T J. Improved sensitivity of profile searches through the use of sequence weights and gap excision. *Comput Appl Biosci.* 10:19-29, 1994.

Thompson, Julie D., Desmond G. Higgins, and Toby J. Gibson, CLUSTAL W: improving the sensitivity of progressive multiple sequence alignment through sequence weighting, position specific gap penalties and weight matrix choice. *Nucleic Acids Research,* 22(22):4673-4680, 1994.

Timberlake W E, Hamer J E. Regulation of Gene Activity during Conidiophore Development in *Aspergillus nidulans,* p. 1-29. In Setlow J K and Hollaender A (ed.), Genetic Engineering 1986; vol 8., Plenum Publishing Corp., New York.

Tong et al., Anticancer Res. 18:719-725 (1998)

Tudzynski, B. and Hoelter, K. Characterization of P450 monooxygenase genes from Gibberella fujikuroi. Unpublished LOCUS CAA76703 525 aa PLN 07 Jan. 1999

Tudzynski, B. and Holter, K. Gibberellin biosynthetic pathway in Gibberella fujikuroi: evidence for a gene cluster. Fungal Genet. Biol. 25 (3), 157-170 (1998) [CAA75565 CAA75566 CAA75567]

Tuite et al., EMBO J. 1:603-608 (1982)

Uchimiya et al., Mol. Gen. Genet. 204:204 (1986)

Valenzuela et al., Nature 298:347-350 (1982)

van den Brink, Hans (J.) M., Robert F. M. van Gorcom, Cees A. M. J. J., van den Hondel, and Peter J. Punt. "Cytochrome P450 Enzyme Systems in Fungi" *Fungal Genetics and Biology* 23, 1-17 (1998).

van den Brink, J., van Zeijl, C., van den Hondel, C. and van Gorcom, R. Cloning and characterization of the NADPH cytochrome P450 oxidoreductase (cprA) gene of *Aspergillus niger*. Unpublished [CAA81550, Z26938].

Wagner et al., Proc. Natl. Acad. Sci. (U.S.A.) 89:6099-6103 (1992)

Walker et al., Proc. Natl. Acad. Sci. (U.S.A.) 89:392-396 (1992)

Wang, Regina W.; Lu, Anthony Y. H. Inhibitory anti-peptide antibody against human CYP3A4. *Drug Metab. Dispos.* 25(6), 762-767, 1997

Weinberg et al., Gene 126:25-33 (1993)

Weisemann et al., Biochimie 73:457-470 (1991)

Wickstrom et al., Proc. Natl. Acad. Sci. (U.S.A.) 85:1028-1032 (1988)

Wong and Neumann Biochem. Biophys. Res. Commun. 107:584-587 (1982)

Wu et al., J. Biol. Chem. 268:10796-10781 (1993)

Wu, et al., Genomics 4:560 (1989)

Yabusaki, Y., Murakami, H. and Ohkawa, H. Primary structure of *Saccharomyces cerevisiae* NADPH-cytochrome P450 reductase deduced from nucleotide sequence of its cloned gene. *J. Biochem.* 103 (6), 1004-1010 (1988) [BAA02936].

Yamano, S., Aoyama, T., McBride, O. W., Hardwick, J. P., Gelboin, H. V. and Gonzalez, F. J. Human NADPH-P450 oxidoreductase: complementary DNA cloning, sequence and vaccinia virus-mediated expression and localization of the CYPOR gene to chromosome 7. Mol. Pharmacol. 36 (1), 83-88 (1989) [A60557]

Yanish-Perron et al. Gene 33:103-119 (1985)

Yolken Rev. Infect. Dis. 4:35 (1982)

Zamechik et al., Proc. Natl. Acad. Sci. (U.S.A.) 83:4143-4146 (1986)

---

What is claimed is:

1. An isolated and purified *Aspergillus ochraceus* 11 alpha hydroxylase polypeptide comprising an amino acid sequence of SEQ ID NO: 2.

2. An isolated and purified *Aspergillus ochraceus* 11 alpha hydroxylase polypeptide comprising an amino acid sequence that is at least 99% identical to the sequence of amino acid residues of SEQ ID NO: 2.

3. An isolated and purified *Aspergillus ochraceus* 11 alpha hydroxylase polypeptide comprising an amino acid sequence that is at least 95% identical to the sequence of amino acid residues of SEQ ID NO: 2.

4. A fusion protein comprising the amino acid sequence of the *Aspergillus ochraceus* 11 alpha hydroxylase of claim 3.

5. An isolated and purified *Aspergillus ochraceus* 11 alpha hydroxylase polypeptide encoded by a nucleic acid wherein said nucleic acid specifically hybridizes under highly stringent conditions to the nucleic acid of SEQ ID NO: 1.

* * * * *

SEQUENCE LISTING

```
<160> NUMBER OF SEQ ID NOS: 68

<210> SEQ ID NO 1
<211> LENGTH: 1774
<212> TYPE: DNA
<213> ORGANISM: Aspergillus ochraceus
<220> FEATURE:
<221> NAME/KEY: CDS
<222> LOCATION: (146)..(1690)
<223> OTHER INFORMATION: Aspergillus ochraceus 11 alpha hydroxylase

<400> SEQUENCE: 1
tggaagtttt tacacttatt atgccggagc cgaaagattc tgagtcgagg ggttggggaa      60
caacactata agacctacaa ccacttggat ttggtgaatt tacacgggca ttatcaaaac     120
agccacaagc tgacagctca ttatc atg ccc ttc ttc act ggg ctt ctg gcg     172
                              Met Pro Phe Phe Thr Gly Leu Leu Ala
                               1               5 att tac cat agt ctc ata ctc gac aac cca gtc caa acc ctg agc acc     220
Ile Tyr His Ser Leu Ile Leu Asp Asn Pro Val Gln Thr Leu Ser Thr
 10              15                  20                  25
```

-continued

```
att gtc gta ttg gcg gca gcg tac tgg ctc gca acg ctc cag ccg agc      268
Ile Val Val Leu Ala Ala Ala Tyr Trp Leu Ala Thr Leu Gln Pro Ser
             30                  35                  40 gac ctt cct gag ctg aat ccc gcc aaa cca ttc gag ttc acc aat cgt      316
Asp Leu Pro Glu Leu Asn Pro Ala Lys Pro Phe Glu Phe Thr Asn Arg
         45                  50                  55 cgt cgt gtt cat gag ttt gtt gaa aat agt aag agc ttg ctt gct cgg      364
Arg Arg Val His Glu Phe Val Glu Asn Ser Lys Ser Leu Leu Ala Arg
     60                  65                  70 ggg agg gaa ttg cac ggg cac gag ccg tac aga ctc atg tct gaa tgg      412
Gly Arg Glu Leu His Gly His Glu Pro Tyr Arg Leu Met Ser Glu Trp
 75                  80                  85 gga tcc ttg att gtc ctg ccc cca gag tgc gcc gac gag ctg cgc aac      460
Gly Ser Leu Ile Val Leu Pro Pro Glu Cys Ala Asp Glu Leu Arg Asn
 90                  95                 100                 105 gac cca aga atg gac ttt gag acg ccc acc acc gac gac tcc cac gga      508
Asp Pro Arg Met Asp Phe Glu Thr Pro Thr Thr Asp Asp Ser His Gly
                110                 115                 120 tat atc cct ggc ttc gac gct ctc aac gca gac ccg aac ctg act aaa      556
Tyr Ile Pro Gly Phe Asp Ala Leu Asn Ala Asp Pro Asn Leu Thr Lys
            125                 130                 135 gtg gtc acc aag tac ctc aca aaa gca ttg aac aag ctt act gct ccg      604
Val Val Thr Lys Tyr Leu Thr Lys Ala Leu Asn Lys Leu Thr Ala Pro
        140                 145                 150 atc tcg cat gaa gcg tcc atc gcc atg aaa gcg gtg ctg ggt gac gat      652
Ile Ser His Glu Ala Ser Ile Ala Met Lys Ala Val Leu Gly Asp Asp
    155                 160                 165 cca gat tgg cgt gag atc tac cca gcc aga gac ttg ctc cag ctc gtc      700
Pro Asp Trp Arg Glu Ile Tyr Pro Ala Arg Asp Leu Leu Gln Leu Val
170                 175                 180                 185 gcc cgg atg tcg aca aga gtg ttc ctt ggc gag gaa atg tgc aat aac      748
Ala Arg Met Ser Thr Arg Val Phe Leu Gly Glu Glu Met Cys Asn Asn
                190                 195                 200 cag gat tgg atc caa acc tca tca caa tac gcg gcc ctt gcc ttc ggt      796
Gln Asp Trp Ile Gln Thr Ser Ser Gln Tyr Ala Ala Leu Ala Phe Gly
            205                 210                 215 gtc ggt gac aag ctt aga ata tac ccg aga atg atc aga ccg ata gta      844
Val Gly Asp Lys Leu Arg Ile Tyr Pro Arg Met Ile Arg Pro Ile Val
        220                 225                 230 cat tgg ttc atg cca tcc tgt tgg gag ctg cgc cga tcg ctg cga cgc      892
His Trp Phe Met Pro Ser Cys Trp Glu Leu Arg Arg Ser Leu Arg Arg
    235                 240                 245 tgc cga cag att ctc acg ccg tac att cac aaa cgc aag tcc ctg aag      940
Cys Arg Gln Ile Leu Thr Pro Tyr Ile His Lys Arg Lys Ser Leu Lys
250                 255                 260                 265 ggg acc acg gac gag cag ggc aag ccc ctt atg ttt gat gat tcc atc      988
Gly Thr Thr Asp Glu Gln Gly Lys Pro Leu Met Phe Asp Asp Ser Ile
                270                 275                 280 gag tgg ttc gag cga gag ctg ggt ccc aac cac gac gcg gtc ctg aag     1036
Glu Trp Phe Glu Arg Glu Leu Gly Pro Asn His Asp Ala Val Leu Lys
            285                 290                 295 cag gtc acg ctc tcc ata gtt gct atc cac acc acg agt gac cta ctc     1084
Gln Val Thr Leu Ser Ile Val Ala Ile His Thr Thr Ser Asp Leu Leu
        300                 305                 310 ttg cag gcc atg agc gat ctc gcg cag aac ccg aaa gtg cta caa gca     1132
Leu Gln Ala Met Ser Asp Leu Ala Gln Asn Pro Lys Val Leu Gln Ala
    315                 320                 325 gtg cgc gag gag gtg gtc cga gtg ctg agc acc gag ggg ctc agc aag     1180
Val Arg Glu Glu Val Val Arg Val Leu Ser Thr Glu Gly Leu Ser Lys
```

```
                330               335                340               345
gtc tcg ctt cac agt ctc aag ctc atg gac agc gcg ttg aag gaa agc    1228
Val Ser Leu His Ser Leu Lys Leu Met Asp Ser Ala Leu Lys Glu Ser
                350                355                360 cag cgt ctc agg cct acg ctt ctc ggc tcc ttt cgt cgg cag gca acg    1276
Gln Arg Leu Arg Pro Thr Leu Leu Gly Ser Phe Arg Arg Gln Ala Thr
            365                370                375 aat gac atc aag ctg aag agc ggg ttt gtc ata aag aaa ggg act aga    1324
Asn Asp Ile Lys Leu Lys Ser Gly Phe Val Ile Lys Lys Gly Thr Arg
                380                385                390 gtc gtg atc gac agc acc cat atg tgg aat ccc gag tat tac act gac    1372
Val Val Ile Asp Ser Thr His Met Trp Asn Pro Glu Tyr Tyr Thr Asp
            395                400                405 cct ctc cag tac gac ggg tac cgc tac ttc aac aag cgg cag aca ccc    1420
Pro Leu Gln Tyr Asp Gly Tyr Arg Tyr Phe Asn Lys Arg Gln Thr Pro
410                415                420                425 ggc gag gac aag aac gcg ttg ctc gtc agc aca agc gcc aac cac atg    1468
Gly Glu Asp Lys Asn Ala Leu Leu Val Ser Thr Ser Ala Asn His Met
                    430                435                440 gga ttc ggt cac ggc gtt cac gcc tgt cct ggc aga ttc ttc gcc tcc    1516
Gly Phe Gly His Gly Val His Ala Cys Pro Gly Arg Phe Phe Ala Ser
                445                450                455 aac gag atc aag att gcc ttg tgt cat atc atc tta aat tat gag tgg    1564
Asn Glu Ile Lys Ile Ala Leu Cys His Ile Ile Leu Asn Tyr Glu Trp
            460                465                470 cgt ctt cca gac ggc ttc aag ccc cag cct ctc aac atc ggg atg act    1612
Arg Leu Pro Asp Gly Phe Lys Pro Gln Pro Leu Asn Ile Gly Met Thr
475                480                485 tat ctg gcg gat ccc aat acc agg atg ctg atc agg cca cgc aag gcg    1660
Tyr Leu Ala Asp Pro Asn Thr Arg Met Leu Ile Arg Pro Arg Lys Ala
490                495                500                505 tat ctg gcg gat ccc aat acc agg atg ctg atcaggccac gcaaggcgga    1710
Tyr Leu Ala Asp Pro Asn Thr Arg Met Leu
                510                515 agtgttattg gtcagtgggt gaagcaagtc gcagaaatgt gtaacaattt ataagaataa    1770
aaaa    1774

<210> SEQ ID NO 2
<211> LENGTH: 515
<212> TYPE: PRT
<213> ORGANISM: Aspergillus ochraceus

<400> SEQUENCE: 2

Met Pro Phe Phe Thr Gly Leu Leu Ala Ile Tyr His Ser Leu Ile Leu
1               5                   10                  15

Asp Asn Pro Val Gln Thr Leu Ser Thr Ile Val Leu Ala Ala
                20                  25                  30

Tyr Trp Leu Ala Thr Leu Gln Pro Ser Asp Leu Pro Glu Leu Asn Pro
            35                  40                  45

Ala Lys Pro Phe Glu Phe Thr Asn Arg Arg Val His Glu Phe Val
    50                  55                  60

Glu Asn Ser Lys Ser Leu Leu Ala Arg Gly Arg Glu Leu His Gly His
65                  70                  75                  80

Glu Pro Tyr Arg Leu Met Ser Glu Trp Gly Ser Leu Ile Val Leu Pro
                85                  90                  95

Pro Glu Cys Ala Asp Glu Leu Arg Asn Asp Pro Arg Met Asp Phe Glu
            100                 105                 110
```

-continued

```
Thr Pro Thr Thr Asp Asp Ser His Gly Tyr Ile Pro Gly Phe Asp Ala
        115                 120                 125

Leu Asn Ala Asp Pro Asn Leu Thr Lys Val Val Thr Lys Tyr Leu Thr
    130                 135                 140

Lys Ala Leu Asn Lys Leu Thr Ala Pro Ile Ser His Glu Ala Ser Ile
145                 150                 155                 160

Ala Met Lys Ala Val Leu Gly Asp Asp Pro Asp Trp Arg Glu Ile Tyr
                165                 170                 175

Pro Ala Arg Asp Leu Leu Gln Leu Val Ala Arg Met Ser Thr Arg Val
                180                 185                 190

Phe Leu Gly Glu Glu Met Cys Asn Asn Gln Asp Trp Ile Gln Thr Ser
            195                 200                 205

Ser Gln Tyr Ala Ala Leu Ala Phe Gly Val Gly Asp Lys Leu Arg Ile
        210                 215                 220

Tyr Pro Arg Met Ile Arg Pro Ile Val His Trp Phe Met Pro Ser Cys
225                 230                 235                 240

Trp Glu Leu Arg Arg Ser Leu Arg Arg Cys Arg Gln Ile Leu Thr Pro
                245                 250                 255

Tyr Ile His Lys Arg Lys Ser Leu Lys Gly Thr Thr Asp Glu Gln Gly
            260                 265                 270

Lys Pro Leu Met Phe Asp Asp Ser Ile Glu Trp Phe Glu Arg Glu Leu
        275                 280                 285

Gly Pro Asn His Asp Ala Val Leu Lys Gln Val Thr Leu Ser Ile Val
    290                 295                 300

Ala Ile His Thr Thr Ser Asp Leu Leu Leu Gln Ala Met Ser Asp Leu
305                 310                 315                 320

Ala Gln Asn Pro Lys Val Leu Gln Ala Val Arg Glu Glu Val Val Arg
                325                 330                 335

Val Leu Ser Thr Glu Gly Leu Ser Lys Val Ser Leu His Ser Leu Lys
            340                 345                 350

Leu Met Asp Ser Ala Leu Lys Glu Ser Gln Arg Leu Arg Pro Thr Leu
        355                 360                 365

Leu Gly Ser Phe Arg Arg Gln Ala Thr Asn Asp Ile Lys Leu Lys Ser
    370                 375                 380

Gly Phe Val Ile Lys Lys Gly Thr Arg Val Val Ile Asp Ser Thr His
385                 390                 395                 400

Met Trp Asn Pro Glu Tyr Tyr Thr Asp Pro Leu Gln Tyr Asp Gly Tyr
                405                 410                 415

Arg Tyr Phe Asn Lys Arg Gln Thr Pro Gly Glu Asp Lys Asn Ala Leu
            420                 425                 430

Leu Val Ser Thr Ser Ala Asn His Met Gly Phe Gly His Gly Val His
        435                 440                 445

Ala Cys Pro Gly Arg Phe Phe Ala Ser Asn Glu Ile Lys Ile Ala Leu
    450                 455                 460

Cys His Ile Ile Leu Asn Tyr Glu Trp Arg Leu Pro Asp Gly Phe Lys
465                 470                 475                 480

Pro Gln Pro Leu Asn Ile Gly Met Thr Tyr Leu Ala Asp Pro Asn Thr
                485                 490                 495

Arg Met Leu Ile Arg Pro Arg Lys Ala Tyr Leu Ala Asp Pro Asn Thr
            500                 505                 510

Arg Met Leu
        515
```

-continued

<210> SEQ ID NO 3
<211> LENGTH: 514
<212> TYPE: PRT
<213> ORGANISM: Aspergillus ochraceus

<400> SEQUENCE: 3

```
Met Pro Phe Phe Thr Gly Leu Leu Ala Ile Tyr His Ser Leu Ile Leu
1               5                   10                  15

Asp Asn Pro Val Gln Thr Leu Ser Thr Ile Val Val Leu Ala Ala Ala
            20                  25                  30

Tyr Trp Leu Ala Thr Leu Gln Pro Ser Asp Leu Pro Glu Leu Asn Pro
        35                  40                  45

Ala Lys Pro Phe Glu Phe Thr Asn Arg Arg Val His Glu Phe Val
 50                  55                  60

Glu Asn Ser Lys Ser Leu Leu Ala Arg Gly Arg Glu Leu His Gly His
65                  70                  75                  80

Glu Pro Tyr Arg Leu Met Ser Glu Trp Gly Ser Leu Ile Val Leu Pro
                85                  90                  95

Pro Glu Cys Ala Asp Glu Leu Arg Asn Asp Pro Arg Met Asp Phe Glu
            100                 105                 110

Thr Pro Thr Thr Asp Asp Ser His Gly Tyr Ile Pro Gly Phe Asp Ala
            115                 120                 125

Leu Asn Ala Asp Pro Asn Leu Thr Lys Val Val Thr Lys Tyr Leu Thr
        130                 135                 140

Lys Ala Leu Asn Lys Leu Thr Ala Pro Ile Ser His Glu Ala Ser Ile
145                 150                 155                 160

Ala Met Lys Ala Val Leu Gly Asp Asp Pro Asp Trp Arg Glu Ile Tyr
                165                 170                 175

Pro Ala Arg Asp Leu Leu Gln Leu Val Ala Arg Met Ser Thr Arg Val
            180                 185                 190

Phe Leu Gly Glu Glu Met Cys Asn Asn Gln Asp Trp Ile Gln Thr Ser
        195                 200                 205

Ser Gln Tyr Ala Ala Leu Ala Phe Gly Val Gly Asp Lys Leu Arg Ile
    210                 215                 220

Tyr Pro Arg Met Ile Arg Pro Ile Val His Trp Phe Met Pro Ser Cys
225                 230                 235                 240

Trp Glu Leu Arg Arg Ser Leu Arg Arg Cys Arg Gln Ile Leu Thr Pro
                245                 250                 255

Tyr Ile His Lys Arg Lys Ser Leu Lys Gly Thr Thr Asp Glu Gln Gly
            260                 265                 270

Lys Pro Leu Met Phe Asp Asp Ser Ile Glu Trp Phe Glu Arg Glu Leu
        275                 280                 285

Gly Pro Asn His Asp Ala Val Leu Lys Gln Val Thr Leu Ser Ile Val
    290                 295                 300

Ala Ile His Thr Thr Ser Asp Leu Leu Leu Gln Ala Met Ser Asp Leu
305                 310                 315                 320

Ala Gln Asn Pro Lys Val Leu Gln Ala Val Arg Glu Glu Val Val Arg
                325                 330                 335

Val Leu Ser Thr Glu Gly Leu Ser Lys Val Ser Leu His Ser Leu Lys
            340                 345                 350

Leu Met Asp Ser Ala Leu Lys Glu Ser Gln Arg Leu Arg Pro Thr Leu
        355                 360                 365

Leu Gly Ser Phe Arg Arg Gln Ala Thr Asn Asp Ile Lys Leu Lys Ser
    370                 375                 380
```

-continued

```
Gly Phe Val Ile Lys Lys Gly Thr Arg Val Val Ile Asp Ser Thr His
385                 390                 395                 400

Met Trp Asn Pro Glu Tyr Tyr Thr Asp Pro Leu Gln Tyr Asp Gly Tyr
            405                 410                 415

Arg Tyr Phe Asn Lys Arg Gln Thr Pro Gly Glu Asp Lys Asn Ala Leu
        420                 425                 430

Leu Val Ser Thr Ser Ala Asn His Met Gly Phe Gly His Gly Val His
    435                 440                 445

Ala Cys Pro Gly Arg Phe Phe Ala Ser Asn Glu Ile Lys Ile Ala Leu
450                 455                 460

Cys His Ile Ile Leu Asn Tyr Glu Trp Arg Leu Pro Asp Gly Phe Lys
465                 470                 475                 480

Pro Gln Pro Leu Asn Ile Gly Met Thr Tyr Leu Ala Asp Pro Asn Thr
                485                 490                 495

Arg Met Leu Ile Arg Pro Arg Lys Ala Glu Ile Asp Met Ala Ser Leu
            500                 505                 510

Thr Val
```

```
<210> SEQ ID NO 4
<211> LENGTH: 2031
<212> TYPE: DNA
<213> ORGANISM: homo sapiens
<220> FEATURE:
<221> NAME/KEY: CDS
<222> LOCATION: (1)..(2031)
<223> OTHER INFORMATION: human oxidoreductase

<400> SEQUENCE: 4
```

```
atg gga gac tcc cac gtg gac acc agc tcc acc gtg tcc gag gcg gtg      48
Met Gly Asp Ser His Val Asp Thr Ser Ser Thr Val Ser Glu Ala Val
1               5                   10                  15 gcc gaa gaa gta tct ctt ttc agc atg acg gac atg att ctg ttt tcg      96
Ala Glu Glu Val Ser Leu Phe Ser Met Thr Asp Met Ile Leu Phe Ser
            20                  25                  30 ctc atc gtg ggt ctc cta acc tac tgg ttc ctc ttc aga aag aaa aaa     144
Leu Ile Val Gly Leu Leu Thr Tyr Trp Phe Leu Phe Arg Lys Lys Lys
        35                  40                  45 gaa gaa gtc ccc gag ttc acc aaa att cag aca ttg acc tcc tct gtc     192
Glu Glu Val Pro Glu Phe Thr Lys Ile Gln Thr Leu Thr Ser Ser Val
50                  55                  60 aga gag agc agc ttt gtg gaa aag atg aag aaa acg ggg agg aac atc     240
Arg Glu Ser Ser Phe Val Glu Lys Met Lys Lys Thr Gly Arg Asn Ile
65                  70                  75                  80 atc gtg ttc tac ggc tcc cag acg ggg act gca gag gag ttt gcc aac     288
Ile Val Phe Tyr Gly Ser Gln Thr Gly Thr Ala Glu Glu Phe Ala Asn
                85                  90                  95 cgc ctg tcc aag gac gcc cac cgc tac ggg atg cga ggc atg tca gcg     336
Arg Leu Ser Lys Asp Ala His Arg Tyr Gly Met Arg Gly Met Ser Ala
            100                 105                 110 gac cct gag gag tat gac ctg gcc gac ctg agc agc ctg cca gag atc     384
Asp Pro Glu Glu Tyr Asp Leu Ala Asp Leu Ser Ser Leu Pro Glu Ile
        115                 120                 125 gac aac gcc ctg gtg gtt ttc tgc atg gcc acc tac ggt gag gga gac     432
Asp Asn Ala Leu Val Val Phe Cys Met Ala Thr Tyr Gly Glu Gly Asp
    130                 135                 140 ccc acc gac aat gcc cag gac ttc tac gac tgg ctg cag gag aca gac     480
Pro Thr Asp Asn Ala Gln Asp Phe Tyr Asp Trp Leu Gln Glu Thr Asp
145                 150                 155                 160 gtg gat ctc tct ggg gtc aag ttc gcg gtg ttt ggt ctt ggg aac aag     528
```

```
Val Asp Leu Ser Gly Val Lys Phe Ala Val Phe Gly Leu Gly Asn Lys
            165                 170                 175 acc tac gag cac ttc aat gcc atg ggc aag tac gtg gac aag cgg ctg        576
Thr Tyr Glu His Phe Asn Ala Met Gly Lys Tyr Val Asp Lys Arg Leu
            180                 185                 190 gag cag ctc ggc gcc cag cgc atc ttt gag ctg ggg ttg ggc gac gac        624
Glu Gln Leu Gly Ala Gln Arg Ile Phe Glu Leu Gly Leu Gly Asp Asp
        195                 200                 205 gat ggg aac ttg gag gag gac ttc atc acc tgg cga gag cag ttc tgg        672
Asp Gly Asn Leu Glu Glu Asp Phe Ile Thr Trp Arg Glu Gln Phe Trp
    210                 215                 220 ccg gcc gtg tgt gaa cac ttt ggg gtg gaa gcc act ggc gag gag tcc        720
Pro Ala Val Cys Glu His Phe Gly Val Glu Ala Thr Gly Glu Glu Ser
225                 230                 235                 240 agc att cgc cag tac gag ctt gtg gtc cac acc gac ata gat gcg gcc        768
Ser Ile Arg Gln Tyr Glu Leu Val Val His Thr Asp Ile Asp Ala Ala
                245                 250                 255 aag gtg tac atg ggg gag atg ggc cgg ctg aag agc tac gag aac cag        816
Lys Val Tyr Met Gly Glu Met Gly Arg Leu Lys Ser Tyr Glu Asn Gln
            260                 265                 270 aag ccc ccc ttt gat gcc aag aat ccg ttc ctg gct gca gtc acc acc        864
Lys Pro Pro Phe Asp Ala Lys Asn Pro Phe Leu Ala Ala Val Thr Thr
        275                 280                 285 aac cgg aag ctg aac cag gga acc gag cgc cac ctc atg cac ctg gaa        912
Asn Arg Lys Leu Asn Gln Gly Thr Glu Arg His Leu Met His Leu Glu
    290                 295                 300 ttg gac atc tcg gac tcc aaa atc agg tat gaa tct ggg gac cac gtg        960
Leu Asp Ile Ser Asp Ser Lys Ile Arg Tyr Glu Ser Gly Asp His Val
305                 310                 315                 320 gct gtg tac cca gcc aac gac tct gct ctc gtc aac cag ctg ggc aaa       1008
Ala Val Tyr Pro Ala Asn Asp Ser Ala Leu Val Asn Gln Leu Gly Lys
                325                 330                 335 atc ctg ggt gcc gac ctg gac gtc gtc atg tcc ctg aac aac ctg gat       1056
Ile Leu Gly Ala Asp Leu Asp Val Val Met Ser Leu Asn Asn Leu Asp
            340                 345                 350 gag gag tcc aac aag aag cac cca ttc ccg tgc cct acg tcc tac cgc       1104
Glu Glu Ser Asn Lys Lys His Pro Phe Pro Cys Pro Thr Ser Tyr Arg
        355                 360                 365 acg gcc ctc acc tac tac ctg gac atc acc aac ccg ccg cgt acc aac       1152
Thr Ala Leu Thr Tyr Tyr Leu Asp Ile Thr Asn Pro Pro Arg Thr Asn
    370                 375                 380 gtg ctg tac gag ctg gcg cag tac gcc tcg gag ccc tcg gag cag gag       1200
Val Leu Tyr Glu Leu Ala Gln Tyr Ala Ser Glu Pro Ser Glu Gln Glu
385                 390                 395                 400 ctg ctg cgc aag atg gcc tcc tcc tcc ggc gag ggc aag gag ctg tac       1248
Leu Leu Arg Lys Met Ala Ser Ser Ser Gly Glu Gly Lys Glu Leu Tyr
                405                 410                 415 ctg agc tgg gtg gtg gag gcc cgg agg cac atc ctg gcc atc ctg cag       1296
Leu Ser Trp Val Val Glu Ala Arg Arg His Ile Leu Ala Ile Leu Gln
            420                 425                 430 gac tgc ccg tcc ctg cgg ccc ccc atc gac cac ctg tgt gag ctg ctg       1344
Asp Cys Pro Ser Leu Arg Pro Pro Ile Asp His Leu Cys Glu Leu Leu
        435                 440                 445 ccg cgc ctg cag gcc cgc tac tac tcc atc gcc tca tcc tcc aag gtc       1392
Pro Arg Leu Gln Ala Arg Tyr Tyr Ser Ile Ala Ser Ser Ser Lys Val
    450                 455                 460 cac ccc aac tct gtg cac atc tgt gcg gtg gtt gtg gag tac gag acc       1440
His Pro Asn Ser Val His Ile Cys Ala Val Val Val Glu Tyr Glu Thr
465                 470                 475                 480
```

```
aag gcc ggc cgc atc aac aag ggc gtg gcc acc aac tgg ctg cgg gcc         1488
Lys Ala Gly Arg Ile Asn Lys Gly Val Ala Thr Asn Trp Leu Arg Ala
                485                 490                 495 aag gag cct gcc ggg gag aac ggc ggc cgt gcg ctg gtg ccc atg ttc         1536
Lys Glu Pro Ala Gly Glu Asn Gly Gly Arg Ala Leu Val Pro Met Phe
        500                 505                 510 gtg cgc aag tcc cag ttc cgc ctg ccc ttc aag gcc acc acg cct gtc         1584
Val Arg Lys Ser Gln Phe Arg Leu Pro Phe Lys Ala Thr Thr Pro Val
    515                 520                 525 atc atg gtg ggc ccc ggc acc ggg gtg gca ccc ttc ata ggc ttc atc         1632
Ile Met Val Gly Pro Gly Thr Gly Val Ala Pro Phe Ile Gly Phe Ile
530                 535                 540 cag gag cgg gcc tgg ctg cga cag cag ggc aag gag gtg ggg gag acg         1680
Gln Glu Arg Ala Trp Leu Arg Gln Gln Gly Lys Glu Val Gly Glu Thr
545                 550                 555                 560 ctg ctg tac tac ggc tgc cgc cgc tcg gat gag gac tac ctg tac cgg         1728
Leu Leu Tyr Tyr Gly Cys Arg Arg Ser Asp Glu Asp Tyr Leu Tyr Arg
                565                 570                 575 gag gag ctg gcg cag ttc cac agg gac ggt gcg ctc acc cag ctc aac         1776
Glu Glu Leu Ala Gln Phe His Arg Asp Gly Ala Leu Thr Gln Leu Asn
            580                 585                 590 gtg gcc ttc tcc cgg gag cag tcc cac aag gtc tac gtc cag cac ctg         1824
Val Ala Phe Ser Arg Glu Gln Ser His Lys Val Tyr Val Gln His Leu
        595                 600                 605 cta aag caa gac cga gag cac ctg tgg aag ttg atc gaa ggc ggt gcc         1872
Leu Lys Gln Asp Arg Glu His Leu Trp Lys Leu Ile Glu Gly Gly Ala
    610                 615                 620 cac atc tac gtc tgt ggg gat gca cgg aac atg gcc agg gat gtg cag         1920
His Ile Tyr Val Cys Gly Asp Ala Arg Asn Met Ala Arg Asp Val Gln
625                 630                 635                 640 aac acc ttc tac gac atc gtg gct gag ctc ggg gcc atg gag cac gcg         1968
Asn Thr Phe Tyr Asp Ile Val Ala Glu Leu Gly Ala Met Glu His Ala
                645                 650                 655 cag gcg gtg gac tac atc aag aaa ctg atg acc aag ggc cgc tac tcc         2016
Gln Ala Val Asp Tyr Ile Lys Lys Leu Met Thr Lys Gly Arg Tyr Ser
            660                 665                 670 ctg gac gtg tgg agc                                                     2031
Leu Asp Val Trp Ser
        675

<210> SEQ ID NO 5
<211> LENGTH: 677
<212> TYPE: PRT
<213> ORGANISM: homo sapiens

<400> SEQUENCE: 5

Met Gly Asp Ser His Val Asp Thr Ser Ser Thr Val Ser Glu Ala Val
1               5                   10                  15

Ala Glu Glu Val Ser Leu Phe Ser Met Thr Asp Met Ile Leu Phe Ser
            20                  25                  30

Leu Ile Val Gly Leu Leu Thr Tyr Trp Phe Leu Phe Arg Lys Lys Lys
        35                  40                  45

Glu Glu Val Pro Glu Phe Thr Lys Ile Gln Thr Thr Leu Thr Ser Val
    50                  55                  60

Arg Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
```

```
                100               105              110
Asp Pro Glu Glu Tyr Asp Leu Ala Asp Leu Ser Ser Leu Pro Glu Ile
            115                 120             125
Asp Asn Ala Leu Val Val Phe Cys Met Ala Thr Tyr Gly Glu Gly Asp
            130                 135             140
Pro Thr Asp Asn Ala Gln Asp Phe Tyr Asp Trp Leu Gln Glu Thr Asp
145                 150                 155                 160
Val Asp Leu Ser Gly Val Lys Phe Ala Val Phe Gly Leu Gly Asn Lys
                165                 170             175
Thr Tyr Glu His Phe Asn Ala Met Gly Lys Tyr Val Asp Lys Arg Leu
            180                 185             190
Glu Gln Leu Gly Ala Gln Arg Ile Phe Glu Leu Gly Leu Gly Asp Asp
            195                 200             205
Asp Gly Asn Leu Glu Glu Asp Phe Ile Thr Trp Arg Glu Gln Phe Trp
210                 215                 220
Pro Ala Val Cys Glu His Phe Gly Val Glu Ala Thr Gly Glu Glu Ser
225                 230                 235                 240
Ser Ile Arg Gln Tyr Glu Leu Val Val His Thr Asp Ile Asp Ala Ala
                245                 250                 255
Lys Val Tyr Met Gly Glu Met Gly Arg Leu Lys Ser Tyr Glu Asn Gln
                260                 265                 270
Lys Pro Pro Phe Asp Ala Lys Asn Pro Phe Leu Ala Ala Val Thr Thr
            275                 280                 285
Asn Arg Lys Leu Asn Gln Gly Thr Glu Arg His Leu Met His Leu Glu
            290                 295                 300
Leu Asp Ile Ser Asp Ser Lys Ile Arg Tyr Glu Ser Gly Asp His Val
305                 310                 315                 320
Ala Val Tyr Pro Ala Asn Asp Ser Ala Leu Val Asn Gln Leu Gly Lys
                325                 330                 335
Ile Leu Gly Ala Asp Leu Asp Val Val Met Ser Leu Asn Asn Leu Asp
                340                 345                 350
Glu Glu Ser Asn Lys Lys His Pro Phe Pro Cys Pro Thr Ser Tyr Arg
            355                 360                 365
Thr Ala Leu Thr Tyr Tyr Leu Asp Ile Thr Asn Pro Pro Arg Thr Asn
370                 375                 380
Val Leu Tyr Glu Leu Ala Gln Tyr Ala Ser Glu Pro Ser Glu Gln Glu
385                 390                 395                 400
Leu Leu Arg Lys Met Ala Ser Ser Ser Gly Glu Gly Lys Glu Leu Tyr
                405                 410                 415
Leu Ser Trp Val Val Glu Ala Arg Arg His Ile Leu Ala Ile Leu Gln
                420                 425                 430
Asp Cys Pro Ser Leu Arg Pro Pro Ile Asp His Leu Cys Glu Leu Leu
            435                 440                 445
Pro Arg Leu Gln Ala Arg Tyr Tyr Ser Ile Ala Ser Ser Ser Lys Val
            450                 455                 460
His Pro Asn Ser Val His Ile Cys Ala Val Val Val Glu Tyr Glu Thr
465                 470                 475                 480
Lys Ala Gly Arg Ile Asn Lys Gly Val Ala Thr Asn Trp Leu Arg Ala
                485                 490                 495
Lys Glu Pro Ala Gly Glu Asn Gly Gly Arg Ala Leu Val Pro Met Phe
            500                 505                 510
Val Arg Lys Ser Gln Phe Arg Leu Pro Phe Lys Ala Thr Thr Pro Val
            515                 520                 525
```

```
Ile Met Val Gly Pro Gly Thr Gly Val Ala Pro Phe Ile Gly Phe Ile
    530                 535                 540

Gln Glu Arg Ala Trp Leu Arg Gln Gln Gly Lys Glu Val Gly Glu Thr
545                 550                 555                 560

Leu Leu Tyr Tyr Gly Cys Arg Ser Asp Glu Asp Tyr Leu Tyr Arg
                565                 570                 575

Glu Glu Leu Ala Gln Phe His Arg Asp Gly Ala Leu Thr Gln Leu Asn
            580                 585                 590

Val Ala Phe Ser Arg Glu Gln Ser His Lys Val Tyr Val Gln His Leu
        595                 600                 605

Leu Lys Gln Asp Arg Glu His Leu Trp Lys Leu Ile Glu Gly Gly Ala
    610                 615                 620

His Ile Tyr Val Cys Gly Asp Ala Arg Asn Met Ala Arg Asp Val Gln
625                 630                 635                 640

Asn Thr Phe Tyr Asp Ile Val Ala Glu Leu Gly Ala Met Glu His Ala
                645                 650                 655

Gln Ala Val Asp Tyr Ile Lys Lys Leu Met Thr Lys Gly Arg Tyr Ser
            660                 665                 670

Leu Asp Val Trp Ser
        675

<210> SEQ ID NO 6
<211> LENGTH: 677
<212> TYPE: PRT
<213> ORGANISM: homo sapiens

<400> SEQUENCE: 6

Met Gly Asp Ser His Val Asp Thr Ser Ser Thr Val Ser Glu Ala Val
1               5                   10                  15

Ala Glu Glu Val Ser Leu Phe Ser Met Thr Asp Met Ile Leu Phe Ser
            20                  25                  30

Leu Ile Val Gly Leu Leu Thr Tyr Trp Phe Leu Phe Arg Lys Lys Lys
        35                  40                  45

Glu Glu Val Pro Glu Phe Thr Lys Ile Gln Thr Leu Thr Ser Ser Val
    50                  55                  60

Arg Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Asn Ala Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Ser Gly Val Lys Phe Ala Val Phe Gly Leu Gly Asn Lys
                165                 170                 175

Thr Tyr Glu His Phe Asn Ala Met Gly Lys Tyr Val Asp Lys Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
```

-continued

```
            210                 215                 220
Pro Ala Val Cys Glu His Phe Gly Val Glu Ala Thr Gly Glu Glu Ser
225                 230                 235                 240

Ser Ile Arg Gln Tyr Glu Leu Val Val His Thr Asp Ile Asp Ala Ala
                245                 250                 255

Lys Val Tyr Met Gly Glu Met Gly Arg Leu Lys Ser Tyr Glu Asn Gln
                260                 265                 270

Lys Pro Pro Phe Asp Ala Lys Asn Pro Phe Leu Ala Ala Val Thr Thr
                275                 280                 285

Asn Arg Lys Leu Asn Gln Gly Thr Glu Arg His Leu Met His Leu Glu
290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Leu Gly Lys
                325                 330                 335

Ile Leu Gly Ala Asp Leu Asp Val Val Met Ser Leu Asn Asn Leu Asp
                340                 345                 350

Glu Glu Ser Asn Lys Lys His Pro Phe Pro Cys Pro Thr Ser Tyr Arg
                355                 360                 365

Thr Ala Leu Thr Tyr Tyr Leu Asp Ile Thr Asn Pro Pro Arg Thr Asn
370                 375                 380

Val Leu Tyr Glu Leu Ala Gln Tyr Ala Ser Glu Pro Ser Glu Gln Glu
385                 390                 395                 400

Leu Leu Arg Lys Met Ala Ser Ser Ser Gly Glu Gly Lys Glu Leu Tyr
                405                 410                 415

Leu Ser Trp Val Val Glu Ala Arg Arg His Ile Leu Ala Ile Leu Gln
                420                 425                 430

Asp Cys Pro Ser Leu Arg Pro Pro Ile Asp His Leu Cys Glu Leu Leu
                435                 440                 445

Pro Arg Leu Gln Ala Arg Tyr Tyr Ser Ile Ala Ser Ser Ser Lys Val
                450                 455                 460

His Pro Asn Ser Val His Ile Cys Ala Val Val Val Glu Tyr Glu Thr
465                 470                 475                 480

Lys Ala Gly Arg Ile Asn Lys Gly Val Ala Thr Asn Trp Leu Arg Ala
                485                 490                 495

Lys Glu Pro Ala Gly Glu Asn Gly Gly Arg Ala Leu Val Pro Met Phe
                500                 505                 510

Val Arg Lys Ser Gln Phe Arg Leu Pro Phe Lys Ala Thr Thr Pro Val
                515                 520                 525

Ile Met Val Gly Pro Gly Thr Gly Val Ala Pro Phe Ile Gly Phe Ile
                530                 535                 540

Gln Glu Arg Ala Trp Leu Arg Gln Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Gln Phe His Arg Asp Gly Ala Leu Thr Gln Leu Asn
                580                 585                 590

Val Ala Phe Ser Arg Glu Gln Ser His Lys Val Tyr Val Gln His Leu
                595                 600                 605

Leu Lys Gln Asp Arg Glu His Leu Trp Lys Leu Ile Glu Gly Gly Ala
                610                 615                 620

His Ile Tyr Val Cys Gly Asp Ala Arg Asn Met Ala Arg Asp Val Gln
625                 630                 635                 640
```

```
Asn Thr Phe Tyr Asp Ile Val Ala Glu Leu Gly Ala Met Glu His Ala
            645                 650                 655
Gln Ala Val Asp Tyr Ile Lys Lys Leu Met Thr Lys Gly Arg Tyr Ser
        660                 665                 670
Leu Asp Val Trp Ser
    675

<210> SEQ ID NO 7
<211> LENGTH: 2322
<212> TYPE: DNA
<213> ORGANISM: Aspergillus ochraceus
<220> FEATURE:
<221> NAME/KEY: CDS
<222> LOCATION: (233)..(2320)
<223> OTHER INFORMATION: Aspergillus ochraceus oxidoreductase

<400> SEQUENCE: 7
cttatttcgt ttaggaagag caccggcttc ggtgtccttc cttaccctct tattcttcct      60
cttctgactc cctttttgtt attgatcgcc catctcggtg aacatttggg atatctttcc    120
ctctccccct cccgccccga ccctccttat cttctcctcc cgtccagcat ttagctcgcc    180
atcgaattcg caattccttc ctcgtgactc ttcatcgctg agcgtcctca tc atg gcg   238
                                                          Met Ala
                                                            1 caa ctc gat act ctc gat ttg gtc gtc ctg gtg gcg ctc ttg gtg ggt      286
Gln Leu Asp Thr Leu Asp Leu Val Val Leu Val Ala Leu Leu Val Gly
        5                  10                  15 agc gtg gcc tac ttc acc aag ggc acc tac tgg gcc gtc gcc aaa gac      334
Ser Val Ala Tyr Phe Thr Lys Gly Thr Tyr Trp Ala Val Ala Lys Asp
 20                  25                  30 cct tat gcc tcg gct ggt ccg gcg atg aat gga ggc gcc aag gcc ggc      382
Pro Tyr Ala Ser Ala Gly Pro Ala Met Asn Gly Ala Lys Ala Gly
 35                  40                  45                  50 aag act cgc gac att gtt cag aaa atg gac gaa act ggc aaa aac tgt      430
Lys Thr Arg Asp Ile Val Gln Lys Met Asp Glu Thr Gly Lys Asn Cys
                 55                  60                  65 gtg att ttc tac ggc tcg caa acc ggt acc gct gag gac tac gcg tcc      478
Val Ile Phe Tyr Gly Ser Gln Thr Gly Thr Ala Glu Asp Tyr Ala Ser
         70                  75                  80 aga ctg gcc aag gaa ggc tcc cag cga ttc ggt ctc aag acc atg gtg      526
Arg Leu Ala Lys Glu Gly Ser Gln Arg Phe Gly Leu Lys Thr Met Val
         85                  90                  95 gcc gat ctg gag gac tac gac tac gaa aac ctg gaa aag ttc ccc gag      574
Ala Asp Leu Glu Asp Tyr Asp Tyr Glu Asn Leu Glu Lys Phe Pro Glu
    100                 105                 110 gac aag gtt gtt ttc ttc gtt ctg gcc act tat ggc gag ggt gaa ccc      622
Asp Lys Val Val Phe Phe Val Leu Ala Thr Tyr Gly Glu Gly Glu Pro
115                 120                 125                 130 acg gat aat gcg gtt gaa ttc tac cag ttc gtc acg ggc gaa gat gct      670
Thr Asp Asn Ala Val Glu Phe Tyr Gln Phe Val Thr Gly Glu Asp Ala
                135                 140                 145 gct ttc gag agc ggc gct acc gcc gac gat aag cct ctg tct tct ctc      718
Ala Phe Glu Ser Gly Ala Thr Ala Asp Asp Lys Pro Leu Ser Ser Leu
            150                 155                 160 aag tat gtc acg ttt ggt ctg ggt aac aac acc tat gag cac tac aac      766
Lys Tyr Val Thr Phe Gly Leu Gly Asn Asn Thr Tyr Glu His Tyr Asn
        165                 170                 175 gct atg gtt cgc aat gtg gac gcc gct ctc aca aag ttc ggc gcc caa      814
Ala Met Val Arg Asn Val Asp Ala Ala Leu Thr Lys Phe Gly Ala Gln
    180                 185                 190
```

```
cgc att ggc tct gct ggt gag ggt gac gac ggc gct ggt aca atg gaa      862
Arg Ile Gly Ser Ala Gly Glu Gly Asp Asp Gly Ala Gly Thr Met Glu
195                 200                 205                 210 gag gat ttc ctg gcc tgg aag gaa ccc atg tgg gct gcc ctt tct gag      910
Glu Asp Phe Leu Ala Trp Lys Glu Pro Met Trp Ala Ala Leu Ser Glu
                215                 220                 225 gcg atg aac ctg caa gag cgc gat gcg gtc tac gag ccg gtc ttc aat      958
Ala Met Asn Leu Gln Glu Arg Asp Ala Val Tyr Glu Pro Val Phe Asn
            230                 235                 240 gtc acc gag gac gag tcc ctg agc ccc gaa gat gag aac gtt tac ctc     1006
Val Thr Glu Asp Glu Ser Leu Ser Pro Glu Asp Glu Asn Val Tyr Leu
            245                 250                 255 ggt gag ccc act caa ggt cat ctc caa ggc gag ccc aag ggc ccg tac     1054
Gly Glu Pro Thr Gln Gly His Leu Gln Gly Glu Pro Lys Gly Pro Tyr
        260                 265                 270 tct gcg cac aac ccg ttc atc gct ccc atc tcc gaa tct cgt gaa ctg     1102
Ser Ala His Asn Pro Phe Ile Ala Pro Ile Ser Glu Ser Arg Glu Leu
275                 280                 285                 290 ttc aac gtc aag gac cgc aac tgt ctg cac atg gaa atc agc atc gcc     1150
Phe Asn Val Lys Asp Arg Asn Cys Leu His Met Glu Ile Ser Ile Ala
                295                 300                 305 ggt agc aac ctc act tac cag act ggt gac cac atc gct gtt tgg ccc     1198
Gly Ser Asn Leu Thr Tyr Gln Thr Gly Asp His Ile Ala Val Trp Pro
            310                 315                 320 acc aac gcc ggt tcc gag gtc gat cgg ttc ctg cag gct ttt ggt ctc     1246
Thr Asn Ala Gly Ser Glu Val Asp Arg Phe Leu Gln Ala Phe Gly Leu
            325                 330                 335 gaa gga aag cgc cac tcc gtc atc aac att aag ggt atc gat gtg acc     1294
Glu Gly Lys Arg His Ser Val Ile Asn Ile Lys Gly Ile Asp Val Thr
340                 345                 350 gct aag gtt ccg att ccc act cct acg acc tat gac gcc gca gtt cgc     1342
Ala Lys Val Pro Ile Pro Thr Pro Thr Thr Tyr Asp Ala Ala Val Arg
355                 360                 365                 370 tac tac ctg gaa gtc tgt gcc ccc gtt tcc cgt cag ttt gtc tcg act     1390
Tyr Tyr Leu Glu Val Cys Ala Pro Val Ser Arg Gln Phe Val Ser Thr
                375                 380                 385 ctc gct gcc ttt gcc cct gat gaa gcg acc aag gcg gag atc gtt cgt     1438
Leu Ala Ala Phe Ala Pro Asp Glu Ala Thr Lys Ala Glu Ile Val Arg
            390                 395                 400 ttg ggt ggc gac aag gac tat ttc cat gag aag att acc aac cga tgc     1486
Leu Gly Gly Asp Lys Asp Tyr Phe His Glu Lys Ile Thr Asn Arg Cys
            405                 410                 415 ttc aac atc gct cag gct ctc cag agc atc acg tcc aag cct ttc acc     1534
Phe Asn Ile Ala Gln Ala Leu Gln Ser Ile Thr Ser Lys Pro Phe Thr
        420                 425                 430 gcc gtc ccg ttc tcc ctg ctt atc gaa ggt atc acc aag ctt cag ccc     1582
Ala Val Pro Phe Ser Leu Leu Ile Glu Gly Ile Thr Lys Leu Gln Pro
435                 440                 445                 450 cgt tac tac tcg atc tcc tcg tct tcc ctg gtt cag aag gac aag att     1630
Arg Tyr Tyr Ser Ile Ser Ser Ser Ser Leu Val Gln Lys Asp Lys Ile
                455                 460                 465 agc att acc gcc gtt gtg gag tcg gtt cgc ttg cct ggt gag gaa cac     1678
Ser Ile Thr Ala Val Val Glu Ser Val Arg Leu Pro Gly Glu Glu His
            470                 475                 480 att gtc aag ggt gtg acc acg aac tat ctt ctc gcg ctc aag gaa aag     1726
Ile Val Lys Gly Val Thr Thr Asn Tyr Leu Leu Ala Leu Lys Glu Lys
            485                 490                 495 caa aac ggc gag cct tcc cct gac ccg cac ggc ttg act tac tct atc     1774
Gln Asn Gly Glu Pro Ser Pro Asp Pro His Gly Leu Thr Tyr Ser Ile
```

```
                500              505              510
act gga ccc cgt aac aag tac gat ggc atc cat gtc ccc gtt cac gtc      1822
Thr Gly Pro Arg Asn Lys Tyr Asp Gly Ile His Val Pro Val His Val
515                 520                 525                 530 cgc cac tcg aac ttc aaa ttg ccc tcg gat ccc tcg cga cct gtg atc      1870
Arg His Ser Asn Phe Lys Leu Pro Ser Asp Pro Ser Arg Pro Val Ile
                535                 540                 545 atg gtt gga ccc ggt act ggt gtt gct cct ttc cgt ggg ttt atc cag      1918
Met Val Gly Pro Gly Thr Gly Val Ala Pro Phe Arg Gly Phe Ile Gln
            550                 555                 560 gag cgt gct gcc ttg gcc gcg aag ggc gag aag gtc gga act acc ttg      1966
Glu Arg Ala Ala Leu Ala Ala Lys Gly Glu Lys Val Gly Thr Thr Leu
        565                 570                 575 ctt ttc ttc ggc tgc cgt aag tcc gac gaa gat ttc ttg tac aag gat      2014
Leu Phe Phe Gly Cys Arg Lys Ser Asp Glu Asp Phe Leu Tyr Lys Asp
    580                 585                 590 gaa tgg aag act ttt cag gag cag ctt ggc gac tcg ctc aag atc atc      2062
Glu Trp Lys Thr Phe Gln Glu Gln Leu Gly Asp Ser Leu Lys Ile Ile
595                 600                 605                 610 act gcc ttc tct cgt gaa tcg gct gag aaa gtc tac gtc cag cac agg      2110
Thr Ala Phe Ser Arg Glu Ser Ala Glu Lys Val Tyr Val Gln His Arg
                615                 620                 625 ctg cgt gag cat gcc gag ctg gtc agt gac ctg ctg aag cag aaa gcc      2158
Leu Arg Glu His Ala Glu Leu Val Ser Asp Leu Leu Lys Gln Lys Ala
            630                 635                 640 act ttc tat gtt tgc ggt gac gct gcc aac atg gcc cgt gaa gtc aac      2206
Thr Phe Tyr Val Cys Gly Asp Ala Ala Asn Met Ala Arg Glu Val Asn
        645                 650                 655 ctc gtg ctt ggg caa atc att gcc aag cag cgc ggt ctc cct gcc gag      2254
Leu Val Leu Gly Gln Ile Ile Ala Lys Gln Arg Gly Leu Pro Ala Glu
    660                 665                 670 aag ggc gag gag atg gtg aag cac atg cgc agc agc ggc agc tac cag      2302
Lys Gly Glu Glu Met Val Lys His Met Arg Ser Ser Gly Ser Tyr Gln
675                 680                 685                 690 gac gat gtc tgg tcc taa aa                                           2322
Asp Asp Val Trp Ser
            695
```

<210> SEQ ID NO 8
<211> LENGTH: 695
<212> TYPE: PRT
<213> ORGANISM: Aspergillus ochraceus

<400> SEQUENCE: 8

```
Met Ala Gln Leu Asp Thr Leu Asp Leu Val Val Leu Ala Leu Leu
1               5                   10                  15

Val Gly Ser Val Ala Tyr Phe Thr Lys Gly Thr Tyr Trp Ala Val Ala
                20                  25                  30

Lys Asp Pro Tyr Ala Ser Ala Gly Pro Ala Met Asn Gly Gly Ala Lys
            35                  40                  45

Ala Gly Lys Thr Arg Asp Ile Val Gln Lys Met Asp Glu Thr Gly Lys
        50                  55                  60

Asn Cys Val Ile Phe Tyr Gly Ser Gln Thr Gly Thr Ala Glu Asp Tyr
65                  70                  75                  80

Ala Ser Arg Leu Ala Lys Glu Gly Ser Gln Arg Phe Gly Leu Lys Thr
                85                  90                  95

Met Val Ala Asp Leu Glu Asp Tyr Asp Tyr Glu Asn Leu Glu Lys Phe
            100                 105                 110
```

```
Pro Glu Asp Lys Val Val Phe Val Leu Ala Thr Tyr Gly Glu Gly
        115                 120                 125

Glu Pro Thr Asp Asn Ala Val Glu Phe Tyr Gln Phe Val Thr Gly Glu
    130                 135                 140

Asp Ala Ala Phe Glu Ser Gly Ala Thr Ala Asp Lys Pro Leu Ser
145                 150                 155                 160

Ser Leu Lys Tyr Val Thr Phe Gly Leu Gly Asn Asn Thr Tyr Glu His
                165                 170                 175

Tyr Asn Ala Met Val Arg Asn Val Asp Ala Ala Leu Thr Lys Phe Gly
            180                 185                 190

Ala Gln Arg Ile Gly Ser Ala Gly Glu Gly Asp Asp Gly Ala Gly Thr
        195                 200                 205

Met Glu Glu Asp Phe Leu Ala Trp Lys Glu Pro Met Trp Ala Ala Leu
    210                 215                 220

Ser Glu Ala Met Asn Leu Gln Glu Arg Asp Ala Val Tyr Glu Pro Val
225                 230                 235                 240

Phe Asn Val Thr Glu Asp Ser Leu Ser Pro Glu Asp Glu Asn Val
                245                 250                 255

Tyr Leu Gly Glu Pro Thr Gln Gly His Leu Gln Gly Glu Pro Lys Gly
            260                 265                 270

Pro Tyr Ser Ala His Asn Pro Phe Ile Ala Pro Ile Ser Glu Ser Arg
        275                 280                 285

Glu Leu Phe Asn Val Lys Asp Arg Asn Cys Leu His Met Glu Ile Ser
    290                 295                 300

Ile Ala Gly Ser Asn Leu Thr Tyr Gln Thr Gly Asp His Ile Ala Val
305                 310                 315                 320

Trp Pro Thr Asn Ala Gly Ser Glu Val Asp Arg Phe Leu Gln Ala Phe
                325                 330                 335

Gly Leu Glu Gly Lys Arg His Ser Val Ile Asn Ile Lys Gly Ile Asp
            340                 345                 350

Val Thr Ala Lys Val Pro Ile Pro Thr Pro Thr Thr Tyr Asp Ala Ala
        355                 360                 365

Val Arg Tyr Tyr Leu Glu Val Cys Ala Pro Val Ser Arg Gln Phe Val
    370                 375                 380

Ser Thr Leu Ala Ala Phe Ala Pro Asp Glu Ala Thr Lys Ala Glu Ile
385                 390                 395                 400

Val Arg Leu Gly Gly Asp Lys Asp Tyr Phe His Glu Lys Ile Thr Asn
                405                 410                 415

Arg Cys Phe Asn Ile Ala Gln Ala Leu Gln Ser Ile Thr Ser Lys Pro
            420                 425                 430

Phe Thr Ala Val Pro Phe Ser Leu Leu Ile Glu Gly Ile Thr Lys Leu
        435                 440                 445

Gln Pro Arg Tyr Tyr Ser Ile Ser Ser Ser Ser Leu Val Gln Lys Asp
    450                 455                 460

Lys Ile Ser Ile Thr Ala Val Val Glu Ser Val Arg Leu Pro Gly Glu
465                 470                 475                 480

Glu His Ile Val Lys Gly Val Thr Thr Asn Tyr Leu Leu Ala Leu Lys
                485                 490                 495

Glu Lys Gln Asn Gly Glu Pro Ser Pro Asp Pro His Gly Leu Thr Tyr
            500                 505                 510

Ser Ile Thr Gly Pro Arg Asn Lys Tyr Asp Gly Ile His Val Pro Val
        515                 520                 525

His Val Arg His Ser Asn Phe Lys Leu Pro Ser Asp Pro Ser Arg Pro
```

-continued

```
                530                 535                 540
Val Ile Met Val Gly Pro Gly Thr Gly Val Ala Pro Phe Arg Gly Phe
545                 550                 555                 560

Ile Gln Glu Arg Ala Ala Leu Ala Ala Lys Gly Glu Lys Val Gly Thr
                565                 570                 575

Thr Leu Leu Phe Phe Gly Cys Arg Lys Ser Asp Glu Asp Phe Leu Tyr
                580                 585                 590

Lys Asp Glu Trp Lys Thr Phe Gln Glu Gln Leu Gly Asp Ser Leu Lys
                595                 600                 605

Ile Ile Thr Ala Phe Ser Arg Glu Ser Ala Glu Lys Val Tyr Val Gln
610                 615                 620

His Arg Leu Arg Glu His Ala Glu Leu Val Ser Asp Leu Leu Lys Gln
625                 630                 635                 640

Lys Ala Thr Phe Tyr Val Cys Gly Asp Ala Ala Asn Met Ala Arg Glu
                645                 650                 655

Val Asn Leu Val Leu Gly Gln Ile Ile Ala Lys Gln Arg Gly Leu Pro
                660                 665                 670

Ala Glu Lys Gly Glu Glu Met Val Lys His Met Arg Ser Ser Gly Ser
                675                 680                 685

Tyr Gln Asp Asp Val Trp Ser
690                 695

<210> SEQ ID NO 9
<211> LENGTH: 695
<212> TYPE: PRT
<213> ORGANISM: Aspergillus ochraceus

<400> SEQUENCE: 9

Met Ala Gln Leu Asp Thr Leu Asp Leu Val Val Leu Ala Leu Leu
1               5                   10                  15

Val Gly Ser Val Ala Tyr Phe Thr Lys Gly Thr Tyr Trp Ala Val Ala
                20                  25                  30

Lys Asp Pro Tyr Ala Ser Ala Gly Pro Ala Met Asn Gly Gly Ala Lys
            35                  40                  45

Ala Gly Lys Thr Arg Asp Ile Val Gln Lys Met Asp Glu Thr Gly Lys
50                  55                  60

Asn Cys Val Ile Phe Tyr Gly Ser Gln Thr Gly Thr Ala Glu Asp Tyr
65                  70                  75                  80

Ala Ser Arg Leu Ala Lys Glu Gly Ser Gln Arg Phe Gly Leu Lys Thr
                85                  90                  95

Met Val Ala Asp Leu Glu Asp Tyr Asp Tyr Glu Asn Leu Glu Lys Phe
                100                 105                 110

Pro Glu Asp Lys Val Val Phe Phe Val Leu Ala Thr Tyr Gly Glu Gly
            115                 120                 125

Glu Pro Thr Asp Asn Ala Val Glu Phe Tyr Gln Phe Val Thr Gly Glu
            130                 135                 140

Asp Ala Ala Phe Glu Ser Gly Ala Thr Ala Asp Asp Lys Pro Leu Ser
145                 150                 155                 160

Ser Leu Lys Tyr Val Thr Phe Gly Leu Gly Asn Asn Thr Tyr Glu His
                165                 170                 175

Tyr Asn Ala Met Val Arg Asn Val Asp Ala Ala Leu Thr Lys Phe Gly
                180                 185                 190

Ala Gln Arg Ile Gly Ser Ala Gly Glu Gly Asp Asp Gly Ala Gly Thr
            195                 200                 205
```

```
Met Glu Glu Asp Phe Leu Ala Trp Lys Glu Pro Met Trp Ala Ala Leu
210                 215                 220

Ser Glu Ala Met Asn Leu Gln Glu Arg Asp Ala Val Tyr Glu Pro Val
225                 230                 235                 240

Phe Asn Val Thr Glu Asp Glu Ser Leu Ser Pro Glu Asp Glu Asn Val
            245                 250                 255

Tyr Leu Gly Glu Pro Thr Gln Gly His Leu Gln Gly Glu Pro Lys Gly
            260                 265                 270

Pro Tyr Ser Ala His Asn Pro Phe Ile Ala Pro Ile Ser Glu Ser Arg
        275                 280                 285

Glu Leu Phe Asn Val Lys Asp Arg Asn Cys Leu His Met Glu Ile Ser
    290                 295                 300

Ile Ala Gly Ser Asn Leu Thr Tyr Gln Thr Gly Asp His Ile Ala Val
305                 310                 315                 320

Trp Pro Thr Asn Ala Gly Ser Glu Val Asp Arg Phe Leu Gln Ala Phe
                325                 330                 335

Gly Leu Glu Gly Lys Arg His Ser Val Ile Asn Ile Lys Gly Ile Asp
            340                 345                 350

Val Thr Ala Lys Val Pro Ile Pro Thr Pro Thr Thr Tyr Asp Ala Ala
        355                 360                 365

Val Arg Tyr Tyr Leu Glu Val Cys Ala Pro Val Ser Arg Gln Phe Val
    370                 375                 380

Ser Thr Leu Ala Ala Phe Ala Pro Asp Glu Ala Thr Lys Ala Glu Ile
385                 390                 395                 400

Val Arg Leu Gly Gly Asp Lys Asp Tyr Phe His Glu Lys Ile Thr Asn
                405                 410                 415

Arg Cys Phe Asn Ile Ala Gln Ala Leu Gln Ser Ile Thr Ser Lys Pro
            420                 425                 430

Phe Thr Ala Val Pro Phe Ser Leu Leu Ile Glu Gly Ile Thr Lys Leu
        435                 440                 445

Gln Pro Arg Tyr Tyr Ser Ile Ser Ser Ser Leu Val Gln Lys Asp
    450                 455                 460

Lys Ile Ser Ile Thr Ala Val Val Glu Ser Val Arg Leu Pro Gly Glu
465                 470                 475                 480

Glu His Ile Val Lys Gly Val Thr Thr Asn Tyr Leu Leu Ala Leu Lys
                485                 490                 495

Glu Lys Gln Asn Gly Glu Pro Ser Pro Asp Pro His Gly Leu Thr Tyr
            500                 505                 510

Ser Ile Thr Gly Pro Arg Asn Lys Tyr Asp Gly Ile His Val Pro Val
        515                 520                 525

His Val Arg His Ser Asn Phe Lys Leu Pro Ser Asp Pro Ser Arg Pro
    530                 535                 540

Val Ile Met Val Gly Pro Gly Thr Gly Val Ala Pro Phe Arg Gly Phe
545                 550                 555                 560

Ile Gln Glu Arg Ala Ala Leu Ala Ala Lys Gly Glu Lys Val Gly Thr
                565                 570                 575

Thr Leu Leu Phe Phe Gly Cys Arg Lys Ser Asp Glu Asp Phe Leu Tyr
            580                 585                 590

Lys Asp Glu Trp Lys Thr Phe Gln Glu Gln Leu Gly Asp Ser Leu Lys
        595                 600                 605

Ile Ile Thr Ala Phe Ser Arg Glu Ser Ala Glu Lys Val Tyr Val Gln
    610                 615                 620

His Arg Leu Arg Glu His Ala Glu Leu Val Ser Asp Leu Leu Lys Gln
```

```
                    625                 630                 635                 640
Lys Ala Thr Phe Tyr Val Cys Gly Asp Ala Ala Asn Met Ala Arg Glu
                        645                 650                 655
Val Asn Leu Val Leu Gly Gln Ile Ile Ala Lys Gln Arg Gly Leu Pro
                660                 665                 670
Ala Glu Lys Gly Glu Glu Met Val Lys His Met Arg Ser Ser Gly Ser
            675                 680                 685
Tyr Gln Asp Asp Val Trp Ser
    690                 695

<210> SEQ ID NO 10
<211> LENGTH: 36
<212> TYPE: DNA
<213> ORGANISM: Homo sapiens primer H. oxred 1A

<400> SEQUENCE: 10
gatcggatcc aatatgggag actcccacgt ggacac                              36

<210> SEQ ID NO 11
<211> LENGTH: 36
<212> TYPE: DNA
<213> ORGANISM: Homo sapiens primer H. oxred 1B

<400> SEQUENCE: 11
gatcggatcc aatatgggag actcccacgt ggacac                              36

<210> SEQ ID NO 12
<211> LENGTH: 22
<212> TYPE: DNA
<213> ORGANISM: homo sapiens primer H. oxred 2A

<400> SEQUENCE: 12
ctctgctctc gtcaaccagc tg                                             22

<210> SEQ ID NO 13
<211> LENGTH: 35
<212> TYPE: DNA
<213> ORGANISM: homo sapiens primer H. oxred2B

<400> SEQUENCE: 13
gatcggtacc ttagctccac acgtccaggg agtag                               35

<210> SEQ ID NO 14
<211> LENGTH: 20
<212> TYPE: DNA
<213> ORGANISM: aspergillus ochraceus primer A. oxred-for1
<220> FEATURE:
<221> NAME/KEY: modified_base
<222> LOCATION: (6)..(6)
<223> OTHER INFORMATION: n = Inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: n = Inosine
<220> FEATURE:
<221> NAME/KEY: misc_feature
<222> LOCATION: (9)..(9)
<223> OTHER INFORMATION: n is a, c, g, or t

<400> SEQUENCE: 14
gacggngcng gtacaatgga                                                20
```

```
<210> SEQ ID NO 15
<211> LENGTH: 26
<212> TYPE: DNA
<213> ORGANISM: aspergillus ochraceus Primer A.oxred-rev1
<220> FEATURE:
<221> NAME/KEY: modified_base
<222> LOCATION: (4)..(4)
<223> OTHER INFORMATION: n = Inosine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (10)..(10)
<223> OTHER INFORMATION: n = Inosine
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (16)..(16)
<223> OTHER INFORMATION: n = Inosine
<220> FEATURE:
<221> NAME/KEY: misc_feature
<222> LOCATION: (16)..(16)
<223> OTHER INFORMATION: n is a, c, g, or t

<400> SEQUENCE: 15
ttangaccan acatcntcct ggtagc                                       26

<210> SEQ ID NO 16
<211> LENGTH: 28
<212> TYPE: DNA
<213> ORGANISM: eschericia coli Primer pSport-for1

<400> SEQUENCE: 16
caagctctaa tacgactcac tataggga                                     28

<210> SEQ ID NO 17
<211> LENGTH: 22
<212> TYPE: DNA
<213> ORGANISM: aspergillus ochraceus Primer A.oxred-rev2

<400> SEQUENCE: 17
caggaaccga tcgacctcgg aa                                           22

<210> SEQ ID NO 18
<211> LENGTH: 25
<212> TYPE: DNA
<213> ORGANISM: aspergillus ochraceus Primer A.oxred-rev3

<400> SEQUENCE: 18
gtcaccctca ccagcagagc caatg                                        25

<210> SEQ ID NO 19
<211> LENGTH: 28
<212> TYPE: DNA
<213> ORGANISM: aspergillus ochraceus Primer A.oxred-rev4

<400> SEQUENCE: 19
ccacattgcg aaccatagcg ttgtagtg                                     28

<210> SEQ ID NO 20
<211> LENGTH: 34
<212> TYPE: DNA
```

```
<213> ORGANISM: eschericia coli Primer pSport-for2

<400> SEQUENCE: 20
gccaagctct aatacgactc actataggga aagc                                     34

<210> SEQ ID NO 21
<211> LENGTH: 27
<212> TYPE: DNA
<213> ORGANISM: aspergillus ochraceus Primer A.oxred-for2

<400> SEQUENCE: 21
gtcgacatgg cgcaactcga tactctc                                             27

<210> SEQ ID NO 22
<211> LENGTH: 31
<212> TYPE: DNA
<213> ORGANISM: aspergillus ochraceus Primer A.oxred-rev5

<400> SEQUENCE: 22
ctcgagttag gaccagacat cgtcctggta g                                        31

<210> SEQ ID NO 23
<211> LENGTH: 24
<212> TYPE: DNA
<213> ORGANISM: aspergillus ochraceus Primer A.oxred-for3

<400> SEQUENCE: 23
ggatccctcg cgacctgtga tcat                                                24

<210> SEQ ID NO 24
<211> LENGTH: 38
<212> TYPE: DNA
<213> ORGANISM: aspergillus ochraceus Primer A.oxred-for4

<400> SEQUENCE: 24
cgaagatttc ttgtacaagg atgaatggaa gacttttc                                 38

<210> SEQ ID NO 25
<211> LENGTH: 36
<212> TYPE: DNA
<213> ORGANISM: aspergillus ochraceus Primer A.oxred-rev6

<400> SEQUENCE: 25
ctgaaaagtc ttccattcat ccttgtacaa gaaatc                                   36

<210> SEQ ID NO 26
<211> LENGTH: 18
<212> TYPE: PRT
<213> ORGANISM: aspergillus ochraceus 11aOH peptide 1

<400> SEQUENCE: 26

Ala Ala Ala Tyr Trp Leu Ala Thr Leu Gln Pro Ser Asp Leu Pro Glu
1               5                   10                  15

Leu Asn

<210> SEQ ID NO 27
<211> LENGTH: 20
<212> TYPE: PRT
<213> ORGANISM: aspergillus ochraceus 11aOH peptide 2

<400> SEQUENCE: 27

Cys Arg Gln Ile Leu Thr Pro Tyr Ile His Lys Arg Lys Ser Leu Lys
1               5                   10                  15
```

```
Gly Thr Thr Asp
        20

<210> SEQ ID NO 28
<211> LENGTH: 21
<212> TYPE: PRT
<213> ORGANISM: aspergillus ochraceus 11aOH peptide 3

<400> SEQUENCE: 28

His Met Gly Phe Gly His Gly Val His Ala Cys Pro Gly Arg Phe Phe
1               5                   10                  15

Ala Ser Asn Glu Ile
            20

<210> SEQ ID NO 29
<211> LENGTH: 20
<212> TYPE: PRT
<213> ORGANISM: homo sapiens oxr peptide 1

<400> SEQUENCE: 29

Cys Thr Tyr Trp Ala Val Ala Lys Asp Pro Tyr Ala Ser Ala Gly Pro
1               5                   10                  15

Ala Met Asn Gly
            20

<210> SEQ ID NO 30
<211> LENGTH: 526
<212> TYPE: PRT
<213> ORGANISM: gibberella fujikuroi CAA75565

<400> SEQUENCE: 30

Met Ala Asn His Ser Ser Ser Tyr Tyr His Glu Phe Tyr Lys Asp His
1               5                   10                  15

Ser His Thr Val Leu Thr Leu Met Ser Glu Lys Pro Val Ile Leu Pro
            20                  25                  30

Ser Leu Ile Leu Gly Thr Cys Ala Val Leu Leu Cys Ile Gln Trp Leu
        35                  40                  45

Lys Pro Gln Pro Leu Ile Met Val Asn Gly Arg Lys Phe Gly Glu Leu
    50                  55                  60

Ser Asn Val Arg Ala Lys Arg Asp Phe Thr Phe Gly Ala Arg Gln Leu
65                  70                  75                  80

Leu Glu Lys Gly Leu Lys Met Ser Pro Asp Lys Pro Phe Arg Ile Met
                85                  90                  95

Gly Asp Val Gly Glu Leu His Ile Leu Pro Pro Lys Tyr Ala Tyr Glu
            100                 105                 110

Val Arg Asn Asn Glu Lys Leu Ser Phe Thr Met Ala Ala Phe Lys Trp
        115                 120                 125

Phe Tyr Ala His Leu Pro Gly Phe Glu Gly Phe Arg Glu Gly Thr Asn
    130                 135                 140

Glu Ser His Ile Met Lys Leu Val Ala Arg His Gln Leu Thr His Gln
145                 150                 155                 160

Leu Thr Leu Val Thr Gly Ala Val Ser Glu Glu Cys Ala Leu Val Leu
                165                 170                 175

Lys Asp Val Tyr Thr Asp Ser Pro Glu Trp His Asp Ile Thr Ala Lys
            180                 185                 190

Asp Ala Asn Met Lys Leu Met Ala Arg Ile Thr Ser Arg Val Phe Leu
        195                 200                 205
```

-continued

```
Gly Lys Glu Met Cys Arg Asn Pro Gln Trp Leu Arg Ile Thr Ser Thr
210                 215                 220

Tyr Ala Val Ile Ala Phe Arg Ala Val Glu Glu Leu Arg Leu Trp Pro
225                 230                 235                 240

Ser Trp Leu Arg Pro Val Val Gln Trp Phe Met Pro His Cys Thr Gln
                245                 250                 255

Ser Arg Ala Leu Val Gln Glu Ala Arg Asp Leu Ile Asn Pro Leu Leu
            260                 265                 270

Glu Arg Arg Arg Glu Glu Lys Ala Glu Ala Glu Arg Thr Gly Glu Lys
        275                 280                 285

Val Thr Tyr Asn Asp Ala Val Glu Trp Leu Asp Asp Leu Ala Arg Glu
    290                 295                 300

Lys Gly Val Gly Tyr Asp Pro Ala Cys Ala Gln Leu Ser Leu Ser Val
305                 310                 315                 320

Ala Ala Leu His Ser Thr Thr Asp Phe Phe Thr Gln Val Met Phe Asp
                325                 330                 335

Ile Ala Gln Asn Pro Glu Leu Ile Glu Pro Leu Arg Glu Glu Ile Ile
            340                 345                 350

Ala Val Leu Gly Lys Gln Gly Trp Ser Lys Asn Ser Leu Tyr Asn Leu
        355                 360                 365

Lys Leu Met Asp Ser Val Leu Lys Glu Ser Gln Arg Leu Lys Pro Ile
    370                 375                 380

Ala Ile Ala Ser Met Arg Arg Phe Thr Thr His Asn Val Lys Leu Ser
385                 390                 395                 400

Asp Gly Val Ile Leu Pro Lys Asn Lys Leu Thr Leu Val Ser Ala His
                405                 410                 415

Gln His Trp Asp Pro Glu Tyr Tyr Lys Asp Pro Leu Lys Phe Asp Gly
            420                 425                 430

Tyr Arg Phe Phe Asn Met Arg Arg Glu Pro Gly Lys Glu Ser Lys Ala
        435                 440                 445

Gln Leu Val Ser Ala Thr Pro Asp His Met Gly Phe Gly Tyr Gly Leu
    450                 455                 460

His Ala Cys Pro Gly Arg Phe Phe Ala Ser Glu Ile Lys Ile Ala
465                 470                 475                 480

Leu Ser His Ile Leu Leu Lys Tyr Asp Phe Lys Pro Val Glu Gly Ser
                485                 490                 495

Ser Met Glu Pro Arg Lys Tyr Gly Leu Asn Met Asn Ala Asn Pro Thr
            500                 505                 510

Ala Lys Leu Ser Val Arg Arg Lys Glu Glu Ile Ala Ile
        515                 520                 525
```

<210> SEQ ID NO 31
<211> LENGTH: 514
<212> TYPE: PRT
<213> ORGANISM: neurospora crassa CAB91316

<400> SEQUENCE: 31

```
Met Glu Arg Leu Asp Ile Lys Ser Ile Thr Asp Pro Ser Ala Thr Pro
1               5                   10                  15

Phe Ser Tyr Leu Val Thr Ala Phe Leu Leu Ala Val Val Val Tyr Ser
                20                  25                  30

Leu Gln Gly Pro Arg Phe Pro Lys Asn Ile Lys His Leu Asn Pro Lys
            35                  40                  45

Gly Pro Leu Glu Phe Ser Asp Thr Arg Pro Lys Lys Glu Phe Val Tyr
        50                  55                  60
```

```
Gly Ser Arg Gln Met Leu Ala Asn Trp Phe Lys Ala Asn Pro Asn Lys
 65                  70                  75                  80

Pro Cys Arg Val Ile Ser Asp Phe Gly Glu Ala Ile Val Leu Pro Pro
                 85                  90                  95

Arg Met Ala Asn Glu Ile Lys Asn Asp Asp Arg Leu Ser Phe Thr Arg
            100                 105                 110

Trp Thr Tyr Lys Ala Phe His Gly His Leu Pro Gly Phe Glu Gly Phe
        115                 120                 125

Gly Glu Ala Ser Arg Glu Ser His Ile Val Gln Glu Val Ile Met Arg
130                 135                 140

Asp Leu Thr Lys Tyr Leu Asn Lys Val Thr Glu Pro Leu Ala Gln Glu
145                 150                 155                 160

Thr Ser Met Ala Met Glu Ala Asn Leu Pro Lys Ala Ala Asn Gly Glu
                165                 170                 175

Trp Ser Thr Ile Asn Leu Arg Ser Lys Ile Leu Pro Ile Val Ala Arg
            180                 185                 190

Ile Ser Ser Arg Val Phe Leu Gly Glu Glu Leu Cys Arg Asn Glu Glu
        195                 200                 205

Trp Leu Lys Val Thr Gln Gln Tyr Thr Ile Asp Gly Phe Gly Ala Ala
210                 215                 220

Glu Asp Leu Arg Leu Trp Pro Ala Ala Leu Arg Pro Ile Val His Trp
225                 230                 235                 240

Phe Leu Pro Ser Cys Gln Arg Ala Arg Ala Asp Val Arg Val Ala Arg
                245                 250                 255

Ser Ile Leu Asp Pro Val Leu Lys Lys Arg Gln Glu Lys Ala Ala
            260                 265                 270

Asn Gly Gly Lys Ala Glu His Asp Asp Ala Ile Glu Trp Phe Glu Arg
        275                 280                 285

Thr Ala Lys Gly Lys Tyr Tyr Asp Pro Ala Val Ala Gln Leu Val Leu
290                 295                 300

Ser Leu Val Ala Ile His Thr Thr Ser Asp Leu Thr Cys Gln Val Met
305                 310                 315                 320

Thr Asn Leu Met Gln Asn Pro Glu Phe Ile Ala Pro Leu Arg Glu Glu
                325                 330                 335

Met Ile Gln Val Leu Ser Glu Gly Gly Trp Lys Lys Thr Ser Leu Tyr
            340                 345                 350

Asn Met Lys Leu Leu Asp Ser Val Ile Lys Glu Ser Gln Arg Val Lys
        355                 360                 365

Pro Thr Gly Val Ala Ser Met Arg Arg Tyr Ala Glu Lys Asp Val Thr
370                 375                 380

Leu Ser Asp Gly Thr Phe Ile Pro Lys Gly Gly Phe Val Ala Val Ser
385                 390                 395                 400

Ala His Asp Met Trp Asn Ser Glu Val Tyr Glu Gln Ala Glu Lys Trp
                405                 410                 415

Asp Gly Arg Arg Phe Leu Arg Met Arg Glu Thr Pro Gly Ala Gly Lys
            420                 425                 430

Glu Asn Val Ala Gln Leu Val Ser Thr Ala Pro Glu His Leu Gly Phe
        435                 440                 445

Gly His Gly Gln His Ala Cys Pro Gly Arg Phe Phe Ala Ala Asn Glu
450                 455                 460

Ile Lys Ile Ala Leu Val His Leu Leu Leu Asn Tyr Glu Trp Arg Leu
465                 470                 475                 480
```

-continued

```
Pro Glu Gly Ser Asp Pro Lys Ile Arg Thr Phe Gly Phe Ser Met Gly
                485                 490                 495

Val Asp Pro Ser Leu Lys Val Glu Tyr Lys Gly Arg Gln Pro Glu Ile
                500                 505                 510

Glu Leu
```

<210> SEQ ID NO 32
<211> LENGTH: 495
<212> TYPE: PRT
<213> ORGANISM: Catharanthus roseus CAB56503

<400> SEQUENCE: 32

```
Leu Leu Phe Cys Phe Ile Leu Ser Lys Thr Thr Lys Lys Phe Gly Gln
1               5                   10                  15

Asn Ser Gln Tyr Ser Asn His Asp Glu Leu Pro Pro Gly Pro Pro Gln
                20                  25                  30

Ile Pro Ile Leu Gly Asn Ala His Gln Leu Ser Gly Gly His Thr His
                35                  40                  45

His Ile Leu Arg Asp Leu Ala Lys Lys Tyr Gly Pro Leu Met His Leu
        50                  55                  60

Lys Ile Gly Glu Val Ser Thr Ile Val Ala Ser Ser Pro Gln Ile Ala
65                  70                  75                  80

Glu Glu Ile Phe Arg Thr His Asp Ile Leu Phe Ala Asp Arg Pro Ser
                85                  90                  95

Asn Leu Glu Ser Phe Lys Ile Val Ser Tyr Asp Phe Ser Asp Met Val
                100                 105                 110

Val Ser Pro Tyr Gly Asn Tyr Trp Arg Gln Leu Arg Lys Ile Ser Met
                115                 120                 125

Met Glu Leu Leu Ser Gln Lys Ser Val Gln Ser Phe Arg Ser Ile Arg
        130                 135                 140

Glu Glu Glu Val Leu Asn Phe Ile Lys Ser Ile Gly Ser Lys Glu Gly
145                 150                 155                 160

Thr Arg Ile Asn Leu Ser Lys Glu Ile Ser Leu Leu Ile Tyr Gly Ile
                165                 170                 175

Thr Thr Arg Ala Ala Phe Gly Glu Lys Asn Lys Asn Thr Glu Glu Phe
                180                 185                 190

Ile Arg Leu Leu Asp Gln Leu Thr Lys Ala Val Ala Glu Pro Asn Ile
                195                 200                 205

Ala Asp Met Phe Pro Ser Leu Lys Phe Leu Gln Leu Ile Ser Thr Ser
        210                 215                 220

Lys Tyr Lys Ile Glu Lys Ile His Lys Gln Phe Asp Val Ile Val Glu
225                 230                 235                 240

Thr Ile Leu Lys Gly His Lys Glu Lys Ile Asn Lys Pro Leu Ser Gln
                245                 250                 255

Glu Asn Gly Glu Lys Lys Glu Asp Leu Val Asp Val Leu Leu Asn Ile
                260                 265                 270

Gln Arg Arg Asn Asp Phe Glu Ala Pro Leu Gly Asp Lys Asn Ile Lys
                275                 280                 285

Ala Ile Ile Phe Asn Ile Phe Ser Ala Gly Thr Glu Thr Ser Ser Thr
        290                 295                 300

Thr Val Asp Trp Ala Met Cys Glu Met Ile Lys Asn Pro Thr Val Met
305                 310                 315                 320

Lys Lys Ala Gln Glu Glu Val Arg Lys Val Phe Asn Glu Glu Gly Asn
                325                 330                 335
```

-continued

```
Val Asp Glu Thr Lys Leu His Gln Leu Lys Tyr Leu Gln Ala Val Ile
            340                 345                 350

Lys Glu Thr Leu Arg Leu His Pro Pro Val Pro Leu Leu Leu Pro Arg
            355                 360                 365

Glu Cys Arg Glu Gln Cys Lys Ile Lys Gly Tyr Thr Ile Pro Ser Lys
            370                 375                 380

Ser Arg Val Ile Val Asn Ala Trp Ala Ile Gly Arg Asp Pro Asn Tyr
385                 390                 395                 400

Trp Ile Glu Pro Glu Lys Phe Asn Pro Asp Arg Phe Leu Glu Ser Lys
                405                 410                 415

Val Asp Phe Lys Gly Asn Ser Phe Glu Tyr Leu Pro Phe Gly Gly Gly
            420                 425                 430

Arg Arg Ile Cys Pro Gly Ile Thr Phe Ala Leu Ala Asn Ile Glu Leu
            435                 440                 445

Pro Leu Ala Gln Leu Leu Phe His Phe Asp Trp Gln Ser Asn Thr Glu
            450                 455                 460

Lys Leu Asn Met Lys Glu Ser Arg Gly Val Thr Val Arg Arg Glu Asp
465                 470                 475                 480

Asp Leu Tyr Leu Thr Pro Val Asn Phe Ser Ser Ser Pro Ala
            485                 490                 495

<210> SEQ ID NO 33
<211> LENGTH: 510
<212> TYPE: PRT
<213> ORGANISM: glycine max AAB94588

<400> SEQUENCE: 33

Met Val Met Glu Leu His Asn His Thr Pro Phe Ser Ile Tyr Phe Ile
1               5                   10                  15

Thr Ser Ile Leu Phe Ile Phe Val Phe Phe Lys Leu Val Gln Arg
            20                  25                  30

Ser Asp Ser Lys Thr Ser Ser Thr Cys Lys Leu Pro Pro Gly Pro Arg
            35                  40                  45

Thr Leu Pro Leu Ile Gly Asn Ile His Gln Ile Val Gly Ser Leu Pro
        50                  55                  60

Val His Tyr Tyr Leu Lys Asn Leu Ala Asp Lys Tyr Gly Pro Leu Met
65                  70                  75                  80

His Leu Lys Leu Gly Glu Val Ser Asn Ile Ile Val Thr Ser Pro Glu
                85                  90                  95

Met Ala Gln Glu Ile Met Lys Thr His Asp Leu Asn Phe Ser Asp Arg
            100                 105                 110

Pro Asp Phe Val Leu Ser Arg Ile Val Ser Tyr Asn Gly Ser Gly Ile
            115                 120                 125

Val Phe Ser Gln His Gly Asp Tyr Trp Arg Gln Leu Arg Lys Ile Cys
        130                 135                 140

Thr Val Glu Leu Leu Thr Ala Lys Arg Val Gln Ser Phe Arg Ser Ile
145                 150                 155                 160

Arg Glu Glu Glu Val Ala Glu Leu Val Lys Lys Ile Ala Ala Thr Ala
                165                 170                 175

Ser Glu Glu Gly Gly Ser Ile Phe Asn Leu Thr Gln Ser Ile Tyr Ser
            180                 185                 190

Met Thr Phe Gly Ile Ala Ala Arg Ala Ala Phe Gly Lys Lys Ser Arg
        195                 200                 205

Tyr Gln Gln Val Phe Ile Ser Asn Met His Lys Gln Leu Met Leu Leu
    210                 215                 220
```

```
Gly Gly Phe Ser Val Ala Asp Leu Tyr Pro Ser Ser Arg Val Phe Gln
225                 230                 235                 240

Met Met Gly Ala Thr Gly Lys Leu Glu Lys Val His Arg Val Thr Asp
            245                 250                 255

Arg Val Leu Gln Asp Ile Ile Asp Glu His Lys Asn Arg Asn Arg Ser
        260                 265                 270

Ser Glu Glu Arg Glu Ala Val Glu Asp Leu Val Asp Val Leu Leu Lys
    275                 280                 285

Phe Gln Lys Glu Ser Glu Phe Arg Leu Thr Asp Asp Asn Ile Lys Ala
290                 295                 300

Val Ile Gln Asp Ile Phe Ile Gly Gly Glu Thr Ser Ser Ser Val
305                 310                 315                 320

Val Glu Trp Gly Met Ser Glu Leu Ile Arg Asn Pro Arg Val Met Glu
            325                 330                 335

Glu Ala Gln Ala Glu Val Arg Arg Val Tyr Asp Ser Lys Gly Tyr Val
        340                 345                 350

Asp Glu Thr Glu Leu His Gln Leu Ile Tyr Leu Lys Ser Ile Ile Lys
    355                 360                 365

Glu Thr Met Arg Leu His Pro Pro Val Pro Leu Leu Val Pro Arg Val
370                 375                 380

Ser Arg Glu Arg Cys Gln Ile Asn Gly Tyr Glu Ile Pro Ser Lys Thr
385                 390                 395                 400

Arg Ile Ile Ile Asn Ala Trp Ala Ile Gly Arg Asn Pro Lys Tyr Trp
            405                 410                 415

Gly Glu Thr Glu Ser Phe Lys Pro Glu Arg Phe Leu Asn Ser Ser Ile
        420                 425                 430

Asp Phe Arg Gly Thr Asp Phe Glu Phe Ile Pro Phe Gly Ala Gly Arg
    435                 440                 445

Arg Ile Cys Pro Gly Ile Thr Phe Ala Ile Pro Asn Ile Glu Leu Pro
450                 455                 460

Leu Ala Gln Leu Leu Tyr His Phe Asp Trp Lys Leu Pro Asn Lys Met
465                 470                 475                 480

Lys Asn Glu Glu Leu Asp Met Thr Glu Ser Asn Gly Ile Thr Leu Arg
            485                 490                 495

Arg Gln Asn Asp Leu Cys Leu Ile Pro Ile Thr Arg Leu Pro
        500                 505                 510

<210> SEQ ID NO 34
<211> LENGTH: 524
<212> TYPE: PRT
<213> ORGANISM: Gibberella fujikuroi CAA75566

<400> SEQUENCE: 34

Met Ser Ile Phe Asn Met Ile Thr Ser Tyr Ala Gly Ser Gln Leu Leu
1               5                   10                  15

Pro Phe Tyr Ile Ala Ile Phe Val Phe Thr Leu Val Pro Trp Ala Ile
            20                  25                  30

Arg Phe Ser Trp Leu Glu Leu Arg Lys Gly Ser Val Val Pro Leu Ala
        35                  40                  45

Asn Pro Pro Asp Ser Leu Phe Gly Thr Gly Lys Thr Arg Arg Ser Phe
    50                  55                  60

Val Lys Leu Ser Arg Glu Ile Leu Ala Lys Ala Arg Ser Leu Phe Pro
65                  70                  75                  80

Asn Glu Pro Phe Arg Leu Ile Thr Asp Trp Gly Glu Val Leu Ile Leu
```

```
                    85                  90                  95
Pro Pro Asp Phe Ala Asp Glu Ile Arg Asn Asp Pro Arg Leu Ser Phe
                100                 105                 110
Ser Lys Ala Ala Met Gln Asp Asn His Ala Gly Ile Pro Gly Phe Glu
                115                 120                 125
Thr Val Ala Leu Val Gly Arg Glu Asp Gln Leu Ile Gln Lys Val Ala
                130                 135                 140
Arg Lys Gln Leu Thr Lys His Leu Ser Ala Val Ile Glu Pro Leu Ser
145                 150                 155                 160
Arg Glu Ser Thr Leu Ala Val Ser Leu Asn Phe Gly Glu Thr Thr Glu
                165                 170                 175
Trp Arg Ala Ile Arg Leu Lys Pro Ala Ile Leu Asp Ile Ile Ala Arg
                180                 185                 190
Ile Ser Ser Arg Ile Tyr Leu Gly Asp Gln Leu Cys Arg Asn Glu Ala
                195                 200                 205
Trp Leu Lys Ile Thr Lys Thr Tyr Thr Thr Asn Phe Tyr Thr Ala Ser
                210                 215                 220
Thr Asn Leu Arg Met Phe Pro Arg Ser Ile Arg Pro Leu Ala His Trp
225                 230                 235                 240
Phe Leu Pro Glu Cys Arg Lys Leu Arg Gln Glu Arg Lys Asp Ala Ile
                245                 250                 255
Gly Ile Ile Thr Pro Leu Ile Glu Arg Arg Arg Glu Leu Arg Arg Ala
                260                 265                 270
Ala Ile Ala Ala Gly Gln Pro Leu Pro Val Phe His Asp Ala Ile Asp
                275                 280                 285
Trp Ser Glu Gln Glu Ala Glu Ala Ala Gly Thr Gly Ala Ser Phe Asp
290                 295                 300
Pro Val Ile Phe Gln Leu Thr Leu Ser Leu Leu Ala Ile His Thr Thr
305                 310                 315                 320
Tyr Asp Leu Leu Gln Gln Thr Met Ile Asp Leu Gly Arg His Pro Glu
                325                 330                 335
Tyr Ile Glu Pro Leu Arg Gln Glu Val Val Gln Leu Leu Arg Glu Glu
                340                 345                 350
Gly Trp Lys Lys Thr Thr Leu Phe Lys Met Lys Leu Leu Asp Ser Ala
                355                 360                 365
Ile Lys Glu Ser Gln Arg Met Lys Pro Gly Ser Ile Val Thr Met Arg
                370                 375                 380
Arg Tyr Val Thr Glu Asp Ile Thr Leu Ser Ser Gly Leu Thr Leu Lys
385                 390                 395                 400
Lys Gly Thr Arg Leu Asn Val Asp Asn Arg Arg Leu Asp Asp Pro Lys
                405                 410                 415
Ile Tyr Asp Asn Pro Glu Val Tyr Asn Pro Tyr Arg Phe Tyr Asp Met
                420                 425                 430
Arg Ser Glu Ala Gly Lys Asp His Gly Ala Gln Leu Val Ser Thr Gly
                435                 440                 445
Ser Asn His Met Gly Phe Gly His Gly Gln His Ser Cys Pro Gly Arg
                450                 455                 460
Phe Phe Ala Ala Asn Glu Ile Lys Val Ala Leu Cys His Ile Leu Val
465                 470                 475                 480
Lys Tyr Asp Trp Lys Leu Cys Pro Asp Thr Glu Thr Lys Pro Asp Thr
                485                 490                 495
Arg Gly Met Ile Ala Lys Ser Ser Pro Val Thr Asp Ile Leu Ile Lys
                500                 505                 510
```

Arg Arg Glu Ser Val Glu Leu Asp Leu Glu Ala Ile
        515                 520

<210> SEQ ID NO 35
<211> LENGTH: 528
<212> TYPE: PRT
<213> ORGANISM: Aspergillus terreus AAD34552

<400> SEQUENCE: 35

Met Thr Val Asp Ala Leu Thr Gln Pro His His Leu Ser Leu Ala
1               5                   10                  15

Trp Asn Asp Thr Gln Gln His Gly Ser Trp Phe Ala Pro Leu Val Thr
            20                  25                  30

Thr Ser Ala Gly Leu Leu Cys Leu Leu Leu Tyr Leu Cys Ser Ser Gly
        35                  40                  45

Arg Arg Ser Asp Leu Pro Val Phe Asn Pro Lys Thr Trp Glu Leu
50                  55                  60

Thr Thr Met Arg Ala Lys Arg Asp Phe Asp Ala Asn Ala Pro Ser Trp
65              70                  75                  80

Ile Glu Ser Trp Phe Ser Gln Asn Asp Lys Pro Ile Arg Phe Ile Val
                85                  90                  95

Asp Ser Gly Tyr Cys Thr Ile Leu Pro Ser Ser Met Ala Asp Glu Phe
            100                 105                 110

Arg Lys Met Lys Glu Leu Cys Met Tyr Lys Phe Leu Gly Thr Asp Phe
        115                 120                 125

His Ser His Leu Pro Gly Phe Asp Gly Phe Lys Glu Val Thr Arg Asp
    130                 135                 140

Ala His Leu Ile Thr Lys Val Val Met Asn Gln Phe Gln Thr Gln Ala
145                 150                 155                 160

Pro Lys Tyr Val Lys Pro Leu Ala Asn Glu Ala Ser Gly Ile Ile Thr
                165                 170                 175

Asp Ile Phe Gly Asp Ser Asn Glu Trp His Thr Val Pro Val Tyr Asn
            180                 185                 190

Gln Cys Leu Asp Leu Val Thr Arg Thr Val Thr Phe Ile Met Val Gly
        195                 200                 205

Ser Lys Leu Ala His Asn Glu Glu Trp Leu Asp Ile Ala Lys His His
    210                 215                 220

Ala Val Thr Met Ala Ile Gln Ala Arg Gln Leu Arg Leu Trp Pro Val
225                 230                 235                 240

Ile Leu Arg Pro Leu Val His Trp Leu Glu Pro Gln Gly Ala Lys Leu
                245                 250                 255

Arg Ala Gln Val Arg Arg Ala Arg Gln Leu Leu Asp Pro Ile Ile Gln
            260                 265                 270

Glu Arg Arg Ala Glu Arg Asp Ala Cys Arg Ala Lys Gly Ile Glu Pro
        275                 280                 285

Pro Arg Tyr Val Asp Ser Ile Gln Trp Phe Glu Asp Thr Ala Lys Gly
    290                 295                 300

Lys Trp Tyr Asp Ala Ala Gly Ala Gln Leu Ala Met Asp Phe Ala Gly
305                 310                 315                 320

Ile Tyr Gly Thr Ser Asp Leu Leu Ile Gly Gly Leu Val Asp Ile Val
                325                 330                 335

Arg His Pro His Leu Leu Glu Pro Leu Arg Asp Glu Ile Arg Thr Val
            340                 345                 350

Ile Gly Gln Gly Gly Trp Thr Pro Ala Ser Leu Tyr Lys Leu Lys Leu

-continued

```
                355                 360                 365
Leu Asp Ser Cys Leu Lys Glu Ser Gln Arg Val Lys Pro Val Glu Cys
        370                 375                 380

Ala Thr Met Arg Ser Tyr Ala Leu Gln Asp Val Thr Phe Ser Asn Gly
385                 390                 395                 400

Thr Phe Ile Pro Lys Gly Glu Leu Val Ala Val Ala Asp Arg Met
                405                 410                 415

Ser Asn Pro Glu Val Trp Pro Glu Ala Lys Tyr Asp Pro Tyr Arg
                420                 425                 430

Tyr Met Arg Leu Arg Glu Asp Pro Ala Lys Ala Phe Ser Ala Gln Leu
        435                 440                 445

Glu Asn Thr Asn Gly Asp His Ile Gly Phe Gly Trp His Pro Arg Ala
    450                 455                 460

Cys Pro Gly Arg Phe Phe Ala Ser Lys Glu Ile Lys Met Met Leu Ala
465                 470                 475                 480

Tyr Leu Leu Ile Arg Tyr Asp Trp Lys Val Val Pro Asp Glu Pro Leu
                485                 490                 495

Gln Tyr Tyr Arg His Ser Phe Ser Val Arg Ile His Pro Thr Thr Lys
                500                 505                 510

Leu Met Met Arg Arg Arg Asp Glu Asp Ile Arg Leu Pro Gly Ser Leu
        515                 520                 525

<210> SEQ ID NO 36
<211> LENGTH: 388
<212> TYPE: PRT
<213> ORGANISM: Gibberella fujikuroi CAA75567

<400> SEQUENCE: 36

Met Lys Tyr Thr Thr Cys Gln Met Asn Ile Phe Pro Ser Leu Trp Ser
1               5                   10                  15

Met Lys Thr Ser Phe Arg Trp Pro Arg Thr Ser Lys Trp Ser Ser Val
            20                  25                  30

Ser Leu Tyr Asp Met Met Leu Arg Thr Val Ala Leu Leu Ser Gly Arg
        35                  40                  45

Ala Phe Val Gly Leu Pro Leu Cys Arg Asp Glu Gly Trp Leu Gln Ala
50                  55                  60

Ser Ile Gly Tyr Thr Val Gln Cys Val Ser Ile Arg Asp Gln Leu Phe
65                  70                  75                  80

Thr Trp Ser Pro Val Leu Arg Pro Ile Ile Gly Pro Phe Leu Pro Ser
                85                  90                  95

Val Arg Ser Val Arg Arg His Leu Arg Phe Ala Ala Glu Ile Met Ala
            100                 105                 110

Pro Leu Ile Ser Gln Ala Leu Gln Asp Glu Lys Gln His Arg Ala Asp
        115                 120                 125

Thr Leu Leu Ala Asp Gln Thr Glu Gly Arg Gly Thr Phe Ile Ser Trp
    130                 135                 140

Leu Leu Arg His Leu Pro Glu Glu Leu Arg Thr Pro Glu Gln Val Gly
145                 150                 155                 160

Leu Asp Gln Met Leu Val Ser Phe Ala Ala Ile His Thr Thr Thr Met
                165                 170                 175

Ala Leu Thr Lys Val Val Trp Glu Leu Val Lys Arg Pro Glu Tyr Ile
            180                 185                 190

Glu Pro Leu Arg Thr Glu Met Gln Asp Val Phe Gly Pro Asp Ala Val
        195                 200                 205
```

-continued

Ser Pro Asp Ile Cys Ile Asn Lys Glu Ala Leu Ser Arg Leu His Lys
210                 215                 220

Leu Asp Ser Phe Ile Arg Glu Val Gln Arg Trp Cys Pro Ser Thr Phe
225                 230                 235                 240

Val Thr Pro Ser Arg Arg Val Met Lys Ser Met Thr Leu Ser Asn Gly
            245                 250                 255

Ile Lys Leu Gln Arg Gly Thr Ser Ile Ala Phe Pro Ala His Ala Ile
        260                 265                 270

His Met Ser Glu Glu Thr Pro Thr Phe Ser Pro Asp Phe Ser Ser Asp
    275                 280                 285

Phe Glu Asn Pro Ser Pro Arg Ile Phe Asp Gly Phe Arg Tyr Leu Asn
290                 295                 300

Leu Arg Ser Ile Lys Gly Gln Gly Ser Gln His Gln Ala Ala Thr Thr
305                 310                 315                 320

Gly Pro Asp Tyr Leu Ile Phe Asn His Gly Lys His Ala Cys Pro Gly
            325                 330                 335

Arg Phe Phe Ala Ile Ser Glu Ile Lys Met Ile Leu Ile Glu Leu Leu
        340                 345                 350

Ala Lys Tyr Asp Phe Arg Leu Glu Asp Gly Lys Pro Gly Pro Glu Leu
    355                 360                 365

Met Arg Val Gly Thr Glu Thr Arg Leu Asp Thr Lys Ala Gly Leu Glu
370                 375                 380

Met Arg Arg Arg
385

<210> SEQ ID NO 37
<211> LENGTH: 525
<212> TYPE: PRT
<213> ORGANISM: Gibberella fujikuroi CAA76703

<400> SEQUENCE: 37

Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
        35                  40                  45

His Val Leu Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
            85                  90                  95

Ile Phe Gln Val Arg Lys Leu Gly Thr Asp Ile Val Ile Pro Pro
        100                 105                 110

Asn Tyr Ile Asp Glu Val Arg Lys Leu Ser Gln Asp Lys Thr Arg Ser
    115                 120                 125

Val Glu Pro Phe Ile Asn Asp Phe Ala Gly Gln Tyr Thr Arg Gly Met
130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
            165                 170                 175

Tyr Ala Leu Thr Lys Glu Met Pro Asp Met Lys Asn Asp Glu Trp Val
        180                 185                 190

```
Glu Val Asp Ile Ser Ser Ile Met Val Arg Leu Ile Ser Arg Ile Ser
            195                 200                 205

Ala Arg Val Phe Leu Gly Pro Glu His Cys Arg Asn Gln Glu Trp Leu
        210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
        275                 280                 285

Leu Ser Trp Met Arg Asp Ala Ala Thr Gly Glu Glu Lys Gln Ile Asp
290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Val Gly Ala
            340                 345                 350

Ser Gly Trp Asp Lys Thr Ala Leu Asn Arg Phe His Lys Leu Asp Ser
        355                 360                 365

Phe Leu Lys Glu Ser Gln Arg Phe Asn Pro Val Phe Leu Leu Thr Phe
370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Thr Glu Phe Asp Gly Phe
            420                 425                 430

Arg Tyr Ser Lys Ile Arg Ser Asp Ser Asn Tyr Ala Gln Lys Tyr Leu
        435                 440                 445

Phe Ser Met Thr Asp Ser Ser Asn Met Ala Phe Gly Tyr Gly Lys Tyr
450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
            500                 505                 510

Ala Arg Leu Cys Val Arg Lys Arg Ser Leu Arg Asp Glu
        515                 520                 525

<210> SEQ ID NO 38
<211> LENGTH: 294
<212> TYPE: PRT
<213> ORGANISM: Fusarium oxysporum CAA57874

<400> SEQUENCE: 38

Met Ala Pro Met Leu Arg Pro Leu Val Tyr Arg Phe Ile Pro Glu Arg
1               5                   10                  15

Ala Arg Ile Lys Asp Gln Trp Thr Lys Gly Arg Lys Arg Val Met Ala
            20                  25                  30

Ser Met Arg Glu Arg Gln Glu Lys Gly Gly Asn Leu Glu Asp Pro Pro
```

```
                35                  40                  45
Thr Met Leu Asp His Leu Ser Asn Gly Arg Asn Glu His Ile Ala Asp
        50                  55                  60

Asp Val Glu Leu Gln Leu Leu His Gln Met Thr Leu Ile Ala Val Gly
65                  70                  75                  80

Thr Val Thr Thr Phe Ser Ser Thr Gln Ala Ile Tyr Asp Leu Val
                85                  90                  95

Ala His Pro Glu Tyr Ile Thr Ile Leu Arg Glu Val Glu Ser Val
            100                 105                 110

Pro Arg Asp Pro Asn Gly Asn Phe Thr Lys Asp Ser Thr Val Ala Met
        115                 120                 125

Asp Lys Leu Asp Ser Phe Leu Lys Glu Ser Gln Arg Phe Asn Ser Pro
        130                 135                 140

Asp Leu Ser Met Ser Asn Leu Lys Asn Tyr Lys Leu Cys Glu Ser Leu
145                 150                 155                 160

Thr Gly His Ser Asn Leu Pro Thr Arg Thr Ile Ala Asp Met Lys Leu
                165                 170                 175

Pro Asp Gly Thr Phe Val Pro Lys Gly Thr Lys Leu Glu Ile Asn Thr
            180                 185                 190

Cys Ser Ile His Lys Asp His Lys Leu Tyr Glu Asn Pro Glu Gln Phe
        195                 200                 205

Asp Gly Leu Arg Phe His Lys Trp Arg Lys Ala Pro Gly Lys Glu Lys
        210                 215                 220

Arg Tyr Met Tyr Ser Ser Ser Gly Thr Asp Asp Leu Ser Trp Gly Phe
225                 230                 235                 240

Gly Arg His Ala Cys Pro Gly Arg Tyr Leu Ser Ala Ile Asn Ile Lys
                245                 250                 255

Leu Ile Met Ala Glu Leu Leu Met Asn Tyr Asp Ile Lys Leu Pro Asp
            260                 265                 270

Gly Leu Ser Arg Pro Lys Asn Ile Glu Phe Glu Val Leu Ala Ser Leu
        275                 280                 285

Asn Ala Cys Ala Asn Ala
        290

<210> SEQ ID NO 39
<211> LENGTH: 510
<212> TYPE: PRT
<213> ORGANISM: Caenorhabditis elegans CAA91268

<400> SEQUENCE: 39

Met Ala Leu Leu Ile Leu Ser Ser Leu Val Ile Ser Ile Phe Thr Phe
1               5                   10                  15

Phe Ile Tyr Ile Ile Leu Ala Arg Arg Glu Arg Phe Lys Leu Arg Glu
                20                  25                  30

Lys Ile Gly Leu Ser Gly Pro Glu Pro His Trp Phe Leu Gly Asn Leu
            35                  40                  45

Lys Gln Thr Ala Glu Arg Lys Glu Lys Leu Gly Tyr Asp Asp Ala Asn
        50                  55                  60

Arg Trp Phe Asn Glu Leu His Glu Gln Tyr Gly Glu Thr Phe Gly Ile
65                  70                  75                  80

Tyr Tyr Gly Ser Gln Met Asn Ile Val Ile Ser Asn Glu Lys Asp Ile
                85                  90                  95

Lys Glu Val Phe Ile Lys Asn Phe Ser Asn Phe Ser Asp Arg Ser Val
            100                 105                 110
```

Pro Ser Ile Tyr Glu Ala Asn Gln Leu Thr Ala Ser Leu Leu Met Asn
    115                 120                 125

Ser Tyr Ser Ser Gly Trp Lys His Thr Arg Ser Ala Ile Ala Pro Ile
    130                 135                 140

Phe Ser Thr Gly Lys Met Lys Ala Met Gln Glu Thr Ile Asn Ser Lys
145                 150                 155                 160

Val Asp Leu Phe Leu Asp Ile Leu Arg Glu Lys Ala Ser Ser Gly Gln
                165                 170                 175

Lys Trp Asp Ile Tyr Asp Asp Phe Gln Gly Leu Thr Leu Asp Val Ile
                180                 185                 190

Gly Lys Cys Ala Phe Ala Ile Asp Ser Asn Cys Gln Arg Asp Arg Asn
        195                 200                 205

Asp Val Phe Tyr His Pro Val Thr Val Lys Ile Thr Ile Asn Asn Phe
    210                 215                 220

Thr Tyr Phe His Ser Ser Pro Gly Thr Phe His Phe Leu Glu Ser
225                 230                 235                 240

Thr Leu Gln Ile His Thr Thr Gly Arg Cys Arg Asn Ser Thr Cys Arg
                245                 250                 255

Arg Thr Val Lys Cys Val Gly Phe Arg Gln Asp Lys Ala Lys Phe Cys
                260                 265                 270

Ser Asp Tyr Glu Arg Arg Gly Gly Glu Gly Ser Asp Ser Val Asp
        275                 280                 285

Leu Leu Lys Leu Leu Asn Arg Glu Asp Asp Lys Ser Lys Pro Met
    290                 295                 300

Thr Lys Gln Glu Val Ile Glu Asn Cys Phe Ala Phe Leu Leu Ala Gly
305                 310                 315                 320

Tyr Glu Thr Thr Ser Thr Ala Met Thr Tyr Cys Ser Tyr Leu Leu Ser
                325                 330                 335

Lys Tyr Pro Asn Val Gln Gln Lys Leu Tyr Glu Glu Ile Met Glu Ala
                340                 345                 350

Lys Glu Asn Gly Gly Leu Thr Tyr Asp Ser Ile His Asn Met Lys Tyr
            355                 360                 365

Leu Asp Cys Val Tyr Lys Glu Thr Leu Arg Phe Tyr Pro Pro His Phe
    370                 375                 380

Ser Phe Ile Arg Arg Leu Cys Arg Glu Asp Ile Thr Ile Arg Gly Gln
385                 390                 395                 400

Phe Tyr Pro Lys Gly Ala Ile Val Cys Leu Pro His Thr Val His
                405                 410                 415

Arg Asn Pro Glu Asn Trp Asp Ser Pro Glu Glu Phe His Pro Glu Arg
                420                 425                 430

Phe Glu Asn Trp Glu Glu Lys Ser Ser Ser Leu Lys Trp Ile Pro Phe
            435                 440                 445

Gly Val Gly Pro Arg Tyr Cys Val Gly Met Arg Phe Ala Glu Met Glu
    450                 455                 460

Phe Lys Thr Thr Ile Val Lys Leu Leu Asp Thr Phe Glu Leu Lys Gln
465                 470                 475                 480

Phe Glu Gly Glu Ala Asp Leu Ile Pro Asp Cys Asn Gly Val Ile Met
                485                 490                 495

Arg Pro Asn Asp Pro Val Arg Leu His Leu Lys Pro Arg Asn
        500                 505                 510

<210> SEQ ID NO 40
<211> LENGTH: 691
<212> TYPE: PRT

-continued

<213> ORGANISM: saccahromyces cerevisiae P450 reductase

<400> SEQUENCE: 40

```
Met Pro Phe Gly Ile Asp Asn Thr Asp Phe Thr Val Leu Ala Gly Leu
1               5                   10                  15

Val Leu Ala Val Leu Leu Tyr Val Lys Arg Asn Ser Ile Lys Glu Leu
            20                  25                  30

Leu Met Ser Asp Asp Gly Asp Ile Thr Ala Val Ser Ser Gly Asn Arg
        35                  40                  45

Asp Ile Ala Gln Val Val Thr Glu Asn Asn Lys Asn Tyr Leu Val Leu
    50                  55                  60

Tyr Ala Ser Gln Thr Gly Thr Ala Glu Asp Tyr Ala Lys Lys Phe Ser
65                  70                  75                  80

Lys Glu Leu Val Ala Lys Phe Asn Leu Asn Val Met Cys Ala Asp Val
                85                  90                  95

Glu Asn Tyr Asp Phe Glu Ser Leu Asn Asp Val Pro Val Ile Val Ser
            100                 105                 110

Ile Phe Ile Ser Thr Tyr Gly Glu Gly Asp Phe Pro Asp Gly Ala Val
        115                 120                 125

Asn Phe Glu Asp Phe Ile Cys Asn Ala Glu Ala Gly Ala Leu Ser Asn
    130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Asp Gly Ala Gly Thr Thr
            180                 185                 190

Asp Glu Asp Tyr Met Ala Trp Lys Asp Ser Ile Leu Glu Val Leu Lys
        195                 200                 205

Asp Glu Leu His Leu Asp Glu Gln Glu Ala Lys Phe Thr Ser Gln Phe
    210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
            260                 265                 270

Ile Val Lys Ser Arg Glu Leu Phe Ser Ser Asn Asp Arg Asn Cys Ile
        275                 280                 285

His Ser Glu Phe Asp Leu Ser Gly Ser Asn Ile Lys Tyr Ser Thr Gly
    290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
            340                 345                 350

Gly Ala Ala Ile Lys His Tyr Leu Glu Ile Thr Gly Pro Val Ser Arg
        355                 360                 365

Gln Leu Phe Ser Ser Leu Ile Gln Phe Ala Pro Asn Ala Asp Val Lys
    370                 375                 380

Glu Lys Leu Thr Leu Leu Ser Lys Asp Lys Asp Gln Phe Ala Val Glu
385                 390                 395                 400
```

```
Ile Thr Ser Lys Tyr Phe Asn Ile Ala Asp Ala Leu Lys Tyr Leu Ser
            405                 410                 415

Asp Gly Ala Lys Trp Asp Asn Val Pro Met Gln Phe Leu Val Glu Ser
        420                 425                 430

Val Pro Gln Met Thr Pro Arg Tyr Tyr Ser Ile Ser Ser Ser Ser Leu
        435                 440                 445

Ser Glu Lys Gln Thr Val His Val Thr Ser Ile Val Glu Asn Phe Pro
    450                 455                 460

Asn Pro Glu Leu Pro Asp Ala Pro Pro Gly Val Gly Val Thr Thr Asn
465                 470                 475                 480

Leu Leu Arg Asn Ile Gln Leu Ala Gln Asn Asn Val Asn Ile Ala Glu
                485                 490                 495

Thr Asn Leu Pro Val His Tyr Asp Leu Asn Gly Pro Arg Lys Leu Phe
            500                 505                 510

Ala Asn Tyr Lys Leu Pro Val His Val Arg Arg Ser Asn Phe Arg Leu
        515                 520                 525

Pro Ser Asn Pro Ser Thr Pro Val Ile Met Ile Gly Pro Gly Thr Gly
    530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
        595                 600                 605

His Ser Arg Leu Pro Asn Thr Lys Lys Val Tyr Val Gln Asp Lys Leu
    610                 615                 620

Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
        675                 680                 685

Asp Val Trp
        690

<210> SEQ ID NO 41
<211> LENGTH: 693
<212> TYPE: PRT
<213> ORGANISM: Aspergillus niger P450 reductase

<400> SEQUENCE: 41

Met Ala Gln Leu Asp Thr Leu Asp Leu Val Leu Ala Val Leu Leu
1               5                   10                  15

Val Gly Ser Val Ala Tyr Phe Thr Lys Gly Thr Tyr Trp Ala Val Ala
                20                  25                  30

Lys Thr Arg Met Pro Leu Pro Ala Pro Arg Met Asn Gly Ala Ala Lys
            35                  40                  45

Ala Gly Lys Thr Arg Asn Ile Ile Glu Lys Met Glu Glu Thr Gly Lys
        50                  55                  60

Asn Cys Val Ile Phe Tyr Gly Ser Gln Thr Gly Thr Ala Glu Asp Tyr
65                  70                  75                  80
```

```
Ala Ser Arg Leu Ala Lys Glu Gly Ser Gln Arg Phe Gly Leu Lys Thr
                85                  90                  95

Met Val Ala Asp Leu Glu Glu Tyr Asp Tyr Glu Asn Leu Asp Gln Phe
                100                 105                 110

Pro Glu Asp Lys Val Ala Phe Phe Val Leu Ala Thr Tyr Gly Glu Gly
                115                 120                 125

Glu Pro Thr Asp Asn Ala Val Glu Phe Tyr Gln Phe Thr Gly Asp
            130                 135                 140

Asp Val Ala Phe Glu Ser Ala Ser Ala Asp Glu Lys Pro Leu Ser Lys
145                 150                 155                 160

Leu Lys Tyr Val Ala Phe Gly Leu Gly Asn Asn Thr Tyr Glu His Tyr
                165                 170                 175

Asn Ala Met Val Arg Gln Val Asp Ala Ala Phe Gln Lys Leu Gly Pro
                180                 185                 190

Gln Arg Ile Gly Ser Ala Gly Glu Gly Asp Asp Gly Ala Gly Thr Met
                195                 200                 205

Glu Glu Asp Phe Leu Ala Trp Lys Glu Pro Met Trp Ala Ala Leu Ser
210                 215                 220

Glu Ser Met Asp Leu Glu Glu Arg Glu Ala Val Tyr Glu Pro Val Phe
225                 230                 235                 240

Cys Val Thr Glu Asn Glu Ser Leu Ser Pro Glu Asp Glu Thr Val Tyr
                245                 250                 255

Leu Gly Glu Pro Thr Gln Ser His Leu Gln Gly Thr Pro Lys Gly Pro
                260                 265                 270

Tyr Ser Ala His Asn Pro Phe Ile Ala Pro Ile Ala Glu Ser Arg Glu
                275                 280                 285

Leu Phe Thr Val Lys Asp Arg Asn Cys Leu His Met Glu Ile Ser Ile
                290                 295                 300

Ala Gly Ser Asn Leu Ser Tyr Gln Thr Gly Asp His Ile Ala Val Trp
305                 310                 315                 320

Pro Thr Asn Ala Gly Ala Glu Val Asp Arg Phe Leu Gln Val Phe Gly
                325                 330                 335

Leu Glu Gly Lys Arg Asp Ser Val Ile Asn Ile Lys Gly Ile Asp Val
                340                 345                 350

Thr Ala Lys Val Pro Ile Pro Thr Pro Thr Thr Tyr Asp Ala Ala Val
                355                 360                 365

Arg Tyr Tyr Met Glu Val Cys Ala Pro Val Ser Arg Gln Phe Val Ala
370                 375                 380

Thr Leu Ala Ala Phe Ala Pro Met Arg Lys Ala Arg Gln Arg Leu Cys
385                 390                 395                 400

Val Trp Val Ala Gln Gly Leu Phe Pro Arg Glu Gly His Gln Pro Met
                405                 410                 415

Leu Gln His Ala Gln Ala Leu Gln Ser Ile Thr Ser Lys Pro Phe Ser
                420                 425                 430

Ala Val Pro Phe Ser Leu Leu Ile Glu Gly Ile Thr Lys Leu Gln Pro
                435                 440                 445

Arg Tyr Tyr Ser Ile Ser Ser Ser Leu Val Gln Lys Asp Lys Ile
            450                 455                 460

Ser Ile Thr Ala Val Val Glu Ser Val Arg Leu Pro Gly Ala Ser His
465                 470                 475                 480

Met Val Lys Gly Val Thr Thr Asn Tyr Leu Leu Ala Leu Lys Gln Lys
                485                 490                 495
```

-continued

```
Gln Asn Gly Arg Ser Leu Ser Arg Pro Ser Arg Leu Asp Leu Leu His
        500                 505                 510

His Gly Pro Arg Asn Lys Tyr Asp Gly Ile His Val Pro Val His Val
        515                 520                 525

Arg His Ser Asn Phe Lys Leu Pro Ser Asp Pro Ser Arg Pro Ile Ile
        530                 535                 540

Met Val Gly Pro Gly Thr Gly Val Ala Pro Phe Arg Gly Phe Ile Gln
545                 550                 555                 560

Glu Arg Ala Ala Leu Ala Ala Lys Gly Glu Lys Val Gly Pro Thr Val
                565                 570                 575

Leu Phe Phe Gly Cys Arg Lys Ser Asp Glu Asp Phe Leu Tyr Lys Asp
            580                 585                 590

Glu Trp Lys Thr Tyr Gln Asp Gln Leu Gly Asp Asn Leu Lys Ile Ile
        595                 600                 605

Thr Ala Phe Ser Arg Glu Gly Pro Gln Lys Val Tyr Val Gln His Arg
    610                 615                 620

Leu Arg Glu His Ser Glu Leu Val Ser Asp Leu Leu Lys Gln Lys Ala
625                 630                 635                 640

Thr Phe Tyr Val Cys Gly Asp Ala Ala Asn Met Ala Arg Glu Val Asn
                645                 650                 655

Leu Val Leu Gly Gln Ile Ile Ala Ala Gln Arg Gly Leu Pro Ala Glu
            660                 665                 670

Lys Gly Glu Glu Met Val Lys His Met Arg Arg Gly Arg Tyr Gln
        675                 680                 685

Glu Asp Val Trp Ser
        690

<210> SEQ ID NO 42
<211> LENGTH: 678
<212> TYPE: PRT
<213> ORGANISM: mus musculus

<400> SEQUENCE: 42

Met Gly Asp Ser His Glu Asp Thr Ser Ala Thr Val Pro Glu Ala Val
1               5                   10                  15

Ala Glu Glu Val Ser Leu Phe Ser Thr Thr Asp Ile Val Leu Phe Ser
            20                  25                  30

Leu Ile Val Gly Val Leu Thr Tyr Trp Phe Ile Phe Lys Lys Lys
        35                  40                  45

Glu Glu Ile Pro Glu Phe Ser Lys Ile Gln Thr Ala Pro Pro Val
    50                  55                  60

Lys Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Lys Ser Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Thr Gly Val Lys Phe Ala Val Phe Gly Leu Gly Asn Lys
                165                 170                 175
```

```
Thr Tyr Glu His Phe Asn Ala Met Gly Lys Tyr Val Asp Gln Arg Leu
            180                 185                 190
Glu Gln Leu Gly Ala Gln Arg Ile Phe Glu Leu Gly Leu Gly Asp Asp
        195                 200                 205
Asp Gly Asn Leu Glu Glu Asp Phe Ile Thr Trp Arg Glu Gln Phe Trp
    210                 215                 220
Pro Ala Val Cys Glu Phe Phe Gly Val Glu Ala Thr Gly Glu Glu Ser
225                 230                 235                 240
Ser Ile Arg Gln Tyr Glu Leu Val His Glu Asp Met Asp Thr Ala
                245                 250                 255
Lys Val Tyr Thr Gly Glu Met Gly Arg Leu Lys Ser Tyr Glu Asn Gln
            260                 265                 270
Lys Pro Pro Phe Asp Ala Lys Asn Pro Phe Leu Ala Ala Val Thr Thr
        275                 280                 285
Asn Arg Lys Leu Asn Gln Gly Thr Glu Arg His Leu Met His Leu Glu
    290                 295                 300
Leu Asp Ile Ser Asp Ser Lys Ile Arg Tyr Glu Ser Gly Asp His Val
305                 310                 315                 320
Ala Val Tyr Pro Ala Asn Asp Ser Thr Leu Val Asn Gln Ile Gly Glu
                325                 330                 335
Ile Leu Gly Ala Asp Leu Asp Val Ile Met Ser Leu Asn Asn Leu Asp
            340                 345                 350
Glu Glu Ser Asn Lys Lys His Pro Phe Pro Cys Pro Thr Thr Tyr Arg
        355                 360                 365
Thr Ala Leu Thr Tyr Tyr Leu Asp Ile Thr Asn Pro Pro Arg Thr Asn
    370                 375                 380
Val Leu Tyr Glu Leu Ala Gln Tyr Ala Ser Glu Pro Ser Glu Gln Glu
385                 390                 395                 400
His Leu His Lys Met Ala Ser Ser Gly Glu Gly Lys Glu Leu Tyr
                405                 410                 415
Leu Ser Trp Val Val Glu Ala Arg Arg His Ile Leu Ala Ile Leu Gln
            420                 425                 430
Asp Tyr Pro Ser Leu Arg Pro Pro Ile Asp His Leu Cys Glu Leu Leu
        435                 440                 445
Pro Arg Leu Gln Ala Arg Tyr Tyr Ser Ile Ala Ser Ser Ser Lys Val
    450                 455                 460
His Pro Asn Ser Val His Ile Cys Ala Val Ala Val Glu Tyr Glu Ala
465                 470                 475                 480
Lys Ser Gly Arg Val Asn Lys Gly Val Ala Thr Ser Trp Leu Arg Thr
                485                 490                 495
Lys Glu Pro Ala Gly Glu Asn Gly Arg Arg Ala Leu Val Pro Met Phe
            500                 505                 510
Val Arg Lys Ser Gln Phe Arg Leu Pro Phe Lys Pro Thr Thr Pro Val
        515                 520                 525
Ile Met Val Gly Pro Gly Thr Gly Val Ala Pro Phe Met Gly Phe Ile
    530                 535                 540
Gln Glu Arg Ala Trp Leu Arg Glu Gln Gly Lys Glu Val Gly Glu Thr
545                 550                 555                 560
Leu Leu Tyr Tyr Gly Cys Arg Arg Ser Asp Glu Asp Tyr Leu Tyr Arg
                565                 570                 575
Glu Glu Leu Ala Arg Phe His Lys Asp Gly Ala Leu Thr Gln Leu Asn
            580                 585                 590
```

-continued

```
Val Ala Phe Ser Arg Glu Gln Ala His Lys Val Tyr Val Gln His Leu
        595                 600                 605

Leu Lys Arg Asp Lys Glu His Leu Trp Lys Leu Ile His Glu Gly Gly
    610                 615                 620

Ala His Ile Tyr Val Cys Gly Asp Ala Arg Asn Met Ala Lys Asp Val
625                 630                 635                 640

Gln Asn Thr Phe Tyr Asp Ile Val Ala Glu Phe Gly Pro Met Glu His
                645                 650                 655

Thr Gln Ala Val Asp Tyr Val Lys Lys Leu Met Thr Lys Gly Arg Tyr
            660                 665                 670

Ser Leu Asp Val Trp Ser
        675

<210> SEQ ID NO 43
<211> LENGTH: 17
<212> TYPE: DNA
<213> ORGANISM: bacteriophage M13 reverse primer

<400> SEQUENCE: 43
caggaaacag ctatgac                                                        17

<210> SEQ ID NO 44
<211> LENGTH: 20
<212> TYPE: DNA
<213> ORGANISM: bacteriophage T7 promoter primer

<400> SEQUENCE: 44
taatacgact cactataggg                                                     20

<210> SEQ ID NO 45
<211> LENGTH: 30
<212> TYPE: DNA
<213> ORGANISM: Aspergillus ochraceus Primer 11alphaOH-for

<400> SEQUENCE: 45
gatcgaattc atgcccttct tcactgggct                                          30

<210> SEQ ID NO 46
<211> LENGTH: 37
<212> TYPE: DNA
<213> ORGANISM: Aspergillus ochraceus Primer 11alphaOH-rev

<400> SEQUENCE: 46
gatctctaga ttacacagtt aaactcgcca tatcgat                                  37

<210> SEQ ID NO 47
<211> LENGTH: 20
<212> TYPE: DNA
<213> ORGANISM: pFastBacI Primer Bacfwd

<400> SEQUENCE: 47
ctgttttcgt aacagttttg                                                     20

<210> SEQ ID NO 48
<211> LENGTH: 19
<212> TYPE: DNA
<213> ORGANISM: pFastBacI Primer PolyA

<400> SEQUENCE: 48
cctctacaaa tgtggtatg                                                      19
```

```
<210> SEQ ID NO 49
<211> LENGTH: 17
<212> TYPE: DNA
<213> ORGANISM: Aspergillus ochraceus Primer 45624-for1

<400> SEQUENCE: 49
gagatcaaga ttgcctt                                                    17

<210> SEQ ID NO 50
<211> LENGTH: 15
<212> TYPE: DNA
<213> ORGANISM: Aspergillus ochraceus Primer 45624-for2

<400> SEQUENCE: 50
cttcgacgct ctcaa                                                      15

<210> SEQ ID NO 51
<211> LENGTH: 17
<212> TYPE: DNA
<213> ORGANISM: Aspergillus ochraceus Primer 45624-rev1

<400> SEQUENCE: 51
gcaatcttga tctcgtt                                                    17

<210> SEQ ID NO 52
<211> LENGTH: 2403
<212> TYPE: DNA
<213> ORGANISM: homo sapiens oxidoreductase partial S90469

<400> SEQUENCE: 52
ggagactccc acgtggacac cagctccacc gtgtccgagg cggtggccga agaagtatct      60
cttttcagca tgacggacat gattctgttt cgctcatcg tgggtctcct aacctactgg     120
ttcctcttca gaaagaaaaa agaagaagtc cccgagttca ccaaaattca gacattgacc     180
tcctctgtca gagagagcag ctttgtggaa aagatgaaga aaacggggag gaacatcatc     240
gtgttctacg gctcccagac ggggactgca gaggagtttg ccaaccgcct gtccaaggac     300
gcccaccgct acgggatgcg aggcatgtca gcggaccctg aggagtatga cctggccgac     360
ctgagcagcc tgccagagat cgacaacgcc ctggtggttt tctgcatggc cacctacggt     420
gagggagacc ccaccgacaa tgcccaggac ttctacgact ggctgcagga cagacgtgtg     480
gatctctctg gggtcaagtt cgcggtgttt ggtcttggga acaagaccta cgagcacttc     540
aatgccatgg gcaagtacgt ggacaagcgg ctggagcagc tcggcgccca gcgcatcttt     600
gagctggggt tgggcgacga cgatgggaac ttggaggagg acttcatcac ctggcgagag     660
cagttctggc cggccgtgtg tgaacacttt gggggtggaag ccactggcga ggagtccagc     720
attcgccagt acgagcttgt ggtccacacc gacatagatg cggccaaggt gtacatgggg     780
gagatgggcc ggctgaagag ctacgagaac cagaagcccc cctttgatgc caagaatccg     840
ttcctggctg cagtcaccac caaccggaag ctgaaccagg aaccgagcg ccacctcatg     900 cacctggaat tggacatctc ggactccaaa atcaggtatg aatctgggga ccacgtggct     960
gtgtacccag ccaacgactc tgctctcgtc aaccagctgg gcaaaatcct gggtgccgac    1020
ctggacgtcg tcatgtccct gaacaacctg gatgaggagt ccaacaagaa gcacccattc    1080
ccgtgcccta cgtcctaccg cacggccctc acctactacc tggacatcac caacccgccg    1140
cgtaccaacg tgctgtacga gctgcgcag tacgcctcgg agccctcgga gcaggagctg    1200
ctgcgcaaga tggcctcctc ctccggcgag ggcaaggagc tgtacctgag ctgggtggtg    1260
```

```
                                             -continued gaggcccgga ggcacatcct ggccatcctg caggactgcc cgtccctgcg gcccccatc    1320 gaccacctgt gtgagctgct gccgcgcctg caggcccgct actactccat cgcctcatcc    1380
tccaaggtcc accccaactc tgtgcacatc tgtgcggtgg ttgtggagta cgagaccaag    1440
gccggccgca tcaacaaggg cgtggccacc aactggctgc gggccaagga gcctgtcggg    1500
gagaacggcg gccgtgcgct ggtgcccatg ttcgtgcgca agtcccagtt acgcctgccc    1560
ttcaaggcca ccacgcctgt catcatggtg ggccccggcc ccggcggtggca ccctttcata    1620 ggcttcatcc aggagcgggc ctggctgcga cagcagggca aggaggtggg ggagacgctg    1680
ctgtactacg gctgccgccg ctcggatgag gactacctgt accgggagga gctggcgcag    1740
ttccacaggg acggtgcgct cacccagctc aacgtggcct ctcccggga gcagtcccac    1800 aaggtctacg tccagcacct gctaaagcaa gaccgagagc acctgtggaa gttgatcgaa    1860
ggcggtgccc acatctacgt ctgtggggat gcacggaaca tggccaggga tgtgcagaac    1920
accttctacg acatcgtggc tgagctcggg gccatggagc acgcgcaggc ggtggactac    1980
atcaagaaac tgatgaccaa gggccgctac tccctggacg tgtggagcta ggggcctgcc    2040
tgccccaccc accccacaga ctccggcctg taatcagctc tcctggctcc ctcccgtagt    2100
ctcctgggtg tgtttggctt ggccttggca tgggcgcagg cccagtgaca aagactcctc    2160
tgggcctggg gtgcatcctc ctcagccccc aggccaggtg aggtccaccg gcccctggca    2220
gcacagccca gggcctgcat gggggcaccg ggctccatgc ctctggagcc tctggccctc    2280
ggtggctgca cagaagggct ctttctctct gctgagctgg cccagcccct ccacgtgatt    2340
tccagtgagt gtaaataatt ttaaataacc tctggccctt ggaataaagt tctgttttct    2400
gta                                                                  2403
```

<210> SEQ ID NO 53
<211> LENGTH: 676
<212> TYPE: PRT
<213> ORGANISM: homo sapiens cytochrome P450 reductase, partial AAB21814

<400> SEQUENCE: 53

```
Gly Asp Ser His Val Asp Thr Ser Ser Thr Val Ser Glu Ala Val Ala
1               5                   10                  15

Glu Glu Val Ser Leu Phe Ser Met Thr Asp Met Ile Leu Phe Ser Leu
            20                  25                  30

Ile Val Gly Leu Leu Thr Tyr Trp Phe Leu Phe Arg Lys Lys Lys Glu
        35                  40                  45

Glu Val Pro Glu Phe Thr Lys Ile Gln Thr Leu Thr Ser Ser Val Arg
    50                  55                  60

Glu Ser Ser Phe Val Glu Lys Met Lys Lys Thr Gly Arg Asn Ile Ile
65                  70                  75                  80

Val Phe Tyr Gly Ser Gln Thr Gly Thr Ala Glu Glu Phe Ala Asn Arg
                85                  90                  95

Leu Ser Lys Asp Ala His Arg Tyr Gly Met Arg Gly Met Ser Ala Asp
            100                 105                 110

Pro Glu Glu Tyr Asp Leu Ala Asp Leu Ser Ser Leu Pro Glu Ile Asp
        115                 120                 125

Asn Ala Leu Val Val Phe Cys Met Ala Thr Tyr Gly Glu Gly Asp Pro
    130                 135                 140

Thr Asp Asn Ala Gln Asp Phe Tyr Asp Trp Leu Gln Glu Thr Asp Val
145                 150                 155                 160

Asp Leu Ser Gly Val Lys Phe Ala Val Phe Gly Leu Gly Asn Lys Thr
```

-continued

```
                165                 170                 175
Tyr Glu His Phe Asn Ala Met Gly Lys Tyr Val Asp Lys Arg Leu Glu
            180                 185                 190
Gln Leu Gly Ala Gln Arg Ile Phe Glu Leu Gly Leu Gly Asp Asp Asp
        195                 200                 205
Gly Asn Leu Glu Glu Asp Phe Ile Thr Trp Arg Glu Gln Phe Trp Pro
    210                 215                 220
Ala Val Cys Glu His Phe Gly Val Glu Ala Thr Gly Glu Glu Ser Ser
225                 230                 235                 240
Ile Arg Gln Tyr Glu Leu Val Val His Thr Asp Ile Asp Ala Ala Lys
            245                 250                 255
Val Tyr Met Gly Glu Met Gly Arg Leu Lys Ser Tyr Glu Asn Gln Lys
        260                 265                 270
Pro Pro Phe Asp Ala Lys Asn Pro Phe Leu Ala Ala Val Thr Thr Asn
    275                 280                 285
Arg Lys Leu Asn Gln Gly Thr Glu Arg His Leu Met His Leu Glu Leu
290                 295                 300
Asp Ile Ser Asp Ser Lys Ile Arg Tyr Glu Ser Gly Asp His Val Ala
305                 310                 315                 320
Val Tyr Pro Ala Asn Asp Ser Ala Leu Val Asn Gln Leu Gly Lys Ile
            325                 330                 335
Leu Gly Ala Asp Leu Asp Val Val Met Ser Leu Asn Asn Leu Asp Glu
        340                 345                 350
Glu Ser Asn Lys Lys His Pro Phe Pro Cys Pro Thr Ser Tyr Arg Thr
    355                 360                 365
Ala Leu Thr Tyr Tyr Leu Asp Ile Thr Asn Pro Pro Arg Thr Asn Val
370                 375                 380
Leu Tyr Glu Leu Ala Gln Tyr Ala Ser Glu Pro Ser Glu Gln Glu Leu
385                 390                 395                 400
Leu Arg Lys Met Ala Ser Ser Ser Gly Glu Gly Lys Glu Leu Tyr Leu
            405                 410                 415
Ser Trp Val Val Glu Ala Arg Arg His Ile Leu Ala Ile Leu Gln Asp
        420                 425                 430
Cys Pro Ser Leu Arg Pro Pro Ile Asp His Leu Cys Glu Leu Leu Pro
    435                 440                 445
Arg Leu Gln Ala Arg Tyr Tyr Ser Ile Ala Ser Ser Ser Lys Val His
450                 455                 460
Pro Asn Ser Val His Ile Cys Ala Val Val Glu Tyr Glu Thr Lys
465                 470                 475                 480
Ala Gly Arg Ile Asn Lys Gly Val Ala Thr Asn Trp Leu Arg Ala Lys
            485                 490                 495
Glu Pro Val Gly Glu Asn Gly Gly Arg Ala Leu Val Pro Met Phe Val
        500                 505                 510
Arg Lys Ser Gln Leu Arg Leu Pro Phe Lys Ala Thr Thr Pro Val Ile
    515                 520                 525
Met Val Gly Pro Gly Thr Gly Trp His Pro Phe Ile Gly Phe Ile Gln
530                 535                 540
Glu Arg Ala Trp Leu Arg Gln Gln Gly Lys Glu Val Gly Glu Thr Leu
545                 550                 555                 560
Leu Tyr Tyr Gly Cys Arg Arg Ser Asp Glu Asp Tyr Leu Tyr Arg Glu
            565                 570                 575
Glu Leu Ala Gln Phe His Arg Asp Gly Ala Leu Thr Gln Leu Asn Val
        580                 585                 590
```

```
Ala Phe Ser Arg Glu Gln Ser His Lys Val Tyr Val Gln His Leu Leu
        595                 600                 605

Lys Gln Asp Arg Glu His Leu Trp Lys Leu Ile Glu Gly Gly Ala His
    610                 615                 620

Ile Tyr Val Cys Gly Asp Ala Arg Asn Met Ala Arg Asp Val Gln Asn
625                 630                 635                 640

Thr Phe Tyr Asp Ile Val Ala Glu Leu Gly Ala Met Glu His Ala Gln
                645                 650                 655

Ala Val Asp Tyr Ile Lys Lys Leu Met Thr Lys Gly Arg Tyr Ser Leu
            660                 665                 670

Asp Val Trp Ser
        675

<210> SEQ ID NO 54
<211> LENGTH: 677
<212> TYPE: PRT
<213> ORGANISM: homo sapiens NADPH-ferrihemoprotein reductase A60557

<400> SEQUENCE: 54

Met Gly Asp Ser His Val Asp Thr Ser Ser Thr Val Ser Glu Ala Val
1               5                   10                  15

Ala Glu Glu Val Ser Leu Phe Ser Met Thr Asp Met Ile Leu Phe Ser
            20                  25                  30

Leu Ile Val Gly Leu Leu Thr Tyr Trp Phe Leu Phe Arg Lys Lys Lys
        35                  40                  45

Glu Glu Val Pro Glu Phe Thr Lys Ile Gln Thr Leu Thr Ser Ser Val
    50                  55                  60

Arg Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Asn Ala Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Ser Gly Val Lys Phe Ala Val Phe Gly Leu Gly Asn Lys
                165                 170                 175

Thr Tyr Glu His Phe Asn Ala Met Gly Lys Tyr Val Asp Lys Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
    210                 215                 220

Pro Ala Val Cys Glu His Phe Gly Val Glu Ala Thr Gly Glu Glu Ser
225                 230                 235                 240

Ser Ile Arg Gln Tyr Glu Leu Val Val His Thr Asp Ile Asp Ala Ala
                245                 250                 255

Lys Val Tyr Met Gly Glu Met Gly Arg Leu Lys Ser Tyr Glu Asn Gln
            260                 265                 270

Lys Pro Pro Phe Asp Ala Lys Asn Pro Phe Leu Ala Ala Val Thr Thr
```

```
                        275                 280                 285
Asn Arg Lys Leu Asn Gln Gly Thr Glu Arg His Leu Met His Leu Glu
    290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Leu Gly Lys
                325                 330                 335

Ile Leu Gly Ala Asp Leu Asp Val Val Met Ser Leu Asn Asn Leu Asp
                340                 345                 350

Glu Glu Ser Asn Lys Lys His Pro Phe Pro Cys Pro Thr Ser Tyr Arg
    355                 360                 365

Thr Ala Leu Thr Tyr Tyr Leu Asp Ile Thr Asn Pro Pro Arg Thr Asn
    370                 375                 380

Val Leu Tyr Glu Leu Ala Gln Tyr Ala Ser Glu Pro Ser Glu Gln Glu
385                 390                 395                 400

Leu Leu Arg Lys Met Ala Ser Ser Gly Glu Gly Lys Glu Leu Tyr
                405                 410                 415

Leu Ser Trp Val Val Glu Ala Arg Arg His Ile Leu Ala Ile Leu Gln
                420                 425                 430

Asp Cys Pro Ser Leu Arg Pro Pro Ile Asp His Leu Cys Glu Leu Leu
                435                 440                 445

Pro Arg Leu Gln Ala Arg Tyr Tyr Ser Ile Ala Ser Ser Ser Lys Val
    450                 455                 460

His Pro Asn Ser Val His Ile Cys Ala Val Val Val Glu Tyr Glu Thr
465                 470                 475                 480

Lys Ala Gly Arg Ile Asn Lys Gly Val Ala Thr Asn Trp Leu Arg Ala
                485                 490                 495

Lys Glu Pro Ala Gly Glu Asn Gly Gly Arg Ala Leu Val Pro Met Phe
                500                 505                 510

Val Arg Lys Ser Gln Phe Arg Leu Pro Phe Lys Ala Thr Thr Pro Val
                515                 520                 525

Ile Met Val Gly Pro Gly Thr Gly Val Ala Pro Phe Ile Gly Phe Ile
    530                 535                 540

Gln Glu Arg Ala Trp Leu Arg Gln Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Gln Phe His Arg Asp Gly Ala Leu Thr Gln Leu Asn
                580                 585                 590

Val Ala Phe Ser Arg Glu Gln Ser His Lys Val Tyr Val Gln His Leu
    595                 600                 605

Leu Lys Gln Asp Arg Glu His Leu Trp Lys Leu Ile Glu Gly Gly Ala
    610                 615                 620

His Ile Tyr Val Cys Gly Asp Ala Arg Asn Met Ala Arg Asp Val Gln
625                 630                 635                 640

Asn Thr Phe Tyr Asp Ile Val Ala Glu Leu Gly Ala Met Glu His Ala
                645                 650                 655

Gln Ala Val Asp Tyr Ile Lys Lys Leu Met Thr Lys Gly Arg Tyr Ser
                660                 665                 670

Leu Asp Val Trp Ser
            675

<210> SEQ ID NO 55
```

<211> LENGTH: 677
<212> TYPE: PRT
<213> ORGANISM: homo sapiens NADPH-cytochrome P450 reductase P16435

<400> SEQUENCE: 55

```
Met Gly Asp Ser His Val Asp Thr Ser Ser Thr Val Ser Glu Ala Val
1               5                   10                  15

Ala Glu Glu Val Ser Leu Phe Ser Met Thr Asp Met Ile Leu Phe Ser
            20                  25                  30

Leu Ile Val Gly Leu Leu Thr Tyr Trp Phe Leu Phe Arg Lys Lys Lys
        35                  40                  45

Glu Glu Val Pro Glu Phe Thr Lys Ile Gln Thr Leu Thr Ser Ser Val
    50                  55                  60

Arg Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Asn Ala Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Ser Gly Val Lys Phe Ala Val Phe Gly Leu Gly Asn Lys
                165                 170                 175

Thr Tyr Glu His Phe Asn Ala Met Gly Lys Tyr Val Asp Lys Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
    210                 215                 220

Pro Ala Val Cys Glu His Phe Gly Val Glu Ala Thr Gly Glu Glu Ser
225                 230                 235                 240

Ser Ile Arg Gln Tyr Glu Leu Val Val His Thr Asp Ile Asp Ala Ala
                245                 250                 255

Lys Val Tyr Met Gly Glu Met Gly Arg Leu Lys Ser Tyr Glu Asn Gln
            260                 265                 270

Lys Pro Pro Phe Asp Ala Lys Asn Pro Phe Leu Ala Ala Val Thr Thr
        275                 280                 285

Asn Arg Lys Leu Asn Gln Gly Thr Glu Arg His Leu Met His Leu Glu
    290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Leu Gly Lys
                325                 330                 335

Ile Leu Gly Ala Asp Leu Asp Val Val Met Ser Leu Asn Asn Leu Asp
            340                 345                 350

Glu Glu Ser Asn Lys Lys His Pro Phe Pro Cys Pro Thr Ser Tyr Arg
        355                 360                 365

Thr Ala Leu Thr Tyr Tyr Leu Asp Ile Thr Asn Pro Pro Arg Thr Asn
    370                 375                 380

Val Leu Tyr Glu Leu Ala Gln Tyr Ala Ser Glu Pro Ser Glu Gln Glu
```

```
                385                 390                 395                 400
Leu Leu Arg Lys Met Ala Ser Ser Gly Glu Gly Lys Glu Leu Tyr
                405                 410                 415

Leu Ser Trp Val Val Glu Ala Arg Arg His Ile Leu Ala Ile Leu Gln
        420                 425                 430

Asp Cys Pro Ser Leu Arg Pro Pro Ile Asp His Leu Cys Glu Leu Leu
            435                 440                 445

Pro Arg Leu Gln Ala Arg Tyr Tyr Ser Ile Ala Ser Ser Ser Lys Val
        450                 455                 460

His Pro Asn Ser Val His Ile Cys Ala Val Val Glu Tyr Glu Thr
465                 470                 475                 480

Lys Ala Gly Arg Ile Asn Lys Gly Val Ala Thr Asn Trp Leu Arg Ala
                485                 490                 495

Lys Glu Pro Ala Gly Glu Asn Gly Gly Arg Ala Leu Val Pro Met Phe
            500                 505                 510

Val Arg Lys Ser Gln Phe Arg Leu Pro Phe Lys Ala Thr Thr Pro Val
        515                 520                 525

Ile Met Val Gly Pro Gly Thr Gly Val Ala Pro Phe Ile Gly Phe Ile
    530                 535                 540

Gln Glu Arg Ala Trp Leu Arg Gln Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Gln Phe His Arg Asp Gly Ala Leu Thr Gln Leu Asn
            580                 585                 590

Val Ala Phe Ser Arg Glu Gln Ser His Lys Val Tyr Val Gln His Leu
        595                 600                 605

Leu Lys Gln Asp Arg Glu His Leu Trp Lys Leu Ile Glu Gly Gly Ala
    610                 615                 620

His Ile Tyr Val Cys Gly Asp Ala Arg Asn Met Ala Arg Asp Val Gln
625                 630                 635                 640

Asn Thr Phe Tyr Asp Ile Val Ala Glu Leu Gly Ala Met Glu His Ala
                645                 650                 655

Gln Ala Val Asp Tyr Ile Lys Lys Leu Met Thr Lys Gly Arg Tyr Ser
            660                 665                 670

Leu Asp Val Trp Ser
        675

<210> SEQ ID NO 56
<211> LENGTH: 679
<212> TYPE: PRT
<213> ORGANISM: Oryctolagus cuniculus NADPH-cytochrome P450 reductase
      P00389

<400> SEQUENCE: 56

Met Ala Asp Ser His Gly Asp Thr Gly Ala Thr Met Pro Glu Ala Ala
1               5                   10                  15

Ala Gln Glu Ala Ser Val Phe Ser Met Thr Asp Val Val Leu Phe Ser
            20                  25                  30

Leu Ile Val Gly Leu Ile Thr Tyr Trp Phe Leu Phe Arg Lys Lys Lys
        35                  40                  45

Glu Glu Val Pro Glu Phe Thr Lys Ile Gln Ala Pro Thr Ser Ser Ser
    50                  55                  60

Val Lys Glu Ser Ser Phe Val Glu Lys Met Lys Lys Thr Gly Arg Asn
65                  70                  75                  80
```

```
Ile Val Val Phe Tyr Gly Ser Gln Thr Gly Thr Ala Glu Glu Phe Ala
            85                  90                  95

Asn Arg Leu Ser Lys Asp Ala His Arg Tyr Gly Met Arg Gly Met Ala
            100                 105                 110

Ala Asp Pro Glu Glu Tyr Asp Leu Ala Asp Leu Ser Ser Leu Pro Glu
            115                 120                 125

Ile Asn Asn Ala Leu Ala Val Phe Cys Met Ala Thr Tyr Gly Glu Gly
            130                 135                 140

Asp Pro Thr Asp Asn Ala Gln Asp Phe Tyr Asp Trp Leu Gln Glu Thr
145                 150                 155                 160

Asp Val Asp Leu Ser Gly Val Lys Tyr Ala Val Phe Gly Leu Gly Asn
            165                 170                 175

Lys Thr Tyr Glu His Phe Asn Ala Met Gly Lys Tyr Val Asp Gln Arg
            180                 185                 190

Leu Glu Gln Leu Gly Ala Gln Arg Ile Phe Glu Leu Gly Met Gly Asp
            195                 200                 205

Asp Asp Ala Asn Leu Glu Glu Asp Phe Ile Thr Trp Arg Glu Gln Phe
            210                 215                 220

Trp Pro Ala Val Cys Glu His Phe Gly Val Glu Ala Thr Gly Glu Glu
225                 230                 235                 240

Ser Ser Ile Arg Gln Tyr Glu Leu Val Leu His Thr Asp Ile Asp Val
            245                 250                 255

Ala Lys Val Tyr Gln Gly Glu Met Gly Arg Leu Lys Ser Tyr Glu Asn
            260                 265                 270

Gln Lys Pro Pro Phe Asp Ala Lys Asn Pro Phe Leu Ala Thr Val Thr
            275                 280                 285

Thr Asn Arg Lys Leu Asn Gln Gly Thr Glu Arg His Leu Met His Leu
            290                 295                 300

Glu Leu Asp Ile Ser Asp Ser Lys Ile Arg Tyr Glu Ser Gly Asp His
305                 310                 315                 320

Val Ala Val Tyr Pro Ala Asn Asp Ser Ala Leu Val Asn Gln Leu Gly
            325                 330                 335

Glu Ile Leu Gly Ala Asp Leu Asp Val Val Met Ser Leu Asn Asn Leu
            340                 345                 350

Asp Glu Glu Ser Asn Lys Lys His Pro Phe Pro Cys Pro Thr Ser Tyr
            355                 360                 365

Arg Thr Ala Leu Thr Tyr Tyr Leu Asp Ile Thr Asn Pro Pro Arg Thr
            370                 375                 380

Asn Val Leu Tyr Glu Leu Ala Gln Tyr Ala Ala Asp Pro Ala Glu Gln
385                 390                 395                 400

Glu Gln Leu Arg Lys Met Ala Ser Ser Ser Gly Glu Gly Lys Glu Leu
            405                 410                 415

Tyr Leu Ser Trp Val Val Glu Ala Arg Arg His Ile Leu Ala Ile Leu
            420                 425                 430

Gln Asp Tyr Pro Ser Leu Arg Pro Pro Ile Asp His Leu Cys Glu Leu
            435                 440                 445

Leu Pro Arg Leu Gln Ala Arg Tyr Tyr Ser Ile Ala Ser Ser Ser Lys
            450                 455                 460

Val His Pro Asn Ser Val His Ile Cys Ala Val Ala Val Glu Tyr Glu
465                 470                 475                 480

Thr Lys Ala Gly Arg Leu Asn Lys Gly Val Ala Thr Ser Trp Leu Arg
            485                 490                 495
```

```
Ala Lys Glu Pro Ala Gly Glu Asn Gly Gly Arg Ala Leu Val Pro Met
            500                 505                 510

Phe Val Arg Lys Ser Gln Phe Arg Leu Pro Phe Lys Ala Thr Thr Pro
            515                 520                 525

Val Ile Met Val Gly Pro Gly Thr Gly Val Ala Pro Phe Ile Gly Phe
            530                 535                 540

Ile Gln Glu Arg Ala Trp Leu Arg Gln Gln Gly Lys Glu Val Gly Glu
545                 550                 555                 560

Thr Leu Leu Tyr Tyr Gly Cys Arg Arg Ala Ala Glu Asp Tyr Leu Tyr
                565                 570                 575

Arg Glu Glu Leu Ala Gly Phe Gln Lys Asp Gly Thr Leu Ser Gln Leu
            580                 585                 590

Asn Val Ala Phe Ser Arg Glu Gln Ala Gln Lys Val Tyr Val Gln His
            595                 600                 605

Leu Leu Arg Arg Asp Lys Glu His Leu Trp Arg Leu Ile His Glu Gly
            610                 615                 620

Gly Ala His Ile Tyr Val Cys Gly Asp Ala Arg Asn Met Ala Arg Asp
625                 630                 635                 640

Val Gln Asn Thr Phe Tyr Asp Ile Val Ala Glu Leu Gly Ala Met Glu
                645                 650                 655

His Ala Gln Ala Val Asp Tyr Val Lys Lys Leu Met Thr Lys Gly Arg
            660                 665                 670

Tyr Ser Leu Asp Val Trp Ser
            675

<210> SEQ ID NO 57
<211> LENGTH: 678
<212> TYPE: PRT
<213> ORGANISM: rattus norveticus NADPH-cytochrome P450 reductase P00388

<400> SEQUENCE: 57

Met Gly Asp Ser His Glu Asp Thr Ser Ala Thr Met Pro Glu Ala Val
1               5                   10                  15

Ala Glu Glu Val Ser Leu Phe Ser Thr Thr Asp Met Val Leu Phe Ser
            20                  25                  30

Leu Ile Val Gly Val Leu Thr Tyr Trp Phe Ile Phe Arg Lys Lys Lys
        35                  40                  45

Glu Glu Ile Pro Glu Phe Ser Lys Ile Gln Thr Thr Ala Pro Pro Val
    50                  55                  60

Lys Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Lys Ser Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Thr Gly Val Lys Phe Ala Val Phe Gly Leu Gly Asn Lys
                165                 170                 175

Thr Tyr Glu His Phe Asn Ala Met Gly Lys Tyr Val Asp Gln Arg Leu
            180                 185                 190
```

-continued

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
    210                 215                 220

Pro Ala Val Cys Glu Phe Phe Gly Val Glu Ala Thr Gly Glu Glu Ser
225                 230                 235                 240

Ser Ile Arg Gln Tyr Glu Leu Val Val His Glu Asp Met Asp Val Ala
            245                 250                 255

Lys Val Tyr Thr Gly Glu Met Gly Arg Leu Lys Ser Tyr Glu Asn Gln
        260                 265                 270

Lys Pro Pro Phe Asp Ala Lys Asn Pro Phe Leu Ala Ala Val Thr Ala
    275                 280                 285

Asn Arg Lys Leu Asn Gln Gly Thr Glu Arg His Leu Met His Leu Glu
290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Ile Gly Glu
            325                 330                 335

Ile Leu Gly Ala Asp Leu Asp Val Ile Met Ser Leu Asn Asn Leu Asp
        340                 345                 350

Glu Glu Ser Asn Lys Lys His Pro Phe Pro Cys Pro Thr Thr Tyr Arg
    355                 360                 365

Thr Ala Leu Thr Tyr Tyr Leu Asp Ile Thr Asn Pro Pro Arg Thr Asn
370                 375                 380

Val Leu Tyr Glu Leu Ala Gln Tyr Ala Ser Glu Pro Ser Glu Gln Glu
385                 390                 395                 400

His Leu His Lys Met Ala Ser Ser Ser Gly Glu Gly Lys Glu Leu Tyr
            405                 410                 415

Leu Ser Trp Val Val Glu Ala Arg Arg His Ile Leu Ala Ile Leu Gln
        420                 425                 430

Asp Tyr Pro Ser Leu Arg Pro Pro Ile Asp His Leu Cys Glu Leu Leu
    435                 440                 445

Pro Arg Leu Gln Ala Arg Tyr Tyr Ser Ile Ala Ser Ser Ser Lys Val
450                 455                 460

His Pro Asn Ser Val His Ile Cys Ala Val Ala Val Glu Tyr Glu Ala
465                 470                 475                 480

Lys Ser Gly Arg Val Asn Lys Gly Val Ala Thr Ser Trp Leu Arg Ala
            485                 490                 495

Lys Glu Pro Ala Gly Glu Asn Gly Gly Arg Ala Leu Val Pro Met Phe
        500                 505                 510

Val Arg Lys Ser Gln Phe Arg Leu Pro Phe Lys Ser Thr Thr Pro Val
    515                 520                 525

Ile Met Val Gly Pro Gly Thr Gly Ile Ala Pro Phe Met Gly Phe Ile
530                 535                 540

Gln Glu Arg Ala Trp Leu Arg Glu Gln Gly Lys Glu Val Gly Glu Thr
545                 550                 555                 560

Leu Leu Tyr Tyr Gly Cys Arg Arg Ser Asp Glu Asp Tyr Leu Tyr Arg
            565                 570                 575

Glu Glu Leu Ala Arg Phe His Lys Asp Gly Ala Leu Thr Gln Leu Asn
        580                 585                 590

Val Ala Phe Ser Arg Glu Gln Ala His Lys Val Tyr Val Gln His Leu
    595                 600                 605

Leu Lys Arg Asp Arg Glu His Leu Trp Lys Leu Ile His Glu Gly Gly
    610                 615                 620

Ala His Ile Tyr Val Cys Gly Asp Ala Arg Asn Met Ala Lys Asp Val
625                 630                 635                 640

Gln Asn Thr Phe Tyr Asp Ile Val Ala Glu Phe Gly Pro Met Glu His
                645                 650                 655

Thr Gln Ala Val Asp Tyr Val Lys Lys Leu Met Thr Lys Gly Arg Tyr
                660                 665                 670

Ser Leu Asp Val Trp Ser
        675

<210> SEQ ID NO 58
<211> LENGTH: 678
<212> TYPE: PRT
<213> ORGANISM: mus musculus NADPH-cytochrome P450 reductase  P37040

<400> SEQUENCE: 58

Met Gly Asp Ser His Glu Asp Thr Ser Ala Thr Val Pro Glu Ala Val
1               5                   10                  15

Ala Glu Glu Val Ser Leu Phe Ser Thr Thr Asp Ile Val Leu Phe Ser
            20                  25                  30

Leu Ile Val Gly Val Leu Thr Tyr Trp Phe Ile Phe Lys Lys Lys Lys
        35                  40                  45

Glu Glu Ile Pro Glu Phe Ser Lys Ile Gln Thr Thr Ala Pro Pro Val
    50                  55                  60

Lys Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Lys Ser Leu Val Val Phe Cys Met Ala Thr Tyr Gly Glu Gly Asp
    130                 135                 140

Pro Thr Asp Asn Ala Gln Asp Phe Tyr Asp Trp Leu Gln Glu Thr Asp
145                 150                 155                 160

Val Asp Leu Thr Gly Val Lys Phe Ala Val Phe Gly Leu Gly Asn Lys
                165                 170                 175

Thr Tyr Glu His Phe Asn Ala Met Gly Lys Tyr Val Asp Gln Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
    210                 215                 220

Pro Ala Val Cys Glu Phe Phe Gly Val Glu Ala Thr Gly Glu Glu Ser
225                 230                 235                 240

Ser Ile Arg Gln Tyr Glu Leu Val Val His Glu Asp Met Asp Thr Ala
                245                 250                 255

Lys Val Tyr Thr Gly Glu Met Gly Arg Leu Lys Ser Tyr Glu Asn Gln
            260                 265                 270

Lys Pro Pro Phe Asp Ala Lys Asn Pro Phe Leu Ala Ala Val Thr Thr
        275                 280                 285

Asn Arg Lys Leu Asn Gln Gly Thr Glu Arg His Leu Met His Leu Glu
    290                 295                 300

```
Leu Asp Ile Ser Asp Ser Lys Ile Arg Tyr Glu Ser Gly Asp His Val
305                 310                 315                 320

Ala Val Tyr Pro Ala Asn Asp Ser Thr Leu Val Asn Gln Ile Gly Glu
            325                 330                 335

Ile Leu Gly Ala Asp Leu Asp Val Ile Met Ser Leu Asn Asn Leu Asp
        340                 345                 350

Glu Glu Ser Asn Lys Lys His Pro Phe Pro Cys Pro Thr Thr Tyr Arg
    355                 360                 365

Thr Ala Leu Thr Tyr Tyr Leu Asp Ile Thr Asn Pro Pro Arg Thr Asn
370                 375                 380

Val Leu Tyr Glu Leu Ala Gln Tyr Ala Ser Glu Pro Ser Glu Gln Glu
385                 390                 395                 400

His Leu His Lys Met Ala Ser Ser Ser Gly Glu Gly Lys Glu Leu Tyr
                405                 410                 415

Leu Ser Trp Val Val Glu Ala Arg Arg His Ile Leu Ala Ile Leu Gln
            420                 425                 430

Asp Tyr Pro Ser Leu Arg Pro Pro Ile Asp His Leu Cys Glu Leu Leu
        435                 440                 445

Pro Arg Leu Gln Ala Arg Tyr Tyr Ser Ile Ala Ser Ser Ser Lys Val
    450                 455                 460

His Pro Asn Ser Val His Ile Cys Ala Val Ala Val Glu Tyr Glu Ala
465                 470                 475                 480

Lys Ser Gly Arg Val Asn Lys Gly Val Ala Thr Ser Trp Leu Arg Thr
                485                 490                 495

Lys Glu Pro Ala Gly Glu Asn Gly Arg Arg Ala Leu Val Pro Met Phe
            500                 505                 510

Val Arg Lys Ser Gln Phe Arg Leu Pro Phe Lys Pro Thr Thr Pro Val
        515                 520                 525

Ile Met Val Gly Pro Gly Thr Gly Val Ala Pro Phe Met Gly Phe Ile
    530                 535                 540

Gln Glu Arg Ala Trp Leu Arg Glu Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Arg Phe His Lys Asp Gly Ala Leu Thr Gln Leu Asn
            580                 585                 590

Val Ala Phe Ser Arg Glu Gln Ala His Lys Val Tyr Val Gln His Leu
        595                 600                 605

Leu Lys Arg Asp Lys Glu His Leu Trp Lys Leu Ile His Glu Gly Gly
    610                 615                 620

Ala His Ile Tyr Val Cys Gly Asp Ala Arg Asn Met Ala Lys Asp Val
625                 630                 635                 640

Gln Asn Thr Phe Tyr Asp Ile Val Ala Glu Phe Gly Pro Met Glu His
                645                 650                 655

Thr Gln Ala Val Asp Tyr Val Lys Lys Leu Met Thr Lys Gly Arg Tyr
            660                 665                 670

Ser Leu Asp Val Trp Ser
            675

<210> SEQ ID NO 59
<211> LENGTH: 678
<212> TYPE: PRT
<213> ORGANISM: Cavia porcellus NADPH-cytochrome P450 reductase P04175
```

<400> SEQUENCE: 59

```
Met Gly Asp Ser Asn Val Asp Thr Gly Thr Thr Ser Glu Met Val
1               5                   10                  15

Ala Glu Val Ser Leu Phe Ser Ala Thr Asp Met Val Leu Phe Ser
            20                  25                  30

Leu Ile Val Gly Leu Leu Thr Tyr Trp Phe Ile Phe Arg Lys Lys
        35                  40                  45

Asp Glu Val Pro Glu Phe Ser Lys Ile Glu Thr Thr Thr Ser Ser Val
    50                  55                  60

Lys Asp Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ala Ala
                100                 105                 110

Asp Pro Glu Glu Tyr Asp Leu Ser Asp Leu Ser Ser Leu Pro Glu Ile
                115                 120                 125

Glu Asn Ala Leu Ala Val Phe Cys Met Ala Thr Tyr Gly Glu Gly Asp
130                 135                 140

Pro Thr Asp Asn Ala Gln Asp Phe Tyr Asp Trp Leu Gln Glu Ala Asp
145                 150                 155                 160

Val Asp Leu Thr Gly Val Lys Tyr Ala Val Phe Gly Leu Gly Asn Lys
                165                 170                 175

Thr Tyr Glu His Phe Asn Ala Met Gly Lys Tyr Val Asp Lys Arg Leu
                180                 185                 190

Glu Gln Leu Gly Ala Gln Arg Ile Phe Asp Leu Gly Leu Gly Asp Asp
                195                 200                 205

Asp Gly Asn Leu Glu Glu Asp Phe Ile Thr Trp Arg Glu Gln Phe Trp
210                 215                 220

Pro Ala Val Cys Glu His Phe Gly Val Glu Ala Thr Gly Glu Glu Ser
225                 230                 235                 240

Ser Ile Arg Gln Tyr Glu Leu Val Val His Thr Asp Met Asp Thr Ala
                245                 250                 255

Val Val Tyr Thr Gly Glu Met Gly Arg Leu Lys Ser Tyr Glu Asn Gln
                260                 265                 270

Lys Pro Pro Phe Asp Ala Lys Asn Pro Phe Leu Ala Val Val Thr Thr
                275                 280                 285

Asn Arg Lys Leu Asn Gln Gly Thr Glu Arg His Leu Met His Leu Glu
                290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Leu Gly Glu
                325                 330                 335

Ile Leu Gly Thr Asp Leu Asp Ile Val Met Ser Leu Asn Asn Leu Asp
                340                 345                 350

Glu Glu Ser Asn Lys Arg His Pro Phe Pro Cys Pro Thr Thr Tyr Arg
                355                 360                 365

Thr Ala Leu Thr Tyr Tyr Leu Asp Ile Thr Asn Pro Pro Arg Thr Asn
                370                 375                 380

Val Leu Tyr Glu Leu Ala Gln Tyr Ala Ser Glu Pro Ser Glu Gln Glu
385                 390                 395                 400

Gln Leu Arg Lys Met Ala Ser Ser Ser Gly Glu Gly Lys Glu Leu Tyr
                405                 410                 415
```

-continued

```
Leu Ser Trp Val Val Glu Ala Arg Arg His Ile Leu Ala Ile Leu Gln
            420                 425                 430
Asp Tyr Pro Ser Leu Arg Pro Pro Ile Asp His Leu Cys Glu Arg Leu
        435                 440                 445
Pro Arg Leu Gln Ala Arg Tyr Tyr Ser Ile Ala Ser Ser Ser Lys Val
    450                 455                 460
His Pro Asn Ser Val His Ile Cys Ala Val Val Glu Tyr Glu Thr
465                 470                 475                 480
Lys Ser Gly Arg Val Asn Lys Gly Val Ala Thr Ser Trp Leu Arg Ala
                485                 490                 495
Lys Glu Pro Ala Gly Glu Asn Gly Arg Arg Ala Leu Val Pro Met Phe
            500                 505                 510
Val Arg Lys Ser Gln Phe Arg Leu Pro Phe Lys Ala Thr Thr Pro Val
        515                 520                 525
Ile Met Val Gly Pro Gly Thr Gly Val Ala Pro Phe Ile Gly Phe Ile
    530                 535                 540
Gln Glu Arg Ala Trp Leu Gln Glu Gln Gly Lys Glu Val Gly Glu Thr
545                 550                 555                 560
Leu Leu Tyr Tyr Gly Cys Arg Arg Ser Asp Glu Asp Tyr Leu Tyr Arg
                565                 570                 575
Glu Glu Leu Ala Gln Phe His Ala Lys Gly Ala Leu Thr Arg Leu Ser
            580                 585                 590
Val Ala Phe Ser Arg Glu Gln Pro Gln Lys Val Tyr Val Gln His Leu
        595                 600                 605
Leu Lys Arg Asp Lys Glu His Leu Trp Lys Leu Ile His Asp Gly Gly
    610                 615                 620
Ala His Ile Tyr Ile Cys Gly Asp Ala Arg Asn Met Ala Arg Asp Val
625                 630                 635                 640
Gln Asn Thr Phe Cys Asp Ile Val Ala Glu Gln Gly Pro Met Glu His
                645                 650                 655
Ala Gln Ala Val Asp Tyr Val Lys Lys Leu Met Thr Lys Gly Arg Tyr
            660                 665                 670
Ser Leu Asp Val Trp Ser
        675
```

<210> SEQ ID NO 60
<211> LENGTH: 19
<212> TYPE: DNA
<213> ORGANISM: Bacteriophage SP6 primer

<400> SEQUENCE: 60
gatttaggtg acactatag                                            19

<210> SEQ ID NO 61
<211> LENGTH: 44
<212> TYPE: DNA
<213> ORGANISM: Artificial Sequence
<220> FEATURE:
<223> OTHER INFORMATION: Synthetic adapter with NotI site and poly dT
      tail
<220> FEATURE:
<221> NAME/KEY: misc_structure
<222> LOCATION: (1)..(1)
<223> OTHER INFORMATION: The first base is phosphorylated

<400> SEQUENCE: 61
gactagttct agatcgcgag cggccgccct tttttttttt tttt               44

-continued

```
<210> SEQ ID NO 62
<211> LENGTH: 16
<212> TYPE: DNA
<213> ORGANISM: Artificial Sequence
<220> FEATURE:
<223> OTHER INFORMATION: Top Strand of a SalI adapter

<400> SEQUENCE: 62
tcgacccacg cgtccg                                                          16

<210> SEQ ID NO 63
<211> LENGTH: 12
<212> TYPE: DNA
<213> ORGANISM: Artificial Sequence
<220> FEATURE:
<223> OTHER INFORMATION: Bottom Strand of a SalI adapter, the first base
      is phosphorylated
<220> FEATURE:
<221> NAME/KEY: misc_structure
<222> LOCATION: (1)..(1)
<223> OTHER INFORMATION: The first base is phosphorylated

<400> SEQUENCE: 63
gcctgcgcac cc                                                              12

<210> SEQ ID NO 64
<211> LENGTH: 21
<212> TYPE: DNA
<213> ORGANISM: homo sapiens oxidoreductase primer 1C

<400> SEQUENCE: 64
gtggaccaca agctcgtact g                                                    21

<210> SEQ ID NO 65
<211> LENGTH: 22
<212> TYPE: DNA
<213> ORGANISM: homo sapiens oxidoreductase primer 2C

<400> SEQUENCE: 65
catcgaccac ctgtgtgagc tg                                                   22

<210> SEQ ID NO 66
<211> LENGTH: 22
<212> TYPE: DNA
<213> ORGANISM: homo sapiens oxidoreductase primer 2D

<400> SEQUENCE: 66
gtacaggtag tcctcatccg ag                                                   22

<210> SEQ ID NO 67
<211> LENGTH: 3710
<212> TYPE: DNA
<213> ORGANISM: Aspergillus niger NADP CYP450 oxidoreductaseZ26838

<400> SEQUENCE: 67
cctgtatcct gataactcct cagcaaatcg gagtaaacag aaggacaagt cattggagta          60
ctaagtagct ccgtgtcaga gacccggaca ggatcagctt ctccgaaccc gagactccgg         120
gcgaaaaggc caccatcgct caggctacca cctgtgttcc ttccgtcgat cgtcctccct         180
cgtttccggc tcacggcccc ccaaattatt gcggtctgct tagcagtggg ttcggcctct         240
ctgttcttcc tggatcacac cacggcttac tttcttatcc ttttcctttt cctttcttcc         300
tttcttcctg ttctccttc ttcctttcca ccccttcttt tcttttaacc ccatagcgtc         360
```

-continued

```
attctttctt ccgttttatc tttggttttg ggacgccgcc accttatctc ggttcctgcc      420
tcggtctccg gtgatcgcac ctggataggc taagcgtagg gaggtgtgac attcttcttt      480
cacctcctct cctttccccg cctcactccg ttcaatcccc cgctccaccc tttcagactc      540
gccatcgtat caagtcgggg cctttgcttg cgccgctgaa cagcctcacc atggcgcaac      600
tcgataccct cgatctggtg gtcctggcgg tgcttttggt gggtagcgtg gcctacttca      660
ccaagggcac ctactgggca gttgcaaaga cccgtatgcc tctaccggcc cgcggatga      720 acggcgccgc taaggctggc aagactcgga acatcattga aagatggaa gaaacgggca      780 agaattgtgt tattttctac ggatcgcaaa ctggaaccgc tgaggactac gcctccagat      840
tggccaagga aggatctcag cgcttcggcc tcaagaccat ggtggctgac ctcgaggaat      900
acgactatga gaacctggac caattcccgg aggacaaggt tgcgttttc gtgctcgcca      960 cctacggaga gggtgagcct acggataatg ctgttgagtt ctaccagttc ttcaccggtg     1020
acgacgttgc ttttgagagc gcgtccgcgg acgagaagcc tctgtccaag ctgaagtatg     1080
ttgctttcgg tctgggtaac aacacttatg agcactacaa cgccatggtt cgtcaagtcg     1140
atgctgcttt ccagaagctc gggccgcagc gtattggttc tgctggcgag ggtgatgacg     1200
gtgccggtac aatggaagaa gacttcttgg cctggaagga gcccatgtgg gcagcactgt     1260
cggagtcgat ggatctcgaa gagcgtgaag cggtctacga acctgttttc tgcgtcaccg     1320
aaaacgagtc cctgagccct gaggacgaga cggtctatct tggagagccc acccagagcc     1380
accttcaggg tactcccaaa ggcccgtact ctgcgcacaa ccccttttatc gccctattg     1440 ccgaatctcg tgagcttttc accgtcaagg atcgcaactg tctgcacatg gaaattagca     1500
tcgctggaag taacttgtcc taccagactg gtgaccacat cgctgtttgg cccacaaacg     1560
ctggtgccga agtggatcgg ttccttcagg tcttcggtct cgagggcaag cgtgattcgg     1620
tcatcaacat caagggtatc gatgttacgg ccaaggtccc aatcccgacc ccgaccacgt     1680
acgatgccgc tgttcggtac tatatggaag tctgcgcccc tgtgtcccgt cagtttgtag     1740
ccactctggc cgcgttcgct ccgatgagga agcaaggca gagattgtgc gtctgggtag     1800
cacaaggact atttccacga gaaggtcacc aaccaatgct tcaacatgcc caggctcttc     1860
agagcatcac gtccaagcct ttctctgctg ttccgttctc tctgcttatt gaaggcatta     1920
cgaagctgca gcctcgctac tactcgatct cttcgtcctc ccttgtccag aaggacaaga     1980
tcagcatcac ggccgttgtg gaatctgttc gtctgcccgg tgcctctcac atggtgaagg     2040
gtgtgactac gaattatctc ctcgcgctca agcagaagca gaacgggcga tccctctccc     2100
gaccctcacg gcttgactta ctccatcacg gtccccggaa caagtacgac ggtatccacg     2160
ttcccgtgca tgttcgccac tcgaacttca gctgccctc tgatccctct cggcccatta     2220 tcatggtttgg tcctggtact ggtgttgctc cttccgtgg tttcattcag aacgtgctg     2280 cttttggcgg caagggcgag aaggttggac ccactgttct cttcttcggt tgccgcaaga     2340
gtgacgagga tttcttgtac aaggatgaat ggaaggtaag atatcttttt ttcttttccg     2400
cagctacctt catacatctc ggatgctaac atatcgcgat tcgcagacct atcaggacca     2460
gcttggagac aacttgaaga tcatcactgc gttctcgcgt gagggtcctc agaaggtcta     2520
cgttcagcac agactccgcg agcactccga acttgtcagc gaccttctga gcagaaagc     2580 taccttctac gtctgtggtg acgctgcaaa catggctcgc gaggttaacc ttgtgcttgg     2640
ccagatcatt gctgcgcagc gtggtctgcc cgccagaaag ggcgaagaaa tggtcaagca     2700
catgcgtaga cgtggacgct accaggaaga tgtgtggtca taatctttca atgcatcgac     2760
```

-continued

```
ttttctttct tgtctatcac gacggccttc tcgatccatt attttattta acgcctagat   2820
gatctttgca tatatactcc gctgattttg cctattcatc tgttttgctt ggcgtggttt   2880
atgtatgcct agtttatttg ttttgtgcac cgaccggcca gccacacatt gaagtggctt   2940
gagcatgagt gcggtagcca gtgtcgaaag aacaggatag acgatcatga ttattgcggg   3000
aacatgttat gccattctgg gcatattgat atctggttgc atgagcccag aggatacgaa   3060
aagatgaatc catatttaat ttgcacaata cttttcgcct tcttcatcta gtaattaaat   3120
taattgagca ctgaccgaac gagctgacac ctgctgctcg aatagccga caacgcattg    3180
acgtgcaaga gatgcataat cattacaatc aacaagtaga ctggtaacta atcactgaa    3240
tactacagtt actgcctact ttcagccaaa aagtaatact gaagatttcg gggaatcaaa   3300
tagaagaaac atgcataagc ccaacctcgg caataccggg agttaagcac agtaaccaaa   3360
accaaaccaa actagaaccg gcgcgcgacc agtgacccat cgtcattccc ggtatcagca   3420
gttcagtcag actggctggc tagcccgaac ccaactgccg caatcatcca tccatcctca   3480
acccgcccct cccatgccaa cctctctact ccgcagagcg agggacaaaa aaatgagatg   3540
cagcaattaa ccacgataat ctagcaaaaa gaaagttaga agccggaaga acatacatat   3600
cgcttttacc gctgttcgac tgcgacgacg ggtcttgaga gcagttccgc cacgtgggcg   3660
aaaagctgga ctgcacacta cttacgctac cctacgctac ctcggtaccc               3710
```

<210> SEQ ID NO 68
<211> LENGTH: 693
<212> TYPE: PRT
<213> ORGANISM: Aspergillus niger NADP CYP450 oxidoreductase CAA81550

<400> SEQUENCE: 68

```
Met Ala Gln Leu Asp Thr Leu Asp Leu Val Leu Ala Val Leu Leu
1               5                   10                  15

Val Gly Ser Val Ala Tyr Phe Thr Lys Gly Thr Tyr Trp Ala Val Ala
                20                  25                  30

Lys Thr Arg Met Pro Leu Pro Ala Pro Arg Met Asn Gly Ala Ala Lys
            35                  40                  45

Ala Gly Lys Thr Arg Asn Ile Ile Glu Lys Met Glu Glu Thr Gly Lys
        50                  55                  60

Asn Cys Val Ile Phe Tyr Gly Ser Gln Thr Gly Thr Ala Glu Asp Tyr
65                  70                  75                  80

Ala Ser Arg Leu Ala Lys Glu Gly Ser Gln Arg Phe Gly Leu Lys Thr
                85                  90                  95

Met Val Ala Asp Leu Glu Glu Tyr Asp Tyr Glu Asn Leu Asp Gln Phe
            100                 105                 110

Pro Glu Asp Lys Val Ala Phe Phe Val Leu Ala Thr Tyr Gly Glu Gly
        115                 120                 125

Glu Pro Thr Asp Asn Ala Val Glu Phe Tyr Gln Phe Thr Gly Asp
    130                 135                 140

Asp Val Ala Phe Glu Ser Ala Ser Ala Asp Glu Lys Pro Leu Ser Lys
145                 150                 155                 160

Leu Lys Tyr Val Ala Phe Gly Leu Gly Asn Asn Thr Tyr Glu His Tyr
                165                 170                 175

Asn Ala Met Val Arg Gln Val Asp Ala Ala Phe Gln Lys Leu Gly Pro
            180                 185                 190

Gln Arg Ile Gly Ser Ala Gly Glu Gly Asp Asp Gly Ala Gly Thr Met
        195                 200                 205
```

```
Glu Glu Asp Phe Leu Ala Trp Lys Glu Pro Met Trp Ala Ala Leu Ser
    210                 215                 220
Glu Ser Met Asp Leu Glu Glu Arg Glu Ala Val Tyr Glu Pro Val Phe
225                 230                 235                 240
Cys Val Thr Glu Asn Glu Ser Leu Ser Pro Glu Asp Glu Thr Val Tyr
                245                 250                 255
Leu Gly Glu Pro Thr Gln Ser His Leu Gln Gly Thr Pro Lys Gly Pro
            260                 265                 270
Tyr Ser Ala His Asn Pro Phe Ile Ala Pro Ile Ala Glu Ser Arg Glu
        275                 280                 285
Leu Phe Thr Val Lys Asp Arg Asn Cys Leu His Met Glu Ile Ser Ile
    290                 295                 300
Ala Gly Ser Asn Leu Ser Tyr Gln Thr Gly Asp His Ile Ala Val Trp
305                 310                 315                 320
Pro Thr Asn Ala Gly Ala Glu Val Asp Arg Phe Leu Gln Val Phe Gly
                325                 330                 335
Leu Glu Gly Lys Arg Asp Ser Val Ile Asn Ile Lys Gly Ile Asp Val
            340                 345                 350
Thr Ala Lys Val Pro Ile Pro Thr Pro Thr Thr Tyr Asp Ala Ala Val
        355                 360                 365
Arg Tyr Tyr Met Glu Val Cys Ala Pro Val Ser Arg Gln Phe Val Ala
    370                 375                 380
Thr Leu Ala Ala Phe Ala Pro Met Arg Lys Ala Arg Gln Arg Leu Cys
385                 390                 395                 400
Val Trp Val Ala Gln Gly Leu Phe Pro Arg Glu Gly His Gln Pro Met
                405                 410                 415
Leu Gln His Ala Gln Ala Leu Gln Ser Ile Thr Ser Lys Pro Phe Ser
            420                 425                 430
Ala Val Pro Phe Ser Leu Leu Ile Glu Gly Ile Thr Lys Leu Gln Pro
        435                 440                 445
Arg Tyr Tyr Ser Ile Ser Ser Ser Ser Leu Val Gln Lys Asp Lys Ile
    450                 455                 460
Ser Ile Thr Ala Val Val Glu Ser Val Arg Leu Pro Gly Ala Ser His
465                 470                 475                 480
Met Val Lys Gly Val Thr Thr Asn Tyr Leu Leu Ala Leu Lys Gln Lys
                485                 490                 495
Gln Asn Gly Arg Ser Leu Ser Arg Pro Ser Arg Leu Asp Leu Leu His
            500                 505                 510
His Gly Pro Arg Asn Lys Tyr Asp Gly Ile His Val Pro Val His Val
        515                 520                 525
Arg His Ser Asn Phe Lys Leu Pro Ser Asp Pro Ser Arg Pro Ile Ile
    530                 535                 540
Met Val Gly Pro Gly Thr Gly Val Ala Pro Phe Arg Gly Phe Ile Gln
545                 550                 555                 560
Glu Arg Ala Ala Leu Ala Ala Lys Gly Glu Lys Val Gly Pro Thr Val
                565                 570                 575
Leu Phe Phe Gly Cys Arg Lys Ser Asp Glu Asp Phe Leu Tyr Lys Asp
            580                 585                 590
Glu Trp Lys Thr Tyr Gln Asp Gln Leu Gly Asp Asn Leu Lys Ile Ile
        595                 600                 605
Thr Ala Phe Ser Arg Glu Gly Pro Gln Lys Val Tyr Val Gln His Arg
    610                 615                 620
```

-continued

```
Leu Arg Glu His Ser Glu Leu Val Ser Asp Leu Leu Lys Gln Lys Ala
625                 630                 635                 640

Thr Phe Tyr Val Cys Gly Asp Ala Ala Asn Met Ala Arg Glu Val Asn
                645                 650                 655

Leu Val Leu Gly Gln Ile Ile Ala Ala Gln Arg Gly Leu Pro Ala Glu
                660                 665                 670

Lys Gly Glu Glu Met Val Lys His Met Arg Arg Arg Gly Arg Tyr Gln
            675                 680                 685

Glu Asp Val Trp Ser
            690
```